(12) United States Patent
Landa et al.

(10) Patent No.: US 9,844,687 B2
(45) Date of Patent: *Dec. 19, 2017

(54) SYSTEMS FOR CUSTOM COLORATION

(71) Applicant: COLORIGHT LTD., Rehovot (IL)

(72) Inventors: Benzion Landa, Nes Ziona (IL);
Efraim Miklatzky, Neve Ilan (IL);
Sagi Abramovich, Raanana (IL); Yacov Mazuz, Rishon-LeZion (IL); Anton Krassilnikov, Holon (IL); Eliyahu Benny, Rishon-LeZion (IL); Gilad Davara, Rehovot (IL); Chen Ofek, Rehovot (IL); Elena Ishkov, Givataim (IL); Lior Shahar, Kiryat Ono (IL);
Daniel Mandelik, Rehovot (IL)

(73) Assignee: COLORIGHT LTD., Rehovot (IL)

( * ) Notice: Subject to any disclaimer, the term of this patent is extended or adjusted under 35 U.S.C. 154(b) by 0 days.

This patent is subject to a terminal disclaimer.

(21) Appl. No.: 14/948,430

(22) Filed: Nov. 23, 2015

(65) Prior Publication Data
US 2016/0175620 A1  Jun. 23, 2016

Related U.S. Application Data

(63) Continuation of application No. 14/005,828, filed as application No. PCT/IB2012/051351 on Mar. 21, 2012, now Pat. No. 9,205,283.
(Continued)

(51) Int. Cl.
*G01J 3/00* (2006.01)
*A61Q 5/10* (2006.01)
(Continued)

(52) U.S. Cl.
CPC .............. *A61Q 5/10* (2013.01); *A45D 19/02* (2013.01); *A45D 44/005* (2013.01); *A45D 44/02* (2013.01);
(Continued)

(58) Field of Classification Search
CPC ........ G01J 3/00; G01J 3/02; G01J 3/10; G01J 3/18; G01J 3/28; G01J 3/42
See application file for complete search history.

(56) References Cited

U.S. PATENT DOCUMENTS

| D246,260 S | 11/1977 | Forrester |
| 4,643,313 A | 2/1987 | Robson |

(Continued)

FOREIGN PATENT DOCUMENTS

| DE | 36 09 962 | 6/1987 |
| DE | 42 05 112 | 8/1993 |

(Continued)

OTHER PUBLICATIONS

Bolduc, Chantal, and Jerry Shapiro. "Hair care products: waving, straightening, conditioning, and coloring." Clinics in dermatology 19.4 (2001): 431-436.

(Continued)

*Primary Examiner* — Abdullahi Nur
(74) *Attorney, Agent, or Firm* — Oblon, McClelland, Maier & Neustadt, L.L.P.

(57) ABSTRACT

Novel systems and methods for performing treatment (e.g., coloration) of keratinous fibers are disclosed. The methods and systems utilize one or more of a dispensing device which is configured to provide customized composition for treating keratinous fibers (e.g., a coloring composition), optionally formed from tablets; an optical reader, for obtaining sufficient characteristics of the keratinous fibers to make a realistic prediction of the outcome of a treatment (e.g., coloring treatment); a computational units for predicting an outcome of a treatment, optionally being interfaced with the dispensing device and for selecting a customized treatment; and tablet formulations which are useful in preparing customized composition for treating keratinous fibers. Further (Continued)

disclosed are rapidly disintegrating tablets for use in the preparation of compositions for treating keratinous fibers.

16 Claims, 53 Drawing Sheets

Related U.S. Application Data

(60) Provisional application No. 61/585,701, filed on Jan. 12, 2012, provisional application No. 61/543,392, filed on Oct. 5, 2011, provisional application No. 61/454,764, filed on Mar. 21, 2011.

(51) Int. Cl.

| | | |
|---|---|---|
| A45D 19/02 | (2006.01) | |
| A45D 44/00 | (2006.01) | |
| A45D 44/02 | (2006.01) | |
| A61K 8/02 | (2006.01) | |
| A61K 8/73 | (2006.01) | |
| A61K 8/81 | (2006.01) | |
| B01F 1/00 | (2006.01) | |
| B01F 13/10 | (2006.01) | |
| B01F 15/02 | (2006.01) | |
| G01N 33/483 | (2006.01) | |
| A61K 8/34 | (2006.01) | |
| A61K 8/40 | (2006.01) | |
| A61K 8/41 | (2006.01) | |
| A61K 8/46 | (2006.01) | |
| A61K 8/49 | (2006.01) | |
| G01N 21/47 | (2006.01) | |

(52) U.S. Cl.
CPC ............ *A61K 8/0216* (2013.01); *A61K 8/347* (2013.01); *A61K 8/40* (2013.01); *A61K 8/415* (2013.01); *A61K 8/463* (2013.01); *A61K 8/494* (2013.01); *A61K 8/4926* (2013.01); *A61K 8/73* (2013.01); *A61K 8/731* (2013.01); *A61K 8/732* (2013.01); *A61K 8/817* (2013.01); *A61K 8/8176* (2013.01); *B01F 1/0022* (2013.01); *B01F 13/1058* (2013.01); *B01F 13/1063* (2013.01); *B01F 15/0216* (2013.01); *G01N 21/4738* (2013.01); *G01N 33/4833* (2013.01); *A45D 2044/007* (2013.01); *A45D 2200/058* (2013.01); *A61K 2800/4324* (2013.01); *A61K 2800/48* (2013.01); *A61K 2800/87* (2013.01); *G01N 2201/06146* (2013.01)

(56) References Cited

U.S. PATENT DOCUMENTS

| | | |
|---|---|---|
| 5,152,305 A | 10/1992 | Niv |
| 5,205,837 A | 4/1993 | Andrean et al. |
| 5,256,866 A | 10/1993 | Conversano et al. |
| 5,424,525 A | 6/1995 | Rockstein et al. |
| 5,660,342 A | 8/1997 | Bock |
| 5,754,283 A | 5/1998 | Keane et al. |
| 5,851,181 A | 12/1998 | Talmor |
| 5,937,865 A | 8/1999 | Dhaliwal |
| 5,990,058 A | 11/1999 | Bac et al. |
| 6,096,359 A | 8/2000 | Bombardelli et al. |
| 6,170,980 B1 | 1/2001 | Martin |
| 6,248,749 B1 | 6/2001 | Demarchez et al. |
| 6,362,885 B1 | 3/2002 | Osumi et al. |
| D457,265 S | 5/2002 | Gebhard |
| D462,808 S | 9/2002 | Swaner et al. |
| 6,529,446 B1 | 3/2003 | de la Huerga |
| 6,547,833 B2 | 4/2003 | Casperson et al. |
| 6,610,266 B2 | 8/2003 | Witham et al. |
| 6,613,311 B2 | 9/2003 | Imperial |
| 6,707,929 B2 | 3/2004 | Marapane et al. |
| 6,764,523 B2 | 7/2004 | Casperson et al. |
| 6,790,240 B2 | 9/2004 | Schulze zur Wiesche et al. |
| 6,818,022 B2 | 11/2004 | Massoni |
| 6,984,377 B2 | 1/2006 | Witham et al. |
| 7,059,333 B2 | 6/2006 | Duqueroie |
| 7,110,117 B2 | 9/2006 | Grossinger et al. |
| 7,204,856 B2 | 4/2007 | Schulze zur Wiesche et al. |
| 7,243,660 B2 | 7/2007 | Capristo |
| 7,304,739 B2 | 12/2007 | Grossinger et al. |
| D568,473 S | 5/2008 | Ashiwa et al. |
| 7,458,992 B2 | 12/2008 | Schmenger et al. |
| 7,463,356 B2 | 12/2008 | Grossinger et al. |
| 7,508,508 B2 | 3/2009 | Grossinger et al. |
| 7,523,018 B2 | 4/2009 | Grossinger et al. |
| D602,633 S | 10/2009 | Spagnuolo |
| D604,855 S | 11/2009 | Shearlaw et al. |
| 7,708,021 B2 | 5/2010 | Ghannad et al. |
| 7,934,512 B2 | 5/2011 | Spagnuolo |
| D646,396 S | 10/2011 | Seki et al. |
| D652,514 S | 1/2012 | Sherwood et al. |
| D652,919 S | 1/2012 | Sherwood et al. |
| D653,811 S | 2/2012 | BenZion |
| D656,620 S | 3/2012 | Altshuler et al. |
| 8,220,469 B1 | 7/2012 | Spagnuolo |
| 8,360,973 B2 | 1/2013 | Bazin et al. |
| D695,903 S | 12/2013 | Tamsiran |
| 2001/0002025 A1 | 5/2001 | Rolf-Dieter et al. |
| 2002/0010556 A1 | 1/2002 | Marapane et al. |
| 2002/0157191 A1 | 10/2002 | Casperson et al. |
| 2002/0194684 A1 | 12/2002 | Schulze zur Wiesche et al. |
| 2003/0028978 A1 | 2/2003 | Schulze zur Wiesche et al. |
| 2004/0000015 A1 | 1/2004 | Grossinger et al. |
| 2004/0013616 A1 | 1/2004 | Witham et al. |
| 2004/0105830 A1 | 6/2004 | Boswell et al. |
| 2004/0221864 A1 | 11/2004 | Capristo |
| 2005/0015895 A1 | 1/2005 | Azizova et al. |
| 2005/0019398 A1 | 1/2005 | Kotharl et al. |
| 2005/0039271 A1 | 2/2005 | Schulze zur Wiesche et al. |
| 2005/0165705 A1 | 7/2005 | Lauper et al. |
| 2005/0177032 A1 | 8/2005 | Grossinger et al. |
| 2005/0244343 A1 | 11/2005 | Witham et al. |
| 2006/0149151 A1 | 7/2006 | Ladjevardi et al. |
| 2006/0195300 A1 | 8/2006 | Grossinger et al. |
| 2007/0159290 A1 | 7/2007 | Grossinger et al. |
| 2007/0265867 A1 | 11/2007 | Lin |
| 2008/0013077 A1 | 1/2008 | Orelli et al. |
| 2008/0068604 A1 | 3/2008 | Grossinger et al. |
| 2008/0256724 A1 | 10/2008 | Bolton et al. |
| 2009/0014523 A1 | 1/2009 | Zhu et al. |
| 2009/0119852 A1 | 5/2009 | Marsh |
| 2011/0038818 A1 | 2/2011 | Onyebuagu et al. |
| 2012/0090725 A1 | 4/2012 | Saranow |
| 2013/0123973 A1 | 5/2013 | Saranow et al. |
| 2013/0334315 A1 | 12/2013 | Vinogradov et al. |
| 2016/0209272 A1* | 7/2016 | Miklatzky ............ A45D 44/005 |

FOREIGN PATENT DOCUMENTS

| | | |
|---|---|---|
| DE | 102 60 880 | 7/2004 |
| DE | 10 2006 008 149 | 8/2007 |
| EP | 0 590 538 | 4/1994 |
| EP | 1 817 976 | 8/2007 |
| EP | 2 081 668 | 7/2009 |
| EP | 2 193 781 | 6/2010 |
| FR | 2 402 446 | 4/1979 |
| FR | 2 532 174 | 3/1984 |
| FR | 2 901 131 | 11/2007 |
| JP | 2000-116622 | 4/2000 |
| JP | 2004-198398 | 7/2004 |
| JP | 2004-212088 | 7/2004 |
| JP | 2007-212140 | 8/2007 |
| JP | 2008-285429 | 11/2008 |
| KR | 20040076861 | 9/2004 |
| WO | WO 2001/0145647 | 10/2001 |
| WO | WO 2002/083282 | 10/2002 |
| WO | WO 2003/012728 | 2/2003 |
| WO | WO 2003/074015 | 9/2003 |
| WO | WO 2004/058202 | 7/2004 |

(56) References Cited

FOREIGN PATENT DOCUMENTS

| WO | WO 2004/082650 | 9/2004 |
|----|----------------|--------|
| WO | WO 2004/101689 | 11/2004 |
| WO | WO 2008/046518 | 11/2004 |
| WO | WO 2009/121643 | 10/2009 |
| WO | WO 2009/152033 | 12/2009 |
| WO | WO 2010/004565 | 1/2010 |
| WO | WO 2010/060601 | 6/2010 |
| WO | WO 2010/100231 | 9/2010 |
| WO | WO 2011/003554 | 1/2011 |
| WO | WO 2012/032671 | 3/2012 |

OTHER PUBLICATIONS

Brown, Keith C., and John F. Corbett. "The role of meta difunctional benzene derivatives in oxidative hair dyeing, II. Reactions with p-amiriophenols." J. Soc. Cosmet. Chem 30 (1979): 191-211.

Brown, Keith C., and John F. Corbett. "The role of the primary intermediate, N, N-bis-(2-hydroxyethyl)-p-phenylenediamine in oxidative hair dyeing." Journal of the Society of Cosmetic Chemists 37.1 (1986): 1-8.

Brown, Keith C., et al. "Oxidative dyeing of keratin fibers." J. Soc. Cosmet. Chem 36 (1985): 31-37.

Brown, Keith C., John F. Corbett and Robert Labinson. "Benzoquinone imines. Part 14. The kinetics and mechanism of the coupling of o-benzoquinone monoimines with m-anninophenols." J. Chem. Soc., Perkin Trans. 2 12 (1978): 1292-1296.

Corbett, J. F. "p-Benzoquinonediimine—a vital intermediate in oxidative hair dyeing." J. Soc. Cosmet. Chem 20 (1969): 253-263.

Corbett, John F. "Benzoquinone imines. Part VI. Mechanism and kinetics of the reaction of p-benzoquinone di-imines with m-Phenylenediamines." J. Chem. Soc. B (1969): 827-.835.

Corbett, John F. "Benzoquinone imines. Part VII. The mechanism and kinetics of the reaction of p.benzoquinone di-imines with monohydric phenols arid the ultraviolet, infrared, and nuclear magrietici resonance spectra of the resulting indoanilines." J. Chem. Soc. B (1970): 1418-1427.

Corbett, John F. "Benzoquinone imines. Part VIII Mechanism and kinetics of the reaction of p-benzoquinone-monoimines with monohydric phenols." J. Chem. Soc. B (1970): 1502-1509.

Corbett, John F. "Hair Colouring." Review of Progress in Coloration and Related Topics 4.1 (1973): 3-7.

Corbett, John F., and Edward P. Gamson, "Benzoquinone imines, Part XI. Mechanism and kinetics of the reaction of p-benzoquinone di-imines with aniline and its derivatives." J. Chem. Soc., Perkin Trans. 2 11 (1972): 1531-1537.

Corbett, John F., Stanley Pohl, and Irma Rodriguez. "Benzoquinone imines, Part XII. Reactions of 2-aminoindamines [2-amino-N-(4-aminophenyl)-p-benzoquinone di-imines] in aqueous solution." J. Chem. Soc., Perkin Trans. 2 7 (1975): 728-734.

Genina, Elina A., et al. "In vitro and in vivo study of dye diffusion into the human skin and hair follicles." Journal of biomedical optics 7.3 (2002): 471-477.

International Preliminary Report on Patentability Chapter 1 for PCT/IB2012/051351. Report Issued Sep. 24, 2013.

Karsheva, M., S. Georgieva, and S. Handjieva. "The Choice of the Thickener—A Way to Improve the Cosmetics Sensory Properties." Journal of the University of Chemical Technology and Metallurgy 42.2 (2007): 187-194.

Kass, G., and L. Hoehm. "Color reactions of oxidation dye intermediates." J. Soc. Cosmet. Chem 12 (1961): 146-154.

Lewis, David, John Mama, and Jamie Hawkes. "A review or aspects of oxidative hair dye chemistry with special reference to N-nitrosamine formation." Materials 6 (2013): 517-534.

Marsh, J., et al. "A new oxidant for hair coloring." International Journal of Cosmetic Science-32.2 (2010): 158-158.

Morel, Olivier JX, and Robert M. Christie. "Current trends in the chemistry of permanent hair dyeing." Chemical reviews 111.4 (2011): 2537-2561.

PCT International Search Report for PCT/IB2012/051351, dated Nov. 9, 2011.

Schmucker-Castner, Julie, and Dilip Desai. "Rheology Modification of Hydrogen Perixode-based Applications Using Cross-linked Polyacrylic Acid Polymers." International journal of cosmetic science 21.5 (1999): 313-325.

Scott, George V., Clarence R. Robbins, and James D. Barnhurst. "Sorption of quaternary ammonium surfactants by human hair." J So Cosmet Chem 20 (1969): 135.

Takahashi, T., Tango, Y. and Shimmoto, K., "Development of a New Hair Color Simulating Apparatus." Journal of Society of Cosmetic Chemists of Japan vol. 37(2003) No. 2, pp. 108-116 Abstract and Figures only.

Tango, Y. and Shimmoto, K., "Development of a device to measure human hair luster," J. Cosmet. Chem, 52, 237-250 (Jul./Aug. 2001).

Tucker, Harold H. "Hair coloring with oxidation dye intermediates." J. Soc. Cosmet. Chem 18 (1967): 609-628.

Underwood, D. L. "Basic elements of dyeing human hair." J. Soc. Cosmet. Chem 12 (1961): 155.

Wakamatsu, Kazumasa, and Shosuke Ito. "Advanced chemical methods in melanin determination." Pigment Cell Research 15.3 (2002): 174-183.

Wang, Liming, et al. "Kinetics and equilibrium of solute diffusion into human hair." Annals of biomedical engineering 40:12 (2012): 2719-2726.

Wolfram, Leszek J., K. Hall, and I. Huy. "The mechanism of hair bleaching." J. Soc. Cosmetic Chem 21 (1970): 875-900.

Office Action dated Aug. 4, 2017, in corresponding Russian Patent Application No. 2013146379/15 (with English-language translation).

* cited by examiner

 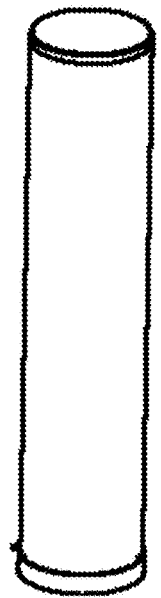
FIG. 4 A  FIG. 4 B
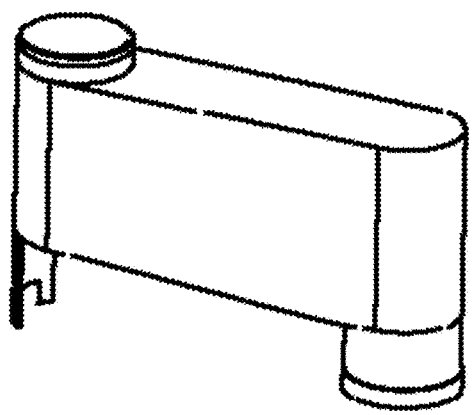 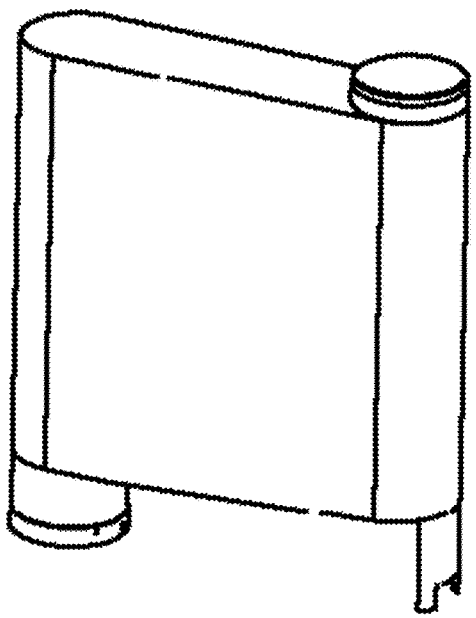
FIG. 4 C  FIG. 4 D

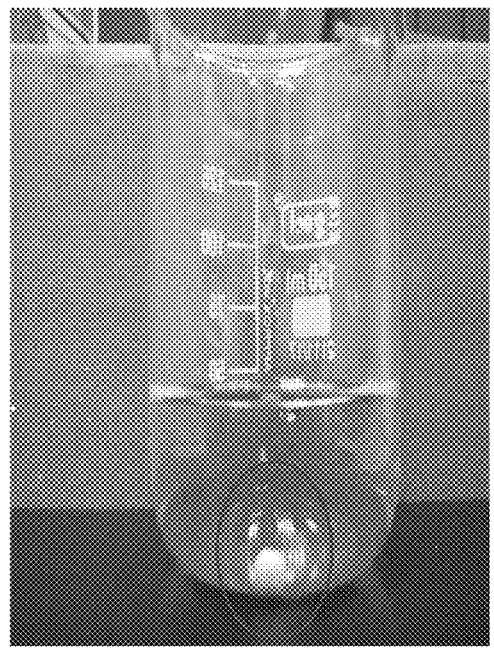
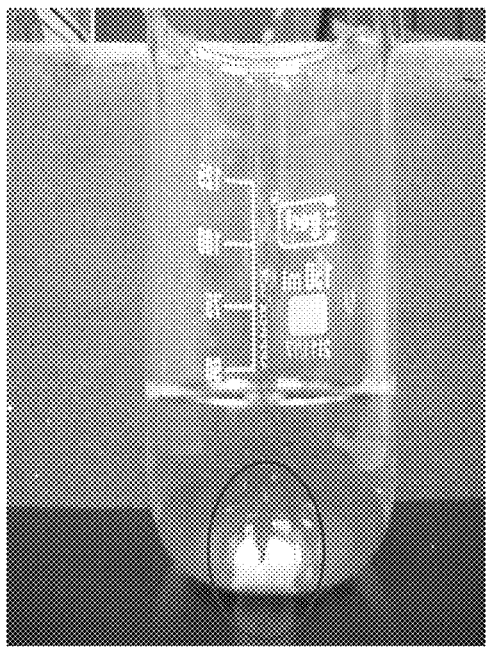
t=0 sec                                    t=3 sec
FIG. 9A                                    FIG. 9B

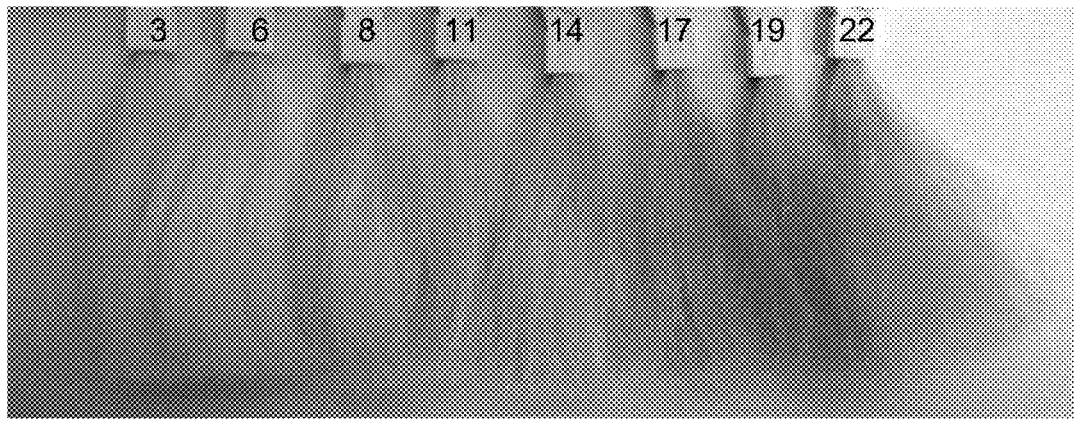
FIG. 15 A Rose 101
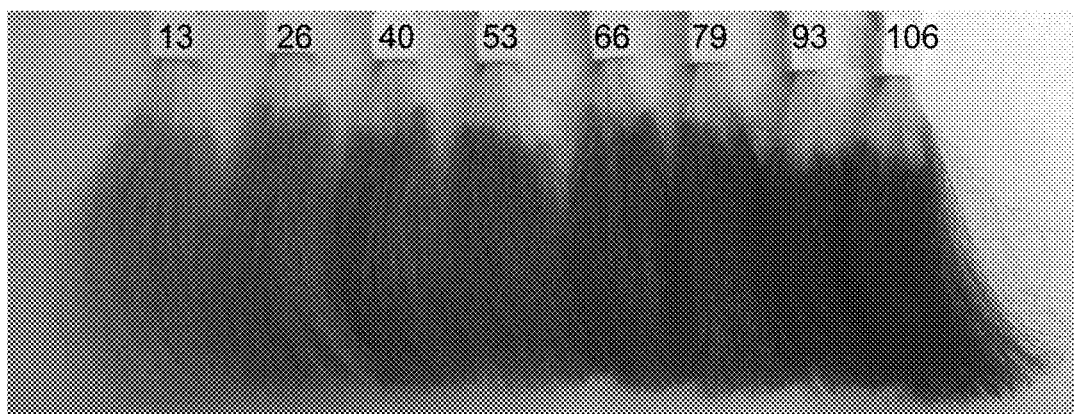
FIG. 15 B Orange 102
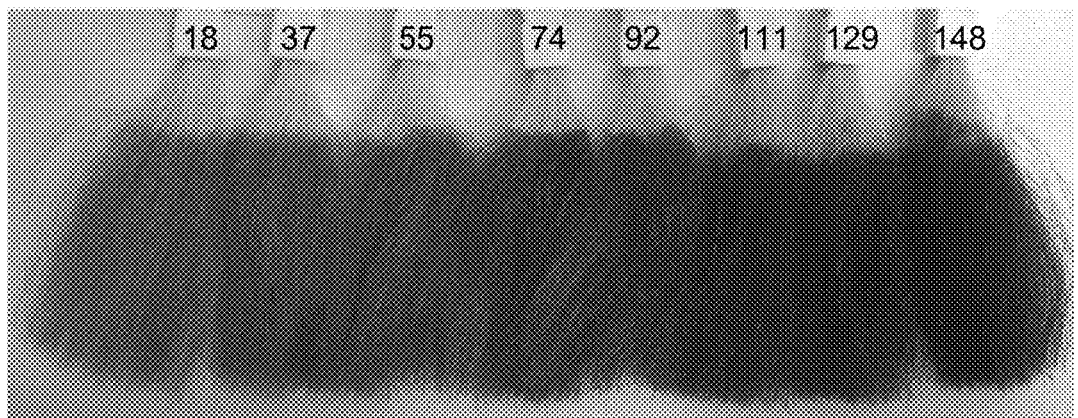
FIG. 15 C Red 103

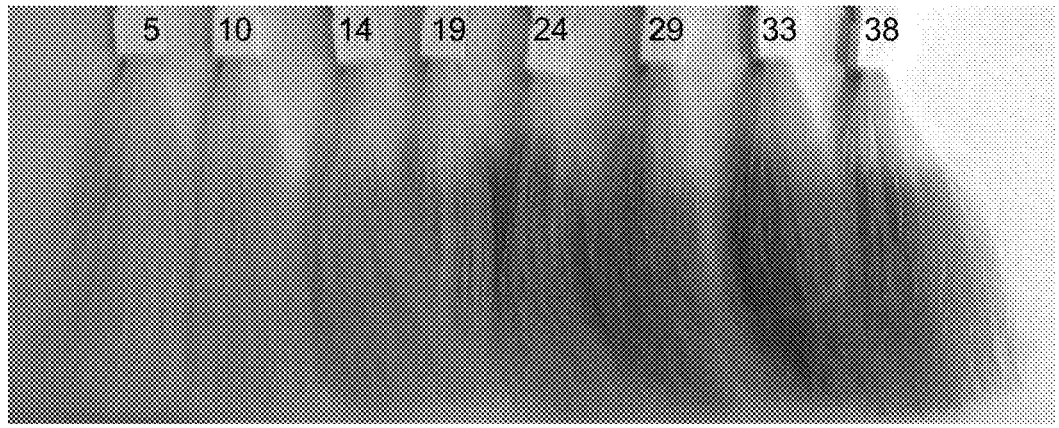
FIG. 15 D Gold 104
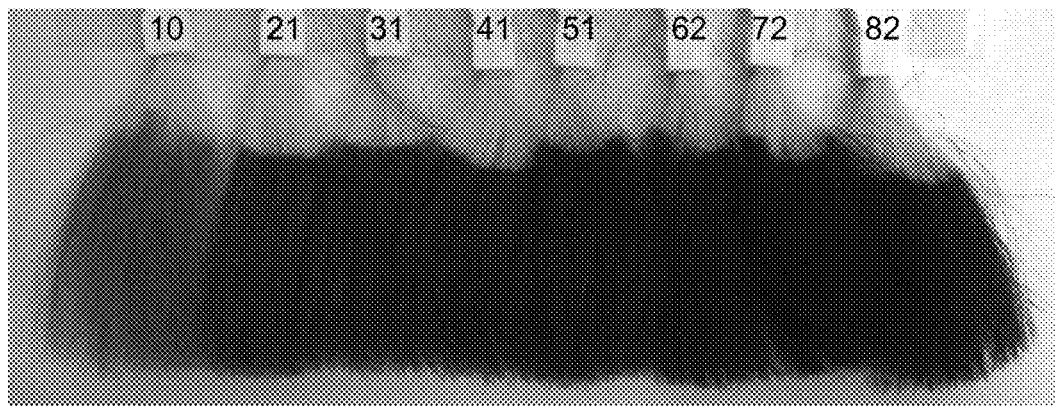
FIG. 15 E Violet 105
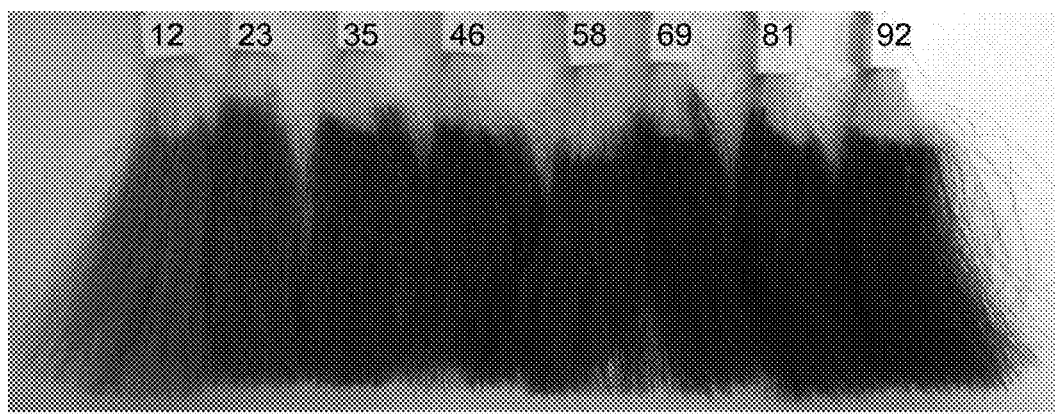
FIG. 15 F Blue 106

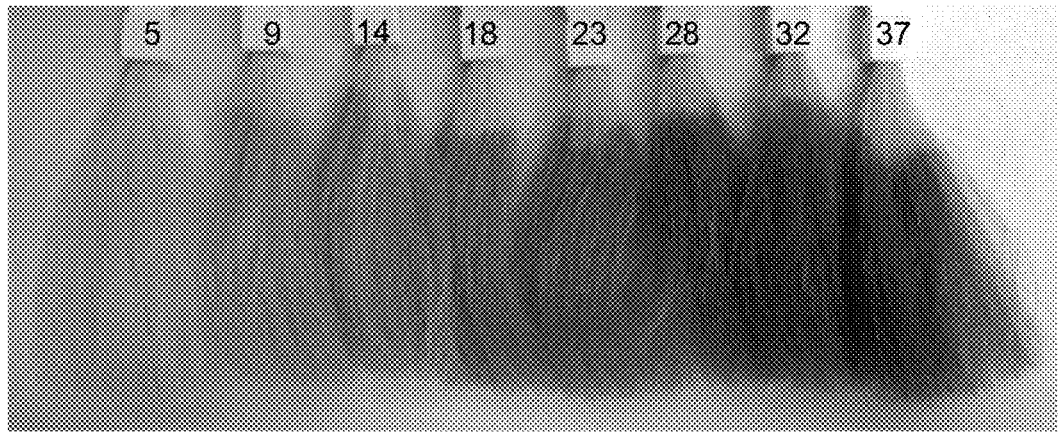
FIG. 15 G Ash 107
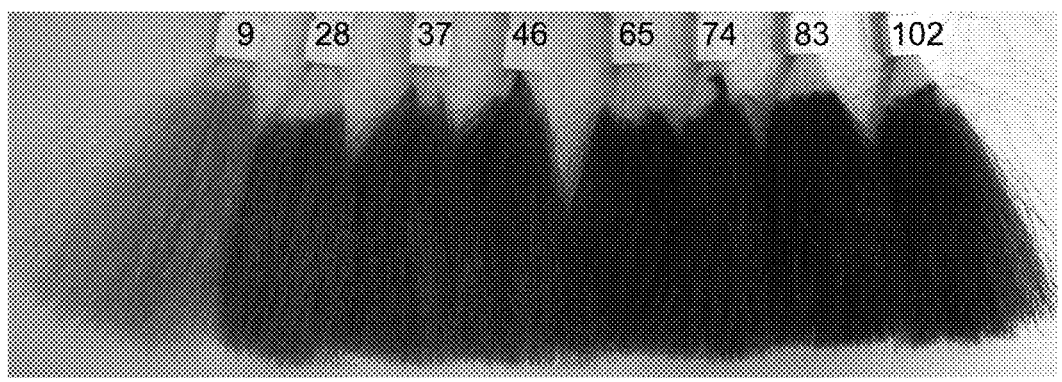
FIG. 15 H Nature 108
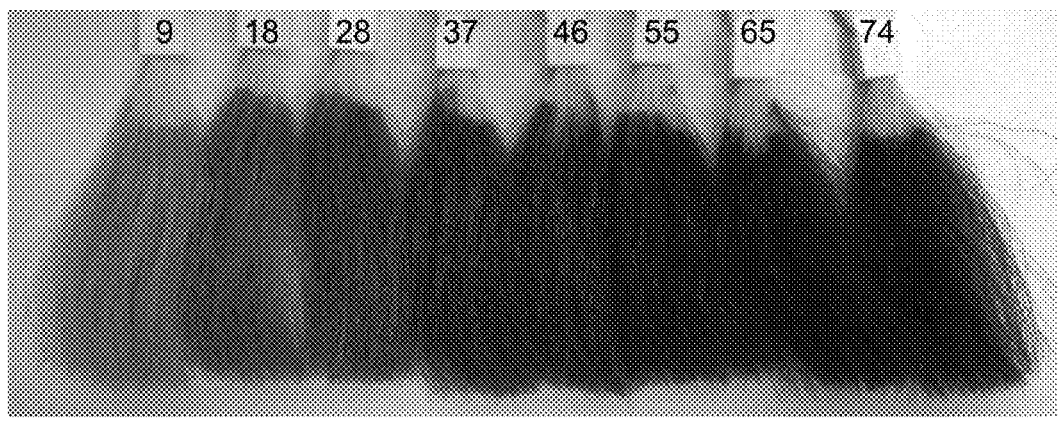
FIG. 15 I Green 109

FIG. 35A Hair with noticeable cuticula
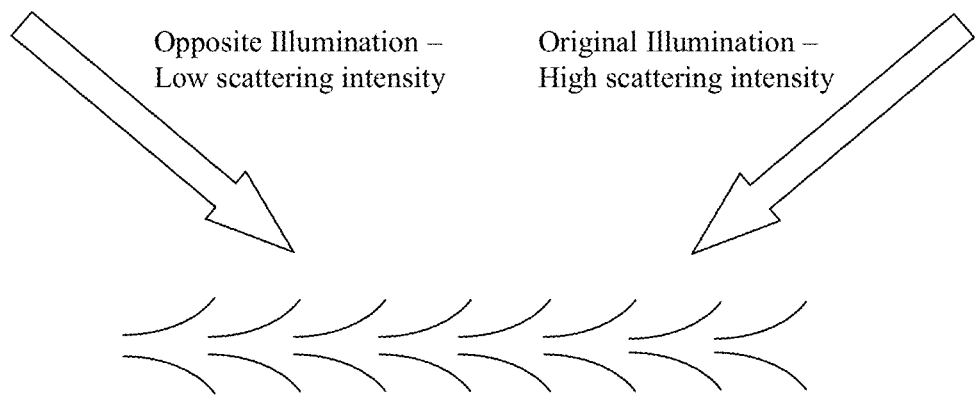
FIG. 35B 'Smooth' Hair
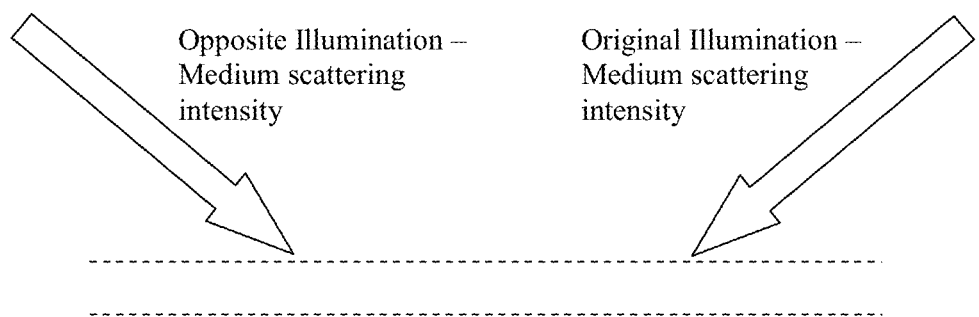

Angles 0° and 180° are parallel to the hair

SYSTEMS FOR CUSTOM COLORATION

CROSS-REFERENCE TO RELATED APPLICATIONS

The present application claims priority to the following patent applications, both of which are hereby incorporated by reference herein in their entirety: PCT/IB2012/51351 filed on Mar. 21, 2012 and U.S. Ser. No. 14/005,828 which is a national phase entry of PCT/IB2012/51351.

FIELD AND BACKGROUND OF THE INVENTION

The present invention, in some embodiments thereof, relates to methods and systems for treating keratinous fibers, and more particularly, but not exclusively, to tablet formulations for treating keratinous fibers such as human hair, to a dispensing device configured for dispensing tablet formulations, to an optical reader for obtaining optical information from keratinous fibers, to a device and method for predicting the results of a treatment operation of keratinous fibers and for selecting a suitable composition for treating keratinous fibers according to the prediction, and to systems for custom treatment of hair and other keratinous fibers which utilize any of the tablet formulations, dispensing device, optical reader and predicting device and method, either alone or in any combination.

Many people wish to alter their appearance by using hair colorants. For this purpose, individuals can either turn to professional salons or buy ready-to-use preparations that can be self-applied by the user. In both cases, the customer identifies his/her desired hair color from a catalog, the appropriate colors or preparations are selected from a finite set of available shades and the pertinent treatments are applied.

Hair colorants are prepared in numerous colors. Usually, a dye color is indicated on the box containing the colorant, either by a color number, a printed example of a color or by means of a sample lock of colored hair.

However, the chemicals of the colorant interact with the chemicals of the uncolored hair and optionally with dye already present in the hair. Thus, even where the same colorant is used, the color of the hair after coloring differs considerably depending on the natural color, or natural color plus old dye mixture of the hair before coloring. For example, in a case where the hair before coloring has a non homogenous mixture of white hair and colored hair, current methods fail to accurately predict the hair color after coloring. Also, in a case where naturally pigmented hair is already colored with artificial colors, the resulting color depends on the combination of original and artificial pigments already present in the hair.

Consequently, it is difficult to predict the color that will result from coloring any person's hair solely from the printing on a box or a sample lock of hair, and a problem often arises that the actual color of the hair after coloring is different from the anticipated color.

In fact, the issue is further complicated by the nature of the coloring process, which chemically changes substances in the hair, including natural hair factors and the artificial colors already present.

Several methods and systems have been developed to predict the final hair color in order to minimize errors and increase customer satisfaction with the use of hair color products. For example, U.S. Pat. No. 6,707,929 describes a method and system for analyzing hair and predicting achievable dyed hair colors. This patent describes methods for identifying an achievable hair color based upon at least one starting hair value of a recipient, for identifying a hair coloring agent based upon at least one starting hair value of a recipient, and for outputting an image for a hair color analyzing system. U.S. Pat. No. 6,707,929 further describes a method for providing a hair-coloring product to a consumer, which is effected by identifying achievable hair colors for the consumer, depicting the achievable colors to the consumer, allowing the consumer to select a desired hair color, and recommending to the consumer a hair-coloring agent to achieve the desired hair color.

Some systems for achieving the above are based on color coordinates. However color coordinates do not sufficiently account for the natural materials in the hair. Improved systems, which utilize a spectrum of the hair and make color calculations based on comparing the hair spectrum with the spectrum of the dye or dye mixture have therefore been developed.

However, even with spectral measurements there is not enough information to characterize the hair and make effective predictions, since natural hair pigments tend to be very absorptive of visible light and are thus hard to distinguish.

Further, the above systems merely manipulate measured colors. As mentioned, hair coloring is a chemical process involving highly active chemicals which have dynamic effects on the hair and on the substances. Thus end results of the dyeing process depend not only on the colors used, but on the way in which these chemical processes are carried out. These processes may have a strong dependence upon initial concentration values of natural and artificial pigments as well as the physical characteristics of the hair, such as its diameter, its permeability and the condition of the cuticles over its surface. These parameters impact both the pace at which chemical reactions take place and the amount of specular reflection that the hair acquires after to coloration, the specular reflection providing a level of shine. Different types of hair colorants exist in the market. A commonly used hair colorant is a permanent dye that achieves an essentially permanent dye effect through oxidative coupling reaction of the dye in the interior of the hair (the hair cortex). A less permanent change in appearance can be obtained from "temporary" hair coloring of the hair surface, and "semi-permanent" and "demi-permanent" coloring providing intermediate colorant penetrations and coloring durations.

Permanent hair coloring is usually achieved by oxidative hair coloring processes. Oxidative hair coloring operates by penetration of a small molecule colorless dye precursor (also known as a primary intermediate), and in many cases also a small molecule dye coupler (also known as a secondary intermediate), into hair swollen by an alkalizing agent such as ammonia. Upon oxidation, either by addition of an oxidizing agent or, for some dyes, by atmospheric oxygen, the dye precursors and couplers react with each other and/or by themselves to produce larger, colored molecules which, due to their increased size, remain trapped inside the hair shaft. Direct dyes, such as azo and HC nitro dyes, which on their own are usually used for temporary coloring, are also used in some permanent hair coloring, often in addition to dye precursors and/or couplers.

In addition to facilitating oxidative coloring processes, oxidizing agents, such as hydrogen peroxide, may also bleach or lighten the hair by destruction of natural melanin pigments within the hair shaft.

Generally, permanent hair colorants are commercially available in wet form. Such coloring preparations usually comprise a 'tint' element, comprising pre-mixed color imparting agents (dye precursors, dye couplers and/or direct dyes) in an alkaline medium, and a 'developer' element, comprising an oxidizing agent. Both elements are supplied in liquid to creamy or paste form, and the two elements are combined immediately prior to application.

For home-use and salon-use, the tint element is generally packaged in a single application container, such as a sealed tube, which reduces exposure of the dyes to oxygen and light and/or the evaporation of pivotal agents such as ammonia. The developer element is less sensitive to degradation and can be supplied in separate tubes or bottles or in large multiple dose containers.

In addition to the stability issues inherent to the oxidative coloring process by currently used wet formulations of hair colorants, these single application-tints also suffer from limited flexibility or reproducibility, and hence from limited options and limited accuracy in cases where customized hair coloring is desired or required. Consumers seeking to use hair colorants desire a large number of color options, reflecting at least the wide range of natural hair colors.

Tint comprising the color imparting agents can be alternatively supplied in powder form, which is mixed before use in an appropriate carrier comprising the necessary additional components. These tint forms exhibit improved stability in comparison with a liquid tint element, due to lower sensitivity to atmospheric oxygen. Nevertheless, such powdery coloring compositions must be protected from exposure to degradation factors to prevent premature deterioration.

U.S. Pat. No. 7,458,992 describes coated dye-containing pellets.

International Patent Application PCT/US2009/046273 (published as WO 2009/152033) discloses a color consultation system for a hair salon where hair colors in powder, granule or particle form are mixed according to the calculations of a processor in order to prepare a hair color treatment for a desired hair color U.S. Pat. No. 6,790,240 describes a shaped body containing a dye precursor, an oxidizing agent and an alkalinizing agent, for preparing coloring compositions by placing the shaped body in a composition containing water. Cellulose-based disintegrants such as microcrystalline cellulose are described for inclusion in the shaped body.

U.S. Pat. No. 7,204,856 describes a shaped body containing a disintegration auxiliary and a thickener, for forming preparations such as hair coloring preparations. Cellulose-based disintegration auxiliaries such as microcrystalline cellulose are described.

U.S. Patent Application having Publication No. 2005/0039271 describes a shaped body, consisting of a dissolution accelerator and an oxidation dye second intermediate in a carrier, for coloring keratinous fibers. The shaped body is free of primary intermediate oxidation dye precursors. The dissolution accelerator may be a gas-evolving component, an enclosed gas, a disintegration aid, or a mixture thereof. Cellulose-based disintegration aids such as microcrystalline cellulose are described.

U.S. Patent Application having Publication No. 2003/0028978 describes a shaped body containing at least one indole derivative and/or indoline derivative, for preparing coloring compositions by placing the shaped body in a composition containing water.

U.S. Pat. No. 5,660,342 describes a mixing device for mixing a liquid with a dry material, particularly a bleaching agent. Tablets of the dry material are smashed, and the broken pieces are then mixed with a liquid.

WO 2010/100231 describes a device for dispensing a coloring composition for keratin fibers, wherein at least 20% of the coloring composition is an anhydrous oil-containing composition. The device comprises three reservoirs, for dispensing a dye composition, an oxidizing composition, and the oil-containing composition, the compositions being dispensed together into a packaging.

EP Patent No. 2081668 describes an apparatus for producing required quantities of cosmetic preparations. Basic preparations are transported, with the aid of electric pumps, from containers in the apparatus to a mixing chamber, and the preparation is dispensed following blending of the components thereof.

Additional background art includes WO 2004/082650; WO 2004/058202; WO 2003/074015; WO 2001/45647; U.S. Patent Application having Publication No. 2002/0194684; FR Patent No. 2901131; U.S. Pat. No. 5,205,837; EP Patent No. 0590538; WO 2009/121643; WO 2008/046518; and EP Patent No. 1817976.

SUMMARY OF THE INVENTION

According to an aspect of some embodiments of the present invention there is provided a system for performing a customized treatment of keratinous fibers, the system comprising:

an optical device for measuring an initial spectrum of the keratinous fibers;

a computer implemented unit for predicting the result of performing the treatment with a pre-determined combination of active agents, and for selecting, based on the predicting, a customized combination of the active agents for effecting a desired treatment; and a mixing unit for mixing the customized combination of active agents, wherein to at least one of the active agents is in a form of a tablet solid formulation as described herein.

According to some embodiments of the present invention, the mixing unit comprises a dispensing device configured for dispensing a selected combination of the tablets.

According to some embodiments of the present invention, the dispensing device is interfaced with the computer-implemented unit.

According to an aspect of some embodiments of the present invention there is provided a system for performing a customized treatment of keratinous fibers, the system comprising:

an optical device for measuring an initial spectrum of the keratinous fibers;

a computer implemented unit for predicting the result of performing the treatment with a pre-determined combination of active agents, and for selecting, based on the predicting, a customized combination of active agents for effecting a desired treatment; and a mixing unit for mixing the customized combination of active agents, wherein the optical device is as described herein.

According to an aspect of some embodiments of the present invention there is provided a system for performing a customized treatment of keratinous fibers, the system comprising:

an optical device for measuring an initial spectrum of the keratinous fibers;

a computer implemented unit for predicting the result of performing the treatment with a pre-determined combination of active agents, and for selecting, based on the predicting, a customized combination of active agents for effecting a desired treatment; and a mixing unit for mixing the customized combination of active agents, wherein the computer implemented unit is operated as a described herein.

According to an aspect of some embodiments of the present invention there is provided a system for performing a customized treatment of keratinous fibers, the system comprising:

an optical device for measuring an initial spectrum of the keratinous fibers;

a computer implemented unit for predicting the result of performing the to treatment with a pre-determined combination of active agents, and for selecting, based on the predicting, a customized combination of active agents for effecting a desired treatment; and a mixing unit for mixing the customized combination of active agents, wherein the mixing unit comprises a dispensing device configured for dispensing a selected amount of at least one of the active agents and being interfaced with the computer implemented unit.

According to an aspect of some embodiments of the present invention there is provided a method of performing a customized treatment of keratinous fibers, the method comprising:

obtaining optical measurements of the keratinous fibers;

predicting a result of treating the keratinous fibers with a pre-determined combination of active agents and selecting, based on the predicting, a customized combination of the active agents for effecting a desired treatment of the keratinous fibers;

preparing a composition comprising the customized combination of active agents; and contacting the keratinous fibers with the composition, wherein obtaining the optical measurements is as described herein.

According to an aspect of some embodiments of the present invention there is provided a method of performing a customized treatment of keratinous fibers, the method comprising:

obtaining optical measurements of the keratinous fibers;

predicting a result of treating the keratinous fibers with a pre-determined combination of active agents while considering the optical measurements;

selecting, based on the predicting, a customized combination of active agents for effecting a desired treatment of the keratinous fibers;

preparing a composition comprising the customized combination of active agents; and contacting the keratinous fibers with the composition, wherein the predicting is in accordance with the methods as described herein.

According to an aspect of some embodiments of the present invention there is to provided a method of performing a customized treatment of keratinous fibers, the method comprising:

obtaining optical measurements of the keratinous fibers;

predicting a result of treating the keratinous fibers with a pre-determined combination of active agents while considering the optical measurements;

selecting, based on the predicting, a customized combination of active agents for effecting a desired treatment of the keratinous fibers;

preparing a composition comprising the customized combination of active agents; and contacting the keratinous fibers with the composition, wherein at least one of the active agents is formulated as a tablet, and selecting the combination comprises selecting a combination of the tablets.

According to some embodiments of the present invention, preparing the composition comprises dispensing the combination of tablets from a dispensing device.

According to some embodiments of the present invention, the dispensing device is interfaced with the computer implemented unit.

According to some embodiments of the present invention, at least one tablet in the combination of tablets is a solid formulation as described herein.

According to some embodiments of the present invention, the dispensing device is as described herein.

In any of the above aspects, the active agents include color imparting agents, thickening agents, oxidizing agents and/or alkalizing agents.

In any of the above aspects, the selecting is further of conditions for contacting the composition with the keratinous fibers, wherein the conditions include, but are not limited to, rate, duration and temperature.

According to an aspect of some embodiments of the present invention there is provided a solid formulation suitable for use in the treatment of keratinous fibers, the formulation being in a form of a tablet and comprising at least one water-insoluble superdisintegrant, and at least one active agent selected from the group consisting of a color imparting agent, an alkalizing agent, an oxidizing agent, and a thickening agent, the superdisintegrant being characterized by a water absorption ratio of at least 0.5.

According to some embodiments of the present invention, the solid formulation is for use in the preparation of a composition for treating keratinous fibers.

According to some embodiments of the present invention, the composition for treating keratinous fibers is a coloring composition.

According to some embodiments of the present invention, the superdisintegrant is characterized by a water absorption ratio that ranges from 0.5 to 2.

According to some embodiments of the present invention, the superdisintegrant is characterized by a water absorption ratio that ranges from 0.6 to 0.9.

According to some embodiments of the present invention, the superdisintegrant is a crosslinked polymer.

According to some embodiments of the present invention, the superdisintegrant is selected from the group consisting of croscarmellose, crospovidone, crosslinked starch, crosslinked alginic acid, crosslinked polyacrylic acid, and a polysaccharide.

According to some embodiments of the present invention, the superdisintegrant is selected from the group consisting of croscarmellose, crospovidone, and crosslinked starch.

According to some embodiments of the present invention, the at least one water-insoluble superdisintegrant is at a concentration in a range of from 0.1 to 10 weight percents of the tablet when uncoated.

According to some embodiments of the present invention, the at least one water-insoluble superdisintegrant is at a concentration in a range of from 0.5 to 5 weight percents of the tablet when uncoated.

According to some embodiments of the present invention, the at least one active agent comprises at least one color imparting agent.

According to some embodiments of the present invention, the at least one active agent consists of the at least one color imparting agent.

According to some embodiments of the present invention, the color imparting agent is selected from the group consisting of a dye precursor, a dye coupler, a direct dye, and any combination thereof.

According to some embodiments of the present invention, the at least one active agent is selected from the group consisting of a direct dye, and a combination of at least one dye precursor and at least one dye coupler.

According to some embodiments of the present invention, a molar ratio of the least one dye precursor and at least one dye coupler ranges from 2:1 to 1:2 and is preferably less than 1.

According to some embodiments of the present invention, the at least one active agent comprises at least one alkalizing agent.

According to some embodiments of the present invention, the at least one active agent consists of the at least one alkalizing agent.

According to some embodiments of the present invention, the at least one active agent comprises at least one oxidizing agent suitable for bleaching hair.

According to some embodiments of the present invention, the at least one active agent consists of the at least one oxidizing agent.

According to some embodiments of the present invention, the at least one oxidizing agent is suitable for reacting with a dye precursor so as to form a dye.

According to some embodiments of the present invention, the active agent comprises at least one thickening agent.

According to some embodiments of the present invention, the solid formulation further comprises ascorbic acid.

According to some embodiments of the present invention, the solid formulation further comprises at least one excipient.

According to some embodiments of the present invention, the solid formulation has a water content of less than 3 weight percents.

According to some embodiments of the present invention, the tablet further comprises a coating.

According to some embodiments of the present invention, the coating comprises at least one coloring agent.

According to some embodiments of the present invention, the coating has a thickness in a range of from 5 µm to 50 µm.

According to some embodiments of the present invention, the tablet has a maximal width in a range of from 2 mm to 10 mm.

According to some embodiments of the present invention, the solid formulation to is substantially spherical or spheroidal, and having an average diameter in a range of from 3 mm to 7 mm.

According to an aspect of some embodiments of the present invention there is provided a composition suitable for use in treating keratinous fibers, the composition comprising an aqueous medium and at least one solid formulation as described herein disintegrated in the medium.

According to some embodiments of the present invention, the composition is characterized by a viscosity suitable for providing sufficient time of contact between the composition and the fibers.

According to some embodiments of the present invention, the composition is suitable for coloring human hair According to some embodiments of the present invention, the composition comprises a plurality of disintegrated tablets, the plurality of tablets being customized for coloring hair of an individual subject.

According to an aspect of some embodiments of the present invention there is provided a method of preparing the composition as described herein, the method comprising contacting the solid formulation with an aqueous medium.

According to an aspect of some embodiments of the present invention there is provided a kit for treating keratinous fibers, the kit comprising at least one set of a plurality of the solid formulations as described herein, the at least one set consisting of a plurality of substantially identical solid formulations.

According to some embodiments of the present invention, the kit comprises at least three of the sets of solid formulations, each of the sets comprises a color imparting agent, wherein the color imparting agents are different from one another in each of the sets.

According to some embodiments of the present invention, the kit further comprises at least one aqueous medium enclosed in a vessel recipient, the medium being selected from the group consisting of an oxidizing medium, an alkalizing medium, and a carrier medium.

According to some embodiments of the present invention, the at least one aqueous medium is suitable for disintegration of the tablets.

According to some embodiments of the present invention, the kit further to comprises at least one additional set of solid formulations, wherein the active agent in the solid formulations in the additional set comprises an alkalizing agent.

According to some embodiments of the present invention, the sets of solid formulations are customized for coloring hair of an individual subject.

According to an aspect of some embodiments of the present invention there is provided a method of preparing the solid formulation as described herein, the method comprising:

forming a mixture comprising the at least one active agent and the at least one superdisintegrant; and compressing the mixture, to thereby form the tablet.

According to some embodiments of the present invention, the mixture comprises a plurality of particles and wherein at least 80 weight percents of the particles have a diameter of 200 µm or less.

According to some embodiments of the present invention, the method further comprises coating the tablet.

According to some embodiments of the present invention, the method further comprises drying the tablet.

According to an aspect of some embodiments of the present invention there is provided a method of treating keratinous fibers, the method comprising:

disintegrating at least one solid formulation as described herein in a first aqueous medium, to thereby obtain a composition comprising the at least one active agent; and contacting the composition with the keratinous fibers for a time period suitable to treat the keratinous fibers.

According to some embodiments of the present invention, the at least solid formulation comprises at least one color imparting agent, the method being for coloring the keratinous fibers.

According to some embodiments of the present invention, the method further comprises, prior to contacting the composition with the fibers, contacting the fibers with a bleaching medium for a time period sufficient to lighten a color of the fibers.

According to some embodiments of the present invention, the method further to comprises preparing the bleaching medium by disintegrating at least one solid formulation which comprises an oxidizing agent in an aqueous medium.

According to some embodiments of the present invention, the method further comprises mixing the at least one solid formulation, before, during and/or after the disintegrating, with an active agent selected from the group consisting of an alkalizing agent, an oxidizing agent, and a thickening agent.

According to some embodiments of the present invention, wherein the method comprises mixing the at least one solid formulation with an oxidizing medium, the oxidizing medium comprising at least one oxidizing agent and a suitable carrier, wherein a concentration of the at least one oxidizing agent in the oxidizing medium being in a range of from 0.5 to 25 weight percents.

According to some embodiments of the present invention, the method comprises mixing the at least one solid formulation with an alkalizing medium, the alkalizing medium comprising at least one alkalizing agent and a suitable carrier, wherein a concentration of the at least one alkalizing agent in the alkalizing medium being in a range of from 0.1 to 15 weight percents.

According to some embodiments of the present invention, the method further comprises selecting the at least one solid formulation from a plurality of solid formulations of different types, wherein the selecting comprises:

establishing initial properties of the keratinous fibers;

selecting a desired customized treatment suiting an individual subject; and determining an amount of solid formulations of each of the types suitable, in combination, for effecting the desired customized treatment.

According to some embodiments of the present invention, the customized treatment comprises customized coloring, and wherein establishing the initial properties comprises measuring an initial reflectance spectrum, and selecting the customized color comprises determining a reflectance spectrum of the customized color, wherein the reflectance spectra are independently converted to a color coordinate presentation.

According to some embodiments of the present invention, determining the amount of solid formulations comprises:

adding to the color coordinate presentation of the initial reflectance spectrum positive or negative contribution of one solid formulation comprising one color to imparting agent providing a basic shade to the color coordinate presentation, thereby calculating an intermediate color coordinate presentation;

and iterating the calculating of the intermediate color presentation upon adding one solid formulation comprising the color imparting agent or upon replacing the solid formulation by a formulation comprising a different color imparting agent, until the difference between the intermediate color coordinate presentation and a desired color coordinate presentation is minimized According to some embodiments of the present invention, the determining further accounts for a positive and/or negative contribution of at least one active agent selected from the group consisting of an alkalizing agent, an oxidizing agent, and a thickening agent in the keratinous fibers to the calculated color coordinate presentation.

According to some embodiments of the present invention, the selecting further accounts for a contribution of individual properties of the keratinous fibers.

According to some embodiments of the present invention, the selecting is effected by one or more computer implemented system.

According to some embodiments of the present invention, the selecting uses a prediction, the prediction of a result of a treatment of keratinous fibers that uses a predetermined composition, the prediction comprising:

measuring an initial spectrum of the keratinous fibers;

determining from the initial spectrum a presence and concentration of respective fiber constituents;

determining a modified concentration of the fiber constituents following bleaching effects of chemical agents in the composition;

determining final concentrations of the fiber constituents following interaction of the chemical agents with colorants in the fiber; and from the final concentrations, predicting a final spectrum of the fiber from which the result of the treatment can be calculated.

According to some embodiments of the present invention, the determining from the initial spectrum a presence and concentration of respective fiber constituents comprises calculating, from the initial spectrum, presence and initial concentrations of keratin, eumelanin, pheomelanin and artificial pigments, and/or wherein determining the modified concentration comprises:

from the predetermined recipe obtaining factors for alkaline agent concentration, hydrogen peroxide concentration, temperature, diameter of hair, condition of hair and its cuticles, ethnicity and exposure duration;

from at least some of the obtained factors, determining modified concentrations of keratin, eumelanin and pheomelanin, or:

from the predetermined recipe obtaining a dye concentration factor; and from the at least some of the factors for dye concentration and at least some of alkaline agent concentration, hydrogen peroxide concentration, temperature, diameter of hair, condition of hair and its cuticles, ethnicity and exposure duration, determining a final concentration of artificial colorant, or wherein predicting the final spectrum of the hair comprises, making the prediction from the from the final concentrations of artificial colorant, keratin, eumelanin, and pheomelanin, predicting a final spectrum of the hair, or wherein a relation between the concentrations of ingredients and the final spectra is determined in the formula of Kubelka Munk.

According to some embodiments of the present invention, the approximation of Kubelka Munk is of the form:

$$\frac{(1-R(\lambda))^2}{2 \cdot R(\lambda)} = \frac{\sum_{n=1}^{N} C_n \cdot K(\lambda)_n}{\sum_{n=1}^{N} C_n \cdot S(\lambda)_n}$$

where:

$R(\lambda)$=The diffused reflectance in wavelength;

$K(\lambda)_n$=The absorption, in wavelength, of the $n^{th}$ ingredient;

$S(\lambda)_n$=The scattering, in wavelength, of the $n^{th}$ ingredient; and $C_n$=The concentration of the $n^{th}$ colorant.

According to some embodiments of the present invention, the diffused reflectance in wavelength—$R(\lambda)$—is obtained from the Sanderson correction formula.

According to some embodiments of the present invention, the predicting a final spectrum, or the determining respective hair constituents, comprises correcting for specular reflection effects, and the correcting for specular reflection effects comprises considering an air to hair boundary and a hair outer region to hair inner region to boundary, and/or the correcting comprises applying a Sanderson correction.

According to some embodiments of the present invention, the Sanderson correction is of the form:

$$R(\lambda) = \frac{R(\lambda)_{meas} - \alpha}{1 - F(\lambda)_{ext} - F(\lambda)_{int} + F(\lambda)_{ext}F(\lambda)_{int} - \alpha F(\lambda)_{int} + F(\lambda)_{int}R(\lambda)_{meas}}$$

Where:

λ=wavelength

α=The relative portion of specular reflectance which propagates to the spectrometer's detector;

R(λ)=Corrected reflectance by Saunderson formula;

$F(\lambda)_{ext}$=The external Fresnel reflectance (specular) from the external side of the hair;

$F(\lambda)_{int}$=The internal Fresnel reflectance between the internal medium of the hair and the hair boundary region.

According to some embodiments of the present invention, the corrected reflectance according to the Sanderson correction—R(λ)—is inserted into the Kubelka Munk approximation, and/or wherein the modified or final concentrations of keratin, eumelanin, pheomelanin and artificial colorant are calculated using a chemical reaction kinetics equation, wherein the calculating the final concentrations further considers taking into account intermediate products appearing from the chemical reactions.

According to some embodiments of the present invention, the measuring is effected by an optical hair measurement device for optical hair measurement, which comprises:

an illumination unit for illuminating hair;

a measuring unit comprising at least one sensor for optically measuring the hair during illumination by the illumination unit; wherein the sensor and a beam from the illumination unit respectively subtend a light diffusion angle at the hair being measured, thereby to ensure that the sensor principally measures light of the illumination beam that is diffused or scattered by the hair.

According to some embodiments of the present invention, the device further comprises a main illumination source and subsidiary illumination sources, and processing electronics to use differential illumination results from respective sources to determine an angle of a hair relative to the main illumination source.

According to some embodiments of the present invention, at least the main illumination source is used for spectroscopy and at least one subsidiary illumination source is used for angular measurement.

According to some embodiments of the present invention, the sensor comprises sensitivity to the visible and near infrared parts of the electromagnetic spectrum.

According to an aspect of some embodiments of the present invention there is provided a device for preparing a customized composition for treating keratinous fibers, the composition comprising a plurality of solid formulations in a tablet form, the device comprising:

a plurality of containers, each container having an outlet suitable for dispensing a tablet; and a dispensing unit for dispensing a pre-determined amount of tablets, the containers and the dispensing unit being attachable to one another.

According to some embodiments of the present invention, the device further comprises a platform, the platform having the plurality of containers attached thereto.

According to some embodiments of the present invention, the containers and the dispensing unit are attachable to one another through the platform.

According to some embodiments of the present invention, the device further comprises at least one funnel configured for channeling tablets dispensed from the container to an outlet.

According to some embodiments of the present invention, the device further comprises one or more optional features selected from the group comprising legs supporting the platform, housings able to enclose at least part of the device, stands for receiving vessels able to contain the customized combination of tablets and user interfaces able to provide or retrieve information relating to the customized combination of tablets.

According to some embodiments of the present invention, the device further comprises means for weighing or counting the tablets to thereby provide the pre-determined amount of the tablets which is dispensed from each of the containers.

According to some embodiments of the present invention, each of the containers individually comprises a different type of tablets, and wherein the customized treatment composition comprises the pre-determined amount of each of the at least one type of the tablets.

According to some embodiments of the present invention, the customized coloring composition comprises a combination of at least two different types of tablets, each of the types of tablets being dispensed from a different container.

According to some embodiments of the present invention, at least one type of the types of tablet comprises a coloring imparting agent.

According to some embodiments of the present invention, the device is configured for dispensing two or more types of tablets, each comprising a different color imparting agent, to thereby provide a pre-determined collection of color imparting agents.

According to some embodiments of the present invention, at least one type of the types of tablets comprises rapidly disintegrating tablets.

According to some embodiments of the present invention, at least one type of the types of tablets comprises an active agent selected from the group consisting of an oxidizing agent, an alkalizing agent and a thickening agent.

According to some embodiments of the present invention, the device is configured for generating at least one medium selected from the group consisting of an alkalizing medium, a bleaching medium, an oxidizing medium and a thickening medium.

According to some embodiments of the present invention, the device further comprises at least one additional compartment containing at least one of the media and configured for dispensing each of the at least medium in a pre-determined amount.

According to some embodiments of the present invention, the device further comprises at least one additional compartment which comprises an aqueous solution and which is in communication with at least a portion of the compartments and which comprises the at least active agent, the device being configured for generating a pre-determined amount of the medium upon contacting a type of the tablets with the aqueous solution.

According to some embodiments of the present invention, the device further comprises a mixing unit for mixing the tablets with the media.

According to some embodiments of the present invention, the device further comprises a printed circuit board to connect electronic components of the device.

According to some embodiments of the present invention, the device further comprises at least one computer-implemented unit.

According to some embodiments of the present invention, the computer-implemented unit (or means) is interfaced with the dispensing unit of each of the containers, and wherein the pre-determined amount of the tablets is selected by the computer-implemented unit.

According to some embodiments of the present invention, the pre-determined amount of the tablets is selected by the computer-implemented means (unit) upon considering initial properties of the keratinous fibers.

According to some embodiments of the present invention, considering the initial properties is effected by an optical measurement instrument.

According to some embodiments of the present invention, the optical measurement instrument comprises:

an illumination unit for illuminating hair;

a measuring unit comprising at least one sensor for optically measuring the hair during illumination by the illumination unit; wherein the sensor and a beam from the illumination unit respectively use wavelengths in the visible and infrared spectral regions, thereby to provide a spectrum of the hair that discriminates both between different natural hair colorants and between different artificial hair colorants.

According to some embodiments of the present invention, the tablets and suitable media are dispensed in the form of a multi-component kit.

According to some embodiments of the present invention, at least one of type of the tablets comprises a solid formulation as described herein.

According to some embodiments of the present invention, each of the tablets is a solid formulation as described herein.

According to an aspect of some embodiments of the present invention there is provided a method for predicting a result of a treatment of keratinous fibers that uses a predetermined composition, comprising:

measuring an initial spectrum of the keratinous fibers;

determining from the initial spectrum a presence and concentration of respective fiber constituents;

determining a modified concentration of the fiber constituents following bleaching effects of chemical agents in the composition;

determining final concentrations of the fiber constituents following interaction of the chemical agents with colorants in the fiber; and from the final concentrations, predicting a final spectrum of the fiber from which the result of the treatment can be calculated.

According to some embodiments of the present invention, the determining from the initial spectrum of a presence and concentration of respective fiber constituents comprises calculating, from the initial spectrum, presence and initial concentrations of keratin, eumelanin, pheomelanin and artificial pigments.

According to some embodiments of the present invention, determining the modified concentration comprises:

from the predetermined recipe obtaining factors for alkalizing agent concentration, oxidizing concentration, temperature, diameter of hair, condition of hair and its cuticles, ethnicity and exposure duration;

from at least some of the obtained factors, determining modified concentrations of keratin, eumelanin and pheomelanin, or:

from the predetermined recipe obtaining a dye concentration factor; and from the at least some of the factors for dye concentration and at least some of alkalizing agent concentration, oxidizing agent concentration, temperature, diameter of hair, condition of hair and its cuticles, ethnicity and exposure duration, determining a final concentration of artificial colorant, or wherein predicting the final spectrum of the keratinous fibers comprises, making the prediction from the final concentrations of artificial colorant, keratin, eumelanin, and pheomelanin, predicting a final spectrum of the keratinous fibers, or wherein a relation between the concentrations of ingredients and the final spectra is determined in the formula of Kubelka Munk.

According to some embodiments of the present invention, the approximation of Kubelka Munk is of the form:

$$\frac{(1-R(\lambda))^2}{2 \cdot R(\lambda)} = \frac{\sum_{n=1}^{N} C_n \cdot K(\lambda)_n}{\sum_{n=1}^{N} C_n \cdot S(\lambda)_n}$$

as defined herein.

According to some embodiments of the present invention, the diffused reflectance in wavelength—$R(\lambda)$—is obtained from the Sanderson correction formula.

According to some embodiments of the present invention, the predicting of a final spectrum, or the determining of respective hair constituents, comprises correcting for specular reflection effects.

According to some embodiments of the present invention, correcting for specular reflection effects comprises considering an air to keratinous fiber boundary and a keratinous fiber outer region to keratinous fiber inner region boundary.

According to some embodiments of the present invention, the correcting comprises applying a Sanderson correction.

According to some embodiments of the present invention, the Sanderson correction is of the form:

$$R(\lambda) = \frac{R(\lambda)_{meas} - \alpha}{1 - F(\lambda)_{ext} - F(\lambda)_{int} + F(\lambda)_{ext} F(\lambda)_{int} - \alpha F(\lambda)_{int} + F(\lambda)_{int} R(\lambda)_{meas}}$$

as defined herein.

According to some embodiments of the present invention, the corrected reflectance according to the Sanderson correction—$R(\lambda)$—is inserted into the Kubelka Munk approximation.

According to some embodiments of the present invention, the modified or final concentrations of keratin, eumelanin, pheomelanin and artificial colorant are calculated using a chemical reaction kinetics equation, wherein the calculating the final concentrations further considers taking into account intermediate products appearing from the chemical reactions.

According to an aspect of some embodiments of the present invention there is to provided a method for predicting a result of a treatment of keratinous fibers that uses a predetermined composition, the method comprising:

measuring an initial spectrum of the keratinous fibers;

from initial concentrations of natural factors of the fibers and from factors obtained form the predetermined composition predicting a final spectrum of the fibers following the treatment;

correcting the final spectrum for specular reflection effects;

further correcting the final spectrum corrected for specular correction effects with a further correction for light scattering effects.

According to some embodiments of the present invention, correcting for specular reflection effects comprises considering an air to keratinous fiber boundary and a keratinous fiber outer region to keratinous fiber inner region boundary, wherein the correcting comprises applying a Sanderson correction, and wherein the Sanderson correction formula comprises:

$$R(\lambda) = \frac{R(\lambda)_{meas} - \alpha}{1 - F(\lambda)_{ext} - F(\lambda)_{int} + F(\lambda)_{ext}F(\lambda)_{int} - \alpha F(\lambda)_{int} + F(\lambda)_{int}R(\lambda)_{meas}}$$

as defined herein.

According to some embodiments of the present invention, the corrected reflectance according to the Sanderson correction—R(λ)—is inserted into the Kubelka Munk approximation.

According to some embodiments of the present invention, the final spectrum is obtained by calculation of final concentrations of keratin, eumelanin, pheomelanin and artificial colorant from initial concentrations using a chemical reaction kinetics equation, and wherein the calculating the final concentrations further considers taking into account intermediate products appearing from the chemical reactions.

According to some embodiments of the present invention, the method further comprises providing a tablet to achieve the final spectrum, the tablet comprising at least one water-insoluble superdisintegrant which swells upon contact with water, and at least one active agent selected from the group consisting of a color imparting agent, an alkalizing agent, an oxidizing agent, and a thickening agent.

According to some embodiments of the present invention, the method further comprises obtaining optical measurements of keratinous fibers, the obtaining comprising:

applying an illumination source to the keratinous fibers;

optically measuring illumination of the keratinous fibers from a diffusion angle in relation to the illumination source, the illumination angle lying between 45 degrees and 135 degrees, thereby to obtain a measurement whose principle components are light that has been diffused or scattered by the hair from the illumination source.

According to an aspect of some embodiments of the present invention there is provided a system for predicting the result of a treatment of keratinous fibers and of preparing a composition therefore, the system comprising:

a spectrometer for measuring an initial spectrum of the keratinous fibers;

a constituent estimation unit for determining from the initial spectrum a presence and concentration of respective hair constituents;

a kinetic chemical reaction modeling unit for a) determining a modified concentration of constituents of the keratinous fibers following bleaching effects of chemical agents in the recipe and b) determining final concentrations of the constituents of the keratinous fibers following interaction of the chemical agents with colorants in the keratinous fibers; and a spectral prediction unit for using the final concentrations to predict a final spectrum of the fibers; and a mixing unit for preparing a composition suitable for the treatment if the final spectrum is approved.

According to some embodiments of the present invention, the keratinous fibers are subject's hair and the subject's hair is initially hair having natural coloration near the roots, or hair having natural coloring far from the roots, or the subject's hair is initially hair having artificial coloration, or initially hair having white coloration, or initially hair containing residue of treatment with perming or curling chemicals.

According to an aspect of some embodiments of the present invention there is provided a device for optical measurement of keratinous fibers, comprising:

an illumination unit for illuminating keratinous fibers;

a measuring unit comprising at least one sensor for optically measuring the to keratinous fibers during illumination by the illumination unit; wherein the sensor and a beam from the illumination unit respectively subtend a light diffusion angle at the keratinous fibers being measured, thereby to ensure that the sensor principally measures light of the illumination beam that is diffused or scattered by the keratinous fibers.

According to some embodiments of the present invention, the measuring unit comprises a plurality of sensors located around the keratinous fibers at an elevation from the azimuth and the illumination unit is positioned perpendicularly to the keratinous fibers.

According to some embodiments of the present invention, the illumination unit comprises a plurality of illumination sources respectively configured to illuminate the keratinous fibers from a plurality of substantially azimuthal angles.

According to some embodiments of the present invention, the light diffusion angle is between 45 and 135 degrees.

According to some embodiments of the present invention, the illumination unit comprises two substantially opposing illumination directions along a hair axis, such that a differential comparison between detections of each respective direction provides an indication of a condition of a hair scapula.

According to some embodiments of the present invention, the illumination unit comprises a light source parallel to a keratinous fibers axis, or at least two illumination sources wherein at least two of the illumination sources illuminate the keratinous fibers from respectively different azimuthal angles.

According to some embodiments of the present invention, the illumination sources are configured to illuminate the keratinous fibers at different times, thereby allowing illumination from respective sources to be measured separately.

According to some embodiments of the present invention, the device further comprises a main illumination source and subsidiary illumination sources, and processing electronics to use differential illumination results from respective sources to determine an angle of a hair relative to the main illumination source, or the processing electronics is configured to use the keratinous fibers angle to correct a spectrum of the keratinous fibers, or the processing electronics is configured to use the differential to illumination results from the multiple illumination sources to distinguish between specular and diffuse light from the keratinous fibers, or wherein at least the main illumination source is used for spectroscopy and at least one subsidiary illumination source is used for angular measurement, or wherein at least a second illumination source is used for spectroscopy.

According to some embodiments of the present invention, there are four illumination sources at a same elevation angle relative to a plane perpendicular to a detection axis, and wherein an azimuth angle with respect to a keratinous fibers axis is 30° for two of the four illumination sources and 150° for a third and a fourth of the illumination sources.

According to some embodiments of the present invention, the sensor comprises sensitivity to the visible and near infrared parts of the electromagnetic spectrum, or wherein the sensor comprises sensitivity to at least the 350-1500 nm wavelength range, or wherein the sensor comprises sensitivity to the 350-750 nm wavelength range, or wherein the sensor comprises sensitivity to at least the 400-950 nm wavelength range, or wherein the sensor comprises at least one calibration region for receiving calibration light and calibrating the optical readings, or the device further comprising a controllably polarizing element, or further comprising a controllably analyzing element, or further comprising grips for holding keratinous fibers in position for measurement.

According to an aspect of some embodiments of the present invention there is provided a device for optical measurement of keratinous fibers, comprising:

an illumination unit for illuminating keratinous fibers;

a measuring unit comprising at least one sensor for optically measuring the keratinous fibers during illumination by the illumination unit; wherein the sensor and a beam from the illumination unit respectively use wavelengths in the visible and infrared spectral regions, thereby to provide a spectrum of the keratinous fibers that discriminates both between different natural colorants in the keratinous fibers and between different artificial colorants in the keratinous fibers.

According to some embodiments of the present invention, the sensor comprises sensitivity to at least the 350-1500 nm wavelength range, or wherein the sensor comprises sensitivity to the 350-750 nm wavelength range, or wherein the sensor comprises sensitivity to at least the 400-950 nm wavelength range, or wherein the sensor comprises at least one calibration region for receiving calibration light and calibrating the optical readings, or comprising at least one known calibrated target to enable real time internal calibration for each measurement, or comprising two known calibrated targets to enable real time internal calibration for different light illumination power.

According to an aspect of some embodiments of the present invention there is provided a method for obtaining optical measurements of keratinous fibers comprising:

applying an illumination source to the keratinous fibers;

optically measuring illumination of the keratinous fibers from a diffusion angle in relation to the illumination source, the illumination angle lying between 45 degrees and 135 degrees, thereby to obtain a measurement whose principle components are light that has been diffused or scattered by the keratinous fibers from the illumination source.

According to some embodiments of the present invention, the method comprises illuminating the keratinous fibers from a plurality of illumination sources at a plurality of angles in sequence including respectively opposing angles and obtaining differential measurements from the opposing angles.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or device according to some aspects of embodiments of the invention can involve performing or completing selected tasks manually, automatically, or a combination thereof. Moreover, according to actual instrumentation and equipment of embodiments of the method and/or device of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of to software instructions being executed by a computer using any suitable operating system. In some embodiments of the invention, one or more tasks according to some embodiments of a method and/or device as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 4A-D show various possible types of containers according to some exemplary embodiments of the invention;

FIGS. 9A-B present images of an exemplary coated tablet formulation according to some embodiments of the present invention (Tablet No. 15 in Table 1E) in 6% (w/w) hydrogen peroxide solution, at t=0 (FIG. 9A) and at t=3 seconds (FIG. 9B);

FIGS. 13A-F present images showing the light fastness of exemplary coated tablets according to some embodiments of the present invention at t=0 (FIG. 13A), and after one month (FIG. 13B), after 3 months (FIG. 13C), after 6 months (FIG. 13D), after 9 months (FIG. 13E) and after one year (FIG. 13F) of illumination.

Figure 14:
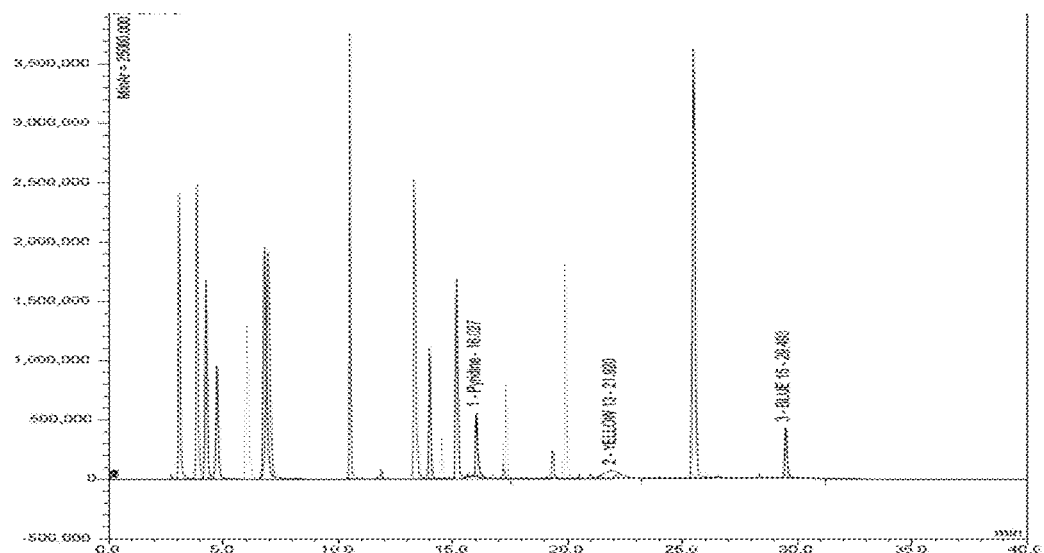
Figure 16A:
Figure 16B:
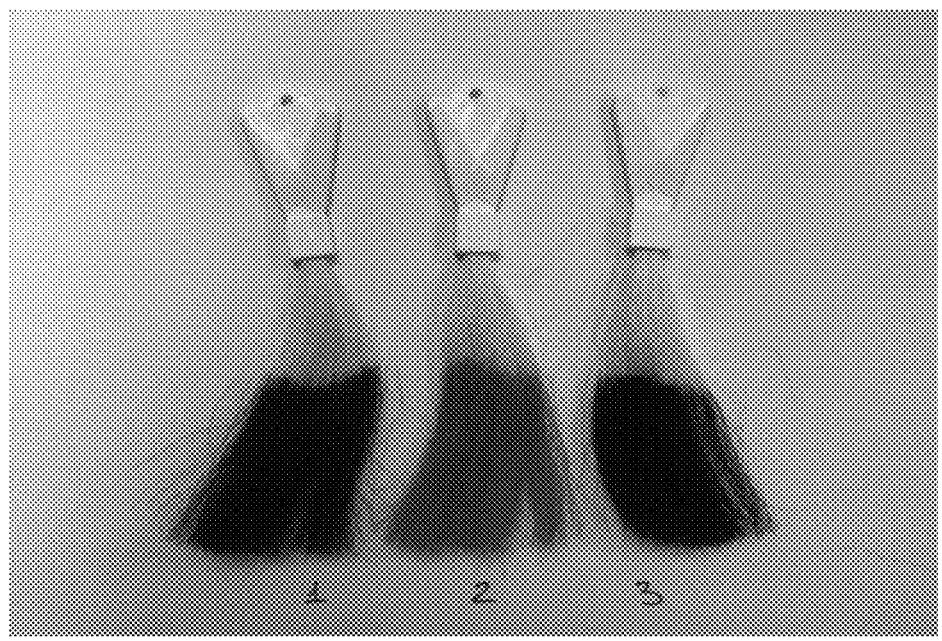
Figure 17:
Figure 18:
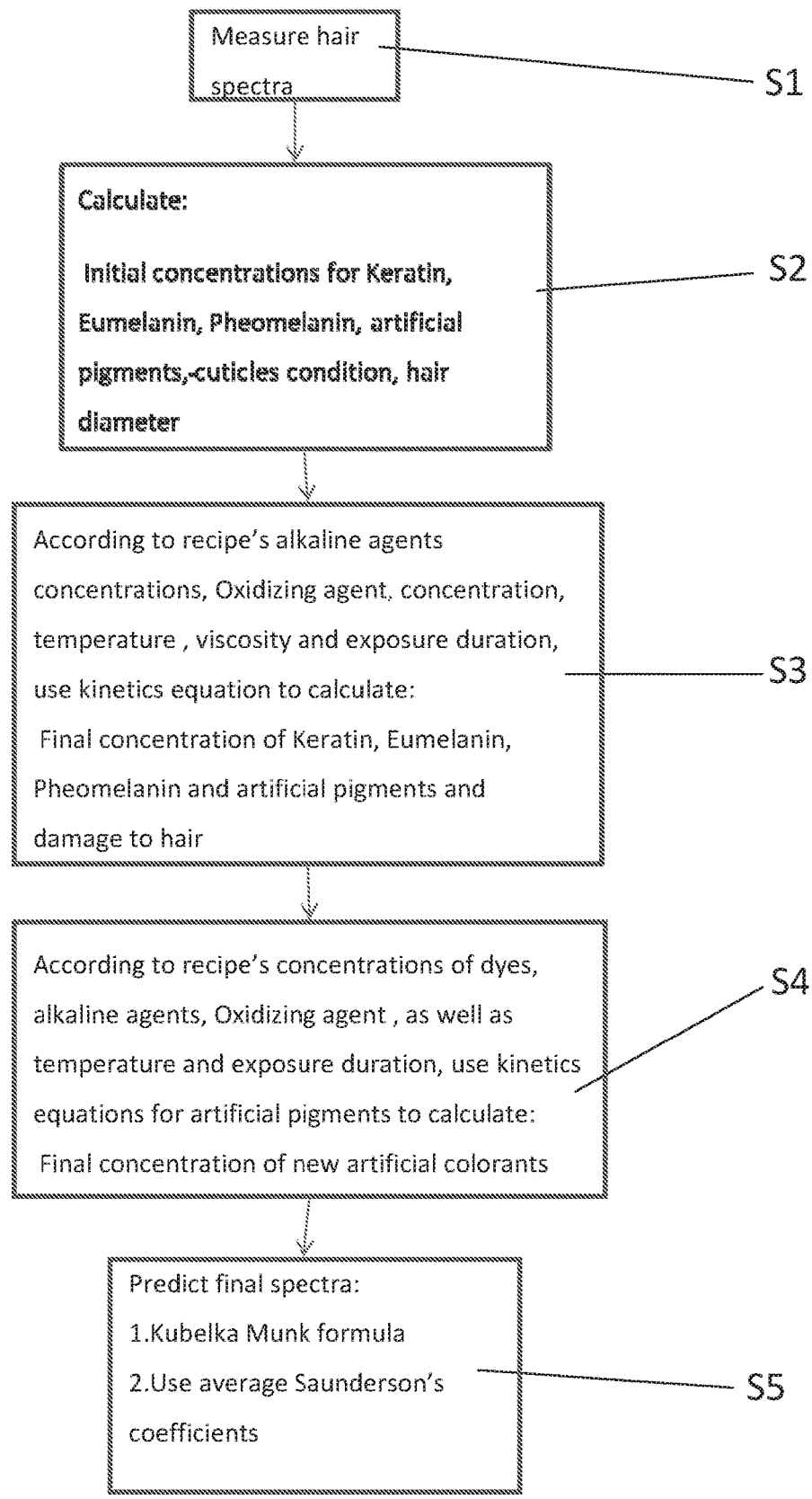
Figure 19:
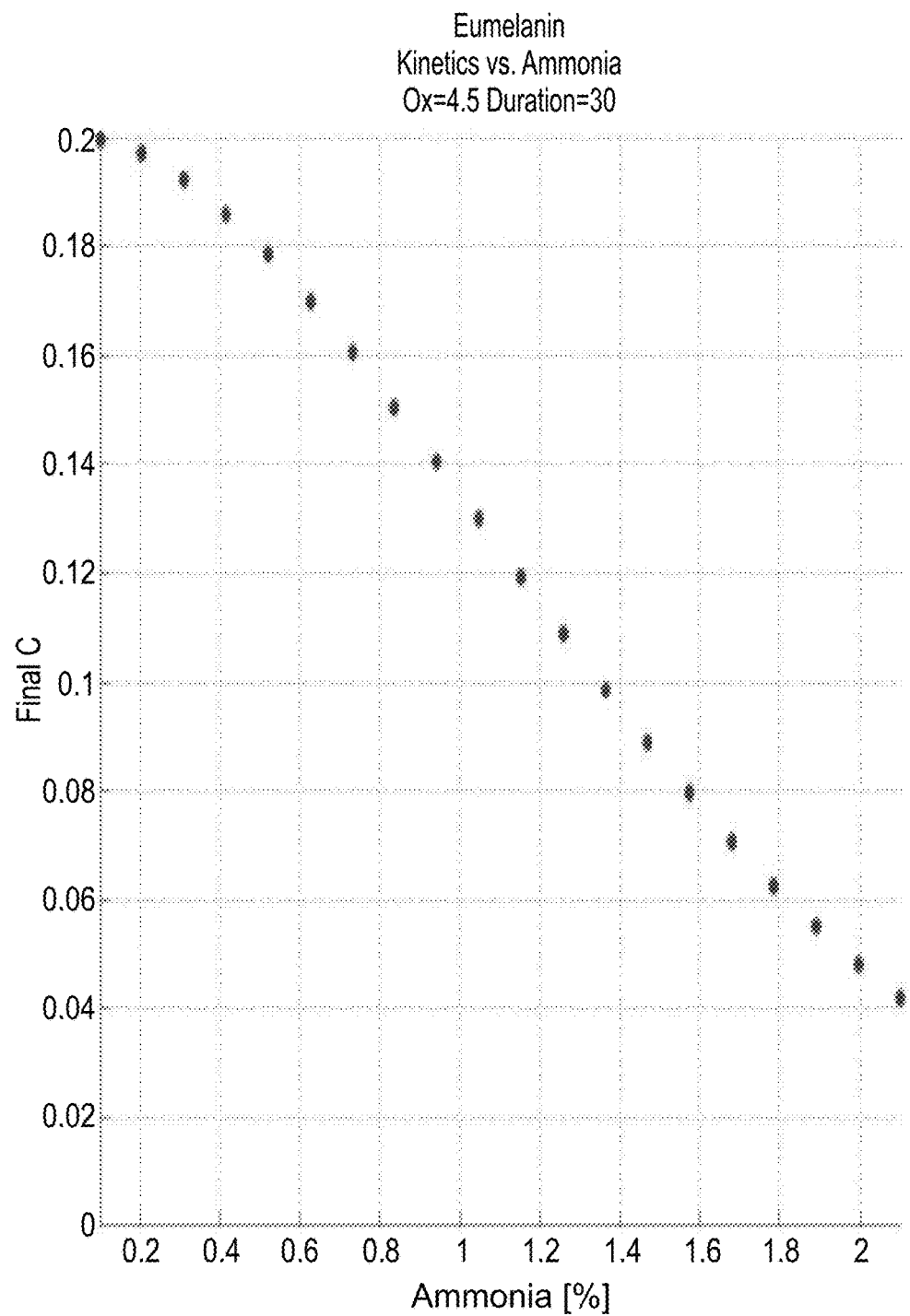
Figure 20:
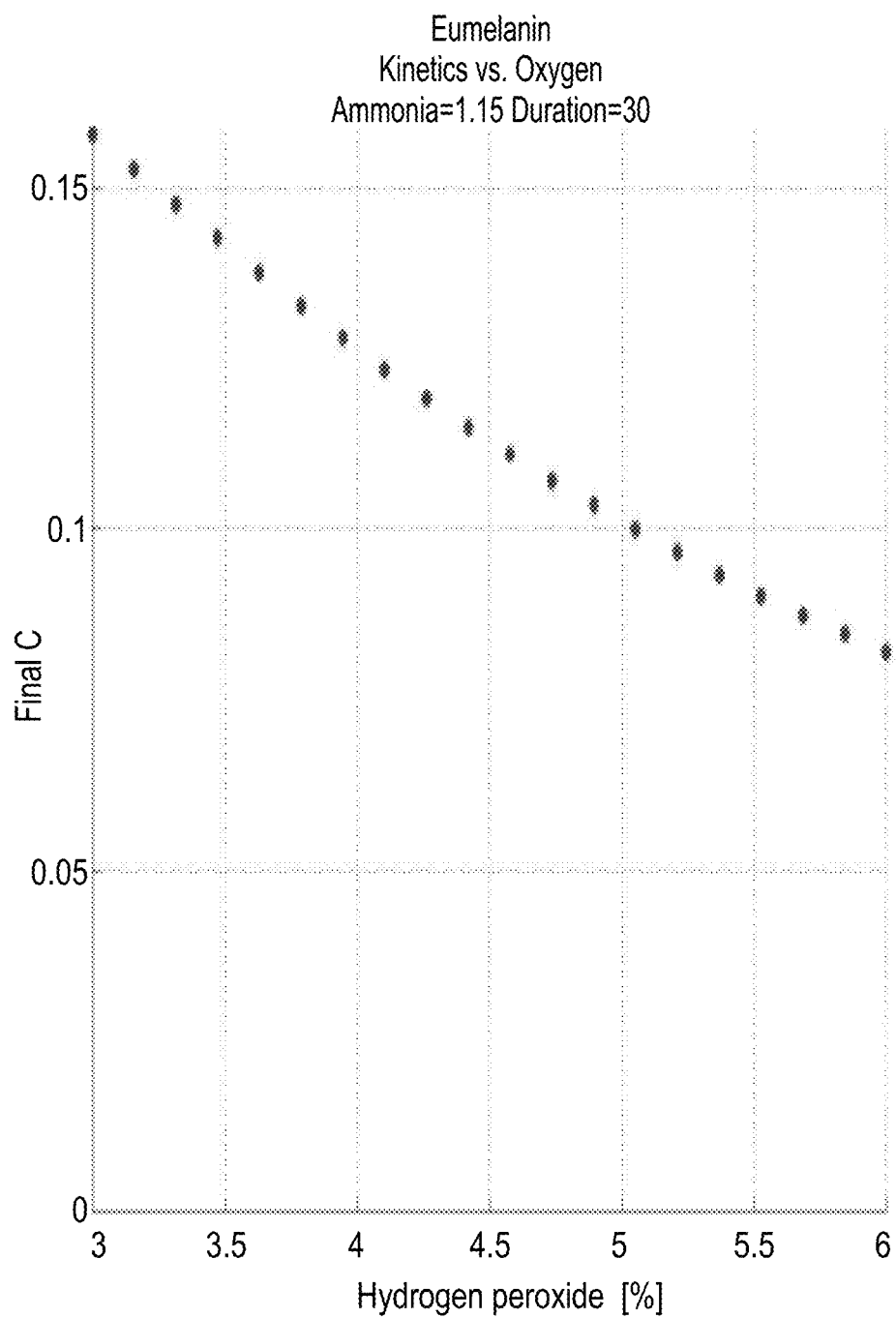
Figure 21:
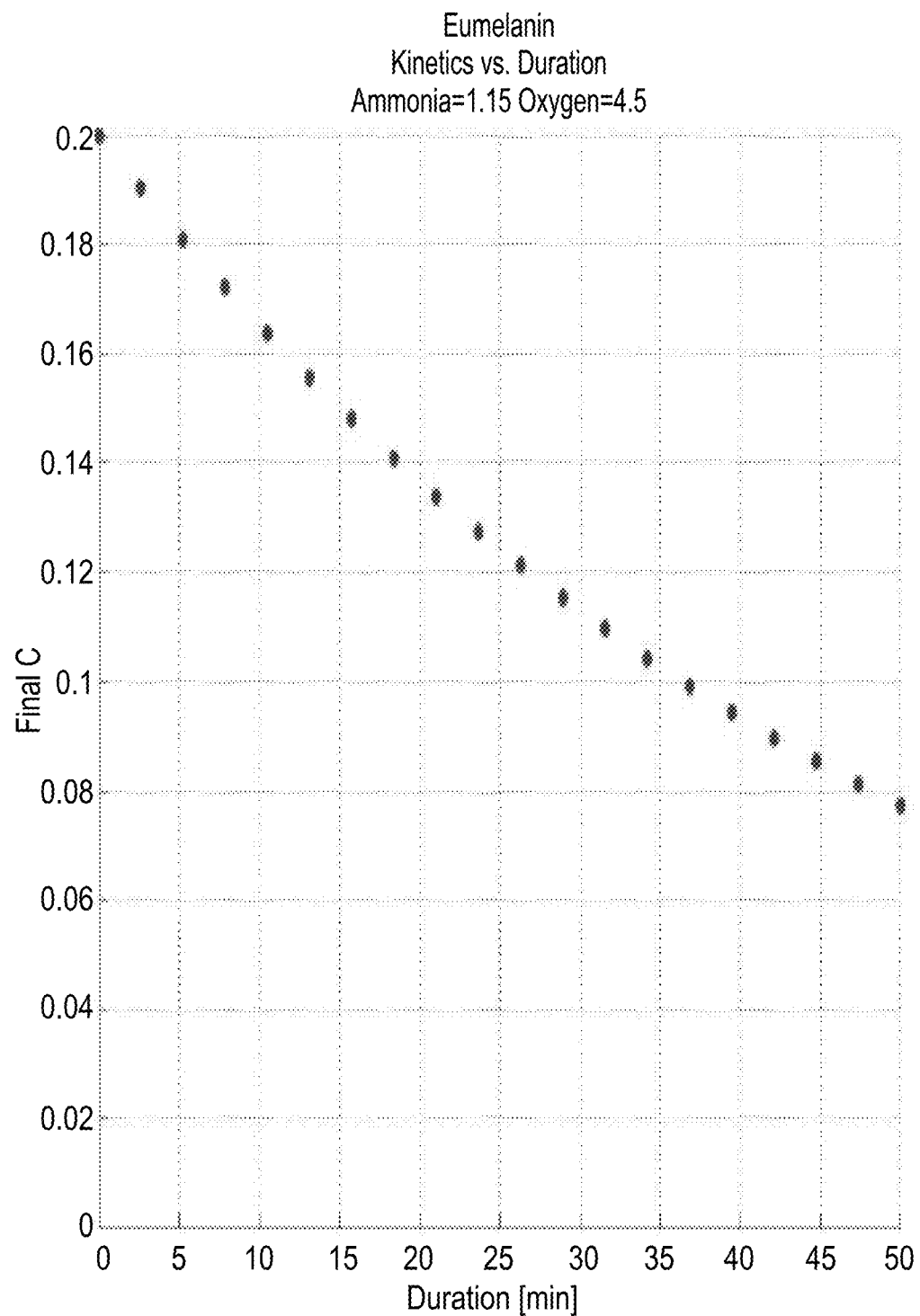
Figure 22:
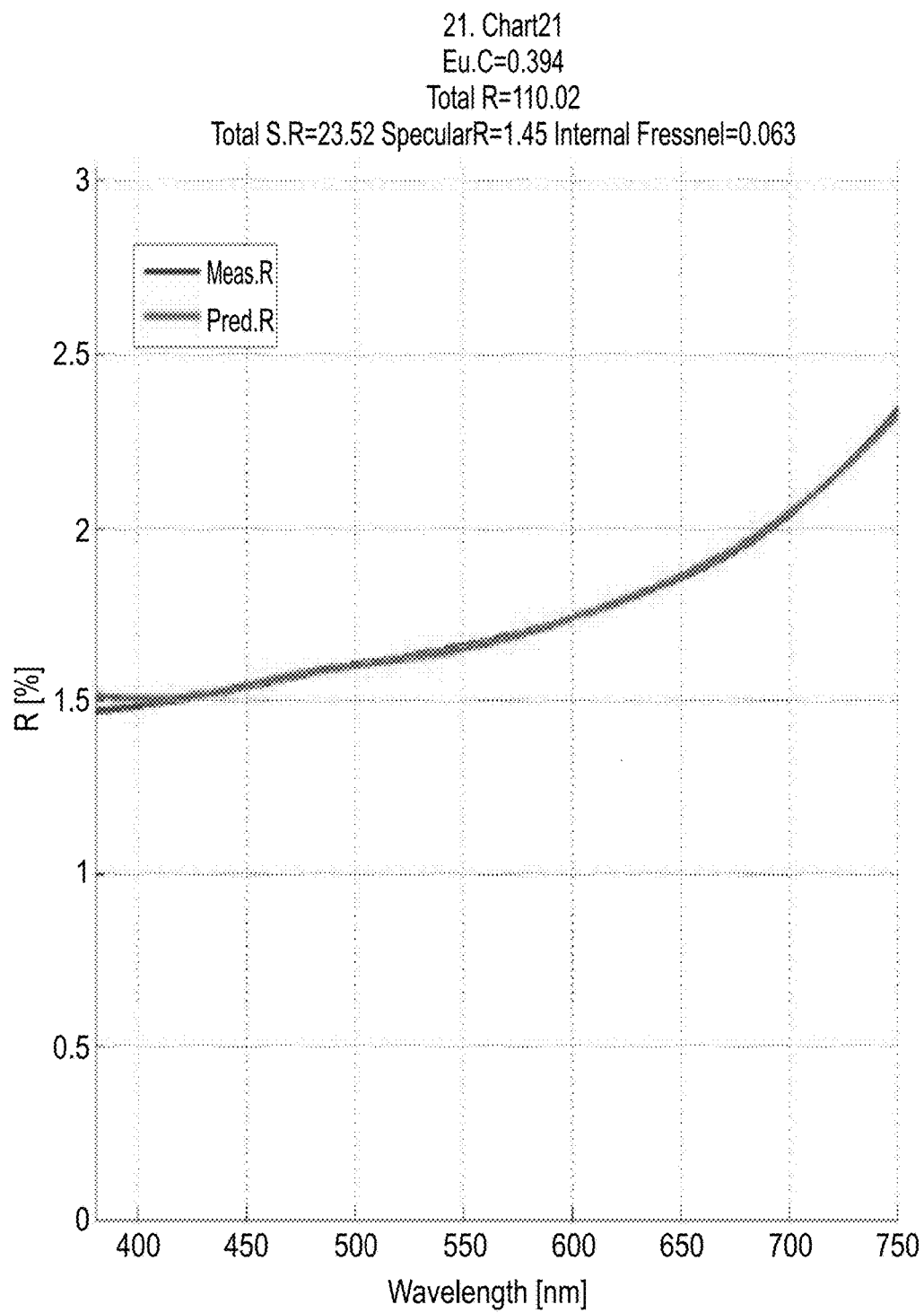
Figure 23:
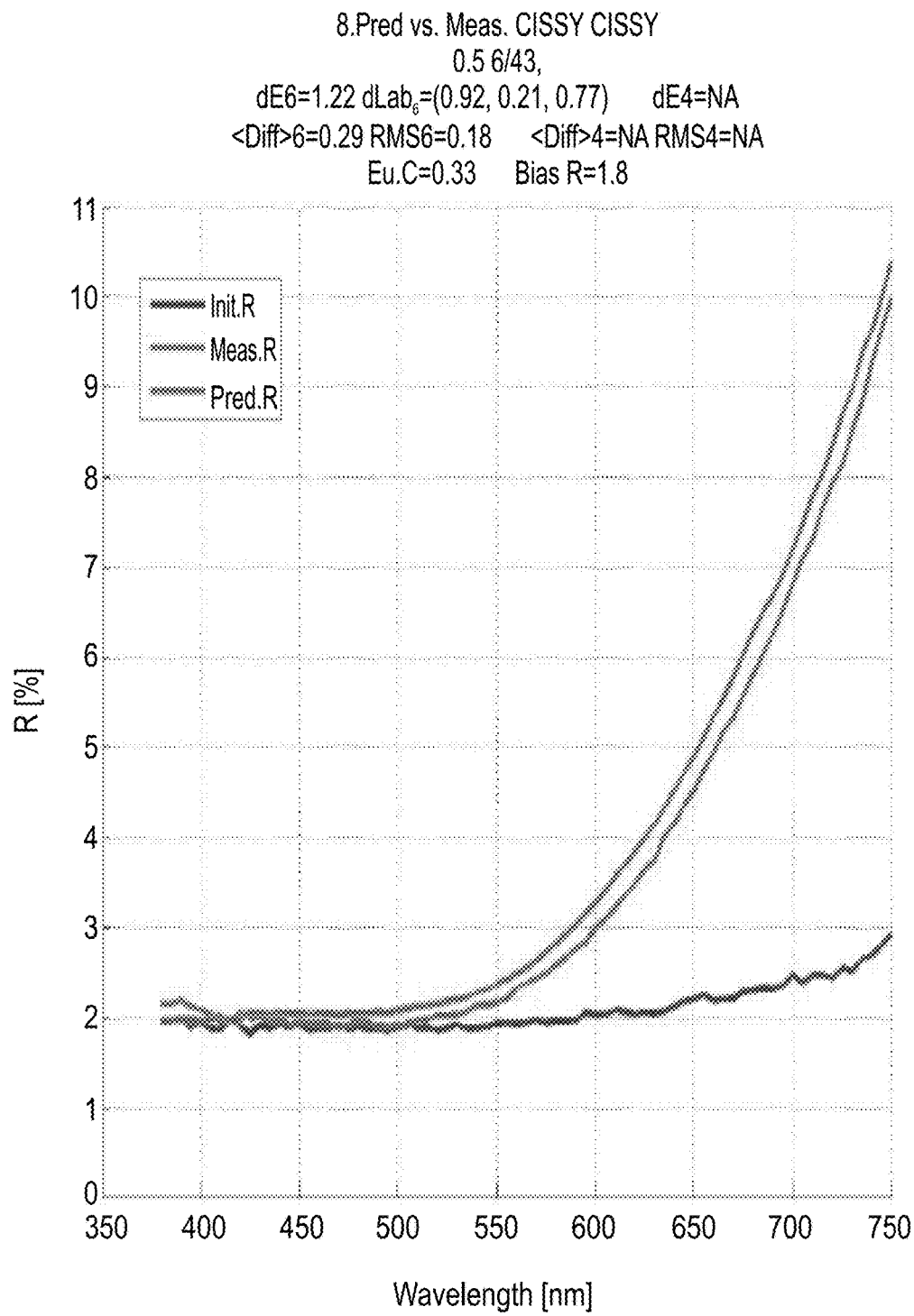
Figure 24:
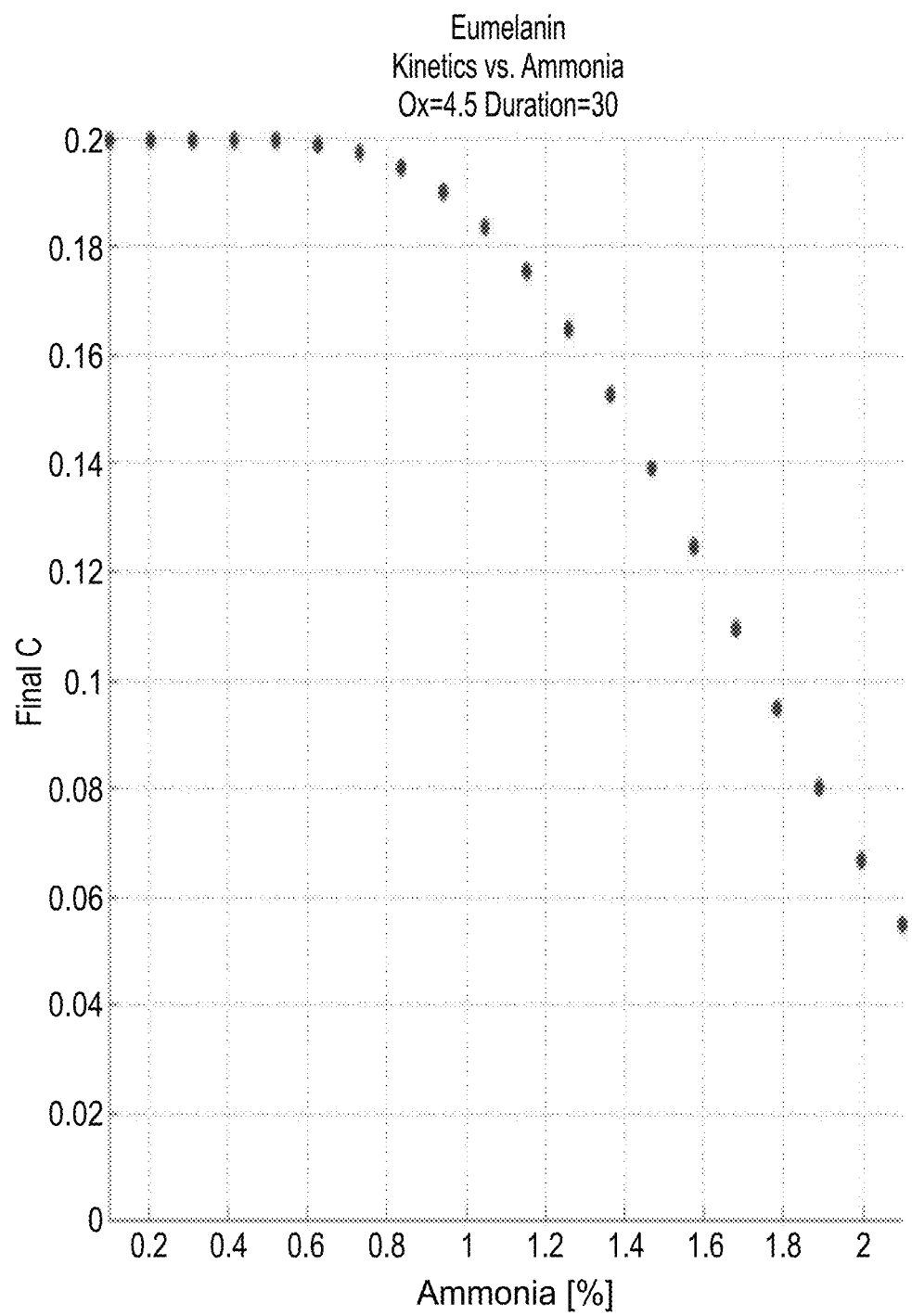
Figure 25:
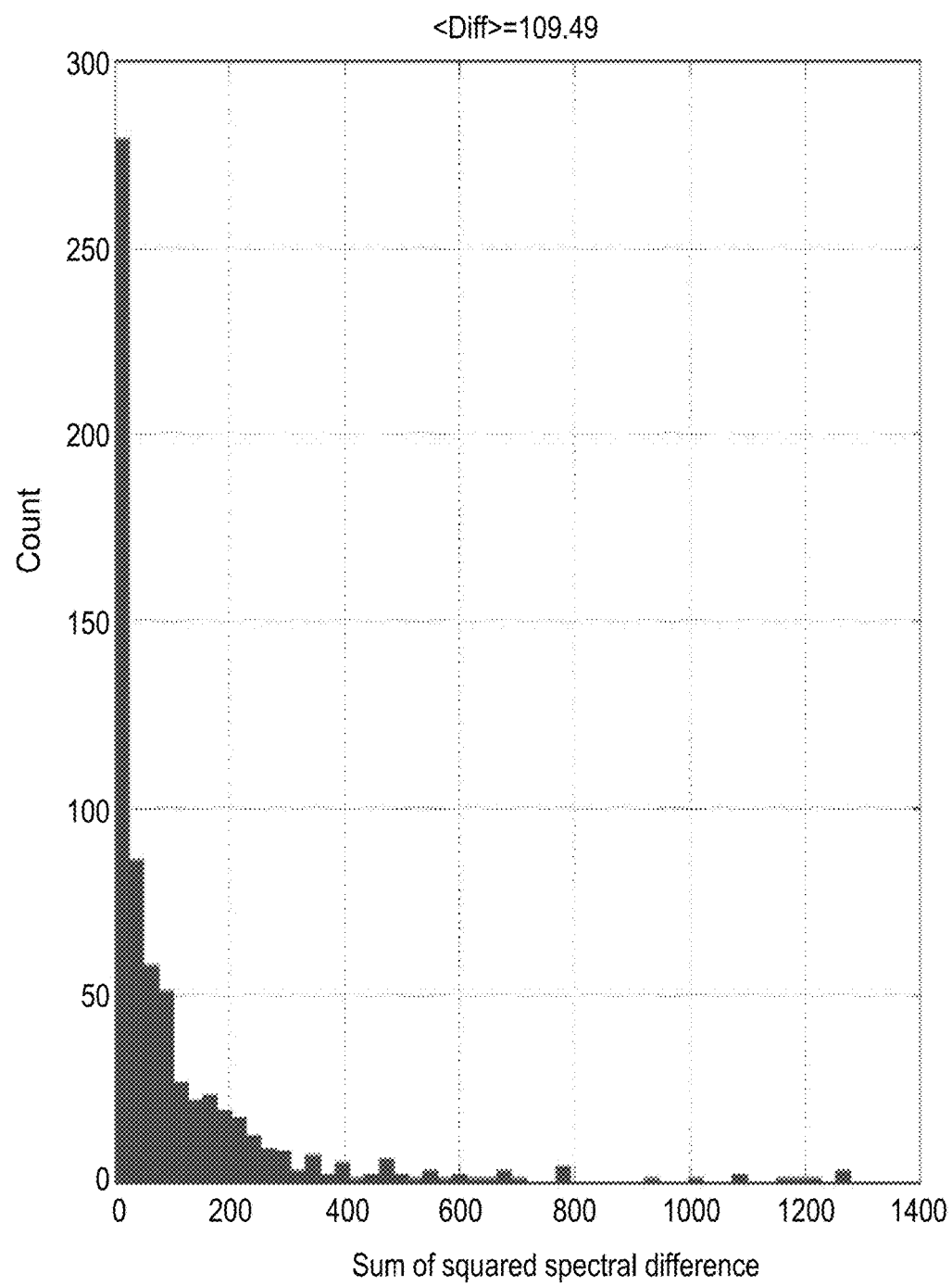
Figure 26:
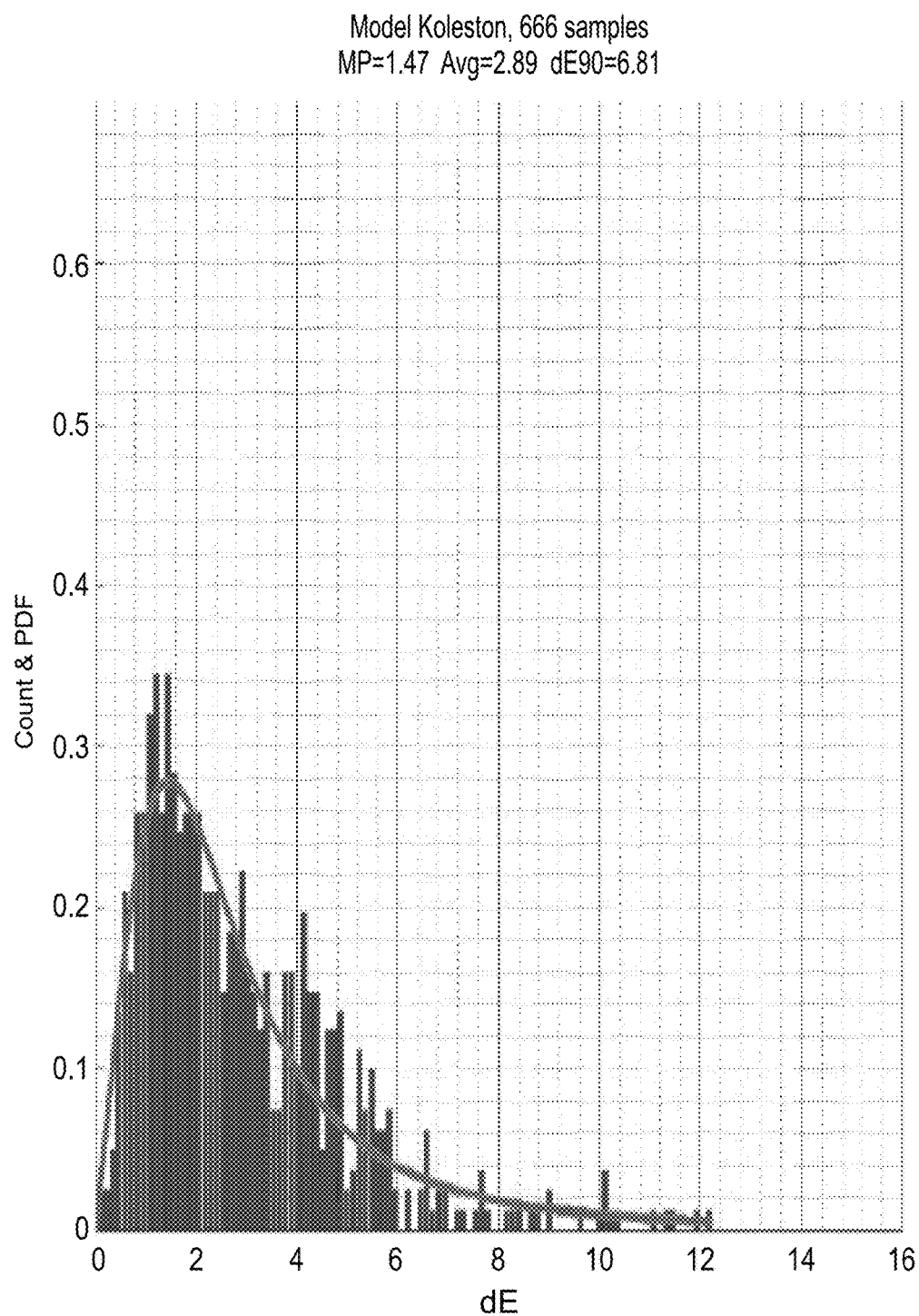
Figure 27:
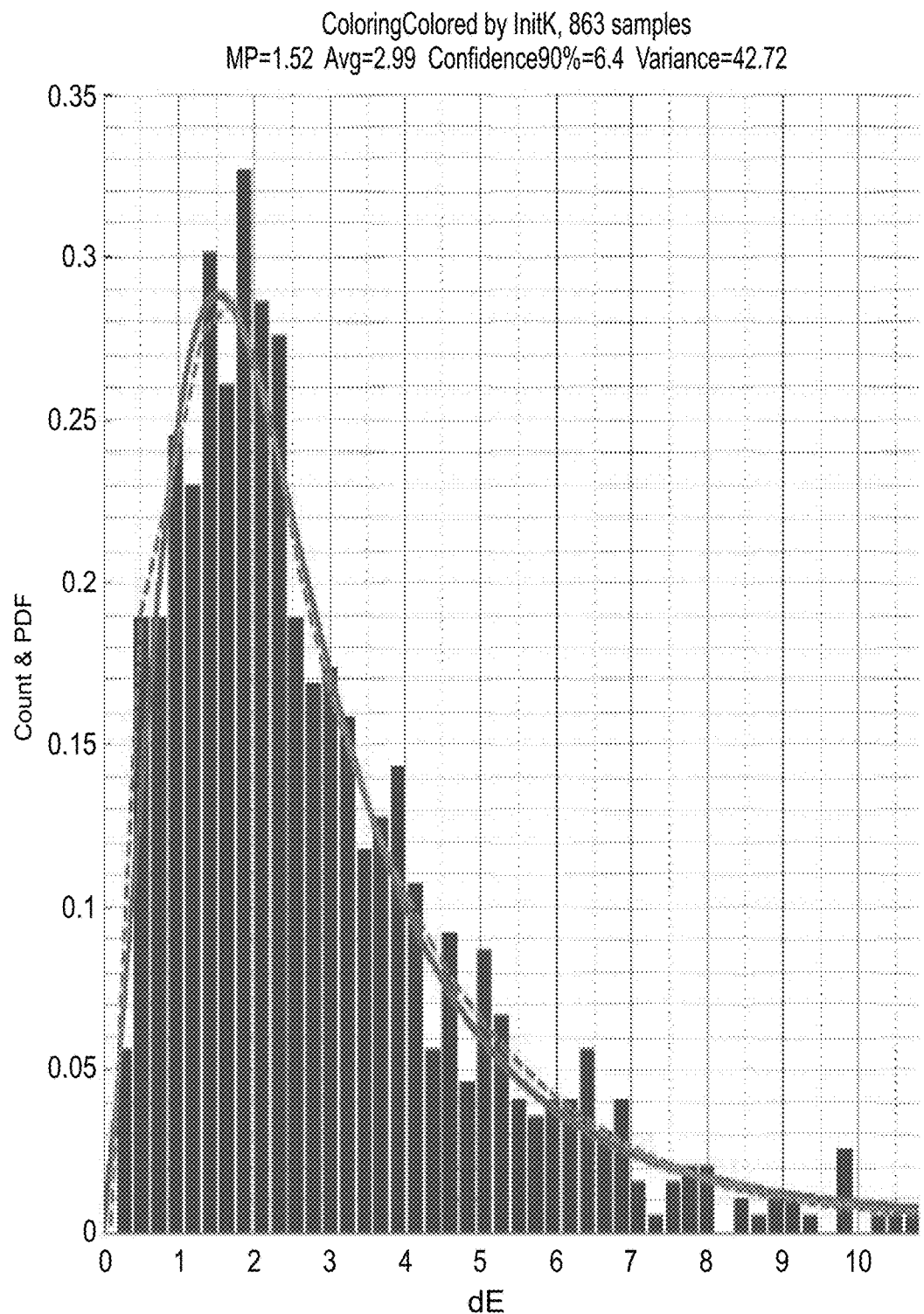
Figure 28:
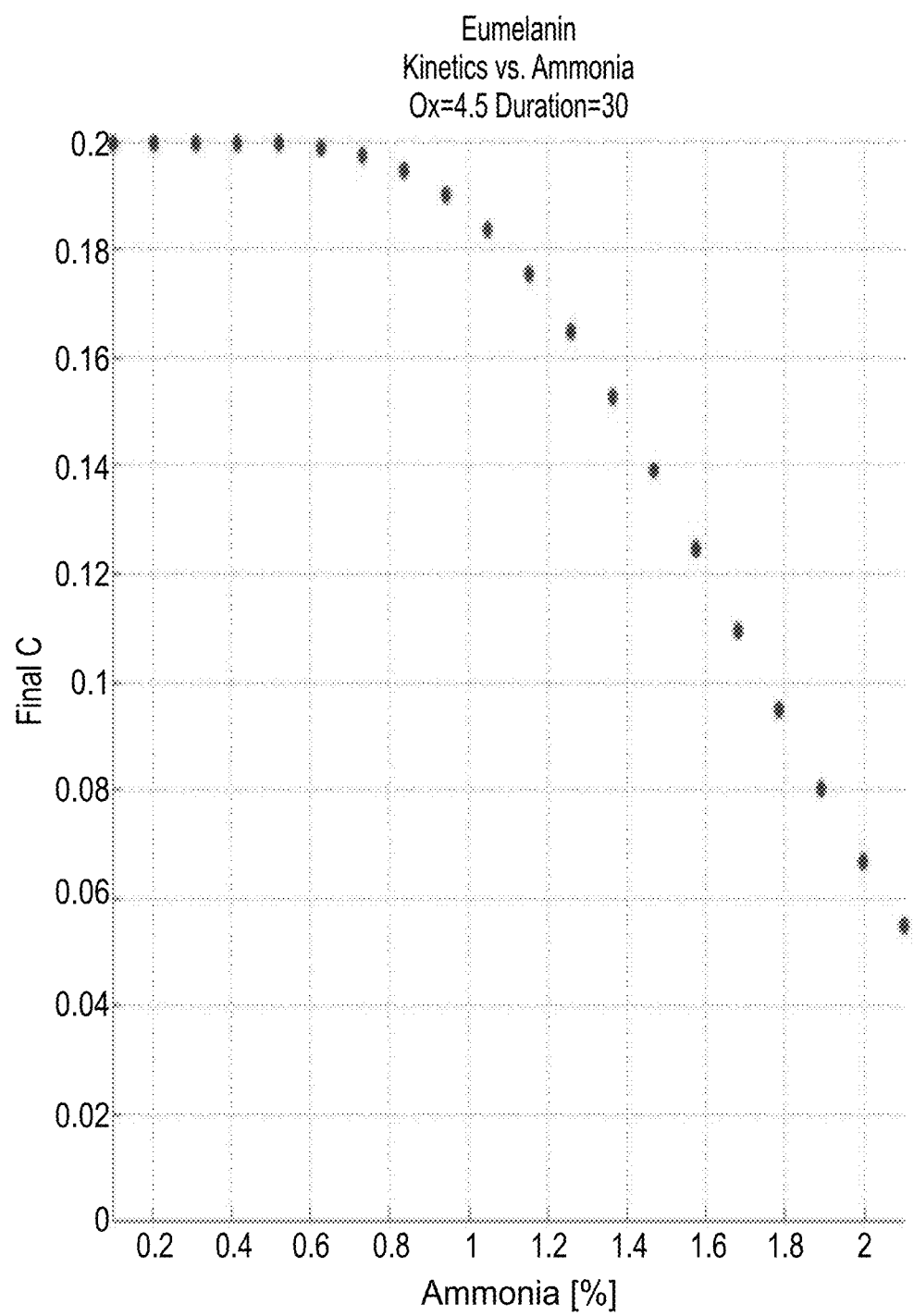
Figure 29:
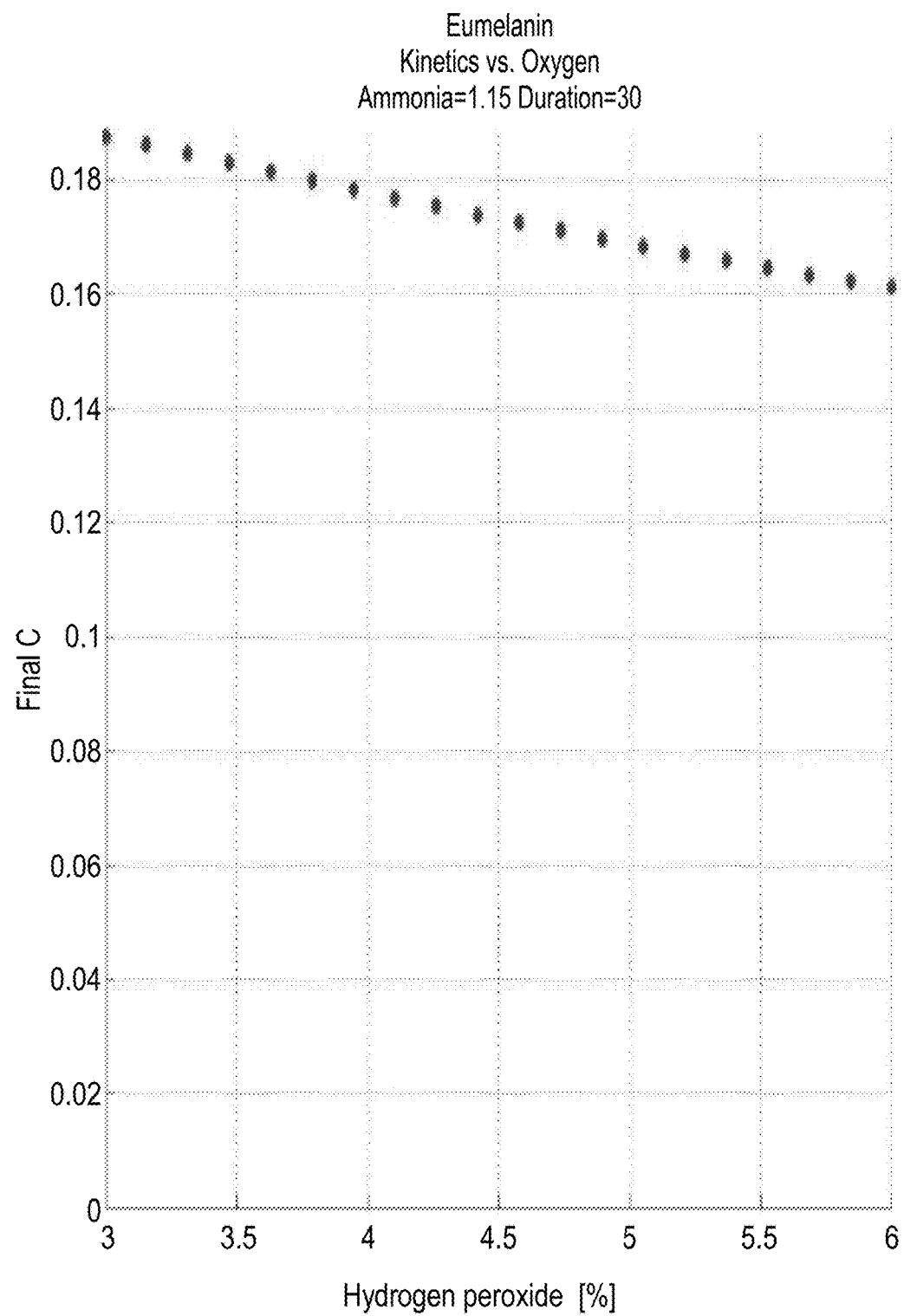
Figure 30:
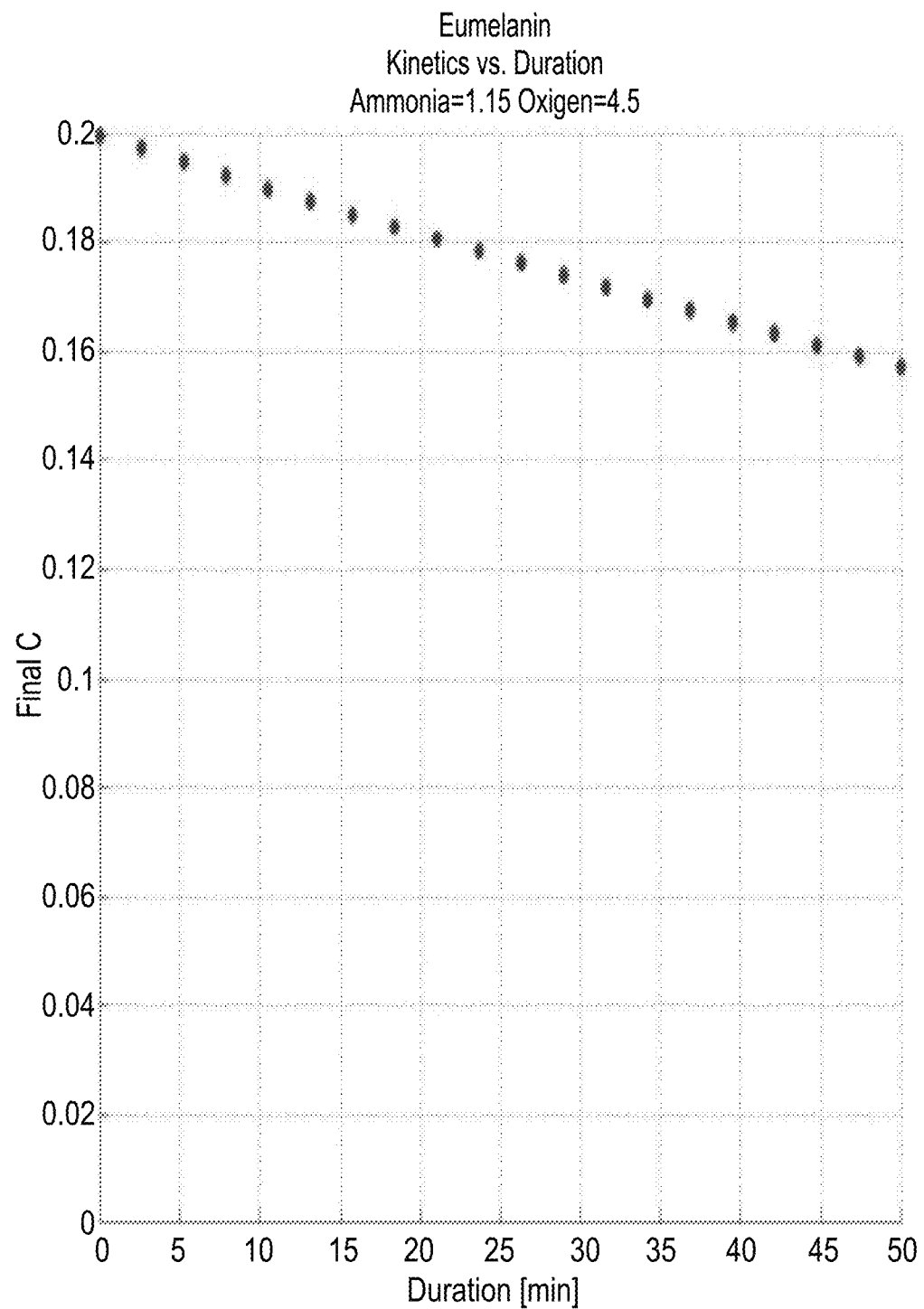
Figure 31:
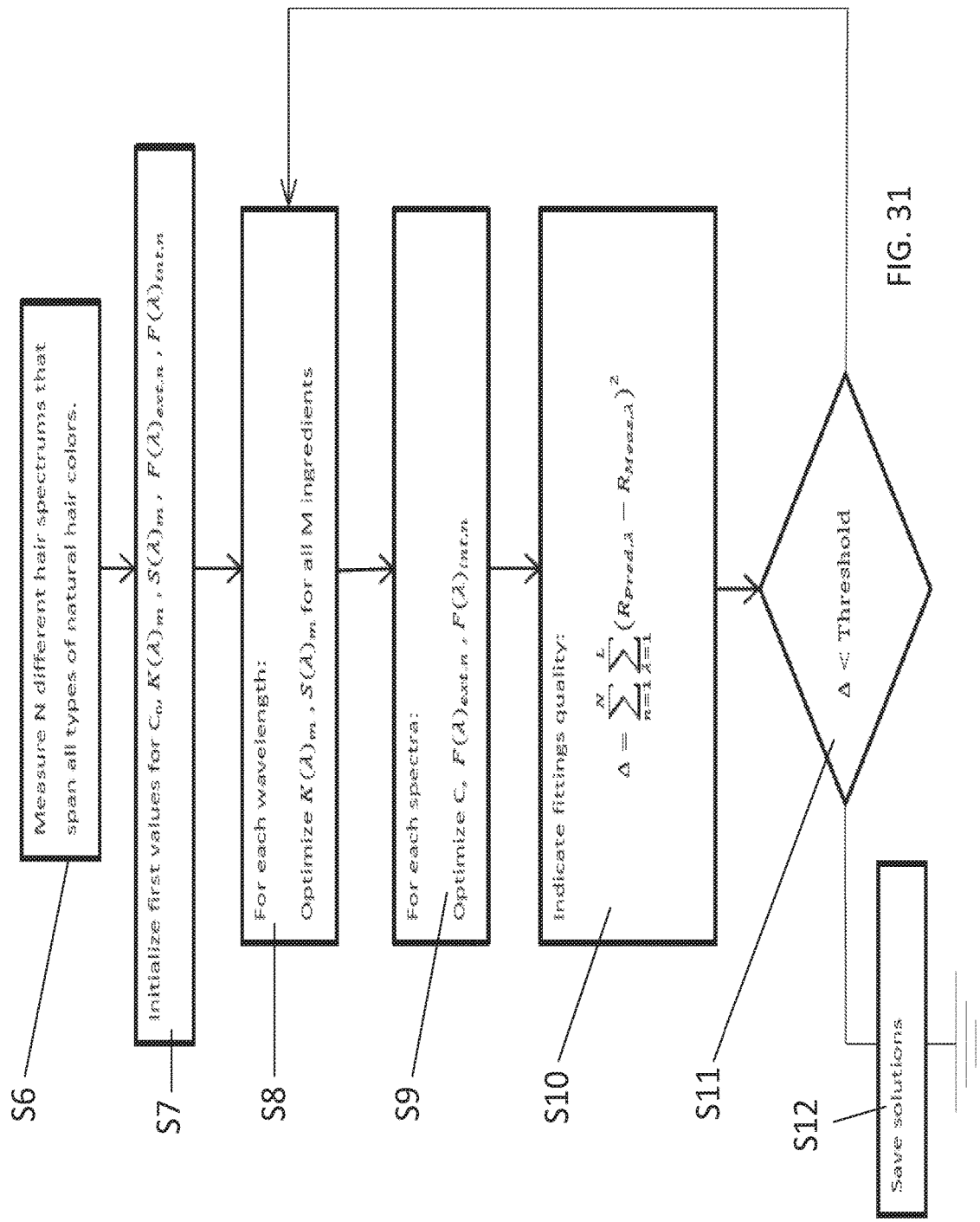

FIG. 14 is a graph showing chromatographic separation of exemplary agents by HPLC;

FIGS. 15A-I show pictures of fibers colored with tablets and methods according to various exemplary embodiments of the invention;

FIGS. 16A-B show natural dark blond Caucasian hair colored with an exemplary green shade formulation at different concentrations (FIG. 16A) and yak hair colored by combinations of an exemplary orange shade formulation and an exemplary violet shade formulation (FIG. 16B) at orange: violet ratios of 1:100 (sample 1), 100:1 (sample 2), and 100:100 (sample 3);

FIG. 17 is an image of human natural red hair without coloring (upper segment of the hair sample), with a red-copper coloring (middle segment), and with coloring using an exemplary violet shade formulation in addition to the red-copper coloring;

FIG. 18 is a simplified flow diagram illustrating operation of a hair color prediction methodology according to an embodiment of the present invention;

FIG. 19 is a simplified graph showing the kinetics of Eumelanin during hair dyeing for different concentrations of ammonia in an environment of fixed hydrogen peroxide and duration;

FIG. 20 a simplified graph showing the kinetics of Eumelanin concentration during hair dyeing for different concentrations of hydrogen peroxide in an environment of fixed ammonia and duration;

FIG. 21 a simplified graph showing the kinetics of Eumelanin concentration during hair dyeing for different durations in an environment of fixed hydrogen peroxide and ammonia;

FIG. 22 is a simplified graph showing a best fit curve to the measurement of natural hair spectra by optimizing the Eumelanin concentration and Pheomelanin concentration using the Kubelka Munk formula and Saunderson's coefficients;

FIG. 23 is a simplified graph of a best-fit curve calculated by Kubelka Munk and the Saunderson correction for coloring natural hair with a known dye recipe which seeks to fit the curve of another measurement;

FIG. 24 is a simplified graph illustrating the distribution of spectral squared differences after optimization according to an embodiment of the present invention;

FIG. 25 is a simplified graph illustrating the distribution of color co-ordinates differences (dE) after optimization of coloring natural undyed hair according to an embodiment of the present invention;

FIG. 26 is a simplified graph illustrating the distribution of spectral squared differences after optimization of coloring dyed hair according to an embodiment of the present invention;

FIG. 27 illustrates coloring against expectation for a series of samples;

FIG. 28 is a simplified graph showing the kinetics of Eumelanin concentration against ammonia concentration, for fixed hydrogen peroxide and duration;

FIG. 29 is a simplified graph showing the kinetics of Eumelanin concentration vs. Hydrogen peroxide rate in the case of a model for initially colored hair, for fixed duration and Ammonia rate of diffusion;

FIG. 30 is a simplified graph showing the kinetics of Eumelanin concentration vs. duration while Ammonia rate and Hydrogen Peroxide rate were kept constant; and FIG. 31 is a simplified flow chart showing a process for extracting factors of natural hair ingredients for calculation.

Figure 32A:
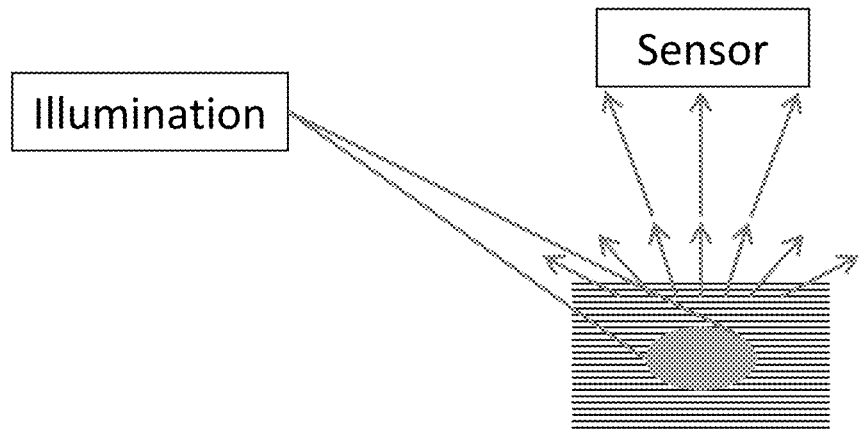
Figure 32B:
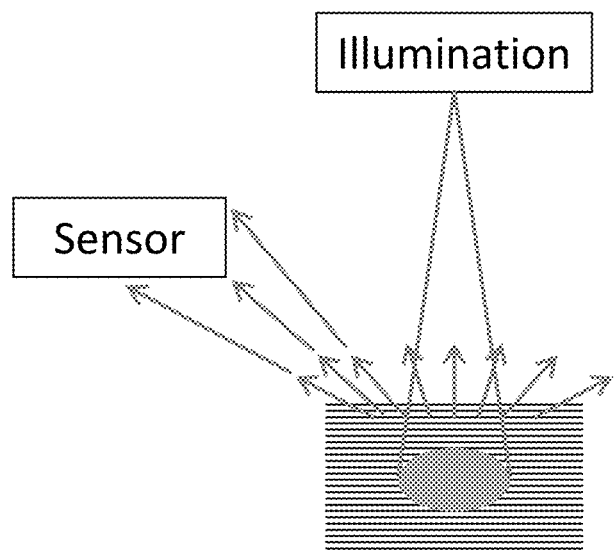
Figure 32C:
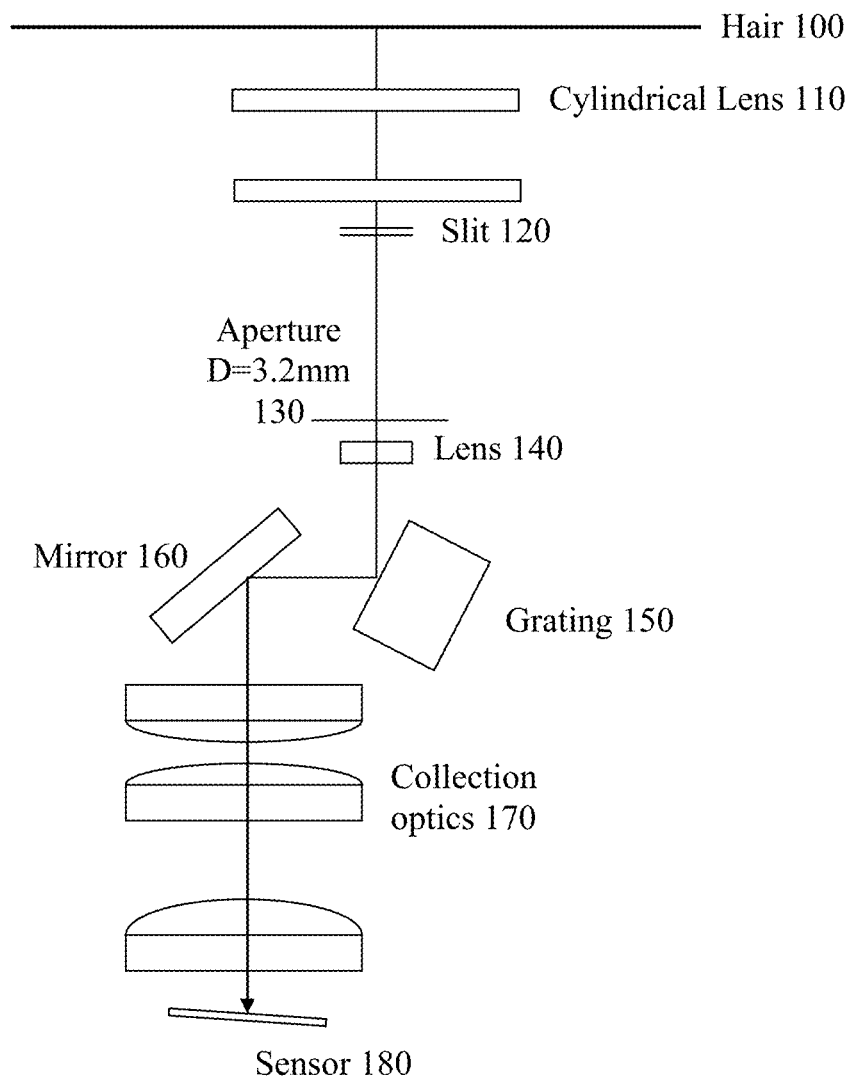
Figure 33A:
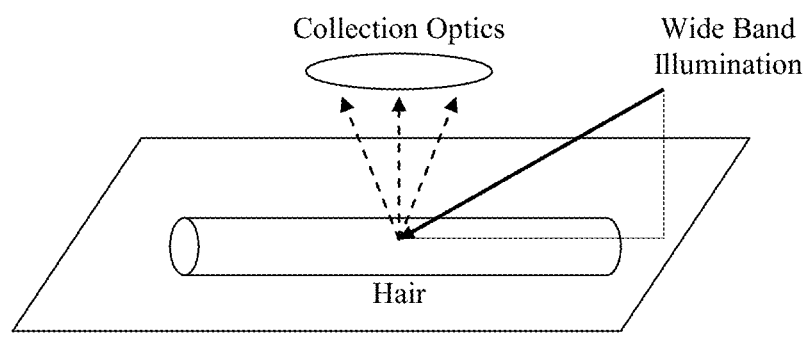
Figure 33B:
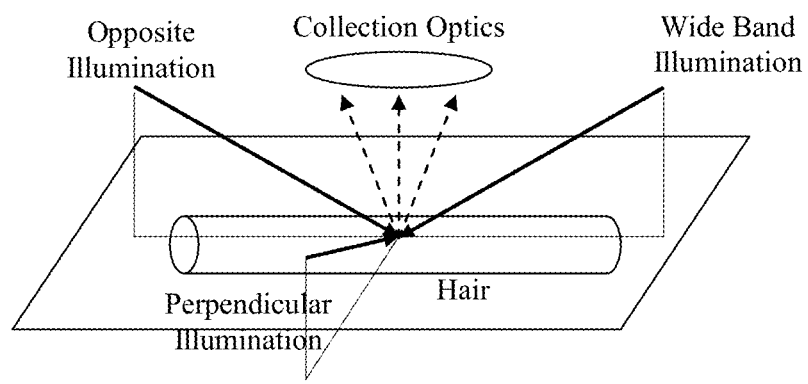
Figure 33C:
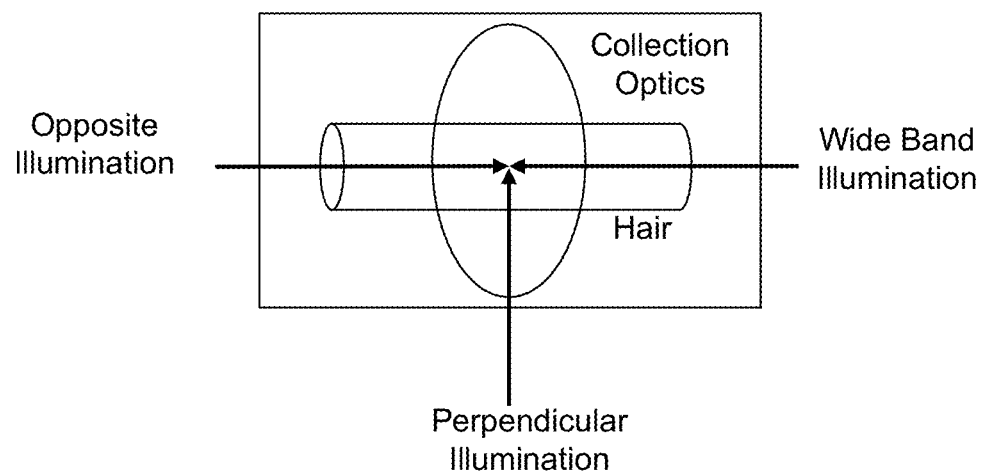
Figure 34A:
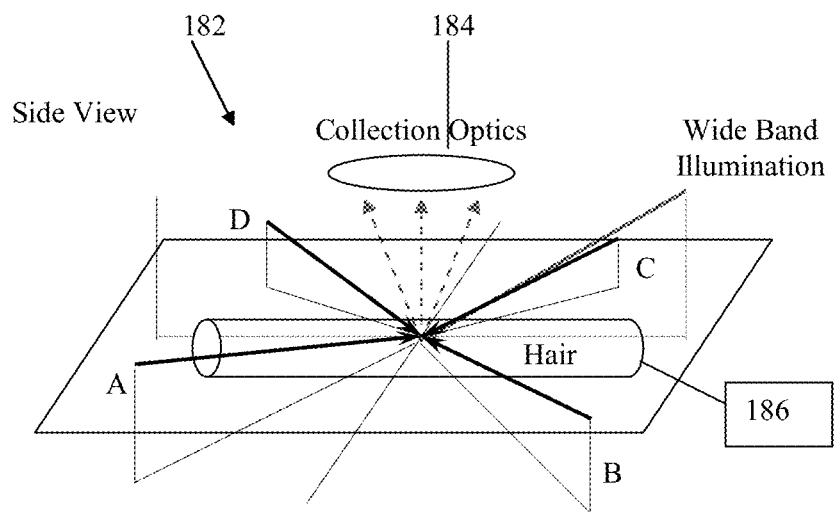

FIG. 32A is a simplified schematic diagram showing an embodiment of the present invention in which hair is illuminated from the azimuth and light is detected from the perpendicular;

FIG. 32B is a simplified schematic diagram showing a variation of the embodiment of FIG. 32A in which hair is illuminated from the perpendicular and light is detected from the azimuth;

FIG. 32C is a diagram showing optics for the illumination and measurement units of FIGS. 32A and 32B;

FIG. 33A is a simplified schematic block diagram illustrating in greater detail the illumination and light collection angles in relation to the hair that is being measured for the embodiment of FIG. 32A;

FIG. 33B is a schematic diagram showing illumination of a hair from two opposite directions of oblique elevation and collection of light at a perpendicular from the hair on the side of the illumination according to the embodiment of FIG. 32A;

FIG. 33C is a schematic diagram showing illumination of the hair according to FIG. 33B seen from above;

FIG. 34A is a simplified side view of a hair reader according to an embodiment of the present invention.

Figure 34B:
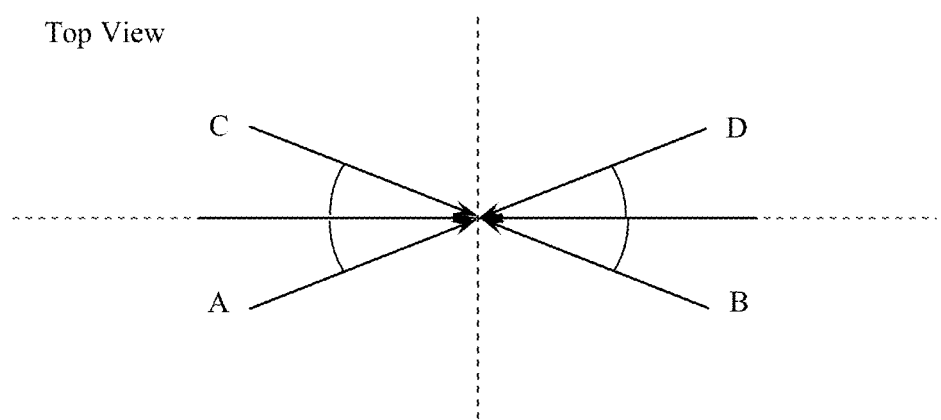
Figure 36:
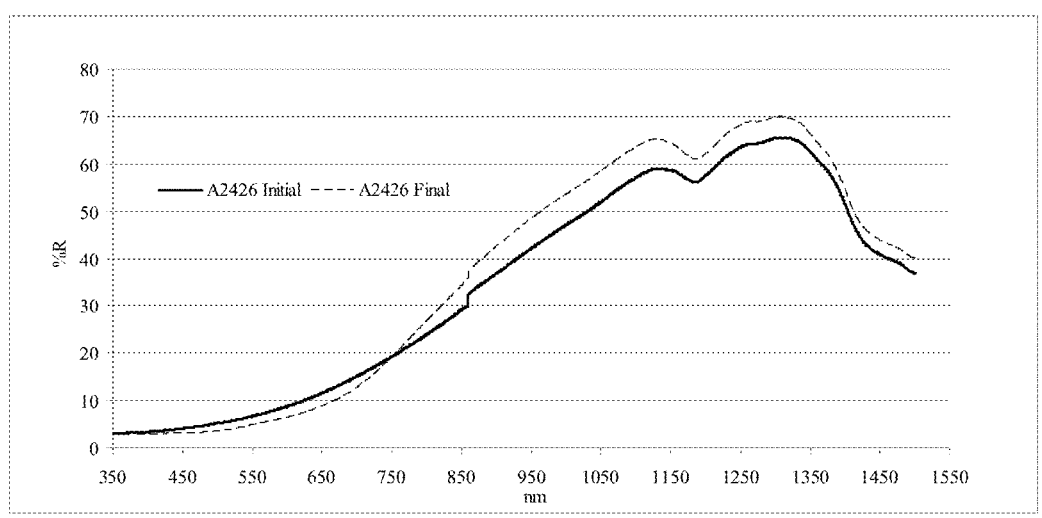
Figure 37:
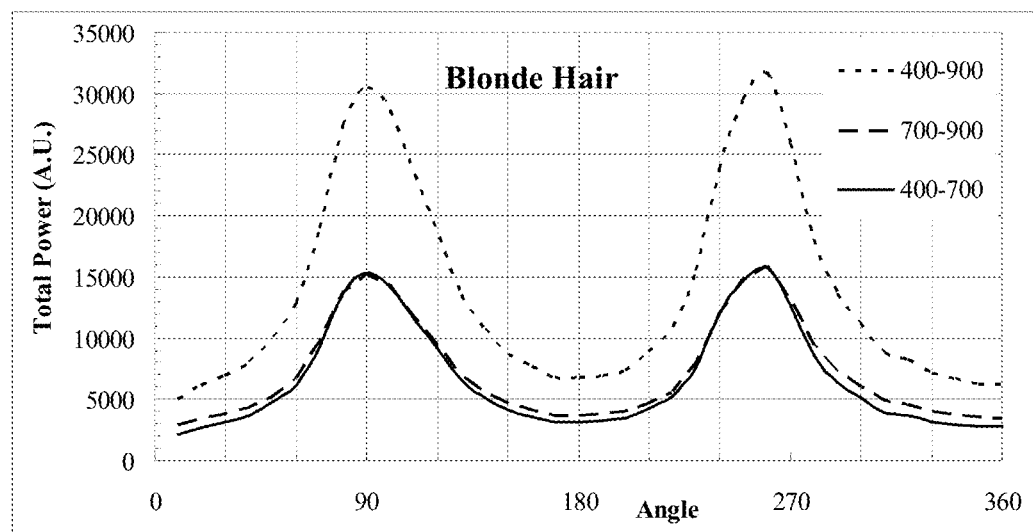
Figure 38:
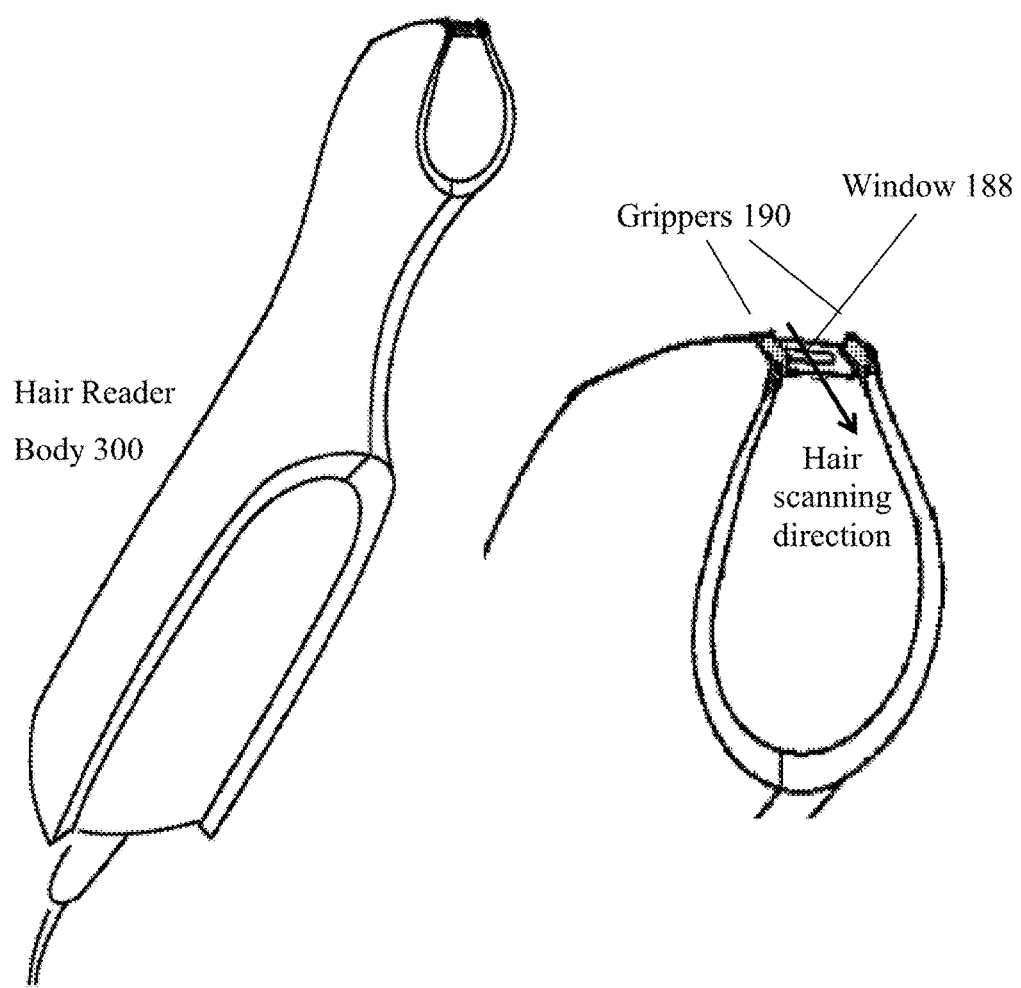
Figure 39A:
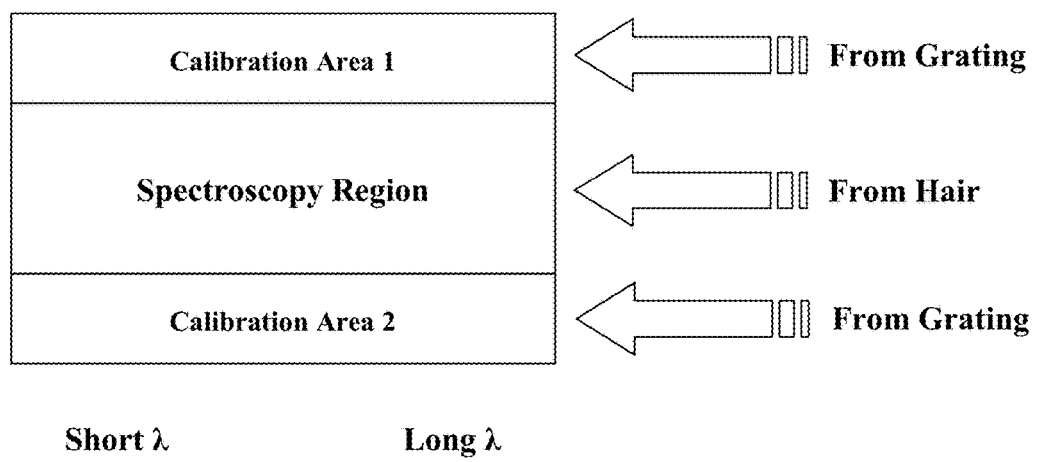
Figure 39B:
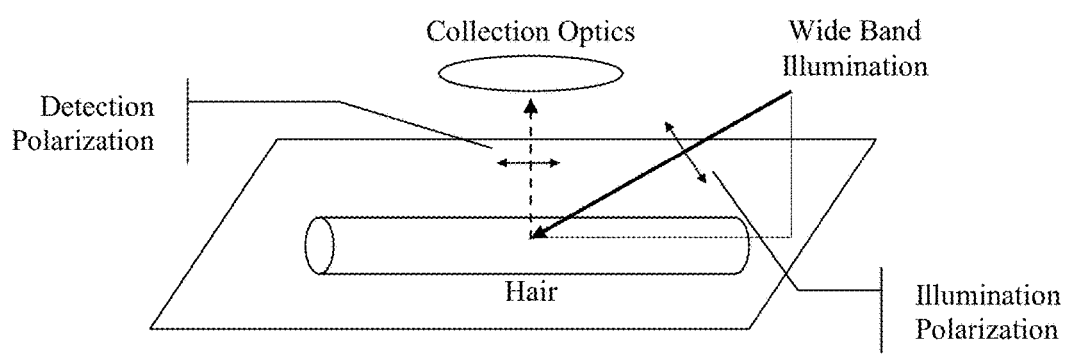
Figure 39C:
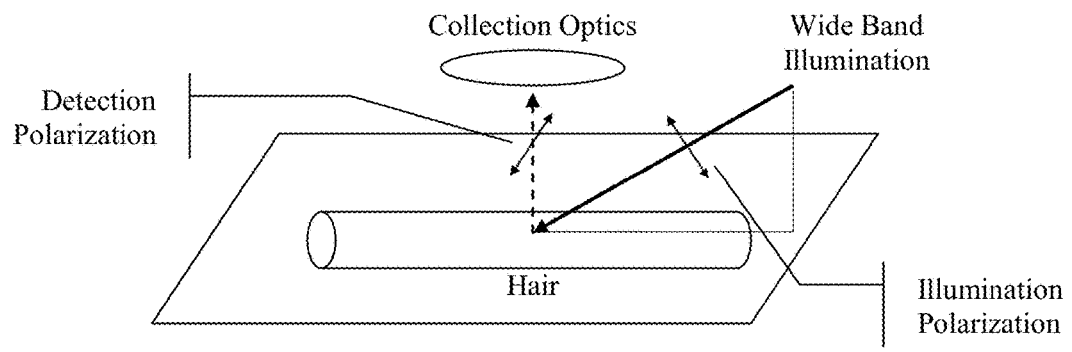

FIG. 34B is a view from above of the hair reader of FIG. 34A;

FIG. 35A shows a hair with a noticeable cuticula where a high scattering intensity is expected for illumination from the right hand side and low scattering intensity from the left hand side;

FIG. 35B shows a hair in which the cuticula is smooth and scattering from the two sides would typically be the same;

FIG. 36 is a simplified graph showing two typical hair spectra as reflection percentages over the range of 350-1550 nm;

FIG. 37 is a simplified graph that illustrates reflectance powers measured from blond hair at different measurement angles;

FIG. 38 is a simplified schematic diagram illustrating mechanical design features of an embodiment of a hair reader according to the present invention;

FIG. 39A is a simplified diagram illustrating calibration using two calibration areas on the sensor according to an embodiment of the present invention;

FIG. 39B, illustrates a block diagram showing illumination of the hair in a given polarization and passing the same polarization at the detection module, according to an embodiment of the present invention; and FIG. 39C is a block diagram showing illumination of the hair in a given polarization and passing of the orthogonal polarization at the detection module according to an embodiment of the present invention.

Figure 40:
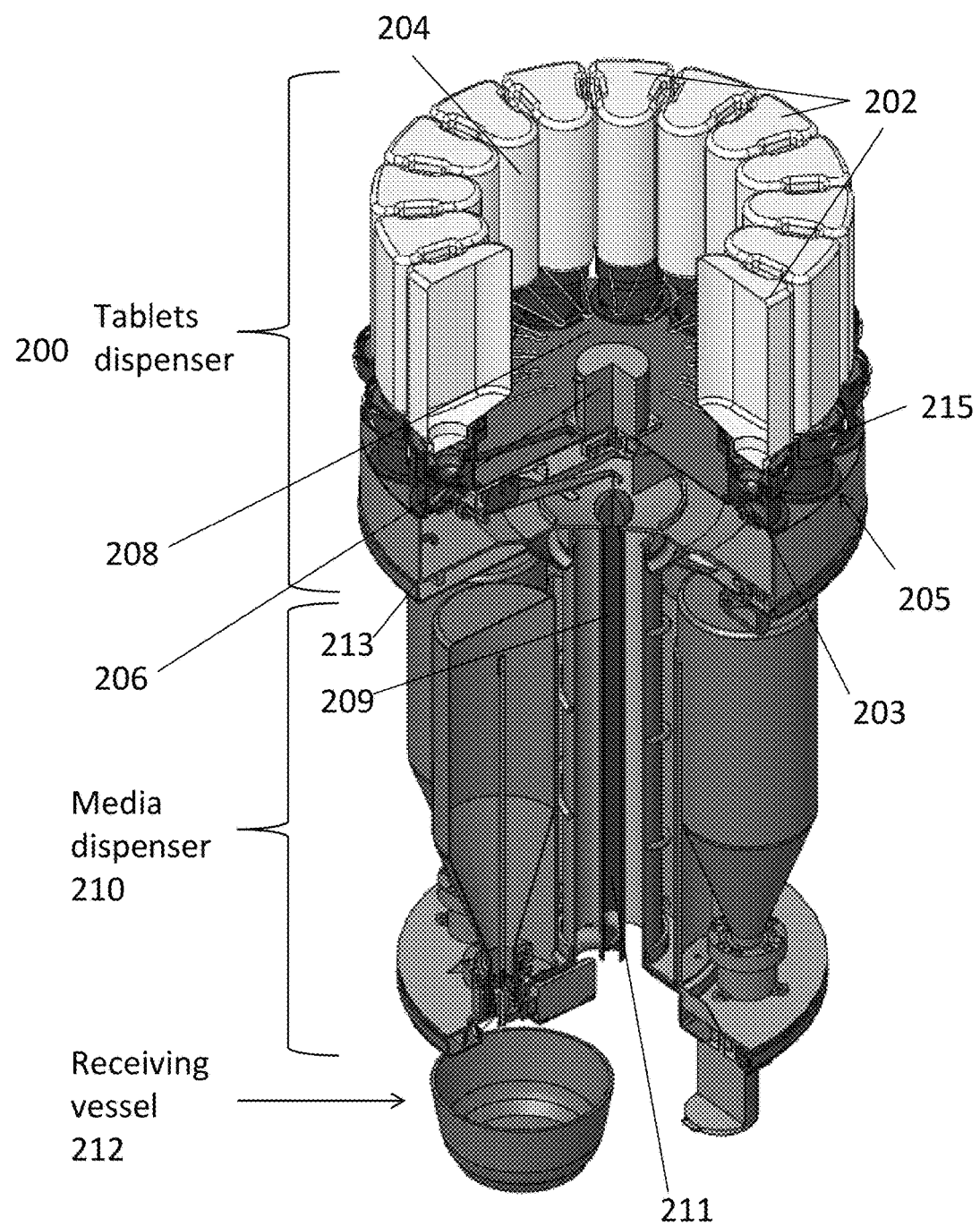
Figure 41:
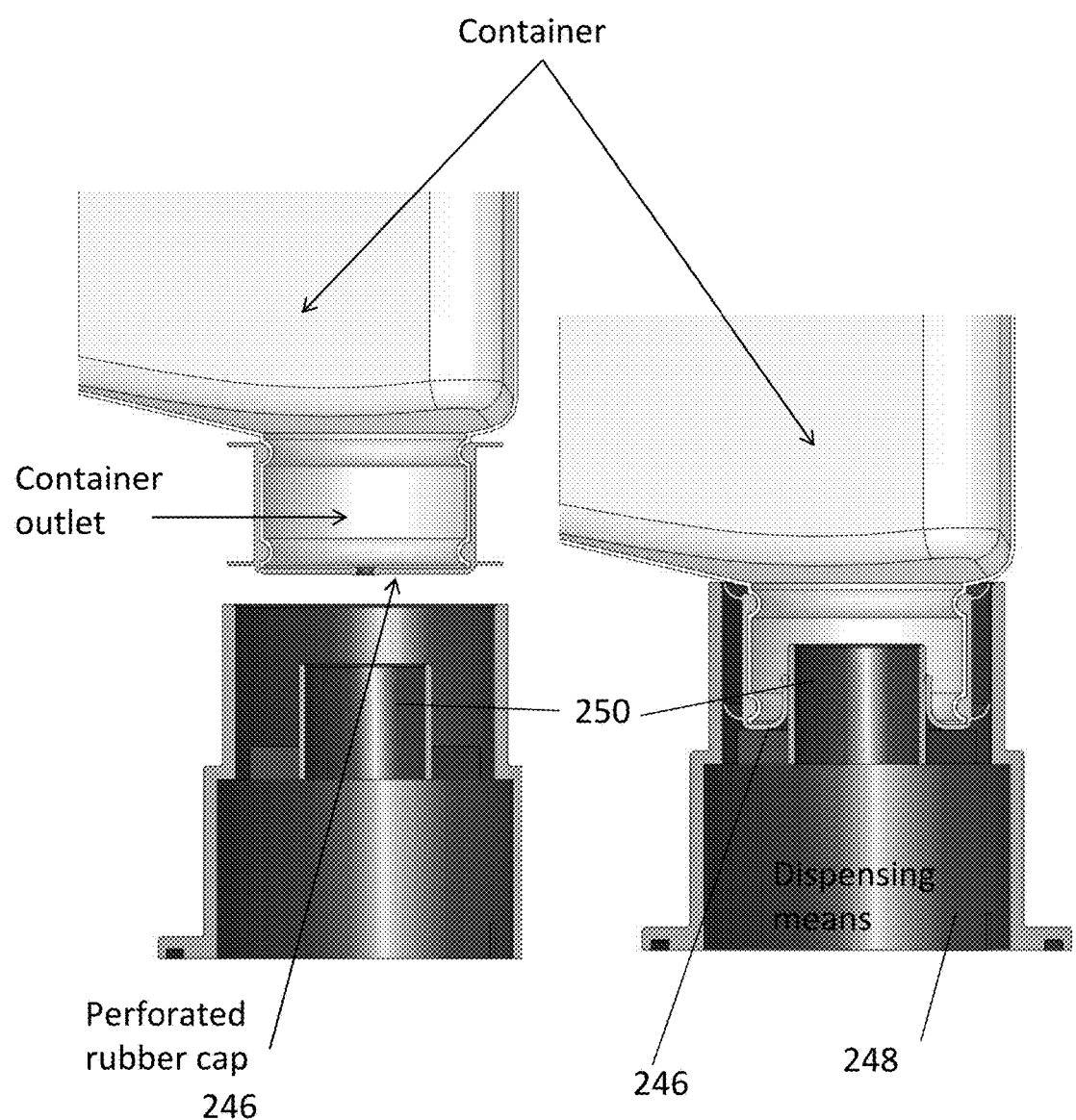
Figure 42:
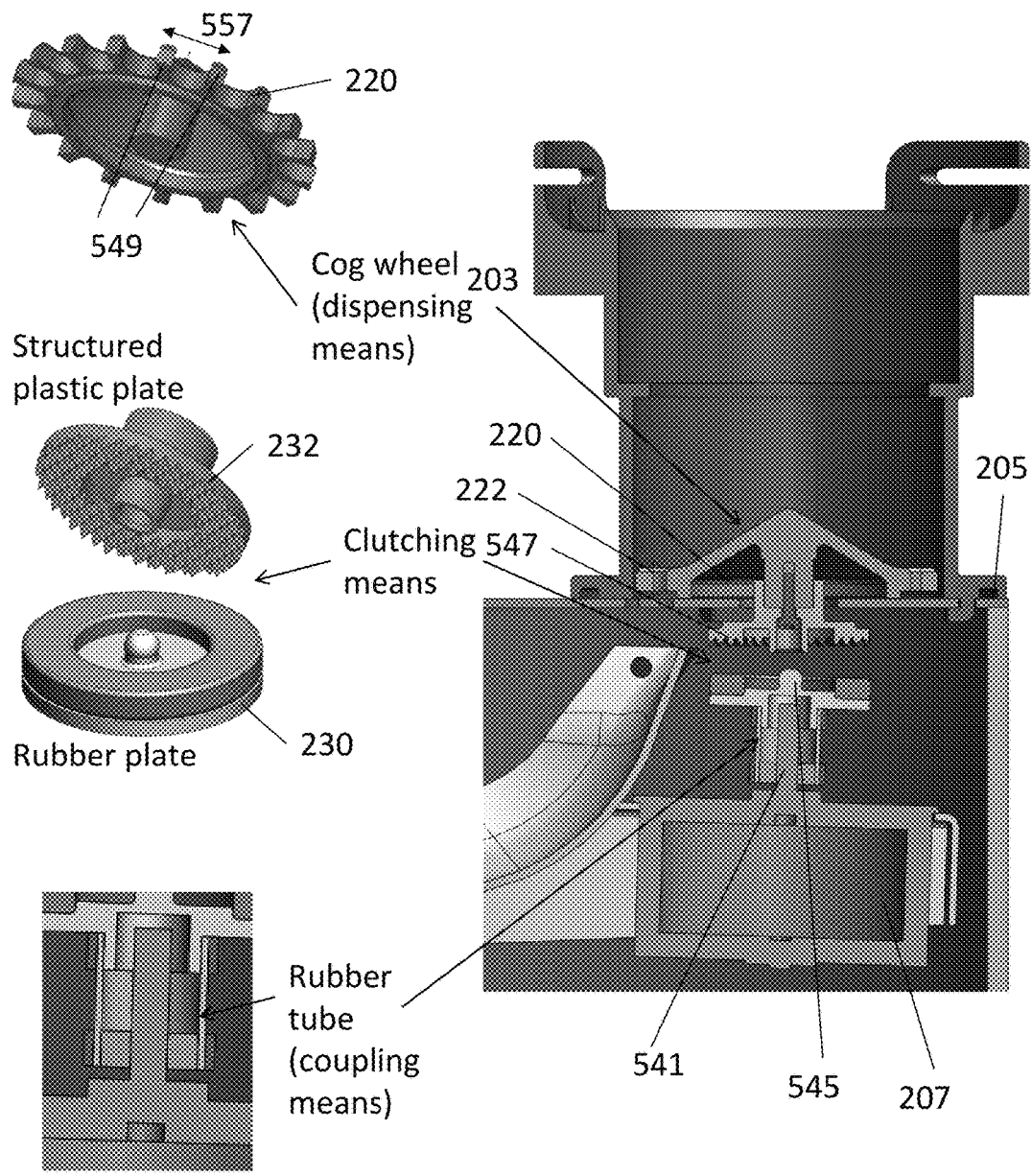
Figure 43:
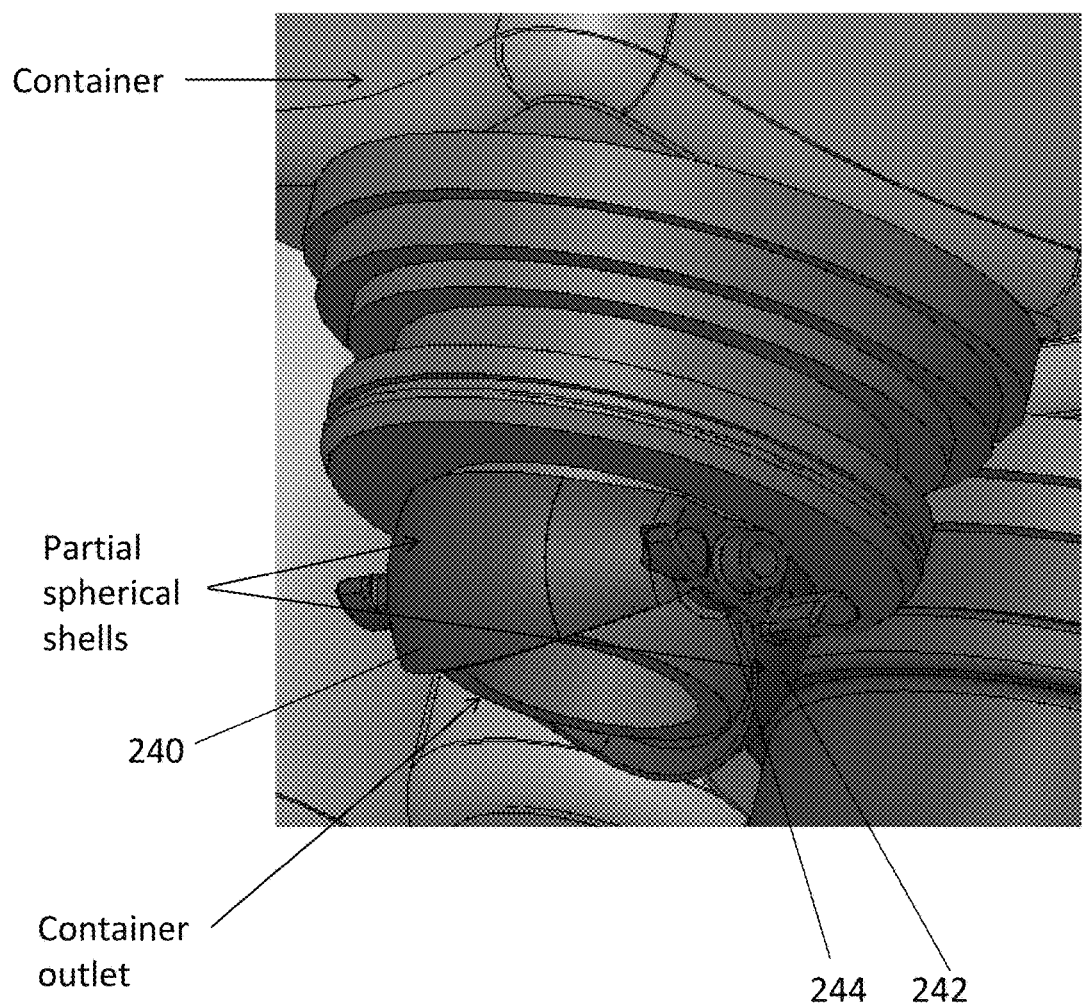
Figure 44:
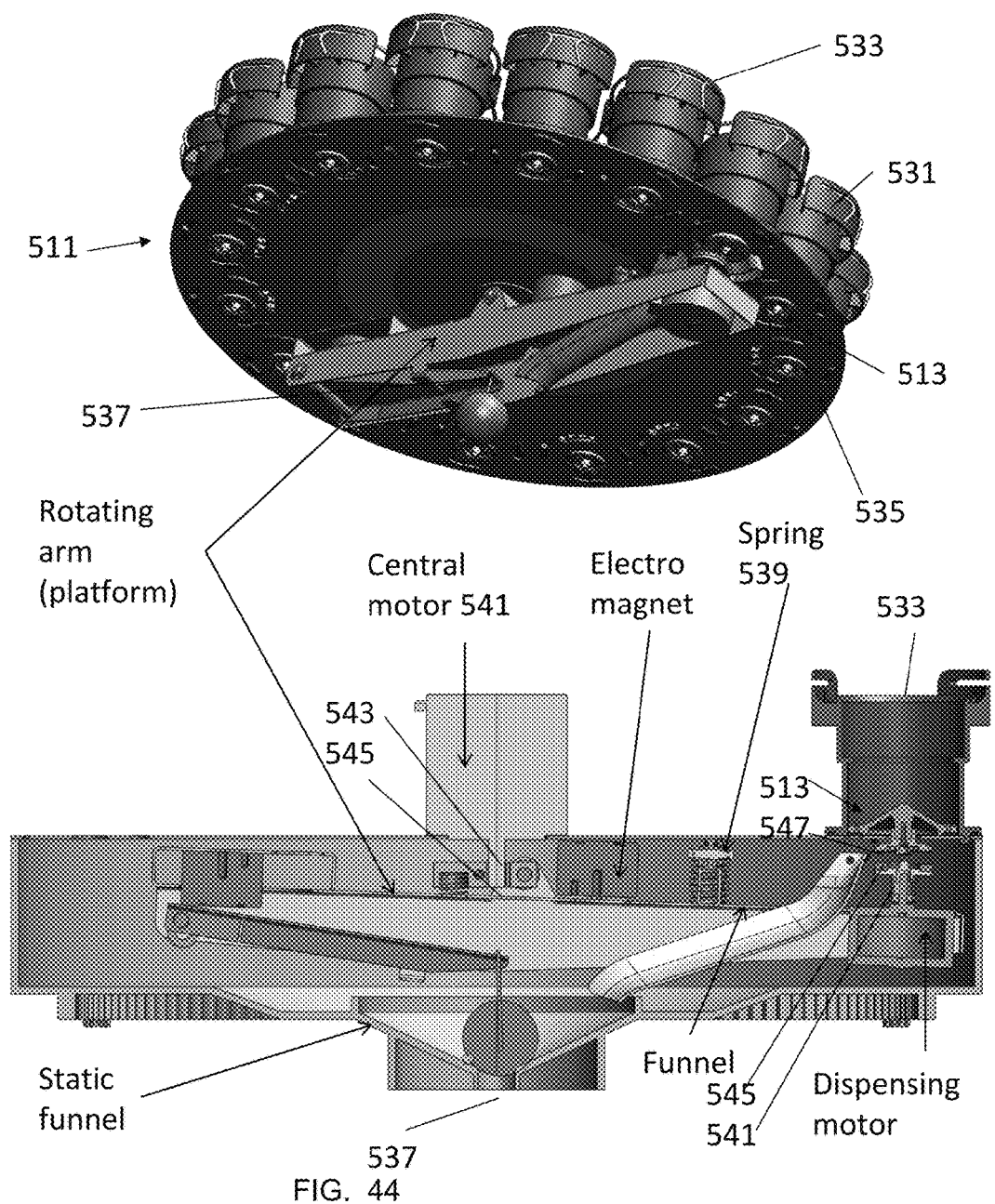
Figure 45:
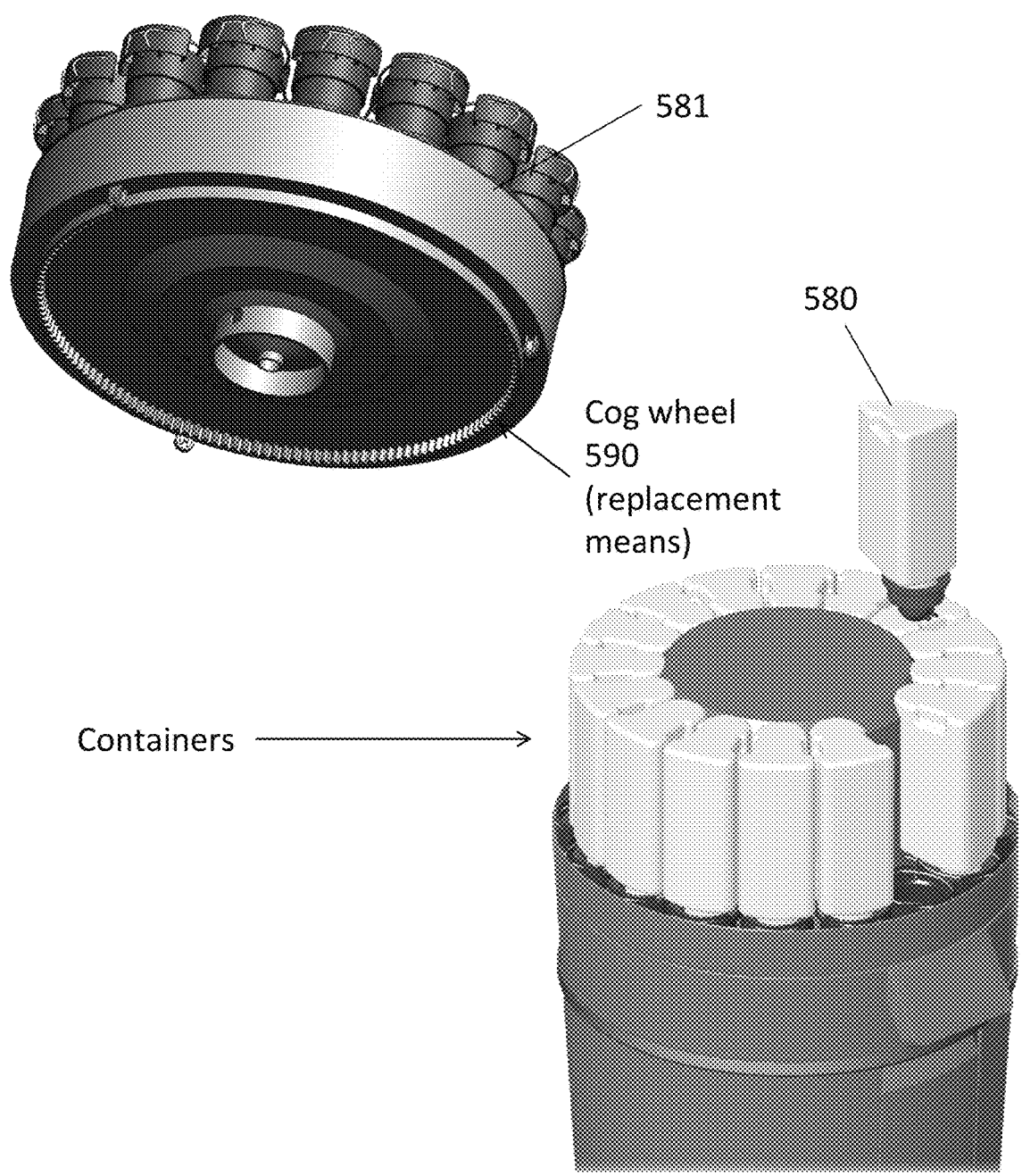
Figure 46:
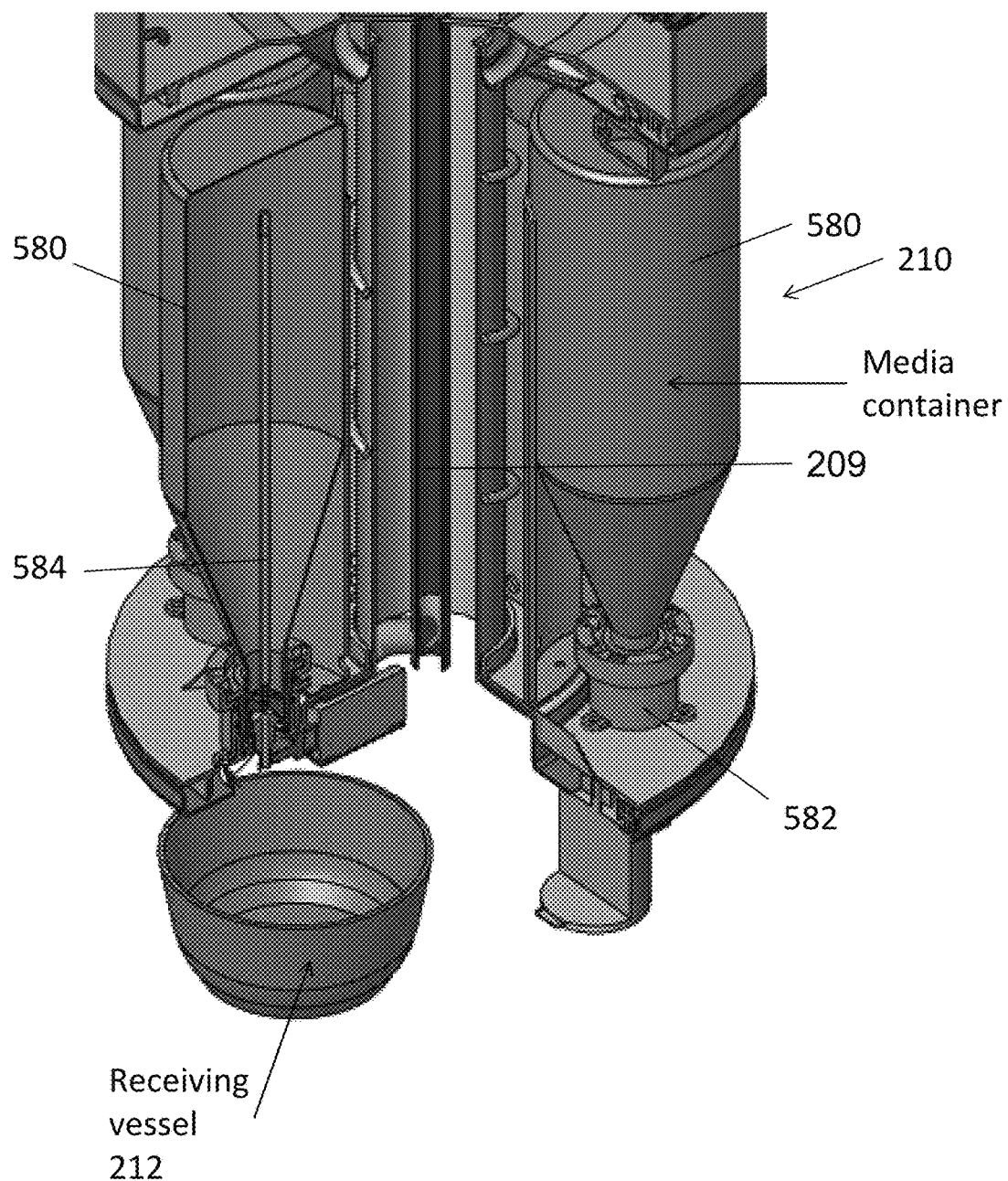
Figure 47:
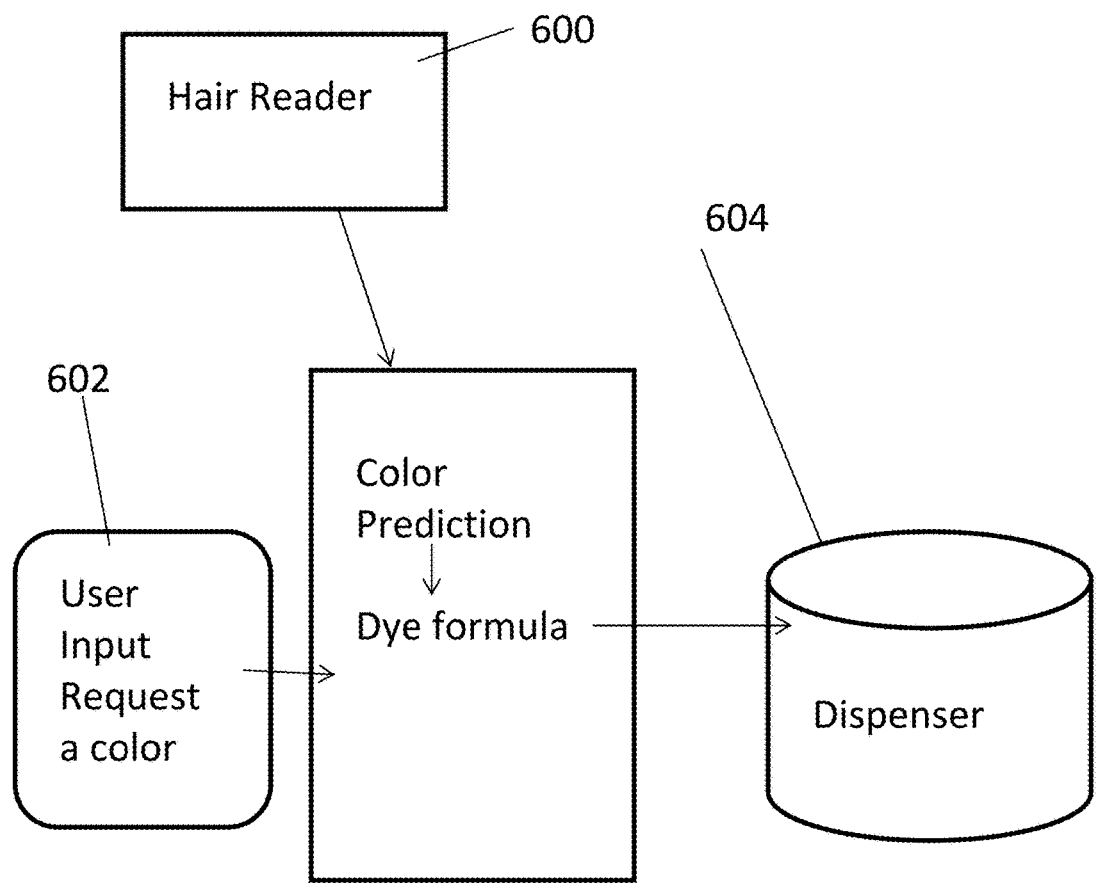

FIG. 40 is an exploded view of a dispensing device according to embodiments of the present invention;

FIG. 41 is a side view showing a container according to an embodiment of the present invention with a perforated rubber cap attached to and detached from the dispenser;

FIG. 42 is a side view and exploded diagram of a dispensing mechanism according to embodiments of the present invention;

FIG. 43 is a simplified diagram illustrating a container with partial spherical shells according to an embodiment of the present invention;

FIG. 44 is a simplified diagram showing a cross-section of the tablet dispenser according to embodiments of the present invention;

FIG. 45 is a simplified diagram showing containers and replacement mechanism according to an embodiment of the present invention;

FIG. 46 is a simplified diagram showing a media dispensing mechanism according to an embodiment of the present invention; and FIG. 47 is a simplified block diagram illustrating the different elements of the present embodiments working together.

DESCRIPTION OF SPECIFIC EMBODIMENTS OF THE INVENTION

The present invention deals with coloring hair Various embodiments relate to methods and systems for treating keratinous fibers, and more particularly, but not exclusively, to tablet formulations for treating keratinous fibers such as human hair, to to an optical reader for obtaining optical information from keratinous fibers, to a device and method for predicting the results of a treatment operation of keratinous fibers and for selecting a composition for treating keratinous fibers according to the prediction, and to systems for custom coloration of hair and other keratinous fibers which utilize any of the tablet formulations, optical reader and predicting device and method, either alone or any combination.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The present inventors have devised and successfully prepared and practiced novel systems and methods for performing treatment (e.g., coloration) of keratinous fibers. These methods and systems comprise a dispensing device which is configured to provide a ready-to-use composition for treating keratinous fibers (e.g., a coloring composition) and optionally, which is configured to provide a ready-to-use, pre-determined composition designed to suit pre-determined treatment (e.g., pre-determined coloring effect; customized treatment).

The dispensing device may optionally be in communication with one or both of an optical reader, which determines the chemical and physical characteristics of the keratinous fibers to be treated, and computational means (computer implemented means or unit) for determining the components, and of concentrations thereof required to provide the pre-determined composition and optionally or alternatively, for determining the rate, duration and temperature for applying the various active agents in the composition. When used in combination, the optical reader and the computational means are designed such that determining the components and their concentrations in the composition is made while considering the chemical and physical characteristics of the keratinous fibers to be treated and the desired result to be achieved, hence for providing a customized treatment.

Embodiments of the present invention therefore relate to an optical reader for obtaining sufficient characteristics of the keratinous fibers to enable making a realistic prediction of the outcome of a treatment (e.g., coloring treatment). An optical reader may be a hand-held tool that measures optical characteristics of the keratinous fibers, to which can then be used to calculate various characteristics of the fibers based on these parameters. The parameters may be used to support planning and recommendation of a treatment procedure, or support estimating the result of the treatment procedure.

Some of the present embodiments are directed to providing an optical reader that utilizes scattered and diffused light and specular reflection from the keratinous fibers being measured, since this gives more accurate measurements that are more useful for prediction and allows information to be obtained about the condition of the fibers, which also contributes to the final appearance. In addition the present embodiments may obtain spectral readings beyond the visible range, where the different natural pigments of the fibers are more easily distinguished. The result provides a significant improvement in the ability to accurately predict the effect of a given treatment on the keratinous fibers The optical reader may use diffused and/or scattered light and take measurements at multiple angles and/or at multiple polarizations. Measurements at different angles and/or polarizations can then be compared. Illumination with different illuminations characteristics at different times and/or at different positions across the measured hair allows for the readings at different angles and/or at different wavelengths and/or at different polarizations to be distinguished.

The optical reader is designed to distinguish in its operation between light diffused from the internal part of the fibers' shaft which gives information regarding the fibers' color and internal ingredients and light scattering from the shaft outer surface which gives information relating to the fibers' condition.

Relative amounts of water in the keratinous fibers or effecting treatment kinetics can be detected, as will be explained.

The spectral range of the optical reader is beyond the visible, and readings in the IR spectrum are used to help compensate for strong absorption of melanin at visible wavelengths.

Both Eumelanin and Pheomelanin absorb much less light at the IR then in the visible. Two different fibers' shafts which are saturated with melanin but actually have different melanin concentrations give very low reflectance intensity at the visible which is not much more than the system noise, making it difficult to distinguish between the to two. The spectral intensity in the IR, however is much more distinguishing, and allows for considerable information to be obtained about the two shafts.

The spectra of artificial dyes and combinations thereof may often be hard to distinguish from melanin in the visible range. Nevertheless, the spectra may differ quite markedly in the near IR range Scattered light provides information about the condition of the fiber cuticula. An estimation of fiber radius from the amount of reflection is also provided.

Polarization of light improves SNR, possibly by excluding glare, and also improves the detection of relative amounts of dyes and natural pigments.

Some embodiments of the present invention further relate to a method for predicting a result of a treatment operation of keratinous fibers that uses a predetermined recipe of the treatment composition (a pre-determined composition).

The present embodiments consider the chemical dynamics of the process in which keratinous fibers are treated. The dynamics may be considered at two levels, the bleaching effects of oxidizing agents in reducing the initial concentrations of natural and artificial pigments, and the interaction of the active agents with the keratinous fibers. Separately, the spectrum finally arrived at is modified to take account of specular reflection.

The above prediction may be carried out based on data obtained from the optical reader, as will be explained in greater detail below.

The present embodiments comprise a method and apparatus for predicting the result of treatment of keratinous fibers in a realistic way. The system of using spectra rather than color coordinates is adopted but the chemical dynamics of the treatment operation are taken into account as are the effects on the end result of light scattering and specular reflection. The optical reader may provide the data on light scattering and/or specular reflection.

Embodiments of the present invention therefore relate to a method for predicting a result of a treatment operation that uses a predetermined composition recipe, which is effected by measuring an initial spectrum of the keratinous fibers to be treated, by obtaining sufficient characteristics of the fibers to make a realistic prediction of the outcome of a treatment; determining from the initial spectrum a presence and concentration of respective constituents; determining a modified concentration of the to constituents following bleaching effects of chemical agents in the recipe; determining final concentrations of the constituents following interaction of the chemical agents with colorants in the fibers; and from the final concentrations, predicting a final spectrum of the keratinous fibers from which the color of the fibers can be calculated. While, preferably, all of these characteristics and acts should be carried out, in some embodiments of the invention, fewer characteristics may be sufficient for good prediction of results.

Embodiments of the present invention relate to a dispensing device which is configured to provide a composition for treating keratinous fibers, upon determining chemical and physical characteristics of the keratinous fibers to be treated. Embodiments of the present invention relate to a dispensing device which is configured to provide a composition for treating keratinous fibers, upon computationally selecting a composition that would impart a desired treatment of the keratinous fibers.

Embodiments of the present invention therefore relate to systems and methods which utilize spectral means for determining chemical and physical characteristics of the keratinous fibers to be treated, computational means for selecting a composition that would impart a desired treatment of the keratinous fibers based on the determined characteristics of the keratinous fibered, and a dispensing device for providing a suitable (customized) composition based on the computational means.

The present inventors have further designed and successfully prepared and practiced rapidly-disintegrating solid formulations, in a form of tablets, particularly substantially spheroidal tablets (i.e., beads), for imparting a desired treatment (e.g., coloring) of keratinous fibers.

The present inventors have further designed and successfully practiced a dispensing device, suitable for dispensing the herein disclosed tablets, and any other tablets for treating keratinous fibers. Such a dispenser can be in communication with one or both of an optical reader and computational means for determining a suitable composition for treating the keratinous fibers (a customized composition or treatment). Optionally, the dispensing device prepares a customized composition or compositions in response to information received from the optical reader and/or the computational means (e.g., as described herein). These compositions can be prepared automatically.

As used herein throughout, the phrase "keratinous fiber" refers to all fibers to comprising keratin structural proteins, including, but not limited to, hair, fur, wool, and silk. The fibers may be located on a living body, e.g., a person or animal, or a non-living body, e.g., a wig, a hairpiece, or other aggregation of non-living keratinous fibers. In some embodiments, the keratinous fibers are hair, and in some embodiments, the fibers are human hair.

It is to be noted that while some embodiments of the present invention are described in the context of hair, utilizing these embodiments in the context of any keratinous fibers as described herein is also contemplated.

As used herein, "treating keratinous fibers" encompasses coloring, bleaching, and any other alteration of the fibers' color.

Herein, "coloring" refers to alteration of a color of a substrate (e.g., keratinous fibers) by introducing a colored substance to substrate. Examples of colored substances include pigments and dyes. The term "coloring" is also referred to herein as "dyeing".

Herein, "bleaching" refers to alteration of a color of a substrate (e.g., keratinous fibers) by reducing an amount of a colored substance (e.g., a natural pigment) in the substrate.

It is to be noted that while some embodiments of the present invention are described in the context of coloring and/or dyeing, utilizing these embodiments in the context of any treatment of keratinous fibers as described herein is also contemplated. Thus, for example, coloring may be effected, coloring and bleaching can be effected and only bleaching can be effected.

Herein the term "customized" with respect to a treatment, composition, combination and other expressions is meant to describe modified or adjusted according to individual specifications and/or preference, so as to achieve a desired end-result (desired effect of keratinous fibers, for example, a desired hair color).

The Systems:

Some embodiments of the present invention relate to systems which are aimed at providing an accurate coloring result when treating keratinous fibers while considering chemical and physical properties of the fibers and a desired result to be achieved by the treatment.

In some embodiments, the systems are configured so as to provide a customized coloring composition for hair of an individual subject.

Such systems may comprise one or more of:

an optical reader measuring specular and/or scattered light from the keratinous fibers to be treated (e.g., hair);

a computer implemented unit or means (also referred to herein as a computational unit or computational means) for predicting the result of the treatment of the keratinous fibers and/or for selecting a recipe for a composition achieving a desired treatment;

a composition which is selected suitable for achieving a desired treatment of the keratinous fibers, or a formulation useful in preparing same; and a dispensing device for providing the selected composition or a selected formulation for preparing the composition or a selected kit for preparing the composition.

In some embodiments, the system further comprises a unit for operating some or all of the abovementioned units, preferably an optionally hand-held unit.

According to some embodiments of the present invention there is provided a system which comprises an optical reader and a computational unit as indicated hereinabove, which is suitable for use in accurately predicting an outcome of a treatment of keratinous fibers by a pre-determined recipe and/or for selecting a treatment composition suitable for achieving a desired effect (customized treatment).

According to some embodiments of the present invention there is provided a system which comprises an optical reader, a computational unit and a dispensing device as indicated hereinabove, which is suitable for use in selecting a treatment composition suitable for achieving a desired effect (customized composition) and for providing the selected composition or agents for forming the selected composition.

According to some embodiments of the present invention there is provided a system which comprises an optical reader, a computational unit, active agents usable for preparing a selected composition for treating keratinous fibers and a dispensing device as indicated hereinabove, which is suitable for use in selecting a treatment composition suitable for achieving a desired effect and for providing the selected composition.

According to some embodiments of the present invention there is provided a system which comprises active agents usable for preparing a composition for treating to keratinous fibers and a dispensing device as indicated hereinabove, which is suitable for providing a selected (customized) composition for treating keratinous fibers.

In any of these embodiments, a color measurement instrument, comprising the optical reader, may be used to establish the initial color of the keratinous fibers.

In any of these embodiments, at least part of the active agents usable for preparing a selected composition is in a form of solid, tablet formulations.

In any of these embodiments, the dispenser is interfaced with the computational unit, the algorithm may determine amounts of tablets to be selected by the dispenser. The algorithm may take into account individual properties of the keratinous fibers to be colored, as described herein.

According to some embodiments of the present invention, in any of the embodiments of a system as described herein which comprises an optical reader, the optical reader is as described herein. The optical reader, which is also referred to herein as hair reader is described hereinbelow in respect of FIGS. 32A-39C.

According to some embodiments, in any of the embodiments of a system as described herein which comprises computational unit, the computational unit is as described herein (and is also referred to as computational means, computer implemented unit or means).

The computational unit and associated prediction algorithm are described herein in respect of FIGS. 18-31.

According to some embodiments, in any of the embodiments of a system as described herein which comprises a composition for treating keratinous fibers, the composition is formed of a solid formulation in a form of tablets as described herein.

According to some embodiments, in any of the embodiments of a system as described herein which comprises a dispensing device, the dispensing device is configured for dispensing tablets, such as the dispensing device as described herein.

In some embodiments, in any of the systems as described herein as utilizing a composition which is made, at least in part, from solid formulation(s), in a form of tablets, the system further comprises a dispenser which is configured for dispensing solid formulation(s), in a form of tablets.

The dispensing device is described herein in respect of FIGS. 1-8 and 40-46.

An exemplary system is depicted in FIG. 47.

According to an aspect of some embodiments of the present invention there is provided a system for performing treatment of keratinous fibers, the system comprising:
  an optical device for measuring an initial spectrum of the keratinous fibers;
  a computer implemented unit for predicting the result of a performing a pre-determined treatment (e.g., the result achieved by coloring hair with a pre-determined coloring composition or recipe), the unit comprising:
    a constituent estimation unit for determining from said initial spectrum a presence and concentration of respective constituents in the keratinous fibers;
    a kinetic chemical reaction modeling unit for a) determining a modified concentration of said constituents following bleaching effects of chemical agents in the recipe and b) determining final concentrations of said constituents following interaction of the chemical agents with colorants in the keratinous fibers; and
    a spectral prediction unit for using said final concentrations to predict a final spectrum of the keratinous fibers;
  a solid formulation in a form of a tablet, the formulation comprising at least one active agent selected from the group consisting of a color imparting agent, an oxidizing agent and an alkalizing agent, and being for use in the preparation of a composition for performing the treatment; and
  a dispensing device configured for dispensing a pre-determined combination of the tablets, and optionally a pre-determined concentration and/or amount of liquid media, and being interfaced with the computer-implemented unit, wherein the pre-combination of the tablets is selected by the computer-implemented unit while considering the initial spectrum of the keratinous fibers and the treatment to be performed.

In some embodiments, the solid formulation utilized in such a system further comprises a water-insoluble superdisintegrant, which optionally is such that swells upon contacting an aqueous solution, as described herein.

In some embodiments, the composition useful for performing the desired treatment is a coloring composition as described herein.

According to an aspect of some embodiments of the present invention there is provided a system for performing treatment of keratinous fibers, the system comprising:
  an optical device for measuring an initial spectrum of the keratinous fibers, the optical device comprising:
    an illumination unit for illuminating hair;
    a measuring unit comprising at least one sensor for optically measuring the keratinous fiber during illumination by the illumination unit; wherein the sensor and a beam from the illumination unit respectively subtend a light diffusion angle at the keratinous fiber being measured, thereby to ensure that the sensor principally measures light of the illumination beam that is diffused or scattered by the keratinous fiber;
  a computer implemented unit for determining from the initial spectrum a presence and concentration of respective constituents in the keratinous fibers,
  a composition comprising at least one active agent selected from the group consisting of a color imparting agent, an oxidizing agent, a thickening agent and an alkalizing agent, the composition being such that an amount and concentration of each of the active agents are selected so as to effect the treatment of the keratinous fibers; and a dispensing device configured for providing the selected composition, the dispensing device being interfaced with the computer-implemented unit, wherein the pre-determined amount of each of the active agents is selected by the computer-implemented unit while considering the initial spectrum of the keratinous fibers and the desired treatment to be performed.

According to an aspect of some embodiments of the present invention there is provided a system for performing treatment of keratinous fibers, the system comprising:

an optical device for measuring an initial spectrum of the keratinous fibers;

a computer-implemented unit for predicting a final spectrum of the fibers following treatment with a selected composition; and a mixer or a dispensing device for preparing the selected composition.

In some embodiments, such a system further comprises active agents as described herein for preparing the selected composition, and in some embodiments, at least part of the active agents is in a form of tablets. In some of these embodiments, the dispensing device is configured to dispense selected amounts and types of tablets so as to provide the selected composition. In some of these embodiments, the dispenser is further configured to dispense selected amounts and concentrations of a liquid media to to be mixed with the tablets or any other form of active agents, so as to provide the selected composition.

The Methods:

According to an aspect of some embodiments of the present invention there are provided methods of treating keratinous fibers, which are effected by executing one or more of the following:

analyzing the keratinous fibers to be treated;

computationally processing the analysis of the fibers to be treated, so as to select the components (active agents) and the concentration of each component in a composition suitable for providing the desired treatment to the keratinous fibers, and optionally so as to select a duration, rate and/or temperature for applying each of the components and/or the composition as a whole;

providing the selected (customized) composition;

and applying it to the keratinous fibers.

The selected (customized) composition can be provided by mixing the components manually or by an automated dispenser.

The selected (customized) composition is advantageously prepared from solid formulations, in a form of tablets, and more advantageously, by rapidly-disintegrating tablets as described herein. An automated dispenser suitable for dispensing tablets is advantageously utilized to this effect.

Further according to an aspect of some embodiments of the present invention there is provided a method for predicting a result of a treatment of a keratinous fibers (e.g., hair coloring operation) that uses a predetermined composition, the method comprising:

measuring an initial spectrum of the keratinous fibers;

determining from the initial spectrum a presence and concentration of respective constituents;

determining a modified concentration of said constituents following bleaching effects of chemical agents in the composition;

determining final concentrations of said constituents following interaction of the chemical agents with colorants in the fibers; and from the final concentrations, predicting a final spectrum of the fibers from which the treatment of the fibers can be calculated.

Further according to an aspect of some embodiments of the present invention there is provided a method for predicting a result of a treatment of keratinous fibers (e.g., hair coloring operation) that uses a predetermined composition (e.g., hair coloring recipe), the method comprising:

measuring an initial spectrum of the keratinous fibers;

from initial concentrations of natural factors of the fibers and from factors obtained form the predetermined composition, predicting a final spectrum of the fibers following the treatment;

correcting the final spectrum for specular reflection effects; and further correcting the final spectrum corrected for specular correction effects with a further correction for light scattering effects.

Such methods can be combined with a method of treating keratinous fibers so as to allow a subject to approve the prediction result or otherwise to modify it as desired, prior to the treatment, so as to allow the subject to determine the composition to be utilized, or to allow a practitioner to select a customized treatment per the desired result.

Further according to an aspect of some embodiments of the present invention there is provided a method for obtaining optical measurements of keratinous fibers (e.g., hair), the method comprising:

applying an illumination source to said fibers;

optically measuring illumination of said fibers from a diffusion angle in relation to the illumination source, the illumination angle lying between 45 degrees and 135 degrees, thereby to obtain a measurement whose principle components are light that has been diffused or scattered by the fibers from the illumination source.

Such a method can be combined with any of the methods described herein for optically measuring an initial spectrum of the keratinous fibers.

According to some embodiments of the present invention, in any of the embodiments of a method as described herein which comprises optical measurements of the keratinous fibers or hair, the optical reader is as described herein.

According to some embodiments, in any of the embodiments of a method as described herein which comprises computational prediction, the prediction is as to described herein.

According to some embodiments, in any of the embodiments of a system as described herein which comprises a composition for treating keratinous fibers, the composition is formed of a solid formulation in a form of tablets as described herein.

According to some embodiments, in any of the embodiments of a method as described herein which comprises providing a selected or pre-determined composition, a dispensing device interfaced with a computational unit is utilized for providing at least part of the components of the selected, customized composition. In some embodiments, the dispensing device is as described herein.

Following is a more detailed description of some embodiments of the methods and systems as described herein.

I. Predicting a Result of a Treatment of Keratinous Fibers:

Reference is now made to FIG. 18 which illustrates an exemplary method for predicting a result of a hair coloring operation that uses a predetermined hair coloring recipe (pre-determined composition). Such a method can be utilized for predicting a result of any treatment of any keratinous fibers.

The term "recipe" is used herein to define a coloring composition with predetermined concentration of active agents such as coloring agents, alkalizing agents, thickening agents and/or oxidizing agents, and/or with predetermined conditions for applying each of these agents or the composition a whole.

In S1 the method obtains an initial spectrum of a subject's hair, typically using a spectrometer.

In S2, the method calculates, from the initial spectrum, initial concentrations of keratin, eumelanin and pheomelanin as well as the initial Sanderson coefficients, which include the light reflected from the surface (both specular and diffused) component of hair and estimation of hair diameter and cuticle condition.

In S3, the method obtains factors regarding the dyeing process from the recipe for alkalizing agent concentration, oxidizing agent concentration, temperature, solutions' viscosity, hair's diameter, cuticles condition and exposure duration.

The factors are used in a chemical reaction kinetic equation to determine modified concentrations of the keratin, eumelanin, pheomelanin, artificial pigments and to the modified values of the Saunderson coefficients. The hair damage is also estimated.

In S4, the recipe is used to provide a color-imparting agent (e.g., dye substance) concentration factor, and the color-imparting agent substance concentration is used together with factors for alkalizing agent concentration, oxidizing agent (e.g., hydrogen peroxide) concentration, temperature, viscosity, hair diameter, hair porosity and exposure duration, in order to determine a final concentration of artificial colorant in the hair In S5, the final concentrations of artificial colorant and of keratin, eumelanin, pheomelanin, artificial pigments and the final values of the Saunderson's coefficients are used together to predict a final spectrum of the hair, using a spectrum calculation process as well as an estimation of damage to hair The final spectrum may be used as is, or may be corrected for light reflected from the surface (both specular and diffused) reflectance effects.

Similarly, the analysis of the initial spectrum to determine the constituents that are present may be corrected for light reflected from the surface (both specular and diffused) effects.

A way of approximation of the reflectance spectrum by having the magnitudes of concentrations of each ingredient as well as their absorption spectrums and scattering spectrums may make use of the Kubelka Munk formula.

The approximation of Kubelka Munk is of the form:

$$\frac{(1-R(\lambda))^2}{2 \cdot R(\lambda)} = \frac{\sum_{n=1}^{N} C_n \cdot K(\lambda)_n}{\sum_{n=1}^{N} C_n \cdot S(\lambda)_n}$$

where:
$R(\lambda)$=The diffused reflectance in wavelength;
$K(\lambda)_n$=The absorption, in wavelength, of the $n^{th}$ ingredient;
$S(\lambda)_n$=The scattering, in wavelength, of the $n^{th}$ ingredient; and
$C_n$=The concentration of the $n^{th}$ colorant.

The internally diffused reflectance in wavelength—$R(\lambda)$—may be obtained from the Sanderson correction formula, as will be discussed in greater detail below.

The predicting a final spectrum in S5 may further comprise correcting for light reflected from the surface (both specular and diffused) reflection effects.

Similarly, the analysis of the initial spectrum to determine the constituents that are present may be corrected for light reflected from the surface (both specular and diffused) reflection effects.

Correcting for light reflected from the surface (both specular and diffused) reflection effects may comprise considering an air to hair boundary and a hair outer region to hair inner region boundary and the cutiles condition.

The correcting may involve applying a Sanderson correction, for example a correction of the form $$R(\lambda) = \frac{R(\lambda)_{meas} - \alpha}{1 - F(\lambda)_{ext} - F(\lambda)_{int} + F(\lambda)_{ext}F(\lambda)_{int} - \alpha F(\lambda)_{int} + F(\lambda)_{int}R(\lambda)_{meas}}$$

where:
$\lambda$=wavelength
$\alpha$=The relative portion of light reflected from the surface (both specular and diffused) reflectance which propagates to the spectrometer's detector;
$R(\lambda)$=Corrected reflectance by Saunderson formula;
$F(\lambda)_{ext}$=The external Fresnel reflectance (light reflected from the surface (both specular and diffused)) from the external side of the hair;
$F(\lambda)_{int}$=The internal Fresnel reflectance between the internal medium of the hair and the hair boundary region.

As mentioned above, the corrected reflectance according to the Sanderson correction—$R(\lambda)$—may be inserted into the Kubelka Munk approximation.

In S3 and S4, the final concentrations of keratin, eumelanin, pheomelanin and artificial colorant may be calculated using a chemical reaction kinetics equation.

The calculating of the final concentrations may take into account intermediate products appearing from said chemical reactions, as will be discussed in greater detail below.

A mixing apparatus may mix a treatment composition according to the recipe when the final result (e.g., color) is approved. The mixing apparatus can be a manual mixer or an automated mixer, optionally in a form of an automated dispensing device, which is configured to provide the calculated final concentrations of each of the color-imparting agent, the oxidizing agent and/or the alkalizing agent, and optionally of a thickening agent, as is further detailed hereinafter. When automated, the mixing device is preferably interfaced with computer-implemented unit which executes the herein described calculations.

The algorithm implementation is now considered in greater detail. The method may be implemented by a computerized process that outputs the optimized recipe of hair treatments for a given initial hair (or any other keratinous fiber) and a definition of desired target treatment (e.g., coloring). The calculations utilize a-priori knowledge of the hair colorants in terms of their optical properties, as well as the evolution imposed, on the natural components in hair, due to different hair treatments. Once these items are defined, given an initial hair coloration, the system considers a plurality of hair treatments. For each treatment the system approximates the final result by physical and chemical formulas. Finally, the system chooses the treatment that best matches the target color (or any other treatment) while minimizing damage to hair and treatment duration. It may be that the same person has several locations on the hair requiring different measurements and different treatments, but with overall considerations. For example, one may have a natural portion with natural coloration close to the scalp and the hair roots, and older hair further away from the scalp which is already colored. The system acquires two measurements respectively, and carries out separate analysis for each part. However, the overall color of the head may take into account the color unity between the two portions, so that the choices for coloration at each part are influenced by the overall aspect of color unity.

The initial hair is measured with a spectrophotometer that includes at least the visible range. The units of the measured spectra are given in terms of relative reflectance, in the sense of the percentage of light that each wavelength reflects from hair. Then, the relation between the spectra and the concentrations to that comprise the hair are analyzed by the formula of Kubelka Munk in the approximation of substance of infinite thickness, with the Saunderson correction formula. The reflectance measurement is comprised of two components: the internally diffused reflectance and the light reflected from the surface (both specular and diffused) component. A diffused reflectance involves dispersing light into equal intensity per every solid angle in the space, while the light reflected from the surface include both a specular portion which keeps the light rays traveling along concrete sector boundaries and a diffused portion, mostly from the cuticles. The internally diffused component obeys the approximation of Kubelka Munk while the light reflected from the surface (both specular and diffused) is treated by the Sanderson correction formula.

Kubelka-Munk (in the approximation of infinite thickness substance):

$$\frac{(1-R(\lambda))^2}{2 \cdot R(\lambda)} = \frac{\sum_{n=1}^{N} C_n \cdot K(\lambda)_n}{\sum_{n=1}^{N} C_n \cdot S(\lambda)_n}$$

where:

$R(\lambda)$=The internally diffused reflectance in wavelength.
$K(\lambda)_n$=The absorption, in wavelength, of the $n^{th}$ ingredient.
$S(\lambda)_n$=The scattering, in wavelength, of the $n^{th}$ ingredient.
$C_n$=The concentration of the $n^{th}$ colorant.

Saunderson Correction:

As mentioned hereinabove, the reflectance is assumed to be comprised of two types: an internally diffused portion, which obeys the formula of Kubelka Munk and a portion of light reflected from the surface (both specular and diffused). The Kubelka Munk model does not take into account the light reflected from the surface (both specular and diffused), which can be considered boundary effects. The light reflected from the surface (both specular and diffused) is due to differences in refraction index between the boundary to air and between the internal medium in hair and the cuticles condition. For example, the differences in refractive index at the boundary between a hair sample and air gives rise to a certain amount of specular reflection while the small cuticles diffuse the light it reflects. The magnitude and angle at which this reflection is reflected depend upon the gloss of the sample, the structural geometry of the sample and the optical setup of the spectrometer. The correction deals with two boundary effects, to one from its external side (air-hair) and the other from its internal side (hair boundary region to hair internal medium). The optical setup is also taken on account in order to describe the relative portion of specular reflection which propagates towards the sensor of the spectrometer.

$$R(\lambda)_{meas} = \alpha + \frac{(1-F(\lambda)_{int})(1-F(\lambda)_{ext})R(\lambda)}{1-F(\lambda)_{int}R(\lambda)}$$

By isolating $R(\lambda)$ we get:

$$R(\lambda) = \frac{R(\lambda)_{meas} - \alpha}{1-F(\lambda)_{ext}-F(\lambda)_{int}+F(\lambda)_{ext}F(\lambda)_{int}-\alpha F(\lambda)_{int}+F(\lambda)_{int}R(\lambda)_{meas}}$$

where:

$\lambda$=wavelength
$\alpha$=The relative portion of light reflected from the surface (both specular and diffused) reflectance which propagates to the spectrometer's detector.
$R(\lambda)$=Corrected reflectance by Saunderson formula. This is actually the portion of reflectance that is due to diffused behavior only.
$F(\lambda)_{ext}$=The external Fresnel reflectance from the external side of the hair (air-hair)
$F(\lambda)_{int}$=The internal Fresnel reflectance between the internal medium of the hair and the boundary (hair boundary to hair internal medium).

Once $R(\lambda)$ is approximated by the Saunderson correction formula, it can be inserted into the Kubelka Munk formula.

Extraction of Optical Properties Among Natural Hair:

The reflectance curve of natural hair is dictated mostly by the different ingredients that it is comprised of. Each ingredient contributes its own absorption and scattering curves in relation to its concentration. Once an illumination spectrum and a reflectance curve are given, the translation to color coordinates is trivial by using standard formulas such as the CIE's.

The optical properties of the ingredients can be calculated by analyzing spectra of different hair samples, and sampling the natural hair space. The amount of ingredients can be chosen arbitrarily during analysis, as long as the number of equations to is not lower than the number of variables. There are possibly many different ingredients in natural hair, however only some of these significantly influence absorption and scattering. Therefore, a decision regarding the maximum allowed error size in the optimization process serves to choose the number of ingredients in hair. The lower the number of ingredients the higher is the calculation error and vice versa.

It was found that a choice of three different ingredients introduces fittings to measurements with low difference errors. These components are strongly correlated to known natural components of hair: Keratin, Eumelanin and Pheomelanin. The Keratin is what the sheath of the hair is made of as well as internal fibers inside the sheath. The Eumelanin and Pheomelanin are two types of Melanin colorant that provide a general class of natural pigments.

Eumelanin is a dark brown pigment which is the most common pigment in most hair, while Pheomelanin is generally present in modest concentrations and contributes to the reddish-yellow tint.

Model for Hair Coloration:

The extraction of absorption and scattering curves among the different hair ingredients requires setting an arbitrary positive non-zero constant value for one of the curves of one of the ingredients for all wavelengths, in order to achieve a set of non-homogeneous equations with a finite set of solutions. For example, one may choose the Keratin's scattering curve to be 1 for all wavelengths.

The process of hair coloration concerns the insertion of dye colorants into hair on the one hand and the reduction of initial Melanin on the other hand. An experiment wherein different natural hair samples were exposed to the chemicals of the dyes, but in the absence of colorants themselves, revealed spectra that spanned beyond the space of natural hairs Thus using extended spectra may reveal additional information about colorants. An approach based on emergence of one additional colorant, with concentration proportionally increasing with the reduction of the Eumelanin concentration was proven to be robust and reliable.

The process of hair coloration is primarily dominated by the concentrations of the colorants, temperature, concentration of the oxidizing agent (e.g., Hydrogen Peroxide), and the percentage of Ammonia, or other alkalizing agent, which dictates the pH level of the solution. These magnitudes strongly influence the rate of reactions during hair coloration.

The reduction of Melanin during exposure to hair dyes is dependent upon its initial concentration, the percentage of the alkalizing agent, percentage of the oxidizing agent, temperature, solution viscosity, hair porosity and exposure duration. A functional relation is characterized empirically from experiments as follows:

$$C_f = f_{KineticsMelanin}(C_i, C_A, C_H, T, t, v, p)$$

where:

$f_{KineticsMelanin}$ = kinetics function of melanin
$C_i$ = initial Melanin's concentration
$C_f$ = final Melanin's concentration
$C_A$ = Concentration of alkalize agent in the solution (e.g., ammonia).
$C_H$ = Concentration of oxidizing agent (e.g., hydrogen peroxide).
T = Temperature
t = duration (exposure time to treatment)
v = viscosity of solution
p = porosity of hair The function $f_{KineticsMelanin}$ monotonically increases with the increase of temperature (T), concentration of alkaline ($C_A$), concentration of oxidizing agent ($C_H$), duration (t) and porosity of hair (p). The function monotonically decreases with increase of viscosity (v).

The coefficients of the function are optimized to exhibit best fit results between predictions of spectrums and measurements of spectrums over known different values of parameters.

Different Kinetics Functions Apply to Eumelanin and Pheomelanin.

Alternatively, no analytical function is introduced, but instead, an empirical grid of measurements set provided with a plurality of different values over all dimensions. The prediction of $C_f$ is then estimated by means of KNN (averaging k nearest neighbors on grid) or standard interpolations.

Summarizing the abovementioned arguments into a mathematical formulation we get, for a given natural hair spectra:

$$\left(\frac{K}{S}\right)_{Meas,i} \equiv \frac{(1-R_i)^2}{2 \cdot R_i} = \frac{K_{ker} + C_{Eu,i} \cdot K_{Eu} + C_{Pheo,i} \cdot K_{Pheo}}{1 + C_{Eu,i} \cdot S_{Eu} + C_{Pheo,i} \cdot S_{Pheo}}$$

Where Ri stands for the initial reflectance after correction by Saunderson's formula.

For example:

After dyeing with specific hair dyes recipe of N dyes the final spectra can be predicted as follows:

$$\left(\frac{K}{S}\right)_{Pred} = \frac{K_{ker} + C_{Eu,f} \cdot K_{Eu} + C_{Pheo,f} \cdot K_{Pheo} + (C_{Eu,i} - C_{Eu,f}) \cdot K_{Adder} + \sum_{n=1}^{N} C_n \cdot K(\lambda)_n}{1 + C_{Eu,f} \cdot S_{Eu} + C_{Pheo,f} \cdot S_{Pheo} + (C_{Eu,i} - C_{Eu,f}) \cdot S_{Adder} + \sum_{n=i}^{N} C_n \cdot S(\lambda)_n}$$

Then, a first spectral prediction is calculated by the Kubelka Munk equation:

$$r_{Pred} = 1 + \left(\frac{K}{S}\right)_{Pred} - \sqrt{\left(\frac{K}{S}\right)_{Pred}^2 + 2*\left(\frac{K}{S}\right)_{Pred}}$$

And the final fitting of a hair spectrum is available by considering the optimized Saunderson coefficients, $\alpha$, $F_{ext}$ and $F_{int}$ for the final spectra:

$$R_{Fitting} = \alpha + \frac{(1 - F_{ext}) \cdot (1 - F_{int}) \cdot r_{Pred}}{1 - F_{int} \cdot r_{Pred}}$$

The magnitudes of the kinetics coefficients $\alpha_1, \alpha_2, \alpha_3, \alpha_4$ and the colorants absorption curves: $K_1, K_2, K_3 \ldots K_N$ and scattering $S_1, S_2, \ldots S_N$ are optimized by processing multiple hair measurements, before and after coloration with known recipes and with appropriate statistical sampling. The optimization seeks to minimize the sum of the spectral squared differences.

Once a reflectance spectra is measured or predicted it may be translated into color coordinates under a chosen desired environmental radiance spectrum. The translation follows the standard CIE color space. The translation of spectra into color coordinates is familiar to those who deal with the art of spectral measurements and to colors.

The distance between the color coordinates of the object and the target may be given by a vector distance:

$$\text{Color distance} \equiv dE = \sqrt{(X_{object} - X_{target})^2 + (Y_{object} - Y_{target})^2 + (Z_{object} - Z_{target})^2}$$

Reference is now made to FIG. 19 which is a simplified graph illustrating the kinetics of Eumelanin's concentration vs. alkalizing agent (e.g., ammonia) rate. Duration, oxidizing agent and temperature were kept constant.

Reference is now made to FIG. 20 which is a simplified graph showing the kinetics of Eumelanin concentration vs. oxidizing agent (e.g., Hydrogen Peroxide) rate. Alkalizing agent (e.g., Ammonia) rate, duration and temperature were kept constant.

Reference is now made to FIG. 21 which is a simplified graph showing kinetics of Eumelanin concentration vs. Exposure duration. Alkalizing agent (e.g., Ammonia) rate, oxidizing agent (e.g., Hydrogen peroxide) rate and temperature were kept constant.

Reference is now made to FIG. 22 which is a simplified graph in which the green curve was best fitted to the measurement of natural hair spectra by optimizing the Eumelanin concentration and Pheomelanin concentration in the Kubelka Munk formula and Saunderson's coefficients.

Reference is here made to FIG. 23 which is a simplified graph in which the green curve is the fitting curve calculated by Kubelka Munk and Saunderson formulas for coloring natural hair with a known dye recipe which seeks to fit the curve of the measurement in the red.

Reference is now made to FIG. 24 which is a simplified graph illustrating the distribution of spectral squared differences after optimization. The optimization process seeks to minimize the sum of the squared spectral difference between predictions to measurements by optimizing models coefficients.

Reference is now made to FIG. 25 which is a simplified graph which shows optimizing coefficients for a model so as to minimize the overall sum of spectral squared differences among a measured set of 666 hair samples. A statistical distribution of the color difference is then calculated.

An algorithm for predicting coloration of initially colored hair requires a measurement to be taken of the initially colored hair. In a first alternative, estimation of colorants is made using an IR signal.

The signal in the IR range at around 950 nm is sensitive to the existence of Melanin and very indifferent to colorants. Therefore, the concentration of natural hair ingredients can be extracted by analyzing the signal in the IR region.

In initially colored hair the components inside are natural hair ingredients and unknown colorants with unknown concentrations. Therefore, an approximation is made to estimate the initial concentrations of each natural hair ingredient according to the IR region and to assign residue absorption or residue scattering to the colorants in hair In the first stage an estimation of N natural hair ingredients are extracted by best fitting (in least squares optimization) the concentration of each ingredient to the measurement at the IR:

$$\left(\frac{K}{S}\right)_{Opt} \equiv \frac{\sum_{n=1}^{N} C_{n,i} \cdot K_n}{\sum_{n=1}^{N} C_{n,i} \cdot S_n} \cong \left(\frac{K}{S}\right)_{Meas} \equiv \frac{(1-r)^2}{2 \cdot r}$$

Then the residues are defined as follows for the entire region of the spectra:

$$\left(\frac{K}{S}\right)_{Meas} \equiv \frac{(1-r)^2}{2 \cdot r} = \begin{cases} \frac{\sum_{n=1}^{N} C_{n,i} \cdot K_n + K_{Res}}{\sum_{n=1}^{N} C_{n,i} \cdot S_n}, & \left(\frac{K}{S}\right)_{Opt} - \left(\frac{K}{S}\right)_{Meas} < 0 \\ \frac{\sum_{n=1}^{N} C_{n,i} \cdot K_n}{\sum_{n=1}^{N} C_{n,i} \cdot S_n + S_{Res}}, & \left(\frac{K}{S}\right)_{Opt} - \left(\frac{K}{S}\right)_{Meas} \geq 0 \end{cases}$$

The magnitude relates to the reflectance after Saunderson's correction and the calculations are processed per each wavelengths increment separately.

The prediction of the final spectra for the initially colored hair, with respect to recipe of N dyes is then formulated as follows:

$$\left(\frac{K}{S}\right)_{Pred} = \frac{\sum_{n=1}^{N} C_{n,f} \cdot K_n + f \cdot K_{Res} + \sum_{n=1}^{N} C_n \cdot K(\lambda)_n}{\sum_{n=1}^{N} C_{n,f} \cdot K_n + f \cdot S_{Res} + \sum_{n=1}^{N} C_n \cdot S(\lambda)_n}$$

Where f stands for a scalar from 0 to 1.

The relation between concentration of natural hair's ingredients final concentrations to initial concentrations is given by the kinetics formula.

As in the case of natural hair, the magnitudes of the residue coefficient f, the to kinetics coefficients and the colorants curves of absorption: $K_1, K_2, \ldots, K_N$ and scattering $S_1, S_2, \ldots, S_N$ are optimized by processing multiple hair measurements, before and after colorations with known recipes.

Reference is now made to FIG. 26, which is a simplified graph illustrating optimization of a model's coefficients for initially colored hair so as to minimize the overall sum of spectral squared differences among a set of 666 measured hair samples. Thereafter, a statistical distribution of the color difference can be calculated.

Reference is now made to FIG. 27, which is a simplified graph showing the kinetics of Eumelanin concentration against ammonia, for fixed hydrogen peroxide and duration.

Reference is now made to FIG. 28, which is a simplified graph showing the kinetics of Eumelanin final concentration vs Ammonia concentration % in the case of a model for initially colored hair Duration and hydrogen peroxide concentration were kept constant.

Reference is now made to FIG. 29, which is a simplified graph showing the kinetics of Eumelanin concentration vs. hydrogen peroxide concentration Ammonia concentration and durations were kept constant.

Reference is now made to FIG. 30, which is a simplified graph showing the kinetics of Eumelanin concentration vs. duration Ammonia and Hydrogen Peroxide concentrations were kept constant.

Reference is now made to FIG. 31 which is a simplified flow chart showing a process for obtaining the natural hair coloring factors and for obtaining ingredients and factors relating to ingredients for products generally used in the hair treatment recipes.

Obtaining a Model for Coloring Natural Hair:

In the above, it has been assumed that factors are known about substances in the recipes and that natural and other hair factors can be derived from the measured hair spectrum. The following is a summary of a system for coloring natural hair according to the above-discussed algorithms that provides the data required by the algorithms.

1. Natural Hair Ingredients:

In stage S6, the process analyzes the spectra of a plurality of natural hairs that span all the space of natural hairs of all colors as per FIG. 13.

a. Number of ingredients. Find how many ingredients are required for best fitting the spectra of the measurements under the assumptions of Kubelka munk and the Saunderson correction—the value of M. Values are then initialized in stage S7. In stage S8, values of K and M are optimized for all M ingredients.

In stage S9 optimizations are carried out for each spectrum. In stage S10 a fitting quality is determined which is compared with a threshold in stage S11. Solutions are saved in stage S12.

b. Save coefficients of Kubelka Munk. This stage keeps the coefficients of K (absorption) and S (scattering) per each ingredient.

2. Melanin Kinetics:

a. Experiment. Prepare an experiment wherein multiple natural hairs that span all the space of natural hairs of all colors are exposed to the materials in the dyes but without the colorants themselves. The treatment includes different durations, temperatures, concentrations of the alkalizing agent, viscosities, and concentrations of the oxidizing agent. Measure all the spectra of all hair in the experiment both before treatment and after treatment.

b. Define new ingredients that appear as bleaching byproducts. Analyze the data in order to extract the emergence of new ingredients within bleached hair and calculate their K (absorption) and S (scattering) as well as their concentrations among the bleached hairs.

c. Extract kinetics functions. Analyze data in order to define the functions that relate the final concentration of each ingredient to its initial concentration, with respect to parameters such as temperature, viscosity, pH level, duration, hair diameter, hair cuticle condition, and concentration of oxidizing agent. The functions may be purely empirical, or may obey diffusion and reaction rate formulae, with appropriate optimized coefficients.

3. Dye Kinetics and Optical Properties:

a. Experiment. Prepare an experiment wherein multiple natural hairs that span all the space of natural hair of all colors are colored with all dyes and their mixtures. Hair dye can include two kinds of coloring agents. One of them is a direct dye that already carries color and migrates as is into hair, while the other agents are different dye precursors and dye couplers that migrate into hair and then chemically interact, with the mediation of oxidizing agents and alkalizing agents, to produce colorant molecules in hair. The treatment includes different dye concentrations, viscosities, durations, temperatures, concentrations of alkalizing agents, and concentrations of oxidizing agents.

Measure all the spectrums of hairs before treatment and after treatment.

b. Define optical properties of colorants. Extract the optical properties of the colorants in terms of their k and s values. Take care to include all possible combinations that can be produced during development of the colorants.

c. Extract kinetics functions. Analyze data in order to define the functions that relate the final concentration of each colorant to its initial concentration, or the concentrations, and reactivity of the different dye precursors and dye couplers that were combined to introduce it into the solution, with respect to parameters such as temperature, viscosity of solution, concentration of alkalizing agent, duration, hair diameter, hair cuticle condition, and concentration of oxidizing agent:

$$C_{colorant_n} = f_n(C_i, C_A, C_p, T, t, v, p)$$

$$C_{colorant\_m} = f_m(C_A, C_p, T, t, v, p, C_{pr\_1}, \ldots, C_{pr\_i}, C_{coupler\_j}, \ldots, C_{coupler\_j})$$

Where:

$f_n(C_i, C_A, C_p, T, t, v, p)$=kinetics function for the n-th "direct" colorant $f_m(C_A, C_p, T, t, v, p, C_{r1}, \ldots, C_{rm})$=kinetics function of the m-th colorant $C_i$=initial "direct" colorant concentration $C_{colorant_n}$=final "direct" colorant concentration.

$C_{colorant\_m}$=final colorant concentration, product of reactants interaction.

$C_{pr\_1}, \ldots, C_{pr\_i}$=concentrations of dye precursors $C_{coupler\_v}, \ldots, C_{coupler\_j}$=concentrations of j dye couplers $C_A$=Concentration of alkalize agent in the solution (e.g., ammonia).

$C_H$=Concentration of oxidizing agent (e.g., hydrogen peroxide).

T=Temperature t=duration (exposure time to treatment)

v=viscosity of solution p=porosity of hair.

The functions may be purely empirical, or might obey reaction and diffusion rate formulae, with appropriate optimized coefficients.

Alternatively to that, no analytical function is introduced, but instead, an empirical grid of measurements set is provided for a plurality of different values over all dimensions. The prediction of $C_{colorant_n}$ and $C_{colorant\_m}$ are then estimated by manner of KNN (averaging k nearest neighbors on grid) or standard interpolations.

II. Optical Reader

According to an aspect of some embodiments of the present invention there is provided an optical reader which measures sufficient characteristics of keratinous fibers to make a realistic prediction of the outcome of a treatment operation of keratinous fibers, as defined herein (e.g., coloring of keratinous fibers such as hair).

Referring now to the drawings, FIG. 32A illustrates a device 10 for optical measurement of keratinous fibers (e.g., hair), comprising an illumination unit 12 for illuminating hair 14.

A measuring unit 16 (not shown in FIG. 32A includes an optical collection system for optically measuring the hair during illumination by the illumination unit. The optical collection system and a beam from the illumination unit respectively subtend a light diffusion angle of between 45 degrees and 135 degrees at the hair being measured and thus ensure that the sensor principally measures light that is diffused or scattered by the hair, as opposed to direct reflection from the outer side of the cubicula or from the cuticula-cortex interface (a Fresnel reflection). Alternatively phrased, illumination beam is incident on the hair, and a resulting beam of diffused light is collected at an angle of 45 to 135 with respect to the illumination beam.

In FIG. 32A the illumination unit is positioned to illuminate said hair from an elevation from the azimuth and the sensor is positioned perpendicularly to said hair. The illumination unit may include multiple illumination sources respectively configured to illuminate said hair from a plurality of substantially azimuthal angles around the hair In FIG. 32B the opposite configuration is used and the measuring unit to comprises a plurality of sensors located around the hair at an elevation from the azimuth. The illumination unit is positioned perpendicularly to the plane of the hair. In both of the above configurations, multiple illumination angles as well as collection angles may be used a third configuration might also be beneficial, in which neither illumination nor collection is perpendicular to the hair such a configuration is used at e.g. 135 deg.

Another possible geometry is illumination and collection from the same direction, e.g. approximately perpendicular to the hair, by using an optical beam-splitter (e.g. 50:50) or a polarizing beam-splitter. In the later possibility, the specular component of the reflection is also removed by choosing cross-polarization configuration.

The illumination unit may include two substantially opposing illumination directions facing each other along a hair axis. A measurement is made for each direction and the measurement-results difference provides an indication of the condition of the hair cuticula, as will be described in greater detail below.

The illumination unit may use light sources which are actually or substantially parallel to the hair axis, albeit from respectively different azimuthal angles around the hair The illumination sources may illuminate the hair at different times. Temporal windowing at the sensor allows illumination from the different sources to be measured separately. Alternatively, the illumination sources may illuminate different regions of the inspected hair. Spatially resolving at the sensor allows illumination from the different sources to be measured separately.

The illumination unit may include a main, wideband illumination source and subsidiary illumination sources. Processing electronics may use differential illumination results by comparing different sources in order to obtain particular kinds of information such as an angle of a hair relative to any illumination source.

The processing electronics may then use the hair angle to correct a hair spectrum for the different illumination angle.

The processing electronics may additionally use differential illumination results to distinguish between specular and diffused reflected light from the hair, each of which gives different information about the hair.

The main illumination source may be used for spectroscopy and the subsidiary illumination sources may be used either for spectroscopy or for angular measurement.

There may be four illumination sources, each at the same elevation angle relative to a plane perpendicular to the detection axis, as will be discussed in greater detail below. In an example, the azimuth angle with respect to a hair axis is 30° for two of the four illumination sources and 150° for a third and a fourth of the illumination sources.

The sensor may detect the visible, near-ultraviolet, ultraviolet, near infrared and infrared parts of the electromagnetic spectrum. As explained, an overall spectrum that covers the visible, the infrared and near infrared parts of the spectrum contain information that allows the melanin-based hair factors to be distinguished. For very dark hair the vast majority of the data required to calculate the melanin concentration is in the NIR & IR. The visible part of the spectrum by contrast enables to define the hair color in any color space such as lab or others, but does not allow calculation of the melanin concentration.

Typical ranges of sensitivity are the 350-1500 nm wavelength range, or the 350-750 nm wavelength range, or the 400-950 nm wavelength range.

As discussed in greater detail below, the sensor may include one or more calibration regions which receive calibration light straight from the optics which has not been reflected by the hair. The calibration light allows the sensor to be calibrated.

A polarizing element, for example a controllable polarizing element, may be inserted at various locations in the optical system.

As discussed below, hair grips may be provided to hold hair in position for measurement.

In use the optical device may apply an illumination source to the hair, then optically measure illumination from a diffusion angle which typically lies between 45 degrees and 135 degrees. The use of the angle is to obtain a measurement whose principle components are light that has been diffused or scattered by the hair, as opposed to direct reflection.

The optical reader is a tool, optionally hand-held, that measures optical characteristics of the hair (or any keratinous fibers). The calculation of hair properties may be made outside the optical reader, for example on the computational unit. The parameters may be used to plan a hair dyeing procedure or any other treatment operation to of keratinous fibers (e.g., coloring, bleaching) and estimate the actual hair color after the operation.

Various optical data may be measured, such as the absorbance spectrum, a specular reflectance spectrum, or a spectrum of light diffused or scattered by the hair or combinations thereof. Also polarization characteristics, or fluorescence characteristics may be measured.

Calculated hair properties may include hair color in the visible range, and relative amounts of melanine in the hair, relative amounts of Eumelanin, relative amounts of Pheomelanin and relatives amount of both Eumelanin and Pheomelanin together, as well as relative amount of hair dyes in the hair, including total dye amounts and amounts of specific dye components.

Other calculations may relate to the relative amount of water in the hair; and a relative extent of features of the hair which affect dyeing kinetics, such as cuticula condition (degree of opening), hair radius, etc. as will be explained in greater detail below.

The optical reader is designed to measure any hair and any hair substitute, where hair and its substitutes can be human hair (natural or dyed), animal hair (natural or dyed), any kind of hair substitute or artificial hair, including wig hair, Creatinine fibers, hair for costumes, etc; and hair made for hair catalogues.

The hair is not limited to head hair or its substitutes but to hair from any part of the body and its substitutes Opto-Mechanical Illumination:

As discussed in respect of FIG. 32A above, the optical reader comprises two modules, an illumination module and a detection module, (among other modules such as calculation, communication etc).

Illumination Module:

An exemplary illumination module contains four LEDs at the following wavelength range:
I: Monochromatic or narrow band 400 (390-410 nm)
II: white or visible (430-750 nm)
III: Monochromatic or narrow band 850 (820-880 nm)
IV: Monochromatic or narrow band 950 (920-980 nm)

The embodiment may use different LEDs or other light sources that illuminate at different wavelength bands.

A variant may use fewer LEDs or more LEDs, for example a further LED that illuminates in the 750-820 nm band may be provided to fill the gap between the $2^{nd}$ and $3^{rd}$ LEDs in the list above.

The LED illumination may be carried out other than simultaneously. Illuminating for spectroscopy purpose may use an illumination intensity level range which is smaller than 1:2 (the ratio between maximum and minimum illumination levels) in order not to get a mixture of different wavelengths in one measured hair area.

The following illumination schedules can be used:
Each LED illuminates at a different time.
The first 2 LEDs (I, II) illuminate at one time and the others (III, IV) at a following time.

The illumination schedules may be used to construct duty cycles for the LEDs.

The LEDs may be mounted in a small package such as ACULED produced by Perkin Elmer. This package allows for a very small distance between the different LEDs, so that illumination impinging on the hair from each LED will be at almost the same angle given a Kohler-like illumination optics is used.

The illumination from the LEDs goes through a lens and may impinge on the hair at a typical angle of 45°. Note that other angles may be used as desired.

The illumination module may be designed to be directional. Specifically the light is directed azimuthally to be parallel to the hair. The idea of the directionality is in order to allow viewing only of the diffused light. Wide NA illumination or other azimuth angles are liable to mix specular and diffused light together.

Detection Module:

The detection module measures the light scattered from the hair (or any keratinous fiber). The intention is that the measurement should separate the effects of at least one of the following: diffused reflection from the fiber cortex, specular reflection of any kind, and absorption.

Reference is now made to FIG. 32C which is a simplified diagram illustrating one possible realization of an optical system suitable for detection. The illumination from the LEDs, which is scattered by the hair 100, passes through a cylindrical lens 110 and a narrow slit 120. After the slit, the light passes a small aperture, in the example a 3.2 mm diameter aperture, 130, and a further lens 140. Wavelength separation is carried out using grating 150.

The light from the grating 150 is deflected using a mirror 160, and collected using a three-lens collection optics 170 onto a sensor 180.

On the sensor, light from different wavelength falls on different columns, due to the effect of the grating 150, therefore obtaining a full spectrum.

Reference is now made to FIGS. 33A and 33B which are respectively schematic block diagrams which show in greater detail the illumination and light collection angles in relation to the hair that is being measured. The main axis of the optics is perpendicular to the hair and found in the same plane defined by the hair and by the illumination angle. The main illumination is a wide band illumination which illuminates the hair at an oblique elevation angle with narrow NA. The collection optics gathers the scattered illumination above the hair in order to create the spectral data.

The detector may for example be a two-dimensional CMOS/CCD sensor 180 with a resolution 1240*1080 such as Aptina MTM9001C125STM. The sensor may detect light over a range from 400 to 1000 nm or wider, thus observing the full illuminating spectrum.

In FIG. 33A the light collection is perpendicular to the hair, thus capturing scattered light. In FIG. 33B the light collection is at an oblique angle. FIG. 33C shows the illumination and light collection from above.

Use Wide Spectrum:

The optical reader creates a spectrum of the hair over a wide range of wavelengths, including the IR region, for example between 400 nm to 950 nm, but may be or even wider, such as between 380 nm and 1500 nm.

This spectrum may be achieved by using illumination sources such as:

A combination of one or more LEDs, as described for the illumination module;

A combination of several monochromatic lasers at wavelengths distributed over the range;

Flash lamps such as Xenon lamps;

Tunable lasers;

White lasers; or

Laser with non-linear elements that split the laser illumination into multiple wavelengths or widen the wavelength to a wide band spectrum One of the main data relevant for recommending a hair treatment (e.g., coloring) procedure is the relative amount of melanin in the hair. In the current embodiment, the relative amount of melanin in the hair is found by fitting the spectrum of the hair to the spectrum of melanin. For finding the relative amount of both types of melanin, a linear function of both spectrums is used in the fitting process.

As explained above, melanin has strong absorption in the visible wavelength. Therefore, it is hard to determine the relative amount thereof, especially in dark hairs, using only visible data. The IR spectrum is used to overcome this problem. In the fitting process, the spectrum in the IR region is used solely or with higher weight than the shorter wavelength part of the spectrum.

Another parameter for the hair treatment is the relative amount of hair dyes that remain from previous hair dyeing treatments or other procedures. The spectrum of the hair dye appears mainly in the visible region and is masked by the spectrum of the melanin. Therefore, as soon as the relative amount of melanin is known, one may subtract the melanin from the measured spectrum to reveal the spectrum of the hair dyes.

The spectrum following melanin subtraction can be used to estimate the relative amount of dyes in the hair and even relative amounts of each dye component.

The contribution of the IR range for calculating the relative amount of melanin begins at 750 nm and even at shorter wavelengths. Therefore, working embodiments may usefully use any spectral range as long as the approximate region of 750 nm is included.

Reference is now made to FIG. 36 which is a simplified graph showing two typical hair spectra as reflection percentages over the range of 350-1550 nm. The solid wide line represents a spectrum of initially light shade hair and the dashed thin line represents a spectrum of the hair after coloring and being a darker shade.

In the IR part of the range—the longer wavelengths—the spectrum of the colored hair—dashed line—shows more reflectance, meaning that the relative amount of melanin is lower. The low level of melanin is an effect of the dyeing procedure. The spectrum in the visible part of the range, which shows less reflective light, means that pigments are absorbed in the hair.

What FIG. 36 shows is that, looking over a wide wavelength region that includes the visible and near IR, provides an advantage in being able to detect relative amounts of both melanin and hair dye.

Looking further to the IR, near 1500 nm, the relative amount of water in the hair may be estimated, since water has a strong absorption near this wavelength.

The relative amount of water in the hair may affect the hair treatment process. For example, the dyeing kinetics in wet hair is different from that of dry hair Therefore it is further advantageous to observe the spectrum up to 1500 nm or even beyond.

The above has explained how to detect relative amounts of melanin, dye color, or water, from looking at a graph, and a curve fitting algorithm has also been mentioned. It will be understood that there are also other algorithms to allow for automated determination of such relative amounts from the spectra.

For example, the spectrum of known hair dyes may be also used in a curve fitting algorithm and the various possible algorithms may use the entire spectrum, specific points within the spectrum or even one point from the spectrum to generate their findings.

The optical reader is not limited to using only the visible and near IR wavelength ranges. Any optical range may be used, such as a combination of one or more of UV, visible, near IR, mid IR and Far IR.

Illumination:

The optical reader may contain multiple illumination sources located at different angles with respect to the hair (or other keratinous fibers to be treated). These sources may be used in order to improve the quality of the measured data by gathering more hair parameters in order to better estimate the dyeing kinetics which are used to plan a dyeing procedure. In addition the hair reader may provide an estimate of the angle between the to hair and the hair reader and correct the measured data using the estimated angle.

Referring again to FIG. 33A, and the main illumination is a wide band illumination which illuminates the hair at an oblique elevation angle with a limited NA. The collection optics gathers the scattered illumination above the hair in order to create the spectral data Finding Hair Cuticula:

Reference is now made to FIG. 33B which is a schematic diagram showing illumination of a hair from two opposite directions of oblique elevation and collection of light at a perpendicular from the hair on the side of the illumination. The first wide band illumination is from an oblique elevation angle as in FIG. 33A. Another illumination beam impinges on the hair at the opposite direction at the azimuth but at the same elevation angle. The scattered illumination from the second direction differs from that of the main illumination since the hair cuticula is not symmetric. The cuticula scatters the illumination from one direction differently from that in the opposite direction. The difference between the scattering intensity depends strongly on the opening degree of the cuticula. FIG. 35A shows a hair with a noticeable cuticula where a high scattering intensity is expected for illumination from the right hand side and low scattering intensity from the left hand side. In FIG. 35B by contrast the cuticula is smooth and scattering from the two sides would typically be the same.

Therefore, the difference between the amount of scattering measured from the main and opposite illumination directions can be used to estimate the opening degree of the cuticula. This opening degree affects the hair kinetics. As the cuticula is more open, the dye enters the hair more rapidly.

It is noted that the second light source may be at other angles and elevations, e.g. not at 180 degrees at azimuth to the main source and not at the same elevation angle. Any angle is satisfactory if the ratio between the scattering of the two sources can be used to estimate the opening of the cuticula.

Hair Radius:

Perpendicular illumination may be used to estimate the radius of the hair, which is also a relevant parameter for the dyeing kinetics.

As the radius of the hair increases, the illumination reflected from a perpendicular illumination source increases.

The angle of the radius measuring source does not have to be precisely at 90 degrees at azimuth to the main source and not at the same elevation angle. Any angle is satisfactory if the returned illumination can be used to estimate the hair radius.

Measuring Angle and Correcting:

The spectral data may have a strong dependency on the angle between the hair and the system optics, that is between the hair and the illumination and detection modules.

In the optical reader, most of the energy measured comes from scattering light from the hair body and surface rather than specular reflected light from the surface. The specular reflection has only a small effect on the relevant measured data (hair visual color, relative amount of melanin, etc.).

Using a different illumination angle (either in elevation or azimuth) may result in more specular reflected light that enters the spectral data.

Reference is now made to FIG. 37, which is a simplified graph that illustrates reflectance powers measured from blond hair at different measurement angles. Three different graphs are shown, solid line for the 400-700 nm wavelength interval, dashed for the 700-900 nm wavelength interval and dotted for the full 400-900 nm wavelength interval. As would be expected, 90 and 270 degrees, the perpendicular directions give maximum reflections, and 0 and 180 degrees, the parallel directions, give minimum reflections.

An embodiment uses multiple light sources at different angles relative to the system optics in order to measure the hair angle and to correct the spectral data therefrom.

Reference is now made to FIG. 34A, which is a simplified side view of a hair reader 400 according to an embodiment of the present invention. FIG. 34B is a view from above of the same.

Collection optics 402 are located perpendicularly to the hair 404. Four light sources, preferably LEDs (A, B, C and D) illuminate the hair in azimuth angle of (30°, 150°, 210° and 330° relative to the hair axis). These sources illuminate one at a time in order to allow separation of their signals at the sensor.

In the nominal case with the hair positioned correctly with respect to the optics, the light collected from each illumination source should be equal, except for the cuticula to effect, which is measured using opposite illumination.

If the hair has a wrong azimuth angle the returned light from source A is different from B, and the returned light from source C is different from D. Furthermore, if the hair has a wrong elevation angle the returned light from source A is different from C, and the returned light from source B is different from D. Nevertheless, using calibrated data, the hair angle may be estimated from the ratio of the four sources. As long as the angle is reasonable the spectral data may be corrected.

If the angle is too large, the operator may be informed about an error in the measurement and may be given the opportunity to rearrange the reader or the hair.

One way of correcting the data may involve using calibrated data. Calibrated data may contain a spectral change relating to different illumination and azimuth angles. The data may consist of full spectrums at different angles or coefficients for linear, parabolic, polynomial or other estimated functions.

The calibrated data may be for a nominal hair or for each hair type or hair color as far as can be learnt from the uncorrected data.

FIG. 34A illustrated four illumination sources. However instead of using four illumination sources, fewer sources may be used.

In an embodiment, three sources A, B and C, are used, and full functionality is nevertheless retained, since all the changes relating to azimuth and elevation angle still affect the sources in pairs.

One or more of the sources may be the sources used for measuring the cuticula or hair radius.

Only two sources need be used for estimating only the azimuth (for example A and B) or only the elevation (for example A and C).

In another embodiment, instead of multiple light sources, the hair angle may be measured using one illumination source and multiple light detectors. Such an embodiment has the advantage of not requiring light toggling.

A further embodiment uses a single sensor that angularly resolves the collected light.

A further embodiment involves a combination of multiple sources and multiple detectors.

The light sources may be at other azimuth angles than described. The elevation angle is not constrained or fixed but may vary for each source or group of sources.

In a further embodiment, instead of using four or fewer illumination sources as discussed above, more sources may be used. Using more sources provides the advantage of using a more accurate angle estimation.

Illumination Sources:

The illumination sources may be activated in a time-sequential order where each source illuminates the hair at a different time. Thus, the scattered light for each source is easy separated by collecting the reflected light of each source at a specific time gate.

In one embodiment the time difference between activating each source is about 1/10 sec, since that coincides with the actual frame rate of the sensor. Therefore, if a set of nine LEDs are used there is about 1 measurement per second. In one embodiment there is a main illumination which contains 4 LEDs, one opposite illumination which is a single LED and the four surrounding LEDs A'-D' making a set of nine.

The opposite illumination and the four surrounding LEDs may in practice be any kind of illumination, LED, group of LEDs, lasers, lamps including flash lamps, etc.

The illumination sources may be narrow band to give only total energy data or may be wide band to gives full or partial spectral data.

Preferred Flow:

The sensor may obtain plenty of images in a short time, and thus multiple measurements can be made. The user may scan the hair using the hair reader and to obtain data for multiple points along the hair A two-dimensional sensor may also enable in-situ calibration using two side areas with specific calibration targets, to cover two dynamic ranges. The same may alternatively be achieved with a 1d sensor, for example by electro-mechanical or electro-optical toggling.

Thus, a hair may be scanned from the hair root up to the hair edge. The hair characteristics, and therefore, the required dyeing procedure and/or the resulted color can be calculated for different portions on the hair, which may have different characteristics.

For each scanning point, the LEDs illuminate according to a predetermined to sequence. The sequence may be for example:

400 nm LED (of ACULED)
Warm white LED (of ACULED)
850 nm LED (of ACULED)
950 nm LED (of ACULED)
Opposite direction LED (optional)
Perpendicular direction LED
LED A
LED B
LED C
LED D When each LED illuminates, the relevant part of the sensor, depending on the wavelength, is sampled by the hair reader electronics.

The data from each LED may be analyzed in real time. If the real time analysis detects improper read data from a given LED (for example too low or too high a reading), the illumination from that LED may be repeated.

Data from one scanning point may be used to analyze a previous or next point. For example, the signal from the opposite direction LED or from LEDs A-D may be averaged from multiple points to get more accurate data.

Mechanical Design:

Reference is now made to FIG. 38, which is a simplified schematic diagram illustrating mechanical design features of an embodiment of a hair reader according to the present invention.

Mechanical features may be designed into the hair reader to obtain better spectroscopy signals from the hair. The optical reader 300 contains two grippers 190 near an optics window 188. The grippers direct hair to be parallel to the illumination, thus improving the signal.

Instead of the grippers any element that directs the hair in the right direction may be used, such as a comb like element.

The grippers may also be slanted toward the center or curled to better hold the hair The optics window 310 may be perpendicular to the hair scanning direction, to therefore allowing averaging of readings from multiple hair fibers.

Source Calibration:

To get an accurate spectrum of the hair, the illumination spectrum may be calibrated. The actual spectral measure is that which is detected by the detector divided by the calibrated data in each wavelength after various offset signals subtraction and nonlinear correction have been applied.

However, the spectrum of the illuminated data need not be fixed. Temperature changes, small mechanical movement, intensity changes of LEDs in time and other reasons may affect the output spectrum.

The optical reader may thus support online calibration of the spectroscopy detector.

Referring now to FIG. 39A, while part of the detector obtains illumination from the hair, part of the detector obtains a signal from the illumination module following the grating without being reflected from the hair. The signal directly from the illumination module and the grating may be used for online calibration. such a signal may be reflected from the in-situ targets.

The calibration may be achieved by taking a single row from the calibrated area, or by averaging some or all rows in the calibration area. Other known statistical methods such as median or average without outliers may be used also.

The calibrated data may be averaged over time, i.e. determining the calibration of the sensor by using calibration measurements at different times.

The calibration area may be constructed from a single part of the sensor or from regions, as shown in FIG. 39A, calibration area 1 and calibration area 2. More than two regions can also be defined.

The illumination can be sampled from any part in the illumination mode between the grating and the hair. The sampling can be carried out by a weak splitter, such as 95/5% where the 5% is passed to the calibration area.

The calibration can be made each specific time or even for every spectrum measurement.

Polarization:

The illumination and detection modules may use polarized light in order to increase signal to noise ratio and in order to improve the detection of relative amounts of material in the hair, including melanin, eumelanin, pheomelanin, hair dyes, water, etc.

The illumination module may illuminate the hair at one or more of the following polarizations:

Polarization parallel to the hair axis.
Polarization perpendicular to the hair axis.
Linear polarization at any angle to the hair axis.

Circular polarization

Any elliptical polarization

The optical reader may allow for switching of the polarization of the illumination module by means of mechanical/optical or electronic switching. The change can be determined automatically or manually. For example there may be different polarizations which give better results for specific hair colors.

The detection module may detect reflected light by filtering or passing any of the polarizations defined for the illumination module.

Switching of the polarization may be carried out at the illumination module or at the sensor.

Referring now to FIG. 39B, and one polarization method is to illuminate the hair in a given polarization and to pass the same polarization at the detection module.

Referring now to FIG. 39C, another method is to illuminate the hair in a given polarization and to pass the orthogonal polarization at the detection module. In either case, the polarization can be controlled by any element that changes the polarization: polarizer, wave plates (including $\lambda/2$ and $\lambda/4$), polarizer rotating prisms, and non-linear elements, and other.

The polarizing element in the illumination module can be placed anywhere between the illumination source and the hair. The polarizing element may even be a part of the illumination source itself (for example, by using a polarized source).

The polarizing element in the detection module can likewise be placed anywhere between the hair and the sensor. It may even be a part of the sensor detector.

The polarizer may have same or different polarizing effect on different wavelengths.

The polarization of the illumination and/or detection module may be changed while scanning the hair One example is getting spectroscopy using two orthogonal polarizations, which may be advantageous when estimation relative amounts of material in the hair The polarization may be determined for a single illumination source, all the illumination sources or any part of them.

If more than one detector exists, the polarization may be determined for a single detector, all the detectors or any part of them.

External Light Suppression:

Another problem that may affect the measurement is getting a signal from external light that impinges on the hair and reaches the spectroscopy detector.

Since external light is not directed, unlike the light of the illumination source, and irrespective of whether directed or not, unwanted signals from the hair due to the external light may reach the detector.

One solution is to take one or more spectrum measurements without using the hair reader illumination sources. The spectrum thus obtained may then be subtracted from the measured spectrum when the internal illumination source is used.

External light suppression measurements may be performed, at the beginning of the hair scanning, at the end, or even during scanning, after any or all illumination pulses.

III. The Solid Formulation:

Solid formulations, suitable for use in the treatment of keratinous fibers are disclosed herein. According to some embodiments of the present invention, the solid formulations have a form of tablets comprising a superdisintegrating agent, which imparts advantageous features to the tablet.

The solid formulations disclosed herein may further comprise color imparting agents (such as dye precursors, dye couplers and direct dyes), and can be used in combination with, or can further comprise, other agents for treating keratinous fibers, such as alkalizing agents and oxidizing agents.

In some embodiments, the solid formulations disclosed herein provide a group to of basic shades in a form of rapidly-disintegrating tablets. Thus, basic shades are individually formulated as tablets, forming the palette of colors at the disposal of the end user, which can be variously combined so as to achieve nearly infinite possibilities of colors and hues.

Solid formulations in a form of tablets are easily and accurately measurable (e.g., by counting) and therefore a desired end color formula can be reproducibly prepared by mixing specific amounts of appropriate basic shade tablets with suitable media, optionally supplemented with alkalizing and/or oxidizing agents and/or other agents useful in coloring keratinous fibers. In some embodiments, part or all other active agents used in the coloring processes (such as alkalizing agents, bleaching agents, oxidizing agents and thickening agents) are provided in the same form of rapidly disintegrating tablets.

The type(s) of color imparting agents comprised in the basic shades and of suitable media and/or active agents to be combined therewith depend upon the type of treatment sought.

For example, for permanent coloring, wherein the color imparting agents penetrate the fiber to its cortex, the basic shade tablets comprise predominantly, but not exclusively, dye precursors and suitable couplers, if necessary. The media suitable for permanent coloring generally comprise alkalizing and oxidizing agents, which can be provided in separate media and/or in separate tablets and/or within at least part of the color imparting tablets used.

For temporary coloring, wherein the color imparting agents remain on the surface of the fiber, the basic shade tablet formulations comprise predominantly, but not exclusively, direct dyes whereby other active agents, such as oxidizing agents and alkalizing agents, are typically not used.

Semi-permanent and demi-permanent coloring correspond to intermediate situations wherein the basic shades may comprise all types of color imparting agents, part of which remain on the surface of the fiber, wherein the other part may penetrate to some extent the fiber cuticle (semi-permanent) or even the fiber cortex (demi-permanent). For semi-permanent coloring, the media generally comprise, if at all, low levels of alkalizing and oxidizing agents, which can be provided in separate media and/or in separate tablets and/or within at least part of color imparting tablets used.

For demi-permanent coloring, the media generally comprise an oxidizing agent in an amount lower than for permanent coloring and an alkalizing agent other than ammonia, both can be provided as separate media and/or in separate tablets and/or within at least part of the color-imparting tablets used.

Certain direct dyes, when used in conjunction with oxidative coloring processes, have sufficient fade-resistance to be used for non-temporary coloring in absence of precursors or couplers and therefore such direct dyes can be used alone, or in admixture with other direct dyes, in basic shade tablets as provided herewith.

The term "basic shade" refers to a color imparting agent or a combination of color imparting agents which provide a primary coloring hue that can be combined with one or more different "basic shades" or primary hues to form a desired end color. The "basic shades" can be considered as the elementary coloring constituents of a palette. The term "basic shade" is also used herein to refer to a set of tablets characterized by a particular color imparting agent or a combination of color imparting agents.

According to an aspect of some embodiments of the invention, there is provided a solid formulation suitable for use in the preparation of a composition for treating keratinous fibers, the formulation being in a form of a tablet, and comprising at least one superdisintegrant, and at least one active agent selected from the group consisting of a color imparting agent, an alkalizing agent, an oxidizing agent and a thickening agent.

In some embodiments, a composition for treating keratinous fibers is a coloring composition, suitable for use (or useful) in coloring keratinous fibers. Such compositions include both compositions that comprise a color imparting agent, as defined herein, and compositions that can be used in combination with a color imparting agent, such as, but not limited to, compositions that comprise any of the other active agents as described herein. For example, compositions comprising an alkalizing agent, which may facilitate introduction of a color imparting agent into a keratinous fiber, compositions comprising an oxidizing agent, which may react with dye intermediates to produce a dye, and compositions comprising a thickening agent, which provide a consistency that facilitates coloring by a color imparting agent, are considered herein to be compositions for treating keratinous fibers.

In some of these embodiments, the active agent comprises a color imparting agent.

The terms "color imparting agents", "color imparting compounds", "color imparting ingredients" and "coloring agents" are interchangeably used herein, and encompass any compound used to impart a color by introducing a colored substance (e.g., dye, pigment), including, but not limited to, oxidation dye precursors, oxidation dye couplers, direct dyes, and any combination thereof.

Solid formulations comprising color imparting agents may form tablets of basic shades, as described herein.

In some embodiments, the solid formulation comprises, optionally in addition to the color imparting agent, any of the other abovementioned active agents. Each of these active agents may be suitable for inclusion in a coloring composition, when combined with a color imparting agent either within the same solid formulation, in a different solid formulation or in any other separate form (e.g., liquid medium such as an aqueous solution).

In some embodiments, at least one color imparting agent is present as an active agent in a solid formulation as described herein, for example, in order to form a color imparted by a coloring composition.

In some embodiments, at least one alkalizing agent is present as an active agent in a solid formulation as described herein, for example, in order to cause keratinous fibers to swell, thereby facilitating penetration of a color imparting agent into the fibers.

In some embodiments, at least one oxidizing agent is present as an active agent in a solid formulation as described herein, for example, in order to oxidize dye precursors in a coloring composition, and/or in order to bleach a color in keratinous fibers (e.g., natural pigmentation).

In some embodiments, at least one thickening agent is present as an active agent in a solid formulation as described herein, for example, in order to obtain a coloring composition consistency which is highly suitable for being applied to and remaining in contact with a surface to be colored (e.g., a relatively high viscosity) with little to no running, dripping, etc.

In some embodiments, a tablet form of solid formulations is formed from a powder and/or granules, for example, by compression of powder and/or granules. Tablets forms may have various porosities and cohesiveness that ultimately impact their disintegration rate (e.g., upon contact with a liquid).

The solid formulation in a tablet form is also referred to herein throughout, interchangeably, as "tablet formulation", "solid formulation" and simply as "tablet".

In some embodiments, a maximal width of a tablet is in a range of from 2 mm to 10 mm. In some embodiments, a maximal width of a tablet is in a range of from 3 mm to 7 mm. In some embodiments, a maximal width of a tablet is in a range of from 4 mm to 6 mm In some embodiments, a maximal width and a minimal width of a tablet are each in a range of from 2 mm to 10 mm. In some embodiments, a maximal width and a minimal width of a tablet are each in a range of from 3 mm to 7 mm. In some embodiments, a maximal width and a minimal width of a tablet are each in a range of from 4 mm to 6 mm In some embodiments, an average diameter of a tablet is in a range of from 2 mm to 10 mm. In some embodiments, an average diameter of a tablet is in a range of from 3 mm to 7 mm. In some embodiments, an average diameter of a tablet is in a range of from 4 mm to 6 mm Average diameters are calculated based on diameters passing through the geometric center of the tablet.

Each of the tablet formulations disclosed herein can be of any geometric shape, as long as the tablets can be individually measured. Suitable shapes include, for example, spheres, cylinders, cubes, discs, and ellipses, and similar spheroid, cuboid, discoid and ellipsoid forms. The spheroid, cylindroid and discoid forms can have oval or circular cross-sections. The shapes may be flattened or elongated, which in the case of a spheroid having a circular cross-section would mean that the thickness of the tablet is respectively less or more than the diameter of the tablet. The tablets can also be marked with an indented or embossed emblem, trademark or other type of mark or identification.

The extent of flattening or elongation of the tablet shape should be compatible with the envisioned dispensing of the tablets. In some embodiments, tablets for automatic dispensing are slightly flattened or elongated, maintaining an approximate symmetrical shape.

In some embodiments, the tablets have convex or rounded outer surfaces. Such tablets are expected to flow or roll over each other more easily than tablets with planar or concave outer surfaces. Tablets which flow or roll easily over each other can to facilitate dispensing (e.g., with a device described herein).

In some embodiments, a solid formulation is substantially spherical or spheroidal, characterized by an average diameter such as described herein.

Various compounds (generally referred to as "disintegrants") may be included in a tablet in order to increase a rate of disintegration.

According to some embodiments of the present invention, the tablet formulations disclosed herein comprise a superdisintegrating agent. Such formulations are uniquely characterized as rapidly disintegrating tablets. Herein and in the art, a "superdisintegrant" refers to a class of ingredients which is particularly effective at inducing disintegration of a solid formulation (e.g., a tablet). In contrast to many disintegrants, superdisintegrants are typically effective at low concentrations. Indeed, in contrast to most other types of disintegrant, high concentrations of superdisintegrant may lead to slower disintegration of solid formulation.

Thus, in some embodiments, a concentration of superdisintegrant in a solid formulation described herein is less than 10 weight percents, for example, in a range of from 0.5 to 10 weight percents. In some embodiments, a concentration of superdisintegrant in a solid formulation described herein is less than 5 weight percents, for example, in a range of from 0.5 to 5 weight percents. In some embodiments, a concentration of superdisintegrant in a solid formulation described herein is less than 3 weight percents, for example, in a range of from 0.5 to 3 weight percents.

The use of such low concentrations is advantageous because, for example, an agent providing an advantageously rapid disintegration of solid formulation is less likely, being at a low concentration, to interfere with the function of other ingredients of a coloring composition. Such interference can be, for example, interaction with other agents in the formulation, which may lead to the formation of toxic or hazardous compounds and/or promoting such interactions and/or interfering with interactions between other agents in the formulation (e.g., dye couplers and dye precursors).

Superdisintegrants are known as hygroscopic compounds which act by absorbing liquid (e.g., water) from a medium when contacted with the medium (e.g., an aqueous medium). Such absorption induces disintegration by causing considerable swelling of the superdisintegrant and/or by enhancing capillary action. A swelling pressure exerted by a swollen superdisintegrants in an outer or radial direction can cause a tablet to burst.

Suitable superdisintegrants according to some embodiments of the present invention, include, but are not limited to, superdisintegrating agents which are characterized by a water absorption ratio of at least 0.5. The water absorption ratio is defined as the change in weight following wetting of the tablet divided by the weight of the dry tablet.

In some embodiments, the superdisintegrating agent is characterized by a water absorption ratio of at least 0.6, at least 0.7, at least 0.8 and at least 0.9. Superdisintegrating agents suitable for use in embodiments of the present invention may also be characterized by a water absorption ratio of 1.0, 1.2, 1.2, 1.3, 1.4, 1.5 and even by higher water absorption ratio of, for example, 2.0.

In some embodiments, the superdisintegrating agent is characterized by a water absorption ratio that ranges from about 0.5 to about 2. In some embodiments, the superdisintegrating agent is characterized by a water absorption ratio that ranges from about 0.5 to about 1.5. In some embodiments, the superdisintegrating agent is characterized by a water absorption ratio that ranges from about 0.6 to 0.9. Any intermediate value within these ranges is contemplated.

However, the abovementioned hygroscopy of superdisintegrants renders such superdisintegrants as being considered incompatible for use with moisture-sensitive ingredients, particularly in formulations which are intended to have a long shelf life.

The present inventors have surprisingly uncovered that superdisintegrants, which a priori are incompatible with color imparting agents (which are generally moisture-sensitive), are suitable for inclusion in the solid formulations according to embodiments of the invention. Despite the hygroscopicity of the superdisintegrant, the solid formulations described herein were shown to exhibit a suitably long shelf life, while exhibiting a desirable disintegration rate of a few seconds (when uncoated).

The superdisintegrant according to some embodiments of the invention is substantially water-insoluble, such that the superdisintegrant remains intact upon contact with an aqueous medium (as well as many media comprising hydrophilic solvents). By remaining intact, the superdisintegrant maintains its ability to induce disintegration.

Herein, "water-insoluble" refers to a solubility of less than 10 grams per kg of water (at 25° C. and pH 7). Thus, in some embodiments, a compound which is insoluble in water, at the indicated condition, at a concentration of more than 10 grams per Kg to water is considered water-insoluble.

In some embodiments, a solubility of a superdisintegrant is less than 3 grams per kg of water (at 25° C. and pH 7). In some embodiments, a solubility of a superdisintegrant is less than 1 gram per kg of water (at 25° C. and pH 7). In some embodiments, a solubility of a superdisintegrant is less than 0.3 gram per kg of water (at 25° C. and pH 7). In some embodiments, a solubility of a superdisintegrant is less than 0.1 gram per kg of water (at 25° C. and pH 7).

Examples of such water-insoluble superdisintegrants include a variety of crosslinked polymers. In some embodiments, a polymer which is quite hydrophilic (e.g., an ionic polymer) interacts abundantly with water molecules, but does not dissolve in water due to the steric hindrance caused by crosslinking.

It is to be appreciated that such water-insoluble superdisintegrants may be chemically similar to polymers used for other purposes, except in respect to water solubility. For example, many water-soluble hydrophilic polymers are used as thickening agents, as dissolution of such a polymer allows the polymer to spread throughout a liquid medium which is to be thickened.

Suitable superdisintegrants include, without limitation, crosslinked celluloses such as croscarmellose (crosslinked carboxymethylcellulose, which is typically used as a sodium salt), for example, Ac-Di-Sol®, Explocel®, Nymcel ZSX®, Pharmacel® XL, Primellose®, Solutab® and VivaSol® superdisintegrants; crospovidone (crosslinked polyvinylpyrrolidone), for example, Crospovidone M®, Kollidon® and Polyplasdone® superdisintegrants; crosslinked starch, such as sodium starch glycolate, for example, Explotab®, Explotab® CLV, ExploSol®, Primojel®, Tablo® and Vivastar® superdisintegrants; crosslinked alginic acids, for example, Satialgine® superdisintegrant; crosslinked polyacrylic compounds such as ion exchange resins, for example, Indion® 414, Tulsion® 339, and Amberlite® IRP resins; and some polysaccharides, such as soy polysaccharide, for example, Emcosoy® superdisintegrant.

Exemplary superdisintegrants include croscarmellose sodium (e.g., Ac-Di-Sol®), crospovidone (e.g., Polyplasdone®) and sodium starch glycolate (e.g., Primojel®).

Calcium silicate is an example of a non-polymeric superdisintegrant. Calcium silicate is a relatively inert mineral characterized by high water absorption, and may be included in some embodiments of the solid formulation at a concentration of up to 40 weight percents, for example, in a range of from 20 to 40 weight percents. However, it is generally less effective than crosslinked polymeric superdisintegrants at low concentrations.

In addition to superdisintegrants, additional materials included in some embodiments of the solid formulation described herein (e.g., excipients) may contribute to the disintegration properties of the solid formulation, although this may not be the primary function of the additional material. Such materials are referred to herein as "disintegration auxiliary agents".

In some embodiments, a disintegration auxiliary agent is water-soluble. In some such embodiments, rapid dissolution of the disintegration auxiliary agent in an aqueous medium (as well as many media comprising hydrophilic solvents) facilitates disintegration of the solid formulation.

In some embodiments, a disintegration auxiliary agent is characterized by low compressibility and cohesiveness, which enhances tablet porosity, and thus facilitates tablet disintegration via capillary action. For example, capillary action may allow a surrounding aqueous medium to penetrate a tablet through its pores. The infiltrating medium fills the pores, dissolving water-soluble ingredients (including, in some embodiments, the disintegration auxiliary agent itself), weakening inter-particulate or inter-granular physical bonds, and/or swelling the superdisintegrant.

Water-soluble disintegration auxiliary agents associated with high tablet porosity can be achieved, for example, by spray drying or agglomeration of water-soluble agents. Examples of such disintegration auxiliary agents include spray-dried lactose monohydrate (e.g., SuperTab® 11SD and SuperTab® 14SD excipients), spray-dried mannitol (e.g., Mannogem® excipient), and agglomerated isomalt (e.g., galenIQ® 720 and galenIQ® 721 excipients).

Aluminum magnesium silicate is an exemplary disintegration auxiliary agent.

In some embodiments, a concentration of aluminum magnesium silicate in a tablet when uncoated is in a range of from 5 to 40 weight percents. In exemplary embodiments, a concentration of aluminum magnesium silicate in a tablet when uncoated is in a range of from 10 to 22 weight percents.

In some embodiments, a disintegration auxiliary agent is a binder which exhibits an intrinsic disintegrating property. Examples of such binders include starch and to cellulose.

Other types of disintegration auxiliary agents which may be included in some embodiments of the invention include exothermic agents (air expansion), non-swellable agents (electric repulsive force), gas releasing agents and enzymatic systems.

In some embodiments, a concentration of a disintegration auxiliary agent is at least 10 weight percents, or at least 15 weight percents, of the tablet (when uncoated). Higher concentrations of such an agent usually correlate with more rapid disintegration.

In some embodiments, the active agent(s) comprises at least one color imparting agent. In some embodiments, a color imparting agent is selected so as to be suitable for coloring keratinous fibers. In some embodiments, a color imparting agent is selected so as to be suitable for coloring human hair (e.g., suitably non-toxic when applied to the head of a human).

It is to be appreciated that rapidly disintegrating tablets are particularly advantageous for tablets comprising color imparting agents. For example, rapid disintegration facilitates mixture of different color imparting agents (e.g., in different types of tablets) in a homogenous manner, as is important in a preparation of a coloring composition. In addition, rapid disintegration ensures that oxidation of all oxidization dye intermediates begins concurrently, thus avoiding the formation of undesirable byproducts, or of dyes which will not be able to penetrate the hair shaft due to increased molecular size. As noted hereinabove, obtaining rapidly-disintegrating tablet formulations containing color imparting agents is not a trivial task.

Examples of suitable types of color imparting agents which may be included in a solid formulation as described herein include a direct dye, a dye precursor, and a dye coupler. Such agents may be included in a solid formulation in any combination thereof, as is discussed in more detail herein.

In some embodiments, a dye precursor is included in combination with a dye coupler, such that a solid formulation comprises at least one direct dye, and/or a combination of at least one dye precursor and at least one dye coupler.

Oxidation dye intermediates, whether dye precursors or dye couplers, are generally aromatic ring or heteroaromatic ring derivatives, most being aromatic diamines, aminophenols, phenols, and/or naphthols.

Oxidation dye intermediates which are able to give deep shades on white hair are to usually categorized as dye precursors. Such precursors generally have two amine groups, and/or one amine and one hydroxy group, at selected positions relative to each other. Dye precursors are generally aromatic diamines, diaminophenols, and/or aminophenols with an amine or hydroxy group ortho or para to an amine group. Pyrimidine and pyrazole derivatives (e.g., substituted pyrimidine, substituted pyrazole), used to develop shades with red highlights, are also generally considered to be dye precursors.

Herein, an "aromatic diamine" refers to a compound comprising an aromatic ring substituted by at least two amine groups.

Herein, the terms "diaminophenols" and "a diaminophenol" encompass any compound which is a substituted phenol, wherein at least two substituents of the phenol ring are amine groups.

Herein, the terms "aminophenols" and "an aminophenol" encompass any compound which is a substituted phenol, wherein at least one substituent of the phenol ring is an amine group.

Dye couplers are oxidation dye intermediates which, on their own, yield only feeble coloring through oxidation, but can be combined with dye precursors to produce stronger shades. The amine and/or hydroxy groups substituting dye couplers are frequently in meta position to each other. Dye couplers include m-phenylene-diamines, m-aminophenols, naphthols, resorcinols, polyphenols, pyrazolones and their derivatives.

Herein, the terms "m-phenylene-diamines" and "an m-phenylene-diamine" encompass substituted and non-substituted m-phenylene-diamine.

Herein, the terms "m-aminophenols" and "an m-aminophenol" encompass substituted and non-substituted m-aminophenol.

Herein, the terms "naphthols" and "a naphthol" encompass substituted and non-substituted 1-naphthol and 2-naphthol.

Herein, the terms "resorcinols" and "a resorcinol" encompass substituted and non-substituted resorcinol (benzene-1, 3-diol).

Herein, the term "polyphenol" encompasses compounds composed to a large extent of covalently linked phenol groups (i.e., aromatic rings substituted by at least one hydroxyl group). In some embodiments, a polyphenol is characterized by having at least 5 aromatic rings, and at least 12 hydroxyl groups attached to aromatic rings, per 1000 Da in molecular weight. In some embodiments, the molecular weight of a polyphenol is at least 500 Da.

A wide variety of dye precursors and dye couplers, suitable for use in the preparation of a coloring composition, will be known to the skilled person. When dye precursors and dye couplers are used in combination (e.g., as active agents in a solid formulation), the dye couplers should be compatible with the dye precursors being used, that is, they can chemically react to form a coloring agent.

Examples of suitable oxidation dye precursors, which may be used alone or in admixture with one another, include, without limitation, 1,3-bis[(4-aminophenyl)(2-hydroxyethyl)amino]-2-propanol; 1,4-bis[(4-aminophenyl)amino]butane; 1,4-diamino-2-(1-methylethyl)benzene; 1,4-diamino-2-(2-hydroxyethoxy)benzene; 1,4-diamino-2-(2-hydroxyethyl)benzene; 1,4-diamino-2-(pyridin-3-yl)benzene; 1,4-diamino-2-(thiophen-2-yl)benzene; 1,4-diamino-2-(thiophen-3-yl)benzene; 1,4-diamino-2,3-dimethylbenzene; 1,4-diamino-2,5-dimethylbenzene; 1,4-diamino-2,6-dimethylbenzene; 1,4-diamino-2-aminomethyl-benzene; 1,4-diamino-2-hydroxymethyl-benzene; 1,4-diamino-2-methoxymethyl-benzene; 1,4-diamino-3,5-diethylbenzene; 1,8-bis(2,5-diaminophenoxy)-3,6-dioxa-octane; 1-[(4-chlorophenyl)methyl]-4,5-diamino-1H-pyrazole; 1-hydroxyethyl-4,5-diaminopyrazole; 2-(2-(acetylamino)ethoxy)-1,4-diamino-benzene; 2-propylamino-5-aminopyridine; 2,4,5,6-tetramino-pyrimidine; 2,5,6-triamino-4-(1H)-pyrimidone; 2,5-diamino-biphenyl; 2,5-diaminopyridine; 2-amino-5-ethoxyphenol; 2-amino-5-methylphenol; 2-amino-6-methylphenol; 2-aminophenol; 2-chloro-1,4-diamino-benzene; 2-chloro-p-phenylenediamine; 2-(3-hydroxy-ethyl-p-phenylenediamine; 4,5-diamino-1-(1-methylethyl)-1H-pyrazole; 4,5-diamino-1-(2-hydroxyethyl)-1H-pyrazole; 4,5-diamino-1-[(4-methylphenyl)methyl]-1H-pyrazole; 4,5-diamino-1-methyl-1H-pyrazole; 4[(2,3-dihydroxypropyl)amino]aniline; 4[(2-methoxyethyl)amino]aniline; 4-[(3-hydroxypropyl)amino]aniline; 4-[di(2-hydroxyethyl)amino]-2-methylaniline; 4-[di(2-hydroxyethyl)amino]aniline; 4-[ethyl(2-hydroxyethyl)amino]aniline; 4-amino-2-(2-hydroxyethyl)phenol; 4-amino-2-(aminomethyl)phenol; 4-amino-2-(hydroxymethyl)phenol; 4-amino-2-(methoxymethyl)phenol; 4-amino-2-[(2-hydroxyethyl)amino]methylphenol; 4-amino-2-fluorophenol; 4-amino-2-methylphenol; to 4-amino-3-(hydroxymethyl)phenol; 4-amino-3-fluorophenol; 4-amino-m-cresol; 4-diethyl-aminoaniline; 4-dimethylaminoaniline; 4-dipropylaminoaniline; 4-methylaminophenol; 4-phenylaminoaniline; 5-aminosalicylic acid; 6-amino-m-cresol; hydroxyethyl-p-phenylenediamine; hydroxypropyl-bis(hydroxyethyl)-p-phenylenediamine; NN-bis(2-hydroxyethyl)-p-phenylenediamine; N-phenyl-p-phenylenediamine; o-aminophenol; p-aminophenol; p-methylaminophenol; p-phenylenediamine; toluene-2,5-diamine; and salts thereof.

Exemplary dye precursors include 4-amino-m-cresol, p-aminophenol, N,N-bis(2-hydroxyethyl)-p-phenylenediamine (e.g., as a sulfate salt), 1-hydroxyethyl-4,5-diaminopyrazole (e.g., as a sulfate salt), and toluene-2,5-diamine (e.g., as a sulfate salt).

Examples of suitable dye couplers, which may be used alone or in admixture with one another, include, without limitation, 1-(2-aminoethoxy)-2,4-diaminobenzene; 1,2,4-trihydroxy-5-methyl-benzene; 1,2,4-trihydroxybenzene; 1,2-dichloro-3,5-dihydroxy-4-methylbenzene; 1,3-di(2,4-diamino-phenoxy)propane; 1,3-diamino-2,4-dimethoxybenzene; 1,3-diamino-4-(2,3-dihydroxy-propoxy)benzene; 1,3-diaminobenzene; 1,3-dihydroxy-2-methylbenzene; 1,3-dihydroxy-benzene; 1,5-dichloro-2,4-dihydroxybenzene; 1,5-dihydroxy-naphthalene; 1,5-naphthalenediol; 1,7-dihydroxynaphthalene; 1-acetoxy-2-methyl-naphthalene; 1-chloro-2,4-dihydroxybenzene; 1-naphthol; 2-(4-amino-2-hydroxyphenoxy)ethanol; 2,3-diamino-6-methoxypyridine; 2,3-dihydroxynaphthalene; 2,3-indolinedione; 2,4-di[(2-hydroxyethyl)amino]-1, 5-dimethoxybenzene; 2,4-diamino-1-(2-hydroxyethoxy)-5-methylbenzene; 2,4-diamino-1-(2-hydroxyethoxy)benzene; 2,4-diamino-1,5-di(2-hydroxyethoxy)benzene; 2,4-diamino-1-ethoxy-5-methylbenzene; 2,4-diamino-1-fluoro-5-methylbenzene; 2,4-diamino-1-methoxy-5-methylbenzene; 2,4-diaminophenoxyacetic acid; 2,4-diaminophenoxyethanol; 2,6-bis(2-hydroxyethyl)aminotoluene; 2,6-diamino-3,5-dimethoxypyridine; 2,6-diaminopyridine; 2,6-dihydroxyethylaminotoluene; 2,6-dimethoxy-3,5-pyridinediamine; 2,7-dihydroxy-naphthalene; 2-[(3-hydroxyphenyl)amino]acetamide; 2-amino-1-(2-hydroxyethoxy)-4-methylaminobenzene; 2-amino-3-hydroxypyridine; 2-amino-3-hydroxypyridine; 2-amino-4-[(2-hydroxyethyl)amino]anisole; 2-amino-4-hydroxyethylamino-anisole; 2-chloro-1,3-dihydroxybenzene; 2-methyl-1-naphthol; 2-methyl-1-naphthol acetate; 2-methyl-1-naphthol; 2-methyl-5-hydroxyethylaminophenol; 2-methylresorcinol; 3,4-diaminobenzoic acid; 3,4-dihydro-6-hydroxy-1,4(2H)-benzoxazine; 3,4-methylenedioxy-aniline; 3,4-methylenedioxyphenol; 3,5-diamino-2,6-dimethoxypyridine; 3-[(2,3-dihydroxy-propyl)amino]-2-methylphenol; 3-[(2-aminoethyl)amino]aniline; 3-[(2-hydroxyethyl)amino]-2-methylphenol; 3-[(2-hydroxyethyl)amino]aniline; 3-[(2-hydroxyethyl)amino]-phenol; 3-[(2-methoxyethyl)amino]phenol; 3-[di(2-hydroxyethyl)amino]aniline; 3-amino-2,4-dichlorophenol; 3-amino-2-chloro-6-methylphenol; 3-amino-2-methylphenol; 3-amino-6-methoxy-2-(methylamino)pyridine; 3-aminophenol; 3-diethylaminophenol; 3-dimethylaminophenol; 3-methyl-1-phenyl-5-pyrazolone; 4-(2-hydroxyethyl-amino)-2-methylphenol; 4-amino-2-di[(2-hydroxyethyl)amino]-1-ethoxybenzene; 4-amino-2-hydroxytoluene; 4-chlororesorcinol; 4-hydroxyindole; 5,6-dihydroxyindole; 5,6-dihydroxyindoline; 5-[(2-hydroxyethyl)amino]-1,3-benzodioxole; 5-[(2-hydroxyethyl)amino]-2-methylphenol; 5-[(2-hydroxyethyl)amino]4-methoxy-2-methylphenol; 5-[(3-hydroxypropyl)amino]-2-methylphenol; 5-amino-2,4-dichlorophenol; 5-amino-2-ethylphenol; 5-amino-2-methoxyphenol; 5-amino-2-methylphenol; 5-amino-4-chloro-2-methylphenol; 5-amino-4-ethoxy-2-methylphenol; 5-amino-4-fluoro-2-methylphenol; 5-amino-4-methoxy-2-methylphenol; 5-amino-6-chloro-o-cresol; 5-hydroxyindole; 5-methyl-2-(1-methylethyl)phenol; 5-methyl-2-aminophenol; 6-amino-3,4-dihydrol, 4(2H)-benzoxazine; 6-bromo-1-hydroxy-3,4-methylenedioxybenzene; 6-hydroxyindole; 7-hydroxyindole; di(2,4-diaminophenoxy)methane; hydroquinone; hydroxy-benzomorpholine; hydroxyethyl-3,4-methylenedioxyaniline; m-aminophenol; m-phenylene-diamine; N-(3-dimethylaminophenyl)urea; resorcinol; and salts thereof.

Exemplary dye couplers include 4-amino-2-hydroxytoluene, m-aminophenol, 2,4-diaminophenoxyethanol (e.g., as a dihydrochloride salt), resorcinol and hydroxyethyl-3,4-methylenedioxyaniline (e.g., as a hydrochloride salt).

It is noted that certain color imparting agents may be considered in the art as either dye precursors or dye couplers. This is the case in particular for some dye intermediates that can self-couple (e.g., 2-amino-3-hydroxypyridine, 2-amino-6-methylphenol, 2-amino-5-ethoxyphenol, 2-propylamino-5-aminopyridine, and 5-methyl-2-aminophenol).

In some embodiments, the dye precursor (or mixture of dye precursors) and the to dye coupler (or mixture of dye couplers) are used in approximately equimolar amounts, that is a ratio of a molar concentration of dye precursor (whether one dye precursor or a sum of a concentration of a plurality of dye precursors) and a molar concentration of dye coupler (whether one dye coupler or a sum of a concentration of a plurality of dye couplers) are approximately 1:1 (e.g., from 2:3 to 3:2, from 4:5 to 5:4).

However, depending on the availability of suitable binding sites, non-equimolar ratios may also be suitable. For example, blocked couplers may bind only one precursor, whereas unblocked couplers, such as resorcinol, may bind two molecules of precursors.

Thus, in some embodiments, a molar ratio of dye precursor and dye coupler is in a range of from 2:1 to 1:2.

As known to persons skilled in the art of hair coloring, certain dye precursors may have a toxicological effect if uncoupled. Hence, in some embodiments, such a dye precursor is combined with a slight molar excess, for example, up to 2% excess, of at least one suitable dye coupler.

In some embodiments, an oxidation dye intermediate (i.e., a dye precursor or dye coupler) is used alone, for example, when the intermediate is self-coupling. In some embodiments, a dye precursor is used as color imparting agent without a dye coupler.

Combinations of dye precursors and dye couplers to form larger colored molecules (oxidation dyes) may comprise two or more dye intermediates. For example, pairs and trios of dye intermediates (e.g., forming dimers or trimers) may comprise one type of precursor for one type of coupler, one type of precursor for two types of couplers and two types of precursors for one type of coupler.

Suitable pairs or trios of precursors and couplers are known in the art of coloring and depend on the chemical structure of each component. For example, precursors selected from the group consisting of:

1-hydroxyethyl-4,5-diamino pyrazole; 2-chloro-p-phenylenediamine; 2-β-hydroxyethyl-p-phenylenediamine; 4-amino-m-cresol; hydroxypropyl-bis(hydroxyethyl)-p-phenylene-diamine; NN-bis(2-hydroxyethyl)-p-phenylene-diamine; N-phenyl-p-phenylenediamine; o-aminophenol; p-aminophenol; p-methylaminophenol; p-phenylenediamine; toluene-2,5-diamine; and salts thereof, can each be coupled with any coupler selected from the group consisting of:

1,5-naphthalenediol; 1-naphthol; 2,4-diaminophenoxy-ethanol; 2,6-diaminopyridine; 2,6-dimethoxy-3,5-pyridinediamine; 2-amino-3-hydroxypyridine; 2-amino-4-hydroxy-ethylamino-anisole; 2-methyl-1-naphthol; 2-methyl-5-hydroxyethylaminophenol; 2-methylresorcinol; 3-aminophenol; 4-(2-hydroxyethyl-amino)-2-methylphenol; 4-amino-2-hydroxytoluene; 5-amino-6-chloro-o-cresol; 5-methyl-2-aminophenol; 6-hydroxyindole; hydroquinone; hydroxybenzomorpholine; hydroxyethyl-3,4-methylenedioxyaniline; m-aminophenol; resorcinol; and salts thereof.

Exemplary precursor-coupler combinations include:
toluene-2,5-diamine (e.g., as a sulfate), m-aminophenol, and resorcinol;
1-hydroxyethyl-4,5-diaminopyrazole (e.g., as a sulfate) and 4-amino-2-hydroxytoluene;
N,N-bis(2-hydroxyethyl)-p-phenylenediamine (e.g., as a sulfate) and 4-amino-2-hydroxy-toluene;
N,N-bis(2-hydroxyethyl)-p-phenylenediamine (e.g., as a sulfate) and 2,4-diamino-phenoxy-ethanol (e.g., as a dihydrochloride);
4-amino-m-cresol and 4-amino-2-hydroxytoluene;
p-aminophenol and 4-amino-2-hydroxy-toluene;
toluene-2,5-diamine (e.g., as a sulfate), 2,4-diaminophenoxyethanol (e.g., as a dihydrochloride), and hydroxy-3,4-methylenedioxyaniline (e.g., as a hydrochloride); and
toluene-2,5-diamine (e.g., as a sulfate) and hydroxy-3,4-methylene-dioxyaniline (e.g., as a hydrochloride).

In some embodiments, a color imparting agent in a solid formulation comprises a combination of at least one dye precursor and at least one dye coupler (e.g., as described herein).

In some embodiments, the dye precursors and/or dye couplers are divided among different tablet-type solid formulations, which may be used in combination with one another to form a coloring composition, for example, in a suitable molar ratio (e.g., a ratio described herein). A suitable molar ratio may be obtained by selecting an appropriate number of each type of tablet.

Direct dyes according to embodiments of the invention can be natural direct dyes to (e.g., henna) and/or synthetic direct dyes (e.g., nitro-, azo-, azine- and anthraquinone-type dyes). At least one direct dye can be included in a solid formulation described herein as sole color imparting agent(s), or in addition to oxidation dye intermediates (e.g., dye precursors and/or dye couplers) as described herein.

In some embodiments, at least one suitable direct dye agent is included in a solid formulation comprising oxidation dye intermediates in order to advantageously modify the shade, brilliance, color intensity or stability of coloring (e.g., permanent coloring) obtained from use of the oxidation dye intermediates.

It is to be appreciated that direct dyes to be used in combination with oxidizing agents (e.g., agents used to oxidize oxidation dye intermediates) should be selected so as to be sufficiently oxidation-resistant.

In some embodiments, direct dyes are a sole color imparting agent(s) in the solid formulation. In some embodiments, such a solid formulation is suitable for preparing a temporary coloring composition. In some embodiments, such a solid formulation is suitable for preparing a longer lasting coloring composition (e.g., semi-permanent composition and/or demi-permanent color composition).

Examples of suitable natural direct dyes, which may be used alone or in admixture with other dyes (e.g., direct dyes), include, without limitation, alizarine, alkannan, alkannin, anthocyanin, apigenin, apocarotenal, atromentin, awobamin, berberine, betanin, bixin, black tea extract, brazilwood, butin/butein, camomile, canthaxanthin, capsanthin, carajuirin, carotene, catechin, chlorophyll A/B, crocetin, curcumin, datiscetin, deoxysantalin, dracorhodin, emblica extract, fisetin, fukugetin, gossypetin, green tea extract, hematine, indigo, isorhamnetin, juglone, kaempferol, lapachol, lawsone, logwood extract, luteolin, lycopene, madder, malclurin, morin, morindadiol, morindanigrin, munjistin, naphthalene, orcein, purpuroxanthin, quercetin, red sandalwood, rhamnazin, rhamnethin, rhamnocitrin, riboflavin, rottlerin, rubiadin, rubiethyric acid, rutin, white tea extract, xanthone, xanthophyll, and zanthorhamnin.

Suitable synthetic direct dyes, which may be used alone or in admixture with other dyes (e.g., direct dyes), include, without limitation, anionic dyes, cationic dyes, aromatic nitro dyes, azine dyes (including indulines and nigrosines), azo dyes, triphenylmethane dyes, and quinone dyes.

Examples of suitable synthetic dyes include, without limitation, 2-amino-6-chloro-4-nitrophenol; 2-hydroxyethyl picramic acid; 2,6-diamino-3-((pyridin-3-yl)azo)pyridine; 3-nitro-p-hydroxyethylaminophenol; 4-amino-3-nitrophenol; 4-hydroxypropylamino-3-nitrophenol; 4-nitro-o-phenylenediamine; hydroxyethyl-2-nitro-p-toluidine; N,N'-bis (2-hydroxyethyl)-2-nitro-p-phenylene-diamine; Acid Black 1; Acid Blue 1; Acid Blue 3; Acid Blue 62; Acid Blue 74; Acid Blue 74 Aluminum Lake; Acid Blue 9; Acid Blue 9

Aluminum Lake; Acid Blue 9 Ammonium Salt; Acid Green 1; Acid Green 25; Acid Green 50; Acid Orange 6; Acid Orange 7; Acid Red 14; Acid Red 14 Aluminum Lake; Acid Red 18; Acid Red 18 Aluminum Lake; Acid Red 184; Acid Red 27; Acid Red 27 Aluminum Lake; Acid Red 33; Acid Red 51; Acid Red 52; Acid Red 87; Acid Red 92; Acid Red 95; Acid Violet 43; Acid Violet 9; Acid Yellow 1; Acid Yellow 23; Acid Yellow 23 Aluminum Lake; Acid Yellow 3; Acid Yellow 3 Aluminum Lake; Acid Yellow 73; Acid Yellow 73 Sodium Salt; Basic Blue 26; Basic Blue 99; Basic Brown 16; Basic Brown 17; Basic Orange 31; Basic Orange 69; Basic Red 1; Basic Red 1:1; Basic Red 51; Basic Red 76; Basic Violet 11:1; Basic Violet 14; Basic Violet 16; Basic Violet 2; Basic Yellow 40; Basic Yellow 57; Basic Yellow 87; Blue 1 Lake; Brilliant Black 1; chromium hydroxide green; chromium oxide greens; curry red; Direct Blue 86; Disperse Black 9; Disperse Blue 377; Disperse Red 17; Disperse Violet 1; Disperse Violet 15; Fast Green FCF; Ferric Ammonium Citrate; HC Blue No. 11; HC Blue No. 12; HC Blue No. 13; HC Blue No. 14; HC Blue No. 15; HC Blue No. 16; HC Blue No. 2; HC Blue No. 7; HC Orange No. 1; HC Orange No. 2; HC Orange No. 5; HC Red No. 1; HC Red No. 10; HC Red No. 11; HC Red No. 13; HC Red No. 14; HC Red No. 15; HC Red No. 3; HC Red No. 7; HC Violet No. 1; HC Violet No. 2; HC Yellow No. 10; HC Yellow No. 13; HC Yellow No. 14; HC Yellow No. 15; HC Yellow No. 2; HC Yellow No. 4; HC Yellow No. 7; HC Yellow No. 9; Pigment Blue 15; Pigment Green 7; Pigment Red 4; Pigment Red 5; Pigment Red 48; Pigment Red 57; Pigment Red 57:1; Pigment Red 63:1; Pigment Red 64:1; Pigment Red 88; Pigment Red 90:1 Aluminum Lake; Pigment Red 112; Pigment Red 190; Pigment Violet 19; Pigment Violet 23; Pigment Yellow 13; Solvent Green 3; Solvent Green 7; Solvent Orange 1; Solvent Red 23; Solvent Red 3; Solvent Red 43; Solvent Red 48; Solvent Red 72; Solvent Red 73; Solvent Violet 13; Solvent Yellow 172; Solvent Yellow 18; Solvent Yellow 29; Solvent Yellow 33; Solvent Yellow 85; Sunset Yellow; tetraaminopyrimidine sulfate; ultramarines; Vat Red 1; and salts thereof.

Exemplary direct dyes include 2-amino-6-chloro-4-nitrophenol, 2,6-diamino-3-((pyridin-3-yl)azo)pyridine, HC Blue No. 15, HC Red No. 10, HC Red No. 11, and HC Yellow No. 13.

In some embodiments, a concentration of color imparting agent in the solid formulation is in a range of from 0.01 to 40 weight percents of the tablet when uncoated. In some embodiments, the concentration is in a range of from 0.5 to 25 weight percents of the tablet when uncoated.

In some embodiments, a concentration of all dye precursors in the solid formulation is in a range of from 0.01 to 25 weight percents of the tablet when uncoated. In some embodiments, the concentration is in a range of from 0.1 to 15 weight percents of the tablet when uncoated. In some embodiments, the concentration is in a range of from 0.1 to 5 weight percents of the tablet when uncoated.

In some embodiments, a concentration of all dye couplers in the solid formulation is in a range of from 0.01 to 15 weight percents of the tablet when uncoated. In some embodiments, the concentration is in a range of from 0.01 to 10 weight percents of the tablet when uncoated.

In some embodiments, a molar ratio of a dye precursor to a dye coupler ranges from 0.1 to 10, or from 0.5 to 5, or from 0.5 to 1.5, or from 0.5 to 1, or from 0.9 to 1. A ratio of about 1 or less is desirable in order to avoid possible formation of harmful compounds.

In some embodiments, a concentration of direct dye in the solid formulation is in a range of from 0.01 to 15 weight percents of the tablet when uncoated. In some embodiments, the concentration is in a range of from 0.1 to 10 weight percents of the tablet when uncoated. Herein, the phrase "weight percents of the tablet when uncoated" means that if the solid formulation is in the form of a coated tablet, only the uncoated portion of the tablet is taken into account when calculating a weight percentage of the component (e.g., dye precursor). Accordingly, any color imparting agents present in the coating are not taken into account.

In some embodiments, the active agent(s) in a solid formulation consist of a color imparting agent(s) (e.g., as described herein), that is, the formulation does not include other types of active agents described herein.

In some embodiments, the active agent(s) in a solid formulation comprises at to least one alkalizing agent.

In some embodiments, the alkalizing agent may be combined in the solid formulation with another active agent described herein (e.g., color imparting agent, thickening agent, oxidizing agent).

In some embodiments, the active agent(s) in a solid formulation consist of an alkalizing agent(s), that is, the formulation does not include other types of active agents described herein.

Suitable alkalizing agents include ammonia and ammonia derivatives (e.g., ammonium salts), organic amines, alkali metal and alkaline earth metal hydroxides, carbonates, carbamates, amino acids, and mixtures thereof.

Suitable alkalizing agents for use according to some embodiments of the invention include, but are not limited to, an alkanolamine, a basic amino acid, a carbonate salt, a carbamate salt, a hydroxide salt, a silicate salt, and any combination thereof.

Examples of suitable alkanolamines including monoalkanolamines, dialkanolamines, trialkanolamines, mono-alkyl-monoalkanol-amines, monoalkyl-dialkanol-amines, and dialkyl-monoalkanol-amines, for example, $C_{1-4}$alkanolamines, di-($C_{1-4}$alkanol)amines, tri-($C_{1-4}$alkanol)amines, mono($C_{1-4}$alkyl)-mono($C_{1-4}$alkanol)-amines, mono($C_{1-4}$alkyl)-di($C_{1-4}$alkanol)-amines, and di($C_{1-4}$alkyl)-mono($C_{1-4}$alkanol)-amines (e.g., monoethanolamine (MEA), diethanolamine (DEA), triethanolamine (TEA), dimethyl MEA, aminobutanol, aminoethyl propanediol, aminomethyl propanediol, bis-hydroxyethyl tromethamine, diethylethanolamine, diisopropanolamine, dimethylamino methylpropanol, isopropanolamine, methylethanolamine, mixed isopropanolamines, triisopropanolamine, tromethamine);

Examples of suitable hydroxide salts include hydroxides of alkali metals (e.g., sodium or potassium hydroxide), hydroxides of alkaline earth metals (e.g., magnesium or calcium hydroxide), and ammonium hydroxide.

Examples of suitable carbonate salts include carbonates of ammonium, alkali metals and alkaline earth metals, such as $Na_2CO_3$, $NaHCO_3$, $K_2CO_3$, $KHCO_3$, $(NH_4)_2CO_3$, $NH_4HCO_3$, $CaCO_3$ and $Ca(HCO_3)_2$);

Examples of suitable carbamate salts include ammonium carbamate;

Examples of suitable basic amino acids include arginine, lysine, oxy-lysine, and histidine. Oligopeptides comprising basic amino acids, and which overall are basic, may also be included.

Examples of suitable silicate salts include sodium silicate and sodium metasilicate.

Additional examples of alkalizing agents which may be utilized in some embodiments include ammonia and alkaline ammonium salts (e.g., ammonium hydroxide); alkylamines (including monoalkylamines, dialkylamines and trialkylamines), for example, $C_{1-4}$alkylamines, di-($C_{1-4}$alkyl)amines, and tri-($C_{1-4}$alkyl)amines (e.g., ethylamine, triethylamine, dipropylamine); alkanediamines such as $C_{1-4}$alkanediamines (e.g., 1,3-diaminopropane); polyalkylene polyamines, such as dimers, trimers, tetramers, oligomers and polymers of the aforementioned alkanediamines (e.g., diethylenetriamine); and heterocyclic amines (such as morpholine);

In some embodiments, the alkalizing agents includes ammonium hydroxide, monoethanolamine (MEA), diethanolamine (DEA), arginine, ammonium carbonate, ammonium hydrogen carbonate, sodium hydroxide, or mixtures thereof.

The quantity of the alkalizing agent to be employed in preparation of a coloring composition can vary over a wide range, depending on the particular alkalizing agent employed and the type of coloring sought.

In some embodiments, the active agent(s) in a solid formulation comprises at least one oxidizing agent.

In some embodiments, the oxidizing agent may be combined in the solid formulation with another active agent described herein (e.g., color imparting agent, thickening agent, alkalizing agent).

In some embodiments, the active agent(s) in a solid formulation consist of an oxidizing agent(s), that is, the formulation does not include other types of active agents described herein.

In some embodiments, the oxidizing agent is suitable for reacting with a dye intermediate (e.g., dye precursor) so as to form a dye (e.g., oxidation dye). Such an oxidizing agent may be used in combination with one or more dye intermediates to described herein, so as to prepare a coloring composition for coloring with an oxidation dye.

Suitable oxidizing agents include, but are not limited to, a peroxide, including hydrogen peroxide and derivatives (e.g., salts and complexes) thereof (e.g., sodium peroxide, urea peroxide, melamine peroxide, polyvinylpyrrolidone hydrogen peroxide complexes), alkyl peroxides and aryl peroxides; inorganic metal peroxide salts such as periodates and perbromates (e.g., sodium periodate, sodium perbromate); inorganic persalt bleaches such as perborates (e.g., sodium, potassium, or ammonium perborate), percarbonates, perphosphates, persulfates (e.g., ammonium, potassium or sodium persulfate) and percarbamides; and mixtures thereof.

In some embodiments, the oxidizing agent is suitable for bleaching keratinous fibers, for example, human hair. Bleaching may comprise bleaching of natural pigmentation. Such an oxidizing agent (also referred to hearing as a "bleaching agent") may be used to prepare a coloring composition which is a bleaching composition, that is, a composition which is intended to affect a color of a surface by bleaching existing color (e.g., natural pigmentation).

Oxidizing agents for use in preparing a bleaching composition are generally not used in combination with a color imparting agent. Rather, a bleaching composition is prepared with at least one bleaching agent, for example, by using a tablet comprising a bleaching agent (e.g., as described herein) without a color imparting agent.

Thus, in some embodiments, the active agent(s) in a solid formulation consists of at least one bleaching agent.

Examples of suitable bleaching agents include, without limitation, persulfate salts (e.g., ammonium, potassium or sodium persulfate).

The quantity of oxidizing agent suitable for formulations according to embodiments of the invention will depend on the particular agent selected and the specific coloring use (e.g., bleaching and/or oxidizing a dye intermediate).

In some embodiments, the active agent(s) in a solid formulation comprises at least one thickening agent.

In some embodiments, the thickening agent may be combined in the solid formulation with another active agent described herein (e.g., color imparting agent, to oxidizing agent, alkalizing agent).

In some embodiments, the active agent(s) in a solid formulation consist of a thickening agent(s), that is, the formulation does not include other types of active agents described herein.

Many compounds known in the art may be suitable for serving as a thickening agent for a coloring composition as described herein.

In some embodiments, the thickening agent is soluble in a solvent used for the coloring composition. Suitable solvents for the coloring composition are described elsewhere herein.

In some embodiments, the thickener is a polymer (e.g., a water-soluble polymer).

Examples of suitable thickening agents for inclusion in some embodiments of the invention include, without limitation, alginate; cellulose derivatives such as carboxymethylcellulose, hydroxyalkylcellulose, and methylcellulose; gums (in modified or non-modified form) such as agar agar, carob bean gum, carrageen gum, ghatti gum, guar gum, gum arabic, karaya gum, tragacanth gum, scleroglucan gum, and xantham gum; fatty alcohols such as cetyl alcohol, oleyl alcohol, and cetearyl alcohol; fatty acids such as oleic acid; pectin, starch, amylose, amylopectin, dextrin; paraffin oil; bentonite; silicic acid; magnesium phyllosilicate; polyacrylamide, poly(2-acrylamido-2-methylpropanesulfonic acid), an acrylate polymer, a polyquarternium, polyvinyl pyrrolidone, polyvinyl alcohol, polyoxypropylene tridecyl ether, and polyoxyethylene tridecyl ether.

It is to be understood that descriptions of multiple polymers (as above) are herein intended to encompass copolymers of any two or more of the described polymers.

Herein, a "polyquarternium" is any compound (e.g., polycationic polymer) designated as such according to the International Nomenclature for Cosmetic Ingredients (INCI).

Herein, "acrylate polymer" includes polymers and copolymers of acrylic acid, methacrylic acid, and esters thereof (e.g., ethyl acrylate, methyl methacrylate), in accordance with INCI nomenclature.

In some embodiments, a concentration of thickening agent(s) in a tablet when uncoated is no more than 80 weight percents. In some embodiments, a concentration of thickening agent(s) in a tablet when uncoated is no more than 50 weight percents. In some embodiments, a concentration of thickening agent(s) in a tablet when uncoated is no more than 20 weight percents.

In some embodiments, the active agent in a solid formulation comprises a combination of different types of active agents described herein.

In some embodiments, the active agent comprises at least one color imparting agent (e.g., as described herein) and at least one alkalizing agent (e.g., as described herein).

In some embodiments, the active agent comprises at least one color imparting agent (e.g., as described herein) and at least one thickening agent (e.g., as described herein).

In some embodiments, the active agent comprises at least one color imparting agent (e.g., as described herein) and at least one oxidizing agent (e.g., as described herein).

In some embodiments, the active agent comprises at least one oxidizing agent (e.g., as described herein) and at least one alkalizing agent (e.g., as described herein).

In some embodiments, the active agent comprises at least one oxidizing agent (e.g., as described herein) and at least one thickening agent (e.g., as described herein).

In some embodiments, the active agent comprises at least one alkalizing agent (e.g., as described herein) and at least one thickening agent (e.g., as described herein).

In some embodiments, the active agent comprises at least one color imparting agent (e.g., as described herein), at least one thickening agent (e.g., as described herein), and at least one alkalizing agent (e.g., as described herein).

In some embodiments, the active agent comprises at least one color imparting agent (e.g., as described herein), at least one oxidizing agent (e.g., as described herein), and at least one alkalizing agent (e.g., as described herein).

In some embodiments, the active agent comprises at least one color imparting agent (e.g., as described herein), at least one oxidizing agent (e.g., as described herein), and at least one thickening agent (e.g., as described herein).

In some embodiments, the active agent comprises at least one thickening agent (e.g., as described herein), at least one oxidizing agent (e.g., as described herein), and at least one alkalizing agent (e.g., as described herein).

In some embodiments, the active agent comprises all types of active agent described herein, that is, at least one color imparting agent (e.g., as described herein), at least one oxidizing agent (e.g., as described herein), at least one thickening agent (e.g., as described herein), and at least one alkalizing agent (e.g., as described herein).

In order to enhance the benefit of providing an active agent in preparation of a coloring composition, in some embodiments an amount of active agent(s) in a tablet described herein is approximately equal to, or less than (e.g., $\frac{1}{2}$, $\frac{1}{3}$, $\frac{1}{4}$, $\frac{1}{5}$, $\frac{1}{10}$, $\frac{1}{20}$, $\frac{1}{50}$), the lowest amount of the active agent(s) likely to be needed for a coloring composition, e.g., an mount suitable for treating (e.g., coloring) the hair of one person.

Consequently, a suitable amount of active agent may be obtained from an integral number of such tablets (e.g., about 2, 3, 4, 5, 10, 20, 50, 100, 150, or 200 tablets).

In some embodiments, an amount of active agent in a tablet is enough so that no more than 100 tablets comprising a color imparting agent(s) are needed to prepare a coloring composition, for example, a coloring composition sufficient to color the hair of at least one human head.

In some embodiments, an amount of active agent in a tablet is enough so that no more than 150 tablets comprising a color imparting agent(s) are needed to prepare a coloring composition (e.g., as described herein).

In some embodiments, an amount of active agent in a tablet is enough so that no more than 100 tablets comprising an active agent described herein (e.g., tablets comprising color imparting agent(s), oxidizing agent(s), alkalizing agent(s) and/or thickening agent(s) are needed to prepare a coloring composition, for example, a coloring composition wherein all of the active agents in the coloring composition (e.g., color imparting agent(s), oxidizing agent(s), alkalizing agent(s), and thickening agent(s)) are derived from tablets such as described herein.

In some embodiments, an amount of active agent in a tablet is enough so that no more than 150 tablets comprising an active agent described herein (e.g., tablets to comprising color imparting agent(s), oxidizing agent(s), alkalizing agent(s) and/or thickening agent(s) are needed to prepare a coloring composition (e.g., as described herein).

In some embodiments, a water content of a solid formulation is less than 5 weight percents of the total weight of a tablet, when uncoated. In some embodiments, a water content of a solid formulation is less than 4 weight percents. In exemplary embodiments, a water content of a solid formulation is less than 3 weight percents. In exemplary embodiments, a water content of a solid formulation is less than 2 weight percents, and in some exemplary embodiments, a water content of a solid formulation is even less than 1.5 weight percents. Water content may optionally be obtained and/or determined as exemplified herein in the Examples.

As demonstrated in the Examples section that follows, the present inventors have uncovered that solid formulations as described herein with reduced water content (of e.g., less than 3 weight percents or less than 2 weight percents) are advantageously characterized by improved stability, due to the hygroscopic nature of some of the components (e.g., the superdisintegrant).

In some embodiments, the solid formulation further comprises at least one excipient (e.g., in addition to the active agent(s) and superdisintegrant(s) described herein). For example, binders and fillers are excipients included in some embodiments. Additional examples of excipients include an anti-adherent, an anti-dandruff agent, an anti-foam agent, anti-oxidants, a binder, a chelating agent, a conditioning agent, an emollient, an emulsifying agent, an exothermic compound, a filler, a fragrance, a free-radical scavenger, a glidant, a hair care agent, a humectant, a lubricant, an odor masking agent, an opacifier, a pearlizing agent, a pH adjusting agents, a plant extract, a preservative, a stabilizing agent, a surfactant, a UV protecting agent, a vitamin, a vitamin precursor, and a wetting agent.

In some embodiments, the excipient comprises a binder and/or filler. In some embodiments, most (>50 weight percents) of the excipients in a solid formulation consist of a binder and/or filler.

In some embodiments, a total concentration of binder and/or filler in a tablet when uncoated is at least 50 weight percents. In some embodiments, the total concentration is at least 60 weight percents. In some embodiments, the total concentration is at least 70 weight percents. In some embodiments, the total concentration is at least 80 weight percents.

A wide variety of water-soluble and water-insoluble binders may be used in the tablets according to embodiments of the invention.

Suitable binders include proteins (such as gelatin); saccharides and their derivatives, including disaccharides (such as sucrose and lactose), and sugar alcohols (such as xylitol, sorbitol and maltitol); polysaccharides and derivatives thereof (e.g., starches, cellulose, and/or modified cellulose); synthetic polymers such as polyvinylpyrrolidone and polyethylene glycol (PEG); alginate; and gums (e.g., acacia gum). Examples of suitable modified cellulose include microcrystalline cellulose, and cellulose ethers such as hydroxypropyl cellulose (HPC).

Suitable fillers include, but are not restricted to, calcium phosphate (e.g., dibasic calcium phosphate), calcium carbonate, silicic acid, and talc.

It is to be appreciated that a particular excipient may fall into more than one of the abovementioned categories. For example, some compounds can be used both as binders to ensure the cohesiveness of the tablet and improve its mechanical strength and as fillers, typically more inert, to provide a convenient dose. Some such compounds are even referred to in the art as binder-fillers. Similarly, some compounds may be considered anti-adherents (e.g., compounds that reduce adhesion between a powder and tablet punch faces, to preventing sticking to tablet punches) or lubricants (e.g., compounds that prevent ingredients from clumping together). Similarly, some glidants (e.g., compounds that improve a flow of the tablet ingredients by reducing inter-particle friction and cohesion) may also act as anti-adherents and/or lubricants.

Suitable anti-adherents include, but are not restricted to, magnesium stearate.

Suitable glidants include, but are not restricted to, calcium silicate, magnesium carbonate, magnesium silicate, silicon dioxide (including fumed silica and colloidal silicon dioxide) and talc (including colloidal talc).

Suitable lubricants include, but are not restricted to, common minerals, such as talc or silica, and fats, such as vegetable stearin, calcium stearate, magnesium stearate, sodium stearyl fumarate and stearic acid.

Suitable antidandruff agents include piroctone olamine, zinc omadine and climbazole.

Examples of suitable anti-foam agents include silicones such as dimethylpolysiloxane and hydrated silica.

Suitable anti-oxidants include, but are not restricted to, ascorbic acid and its salts and derivatives (such as sodium ascorbate, erythorbic acid, ascorbyl palmitate, ascorbyl laurate), mercaptans and inorganic sulfites (such as sodium sulfite, sodium bisulfite, sodium metabisulfite, potassium sulfite, and thioglycolic acid), butylated hydroxytoluene (BHT), butylated hydroxyanisole (BHA) and sodium dithionite. Such antioxidants can be present in the tablets of the invention and/or in the suitable media up to 15% by weight. Typically, such antioxidants can account to up to 5% by weight of the final coloring formulae according to the invention.

Ascorbic acid is an exemplary excipient. Without being bound by any particular theory, it is believed that ascorbic acid advantageously and effectively acts as an antioxidant in tablets such as described herein, while also reducing disintegration time, as exemplified herein. Exemplary concentrations of ascorbic acid are in a range of from 1 to 3 weight percents.

Suitable surfactants include cosmetically acceptable anionic, cationic, zwitterionic, and non-ionic surfactants.

Suitable anionic surfactants include alkyl phosphate, alkyl carboxylate, alkyl sulfate, and alkyl sulfonate type surfactants. Examples of suitable anionic surfactants include α-olefinsulfonate and its salts, and alkali salts of sulfosuccinic acid half-esters.

Examples of suitable cationic surfactants include long-chained quaternized ammonium compounds, for example, behenyl trimethyl ammonium chloride, benzyl tetradecyl-dimethyl-ammonium chloride, cetyl pridinium chloride, cetyl trimethyl ammonium chloride, dimethyl dihydrogenated-tallow ammonium chloride, dimethyl stearyl ammonium chloride, dimethyl-stearyl benzyl ammonium chloride, lauryl dimethylbenzyl ammonium chloride, lauryl-trimethyl-ammonium chloride, stearyl trimethyl ammonium chloride, trimethylacetyl-ammonium bromide, and tris-(oligooxy-ethyl)alkylammonium phosphate.

Examples of suitable zwitterionic surfactants include betaines (such as fatty acid-amidoalkylbetaine and sulfobetaine) and long-chained alkylamino acids (such as cocoaminoacetate, cocoamino-propionate, sodium cocoamphopropionate and sodium cocoamphoacetate).

Examples of suitable non-ionic surfactants include polyethoxylated alcohols, polyethoxylated alkyl phenols, polyethoxylated glyceryl esters, and polyethoxylated organic ethers derived from fatty acids.

In some embodiments, a concentration of such surfactants is no more than 15 weight percents.

Suitable emulsifying agents include, but are not restricted to, fatty acids (such as behenic acid, stearic acid, myristic acid, palmitic acid and oleic acid) and anionic, cationic, zwitteronic and nonionic surfactants (e.g., as described herein).

In some embodiments, a concentration of such emulsifying agents is no more than 30 weight percents.

A "pH adjusting agent" refers to acidifying agents and alkalizing agents. Numerous suitable acidifying agents are known in the art of formulation including, but not limited to, acetic acid, citric acid, fumaric acid, hydrochloric acid, lactic acid, maleic acid, malic acid, nitric acid, phosphoric acid, propionic acid, sodium phosphate monobasic, sulfuric acid and tartaric acid. Suitable alkalizing agents include for example ammonium hydroxide, ammonium carbonate, diethanolamine, monoethanolamine, potassium hydroxide, sodium bicarbonate, sodium borate, sodium carbonate, sodium hydroxide, sodium phosphate dibasic and trolamine Food acids and bases such as allantoin, bisabolol, pyrrolidonecarboxylic acids and salts thereof are also suitable.

It is to be appreciated that an alkalizing agent is used at considerably lower concentrations when used as a pH adjusting agent as described herein than when used as an active agent as described herein.

In some embodiments, a concentration of such pH adjusters is no more than 5 weight percents.

Suitable chelating agents include, but are not restricted to, ethylenediaminetetraacetic acid (EDTA) and its salts (such as disodium EDTA), ethylenediamine disuccinic acid (EDDS) and its salts, nitrilotriacetic acid (NTA), β-alaninediacetic acid, phosphonic acids (such as etidronic acid), pyrophosphates, and zeolites.

In some embodiments, a concentration of such chelating agents is no more than 5 weight percents.

Suitable fragrances include those from natural or synthetic sources. Natural fragrances include extracts and essential oils from flowers, stems, leaves, fruits, roots, woods, herbs, grasses, resins, balsams and animal raw ingredients (e.g., aniseed bergamot, cardamom, civet, myrrh, mace, patchouli, pine, rose, sandalwood, and tarragon). Synthetic fragrances include ester, ether, aldehyde, ketone, alcohol and hydrocarbon compounds (e.g., benzyl acetate, benzyl ethyl ether, citronellal, methyl cedryl ketone, anethole, and terpenes).

In some embodiments, a concentration of such fragrances is no more than 5 weight percents.

Suitable conditioning agents include, but are not restricted to, cationic surfactants (e.g., as described herein), cationic polymers (e.g., a polyquaternium), silicones (e.g., silicone oils, cationic silicones, silicone gums, high refractive silicone and silicone resins), organic conditioning oils (e.g., hydrocarbon oils, polyolefins, and fatty esters), alkylamidoamines, phospholipids (e.g., soybean lecithin, egg lecithin and cephalins) and quaternary compounds (e.g., centrimonium chloride).

In some embodiments, a concentration of such conditioning agents is no more than 5 weight percents.

Suitable humectants include water-soluble liquid polyols (e.g., glycerin, propylene glycol, hexylene glycol, butylene glycol, dipropylene glycol), polyalkylene glycols, urea, and mixtures thereof.

In some embodiments, a concentration of such humectants is no more than 30 weight percents.

Suitable hair-care agents include, but are not restricted to, betaine, cationic polymers (e.g., as described herein) or resins, cholesterol, lanolin derivatives, pantothenic acid, and vitamins.

Suitable vitamins include vitamins A, $B_3$, $B_5$, $B_6$, C, E, F and H, and provitamins (vitamin precursors) thereof.

In some embodiments, a concentration of such hair care agents is no more than 5 weight percents.

Suitable UV protecting agents include, but are not restricted to derivatized benzophenones (such as uvinol), benzotriazole, cinnamic acid derivatives, coumarin, p-aminobenzoic acid, salicylic acid, and triazines.

In some embodiments, a concentration of such UV protecting agents is no more than 5 weight percents.

Suitable preservatives (in addition to antioxidants) include antimicrobial agents which prevent and/or retard bacterial growth, and thus protect cosmetic products from spoilage.

Suitable pearlizing agents include compounds such as ethylene glycol monostearate and ethylene glycol distearate, and PEG-3 distearate.

In some embodiments, a concentration of such pearlizing agents is no more than 10 weight percents.

An "exothermic compounds: refers herein to a compound which releases heat upon contact with a medium in which a tablet is disintegrated (e.g., to prepare a coloring composition). Examples of exothermic compounds suitable for inclusion in a solid formulation include, but are not restricted to, calcium chloride, calcium oxide, sodium acetate, and combinations thereof.

In some embodiments, tablet disintegration is enhanced by heat released by the exothermic compound. In such embodiments, the exothermic compound may be considered a disintegration auxiliary agent.

In some embodiments, the solid formulation comprises microcrystalline cellulose in a concentration in a range of from 57 to 70 weight percents. Avicel® PH-200 is an exemplary microcrystalline cellulose.

In some embodiments, the solid formulation comprises lactose (e.g., spray-dried lactose) in a concentration in a range of from 21 to 27 weight percents. SuperTab® 11SD is an exemplary lactose.

In some embodiments, the solid formulation comprises croscarmellose (e.g., sodium croscarmellose) in a concentration in a range of from 1.75 to 3.25 weight percents (e.g., 2 weight percents or 3 weight percents). AC-Di-Sol® SD711 is an exemplary croscarmellose.

In some embodiments, the solid formulation comprises magnesium stearate in a concentration in a range of from 0.75 to 3.25 weight percents (e.g., 1 weight percent or to 3 weight percents).

In some embodiments, the solid formulation comprises ascorbic acid in a concentration in a range of from 0.75 to 1.25 weight percent. In exemplary embodiments, the concentration is about 1 weight percent.

In exemplary embodiments, the solid formulation consists of at least color imparting agent, and excipients consisting of microcrystalline cellulose in a concentration in a range of from 57 to 70 weight percents, spray-dried lactose in a concentration in a range of from 21 to 27 weight percents, croscarmellose in a concentration in a range of from 1.75 to 3.25 weight percents, magnesium stearate in a concentration in a range of from 0.75 to 3.25 weight percents, and ascorbic acid in a concentration in a range of from 0.75 to 1.25 weight percent.

In some embodiments, the concentrations of microcrystalline cellulose and lactose are approximately correlated, such that a concentration of both microcrystalline cellulose and lactose is relatively high when the total concentration of other ingredients is relatively low, and vice versa. In some embodiments, a concentration of lactose is between 35.0% and 39.0% of the concentration of microcrystalline cellulose. In some embodiments, a concentration of lactose is between 36.0% and 38.2% of the concentration of microcrystalline cellulose. In some embodiments, a concentration of lactose is between 37.6% and 38.1% of the concentration of microcrystalline cellulose.

In some embodiments, the color imparting agent(s) in a tablet (e.g., a tablet comprising the abovementioned excipients) consist of toluene-2,5-diamine, m-aminophenol, and resorcinol, the agents imparting a "natural" shade. Toluene-2,5-diamine sulfate is an exemplary form of toluene-2,5-diamine. In exemplary embodiments, a concentration of toluene-2,5-diamine (e.g., toluene-2,5-diamine sulfate) in a tablet when uncoated is about 9.93 weight percents, a concentration of m-aminophenol is about 0.91 weight percent, and a concentration of resorcinol is about 4.05 weight percents.

In some embodiments, the color imparting agent(s) in a tablet (e.g., a tablet comprising the abovementioned excipients) consist of 2-amino-6-chloro-4-nitrophenol, the agent imparting a gold shade. In exemplary embodiments, a concentration of 2-amino-6-chloro-4-nitrophenol in a tablet when uncoated is about 1.55 weight percents.

In some embodiments, the color imparting agent(s) in a tablet (e.g., a tablet to comprising the abovementioned excipients) consist of 4-amino-m-cresol, 4-amino-2-hydroxytoluene, and 2-amino-6-chloro-4-nitrophenol, the agents imparting an orange shade. In exemplary embodiments, a concentration of 4-amino-m-cresol in a tablet when uncoated is about 0.43 weight percent, a concentration of 4-amino-2-hydroxytoluene is about 0.43 weight percent, and a concentration of 2-amino-6-chloro-4-nitrophenol is about 11.7 weight percents.

In some embodiments, the color imparting agent(s) in a tablet (e.g., a tablet comprising the abovementioned excipients) consist of 1-hydroxyethyl-4,5-diaminopyrazole, 4-amino-2-hydroxytoluene, and HC Red No. 10 & 11, the agents imparting a red shade. 1-Hydroxyethyl-4,5-diaminopyrazole sulfate is an exemplary form of 1-hydroxyethyl-4,5-diaminopyrazole. In exemplary embodiments, a concentration of 1-hydroxyethyl-4,5-diaminopyrazole (e.g., 1-hydroxyethyl-4,5-diaminopyrazole sulfate) in a tablet when uncoated is about 6.3 weight percents, a concentration of 4-amino-2-hydroxytoluene is about 3.3 weight percents, and a concentration of HC Red No. 10 & 11 is about 0.075 weight percent.

In some embodiments, the color imparting agent(s) in a tablet (e.g., a tablet comprising the abovementioned excipients) consist of N,N-bis(2-hydroxyethyl)-p-phenylenediamine, and 4-amino-2-hydroxytoluene, the agents imparting a violet shade. N,N-bis(2-hydroxyethyl)-p-phenylenediamine sulfate is an exemplary form of N,N-bis(2-hydroxyethyl)-p-phenylenediamine. In exemplary embodiments, a concentration of N,N-bis(2-hydroxyethyl)-p-phenylenediamine (e.g., N,N-bis(2-hydroxyethyl)-p-phenylenediamine sulfate) in a tablet when uncoated is about 9.25 weight percents, and a concentration of 4-amino-2-hydroxytoluene is about 3.9 weight percents.

In some embodiments, the color imparting agent(s) in a tablet (e.g., a tablet comprising the abovementioned excipients) consist of toluene-2,5-diamine, 2,4-diamino-phenoxyethanol, and hydroxyethyl-3,4-methylene-dioxyaniline, the agents imparting an "ash" shade. Toluene-2,5-diamine sulfate is an exemplary form of toluene-2,5-diamine. 2,4-Diamino-phenoxyethanol dihydrochloride is an exemplary form of 2,4-diamino-phenoxyethanol. Hydroxyethyl-3,4-methylene-dioxyaniline hydrochloride is an exemplary form of hydroxyethyl-3,4-methylene-dioxyaniline. In exemplary embodiments, a concentration of toluene-2,5-diamine (e.g., toluene-2,5-diamine sulfate) in a tablet when uncoated is about 0.24 weight percent, a concentration to of 2,4-diamino-phenoxyethanol (e.g., 2,4-diamino-phenoxyethanol dihydrochloride) is about 0.22 weight percent, and a concentration of hydroxyethyl-3,4-methylene-dioxyaniline (e.g., hydroxyethyl-3,4-methylene-dioxyaniline hydrochloride) is about 0.46 weight percent.

In some embodiments, the color imparting agent(s) in a tablet (e.g., a tablet comprising the abovementioned excipients) consist of p-aminophenol, and 4-amino-2-hydroxytoluene, the agents imparting a rose shade. In exemplary embodiments, a concentration of p-aminophenol in a tablet when uncoated is about 0.35 weight percent, a concentration of 4-amino-2-hydroxytoluene is about 0.45 weight percent weight percent.

In some embodiments, the color imparting agent(s) in a tablet (e.g., a tablet comprising the abovementioned excipients) consist of toluene-2,5-diamine, hydroxyethyl-3,4-methylene-dioxyaniline, HC Yellow No. 13, 2,6-diamino-3-((pyridine-3-yl)azo)pyridine, and HC Blue No. 15, the agents imparting a green shade. Toluene-2,5-diamine sulfate is an exemplary form of toluene-2,5-diamine. Hydroxyethyl-3,4-methylene-dioxyaniline hydrochloride is an exemplary form of hydroxyethyl-3,4-methylene-dioxyaniline. In exemplary embodiments, a concentration of toluene-2,5-diamine (e.g., toluene-2,5-diamine sulfate) in a tablet when uncoated is about 3.46 weight percents, a concentration of hydroxyethyl-3,4-methylene-dioxyaniline (e.g., hydroxyethyl-3,4-methylene-dioxyaniline hydrochloride) is about 3.43 weight percents, a concentration of HC Yellow No. 13 is about 2 weight percents, a concentration of 2,6-diamino-3-((pyridine-3-yl)azo)pyridine is about 0.025 weight percent, and a concentration of HC Blue No. 15 is about 0.025 weight percent.

In some embodiments, the color imparting agent(s) in a tablet (e.g., a tablet comprising the abovementioned excipients) consist of N,N-bis(2-hydroxyethyl)-p-phenylenediamine, 2,4-diamino-phenoxyethanol, and HC Blue No. 15, the agents imparting a blue shade. N,N-bis(2-hydroxyethyl)-p-phenylenediamine sulfate is an exemplary form of N,N-bis(2-hydroxyethyl)-p-phenylenediamine. 2,4-Diamino-phenoxyethanol dihydrochloride is an exemplary form of 2,4-diamino-phenoxyethanol. In exemplary embodiments, a concentration of N,N-bis(2-hydroxyethyl)-p-phenylenediamine (e.g., NN-bis(2-hydroxyethyl)-p-phenylenediamine sulfate) in a tablet when uncoated is about 6.2 weight percents, a concentration of 2,4-diamino-phenoxyethanol (e.g., 2,4-diamino-phenoxyethanol dihydrochloride) is about 5.05 weight percents, and a concentration of HC Blue No. 15 is about 0.2 weight percent.

In some embodiments, a composition, kit, device and/or a method of coloring as described herein utilizes some or all of the abovementioned tablets, such that the abovementioned "natural", gold, orange, red, violet, ash, rose, green and/or blue shades serve as basic shades.

In some embodiments, the solid formulations described herein are packaged in low water transmission individual packaging, in order to minimize exposure to atmospheric moisture.

Coated Formulations:

In some embodiments, the tablet further comprises a coating. Thus, in some embodiments, a solid formulation as described herein comprises a coated tablet.

As exemplified herein, a coating may surprisingly be beneficial to rapidly-disintegrating tablets as disclosed herein, although a coating may slow a rate of tablet disintegration.

The coating may have advantageous properties, such as, but not necessarily, protecting tablet ingredients (e.g., by reducing or preventing their exposure to moisture, atmospheric oxygen and/or UV light) and/or improving tablet mechanical strength of the tablet (e.g., by reducing a friability and/or increasing a hardness thereof).

Thus, in some embodiments, a coating increases a shelf life of a tablet.

In some embodiments, a coating reduces dusting. Reduction of dusting may result in a safer working environment.

Suitable coatings may optionally be selected to retain some permeability so a solvent of a medium which triggers disintegration (e.g., water-permeability), while preventing premature moisture-derived degradation.

Suitable coating materials include, but are not restricted to, polymer and co-polymer coatings such as carboxymethylcellulose (CMC), ethyl cellulose (EC), hydroxypropylcellulose (HPC), hydroxypropyl methylcellulose (HPMC), methyl hydroxyethyl cellulose (MHEC), polyethylene glycol (PEG), polyvinyl alcohol (PVA), polyvinylpyrrolidone (PVP), copolymers thereof (e.g., polyvinyl alcohol-polyethylene glycol (PVA:PEG) copolymer). Certain sugar-based coatings (e.g., xanthan:sugar) to providing similar properties may also be suitable.

Exemplary coating materials include PEG, PVA, PVA: PEG copolymer, HPMC, and xanthan:sugar.

In exemplary embodiments, the coating consists of polyvinyl alcohol and a pigment (e.g., a synthetic pigment). Kollicoat® IR coating polymer is an exemplary polyvinyl alcohol. Exemplary pigments include Pigment Green 7 (CAS No. 1328-45-6) and Pigment Yellow 73 (CAS No. 13515-40-7). An exemplary concentration of polyvinyl alcohol in the coating is about 80 weight percents, and the remainder is pigment.

In exemplary embodiments, such a coating is obtained using a coating solution consisting of the coating materials in about 95 weight percents water (e.g., with about 4 weight percents polyvinyl alcohol, and about 1 weight percent pigment).

The coating may comprise at least one excipient described herein. It is to be appreciated that a coating is a logical location for certain types of excipients (e.g., UV protecting agents).

In some embodiments, a thickness (i.e., average thickness) of the coating is in a range of from 1 μm to 100 μm. In some embodiments, an average thickness of the coating is in a range of from 5 μm to 50 μm. In some embodiments, an average thickness of the coating is in a range of from 10 μm to about 40 μm.

In some embodiments, a weight of a coating of a tablet is in a range of from 0.1 to 10 weight percents of the tablet when uncoated. In some embodiments, a weight of a coating of a tablet is in a range of from 1 to 5 weight percents of the tablet when uncoated. In some embodiments, a weight of a coating of a tablet is in a range of from 1.5 to 3.5 weight percents of the tablet when uncoated.

In some embodiments, the coating comprises at least one coloring agent. The coloring agent may be a color imparting agent described herein (e.g., a direct dye) or a coloring agent which is not particularly suitable for preparing a coloring composition.

As the coating represents a small percentage of the solid formulation, such a coloring agent in a coating will not necessarily affect a color imparted by the coloring composition formed using the solid formulation.

Thus, for example, in some embodiments, the coating coloring agent and/or a color of the coating may be of a different color than a color imparted by the color imparting agent(s) of a tablet.

In some embodiments, a coating coloring agent (and/or a color of the coating obtained with such a color imparting agent) is indicative of the color imparting agent(s), if present, in a tablet. For example, a color of the coating may be substantially the same as a color imparted by color imparting agents in the tablet, and/or a particular color (e.g., a light color) of a coating may be indicative of a tablet without a color imparting agent (e.g., a tablet comprising a bleaching agent)

In some embodiments, a tablet coating enables immediate initiation of tablet disintegration upon contact with a suitable medium.

In some embodiments, a tablet coating provides control over the timing of disintegration, for example by providing delayed disintegration. In some embodiments, such a tablet is suitable for use in combination with at least one tablet which disintegrates immediately, such that tablets can disintegrate in a pre-determined sequence. For example, selection of suitable coatings can allow tablets comprising color imparting agent(s) and/or oxidizing agent(s) to rapidly disintegrate in a medium, whereas tablets comprising alkalizing agent(s) and/or thickening agent(s) disintegrate later in the same medium.

In another example, a delayed thickening of a medium can be achieved by using thickening tablets wherein the viscosity modifying agent is released in non-viscous pre-form which is later "activated" to its viscous form using a delayed disintegration alkalizing tablet. Activation may be by providing a pH suitable for the thickening of the medium, in addition to the pH of the coloring process.

Hardness of a solid formulation is a measure of mechanical strength measured as the compressive pressure of fracture, which can be measured, for example, using standard industry tablet hardness testing machines.

In some embodiments, a hardness of a solid formulation is selected to be suitable for one or more intended purposes of the formulation, which may include for example: a) to sustain coating conditions; b) to sustain handling and storing conditions; c) to sustain dispensing conditions; and/or d) to enable disintegration.

Therefore, increase or decrease in hardness values between subsequent steps from the manufacturing process to end-use can be acceptable, as long as the hardness at to each step serves its purpose and the final hardness of a tablet at the point of use is compatible with the selected conditions (e.g., dispensing conditions).

In some embodiments, a hardness of a tablet when uncoated which is sufficient to prevent undesired tablet fracture and withstand the coating process (if the tablet is coated) is of at least 1.0 kgf. In some embodiments, a hardness of an uncoated tablet is in a range of from 1.0 kgf to 6.0 kgf. In some embodiments, a hardness of an uncoated tablet is in a range of from 3.0 kgf to 5.0 kgf.

Without being bound by any particular theory, it is believed that excessively high hardness of a tablet when uncoated may be associated with a low porosity, which may be detrimental to tablet disintegration.

In embodiments, wherein tablets are not further coated, the hardness of the uncoated tablets should be compatible with their later handling, storing and dispensing.

In embodiments wherein tablets are coated, hardness after coating is related to the tablet hardness before coating, and depends upon a variety of factors including, for example, the type of coating, the coating thickness, the storage conditions and the storage duration.

In some embodiments, a hardness of a coated tablet is in a range of from 2.0 kgf to 8.0 kgf.

Solid Formulation Properties:

Solid formulations described herein may be characterized by a short disintegration time, for example, in deionized water and/or an aqueous solution of hydrogen peroxide. Measurement of disintegration times may be performed as described in the Examples section.

In some embodiments, a disintegration time of a solid formulation in deionized water is no more than 3 minutes. In some embodiments, a disintegration time of a solid formulation in deionized water is no more than 2 minutes. In some embodiments, a disintegration time of a solid formulation in deionized water is no more than 1 minute, and can even last a few seconds (e.g., from 3 to 30 seconds).

In some embodiments, a disintegration time of a solid formulation in an aqueous solution of hydrogen peroxide (9%) is no more than 5 minutes. In some embodiments, a disintegration time of a solid formulation in an aqueous solution of hydrogen peroxide (9%) is no more than 4 minutes. In some embodiments, a disintegration time of a solid to formulation in an aqueous solution of hydrogen peroxide (9%) is no more than 3 minutes.

In some embodiments, exemplary solid formulations as described herein disintegrate in an aqueous solution of hydrogen peroxide (6%) within a few seconds (see, FIGS. 9A-B).

In some embodiments, a friability of a tablet (determined as described herein) is no more than 0.5%. In some embodiments, a friability of a tablet (determined as described herein) is no more than 0.37%.

Herein, friability of tablets is determined by measuring weight loss upon rotating tablets 25 times at a speed of 25 rotations per minute, using a friability test apparatus (e.g., a Thermonik Campbell Electronics FTA-20), as described in the Examples section herein.

In some embodiments, the tablets exhibit an increase in weight of less than 3%, upon storage for one month under open air, at a relative humidity of 52%, and a temperature of 22.8° C. In some embodiments, the tablets exhibit an increase in weight of less than 2%.

In some embodiments, wherein a tablet comprises a coating, and the coating has a color (e.g., a color other than white), the coating color does not visibly fade upon receiving 3 months of direct sunlight. In some embodiments, the coating color does not visibly fade upon receiving 6 months of direct sunlight.

Exposure to direct sunlight may be performed as described herein in the Examples section. It is to be understood that direct sunlight for a given time period of time may be simulated, that is, exposure to an amount of light which is equivalent to direct sunlight for such a time period, as exemplified herein.

Herein, "visibly fade" refers to fading which is noticeable to an average human observer.

As exemplified herein, the tablets described herein remain substantially free of microbiological contamination for at least 3 weeks, at least 10 weeks, and even at least 24 weeks, when stored under suitable (but not particularly demanding) conditions (e.g., dry conditions).

Thus, in some embodiments, the solid formulation tablets are substantially free to of microbiological contamination, for example, microbiological contamination is at a level of less than 10 colony forming units/gram formulation.

The number of colony forming units may be determined as described in the Example section herein.

In some embodiments, the tablets exhibit at least two of the abovementioned properties (i.e., a disintegration time in water as described herein, a disintegration time in aqueous hydrogen peroxide as described herein, a friability as described herein, a minimal weight increase upon storage as described herein, a coating color stability as described herein, and/or an absence of microbiological contamination as described herein). In some embodiments, the tablets exhibit at least three of the abovementioned properties. In some embodiments, the tablets exhibit at least four of the abovementioned properties. In some embodiments, the tablets exhibit at least five of the abovementioned properties. In some embodiments, the tablets exhibit all six of the abovementioned properties.

For example, a disintegrating tablet comprising an alkalizing agent, oxidizing agent, and/or thickening agent may consist largely of the active agent therein, in a dry form, if the active agent exhibits suitable properties (e.g., solubility). Thus, the active agent may comprise at least 50 weight percents, at least 60 weight percents, at least 70 weight percents, at least 80 weight percents, at least 90 weight percents, and even 100 weight percents of such a tablet.

In some embodiments, a disintegrating tablet is prepared from ammonium carbonate and/or bicarbonate (alkalizing agent).

In some embodiments, a disintegrating tablet is prepared from silicic acid (thickening agent).

In some embodiments, a disintegrating tablet is prepared from an oxidizing salt such as a periodate, a perbromate, a perborate, a percarbonate, a perphosphate, a persulfate, and/or a percarbamide (oxidizing agents).

In some embodiments, the solid formulation is suitable for use in coloring human hair, e.g., by being suitable for preparing a coloring composition suitable for coloring human hair.

In such formulations, ingredients are selected so as to be cosmetically to acceptable, at least in the amounts used in such a coloring composition. The acceptability of ingredients can be readily determined by those of skill in the cosmetic arts, for example, based on determinations of a regulatory agency, and such information is updated regularly.

When intended for human use, the color-imparting agents and the other ingredients or additives of the compositions described herein should fulfill the safety requirements applicable to such cosmetic products. In particular, the ingredients are selected for their compatibility with one another and for their lack of toxicity to the hair and scalp. When applicable, the tablet or media constituents can be salt or solvate derivatives of the above-listed parent compounds and, for example, the color imparting agents may be used in the form of cosmetically acceptable salts or solvates of the parent dye.

The term "cosmetically acceptable", as used herein, refer to constituent ingredients, including the color imparting agents, their salts and/or solvates, that are safe and effective for topical use in mammals, in particular in humans, and that possess or are compatible with the desired coloring activity, are considered as safe, and do not cause undue toxicity, irritation, allergic reaction and the like. Such regulatory information is updated from time to time and readily available.

Cosmetically acceptable salts include salts of acidic or basic groups. Cosmetically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate salts. Certain compounds of the invention can form cosmetically acceptable salts with various amino acids. Suitable base salts include, but are not limited to, aluminum, calcium, lithium, magnesium, potassium, sodium, zinc, and diethanolamine salts. Cosmetically acceptable solvates include, but are not limited to, hydrates, ethanolates and methanolates.

As a solid formulation should be suitable for preparing a coloring composition, it is to be appreciated that the ingredients of a solid formulation, as a whole, should be suitable for preparing a given coloring composition, for example, a composition to comprising a particular medium (e.g., a solvent, a cream, a gel). Thus, in some embodiments, all ingredients are selected to be suitable for use in combination with the same medium of a coloring composition.

Process of Preparing Solid Formulations:

Solid formulations as described herein may be prepared in a tablet form by compression techniques.

Hence, according to another aspect of embodiments of the invention, there is provided a method of preparing a solid formulation described herein. The method comprises forming a mixture comprising at least one superdisintegrant and at least one active agent to be included in the solid formulation (e.g., as described herein); and compressing the mixture to thereby form the tablet described herein. In some embodiments, the mixture comprises all ingredients to be included in the tablet when uncoated (e.g., ingredients described herein).

For example, in direct compression tabletting, a measured volume of a mixture fills a die. Then a lower punch and an upper punch uniaxially compress the mixture within the die.

In some embodiments, the ingredients, or a portion of the ingredients, are provided as dry powders.

In some embodiments, the ingredients, or a portion of the ingredients, are ground and/or granulated before being mixed and compressed to form the tablets described herein. Tablet ingredients can be granulated by any granulating method known in the art. In some embodiments, granulation is by dry granulation.

As known in the art of tablet-pressing, it is advantageous for all ingredients be somewhat uniform in bulk density to avoid ingredient segregation during the tabletting process. When ingredients have similar material densities, approximate size uniformity of the ingredients' particles ensures that homogeneous concentrations and doses are delivered with each tablet. In some embodiments, such approximate size uniformity is obtained by grinding (e.g., by cutter milling, hammer milling, etc.) and/or by sieving.

In some embodiments, ingredients are provided as free-flowing powders, for example, in order to ensure uniform tablet weight.

In some embodiments, a size of the particles in the mixture is generally below to 200 µm. Thus, in some embodiments, at least 70 weight percents of the particles in the mixture have a diameter of 200 µm or less. In some embodiments, at least 80 weight percents of the particles in the mixture have a diameter of 200 µm or less. In some embodiments, at least 90 weight percents of the particles in the mixture have a diameter of 200 µm or less.

In some embodiments, a size of the particles in the mixture is generally in a range of from 20 µm to 150 µm. Thus, in some embodiments, at least 70 weight percents of the particles in the mixture have a diameter in a range of from 20 µm to 150 µm. In some embodiments, at least 80 weight percents of the particles in the mixture have a diameter in a range of from 20 µm to 150 µm. In some embodiments, at least 90 weight percents of the particles in the mixture have a diameter in a range of from 20 µm to 150 µm.

In some embodiments, a size of the particles in the mixture is generally in a range of from 40 µm to 120 µm. Thus, in some embodiments, at least 70 weight percents of the particles in the mixture have a diameter in a range of from 40 µm to 120 µm. In some embodiments, at least 80 weight percents of the particles in the mixture have a diameter in a range of from 40 µm to 120 µm. In some embodiments, at least 90 weight percents of the particles in the mixture have a diameter in a range of from 40 µm to 120 µm.

In some embodiments, a size of the particles of color imparting agent in the mixture is generally below 200 µm. Thus, in some embodiments, at least 70 weight percents of the particles of color imparting agent in the mixture have a diameter of 200 µm or less. In some embodiments, at least 80 weight percents of the particles of color imparting agent in the mixture have a diameter of 200 µm or less. In some embodiments, at least 90 weight percents of the particles of color imparting agent in the mixture have a diameter of 200 µm or less.

In some embodiments, a size of the particles of color imparting agent in the mixture is generally in a range of from 20 µm to 150 µm. Thus, in some embodiments, at least 70 weight percents of the particles of color imparting agent in the mixture have a diameter in a range of from 20 µm to 150 µm. In some embodiments, at least 80 weight percents of the particles of color imparting agent in the mixture have a diameter in a range of from 20 µm to 150 µm. In some embodiments, at least 90 weight percents to of the particles of color imparting agent in the mixture have a diameter in a range of from 20 µm to 150 µm.

In some embodiments, a size of the particles of color imparting agent in the mixture is generally in a range of from 40 µm to 120 µm. Thus, in some embodiments, at least 70 weight percents of the particles of color imparting agent in the mixture have a diameter in a range of from 40 µm to 120 µm. In some embodiments, at least 80 weight percents of the particles of color imparting agent in the mixture have a diameter in a range of from 40 µm to 120 µm. In some embodiments, at least 90 weight percents of the particles of color imparting agent in the mixture have a diameter in a range of from 40 µm to 120 µm.

Some ingredients may be commercially available as particles within a desired size range. Others may optionally be sieved to reduce the amount of undersized or oversized particles. If needed, certain ingredients may optionally be pre-ground with any suitable grinding machine available, and optionally further sieved to achieve the desired uniformity. The ingredients, whether or not ground and/or sieved, may optionally then be mixed to form a mixture suitable for the manufacture of homogeneous formulations. Certain ingredients may be subject to safety regulations, and any process employing such ingredients should be carried out with all due care. For example, some color imparting agents may be toxic, if inhaled, and should be handled accordingly in any process involving dust formation.

In some embodiments, the process or processes involved in the preparation of tablets according to the invention are performed in dry conditions. In some embodiments, dry conditions comprise a relative humidity of less than 20%. In some embodiments, dry conditions comprise a relative humidity of less than 10%. In some embodiments, dry conditions comprise a relative humidity of less than 5%. In some embodiments, dry conditions comprise a relative humidity of less than 2%.

Generally, the greater the pressure applied during compression the harder the tablet produced. As discussed herein, tablets described herein should to be hard enough to provide the mechanical strength required to maintain their integrity, for instance during manufacture, storage, transport and handling, while being friable enough to allow their disintegration upon contact with an appropriate medium. Compression pressure may optionally be controlled, for example, by the final closure distance to between the punches.

In some embodiments, compressing is performed under conditions (e.g., compression pressure) which result in the tablet having a hardness described herein (for an uncoated tablet).

The tablet geometry is determined by the shape of the punches, the volume of the die and the position of the punches in relation to each other during compression.

In some embodiments, the aforementioned parameters are selected so as to provide a tablet geometry described herein.

In some embodiments, spheroid tablets (e.g., as described herein) are prepared by direct-compression tabletting using a "modified ball" tablet punch having a rounded concave punch shape, and by selecting a proper compression force/pressure. At a given compression pressure, a tablet thickness similar to the punch diameter can be achieved providing for tablets having a close to spherical shape.

A lower compression pressure would be suitable for the preparation of elongated capsules, whereas a higher compression pressure would be suitable for the preparation of flattened tablets.

In some embodiments, the process further comprises coating the tablet obtained by compression (e.g., to obtain a coating described herein).

There are several suitable methods of tablet coating known in the art, for example, dry coating, film coating, fluid bed coating, perforated and non-perforated pan coating, Wurster coating, solid wall pan coating, "Sugar coating", and top coating. Any method that can be used to coat an uncoated tablet described herein (e.g., an uncoated tablet characterized by a hardness described herein) and would result in a coated tablet described herein (e.g., a coated tablet characterized by a hardness described herein) is suitable.

In some embodiments, agents used to form coatings are suspended or dissolved in a suitable liquid. Suitable liquids include water, polyhydric alcohols (such as ethylene glycol, propylene glycol and glycerin), ethyl acetate, methylene dichloride, oils (including natural or synthetic oils, such as plant oils, paraffin and silicone oils), and combinations thereof. Selection of a suitable solvent for suspending or dissolving a coating agent is within the capabilities of persons skilled in the art of tablet coating.

In some embodiments, water is the predominant solvent of the liquid, and other to liquids (e.g., alcohols, oils), if used, are in an amount sufficient to improve the miscibility of a coating agent.

In some embodiments, lower aliphatic alcohols (e.g., methanol, ethanol, and propanol) and ketones (e.g., acetone and butanone) are used as solvent.

An exemplary coating method for tablets of the invention comprises spray coating using a perforated pan spray coater. In such a coating method, a spray gun(s) applies a coating to the tablets at a desired flow rate of coating solution and pattern of propelling gas while the pan rotates, ensuring the tablets are coated evenly.

In some embodiments, the tablets are concurrently dried by heated gas (usually air), for example, blown from an upper duct through the pan which exits through the pan perforations.

The temperature of the heated air may optionally be controlled by an inlet gas temperature control. The temperature may optionally be monitored at the level of the exhaust duct below the product bed. In some embodiments, the tablets are assumed to be at about the same temperature as measured at the exhaust.

In some embodiments, coating quality is improved by performing anti-dusting and/or tablet pre-heating steps before the previously described coating process.

Without being bound by ant particular theory, it is believed that the perforated pan coating method described herein is advantageous due to a short exposure of the tablets to the coating solution, which is a result of continuous heating and drying. The short exposure is believed to enhance stability of the core of the tablet, especially of reactive ingredients therein.

In exemplary embodiments, the process further comprises drying the tablet. In an exemplary embodiment, drying is effected in a vacuum oven.

In some embodiments, drying is effected at a temperature of 30-80° C. (e.g., 40° C.), under reduced pressure (of e.g., 15 mbar).

In some embodiments, dying is effected during a time period of at least 10 hours (e.g., about 20 hours).

Tablets may optionally be dried when coated or when uncoated. In an exemplary process, coated tablets are dried.

As exemplified herein, drying (e.g., as described herein) may reduce a water content of a tablet to less than 3 weight percents, and even to less than 2 weight percents or less than 1 weight percent.

In some embodiments, the process further comprises sublimation (e.g., freeze drying of tablet ingredients), which may optionally promote dissolution or disintegration.

Compositions:

The rapidly-disintegrating tablets (both coated and uncoated) disclosed herein can be advantageously used for forming compositions for treating keratinous fibers. The composition can be, for example, a coloring composition or any composition useful in a coloring process of keratinous fibers, as defined herein.

According to another aspect of embodiments of the invention, there is provided a composition suitable for use in treating keratinous fibers. The composition comprises an aqueous medium and at least one of the solid formulations as described herein disintegrated in the medium.

Herein, the phrase "aqueous medium" encompasses water, aqueous solutions and aqueous suspensions.

Herein, the phrase "aqueous solution" refers to a solution in which more than 50 weight percents of the solvent consists of water. The remainder of the solvent may be, for example, a water-miscible co-solvent. Examples of suitable co-solvents in an aqueous solution include lower aliphatic alcohols (e.g., ethanol, propanol and isopropanol), and polyhydric alcohols (e.g., ethylene glycol, propylene glycol and glycerine), and combinations thereof.

Herein, the phrase "aqueous suspension" refers to a suspension wherein the continuous phase is water or an aqueous solution (as defined herein). Examples of an aqueous suspension include oil-in-water emulsions (e.g., creams), aqueous gels, and aqueous suspensions of surfactants (e.g., surfactant micelles in an aqueous solution).

Examples of suitable oils for inclusion in aqueous media (e.g., in oil-in-water emulsions) include natural or synthetic oils, such as plant oils, paraffin and silicone oils), and combinations thereof.

Examples of surfactants which may be included in aqueous media include soap (e.g., ammonium or potassium oleate), and oxyethylenated non-ionic surfactants (such to polyalkoxylated or polyglycerolated fatty alcohols).

The aqueous medium may further comprise at least one active agent described herein, that is, an active agent which is not derived from disintegration of a tablet.

In some embodiments, the aqueous medium comprises at least one oxidizing agent (e.g. as described herein), such that the medium is an oxidizing medium.

In some embodiments, the aqueous medium comprises at least one alkalizing agent (e.g. as described herein), such that the medium is an alkalizing medium.

In some embodiments, the aqueous medium comprises at least one thickening agent (e.g. as described herein), such that the medium is a thickening medium.

In some embodiments, the aqueous medium comprises at least one color imparting agent (e.g. as described herein), such that the medium is a color imparting medium.

In some embodiments, the aqueous medium comprises at least one oxidizing agent (e.g. as described herein) and at least one alkalizing agent (e.g., as described herein), such that the medium is an oxidizing medium and an alkalizing medium.

In some embodiments, the aqueous medium comprises at least one oxidizing agent (e.g. as described herein) and at least one thickening agent (e.g., as described herein), such that the medium is an oxidizing medium and a thickening medium.

In some embodiments, the aqueous medium comprises at least one alkalizing agent (e.g. as described herein) and at least one thickening agent, such that the medium is an alkalizing medium and a thickening medium.

In some embodiments, the aqueous medium comprises at least one oxidizing agent (e.g. as described herein), at least one alkalizing agent (e.g., as described herein), and at least one thickening agent (e.g., as described herein).

In some embodiments, the composition comprises at least one color imparting agent. Such a composition is referred to herein as a coloring composition. The color imparting agent(s) may be a component of the aqueous medium (e.g., a color imparting medium) or a component of a solid formulation (e.g., as described herein).

In some embodiments, the solid formulation comprises at least one color imparting agent as an active agent (e.g., as described herein). In some embodiments, to the composition further comprises at least one additional active agent which is an alkalizing agent, oxidizing agent and/or thickening agent (e.g., as described herein). The alkalizing agent(s), oxidizing agent(s) and/or thickening agent(s) may be a component of the aqueous medium (e.g., an alkalizing medium, oxidizing medium, and/or thickening medium described herein) and/or a component of a solid formulation (e.g., as described herein).

In some embodiments, the composition comprises at least one solid formulation comprising at least one color imparting agent disintegrated in an aqueous medium comprising at least one additional active agent which is an alkalizing agent, oxidizing agent and/or thickening agent (e.g., an alkalizing medium, oxidizing medium, and/or thickening medium described herein).

In some embodiments, such a composition is suitable for use in coloring human hair (e.g., as described herein).

As the composition comprises a disintegrated solid formulation as described herein, it is to be appreciated that the composition will comprise substantially all of the ingredients of the solid formulation (e.g., excipients, superdisintegrants, disintegration auxiliary agents), as described herein.

The composition may be, for example, a composition prepared according to any method described hereinbelow.

Each active agent in the composition may result from disintegration of a solid formulation comprising that active agent (e.g., a solid formulation described herein) or be added to the composition from a different source, such as a solid (e.g., a powder), a liquid medium (e.g., a medium described herein), etc.

In some embodiments, the composition comprises a plurality of disintegrated tablets (e.g., tablets comprising color imparting agent(s), tablets comprising oxidizing agent(s), tablets comprising alkalizing agent(s), and/or tablets comprising thickening agent(s)), the plurality of tablets being customized for coloring hair of an individual subject.

In some embodiments, the aqueous medium is customized for coloring hair of an individual subject. For example, the type of active agent(s) in the aqueous medium and concentration(s) thereof may be customized for an individual.

For example, the tablets and/or medium may be selected so as to take into to account the initial hair color of an individual, which may be affected by natural pigmentation, hair reflectance, previous coloring, and/or other chemical agents present in or on hair, and the final color desired by an individual (e.g., color imparting agents are selected so as to achieve the desired color beginning from the initial color; the type of hair of an individual (e.g., European, Asiatic, African, etc.; straight, wavy, curly, or kinky; thin or coarse; dry, normal or oily); a desired type of coloring process, for example, permanent coloring, semi-permanent coloring, demi-permanent coloring, temporary coloring, and/or decoloring (e.g., bleaching); and/or any sensitivities of an individual (e.g., avoiding or minimizing components to which an individual is allergic or otherwise sensitive to). Customizing based on an initial color and a desired color may be performed based on an analysis of how to go from an initial color to a desired color, as described herein (see, for example, Section I).

It is to be appreciated that the aforementioned types of coloring process may use different types of color imparting agent (if any), and/or amounts of alkalizing agent, as described herein.

In some embodiments, a viscosity of the composition is suitable for providing sufficient time of contact between the composition and the fibers to be colored, as described herein.

Viscosity may depend on many components in the composition, including components in the aqueous medium and/or components in one or more disintegrated tablets.

In some embodiments, viscosity is determined primarily by an amount of thickening agent(s). In some embodiments, the thickening agent(s) is released from a disintegrating tablet.

In some embodiments of the various aspects of embodiments of the invention (e.g., methods, devices, kits described herein), a disintegrating tablet comprising an active agent described herein is not necessarily a disintegrating tablet according to embodiments of the invention (e.g., comprising a superdisintegrant as described herein).

A coloring composition as described herein, or any other composition for treating keratinous fibers as described herein, can have a final form of liquid (e.g., an aqueous solution), a cream, a gel, a lotion, an emulsion, a paste, and any other acceptable forms in the field of hair coloring. The final form is determined as desired, be selecting suitable ingredients and concentrations thereof (e.g., a thickening agent).

Kits:

Solid formulations in a tablet form, as described herein, are highly useful for coloring keratinous fibers, particularly when different active agents described herein are used in combination, for example, by using different solid formulations described herein in order to provide some or all of the active agents desirable for coloring.

In addition, solid formulations in tablet form which comprise at least one color imparting agent, as described herein, are particularly useful in combinations comprising solid formulations with different color imparting agents. Such tablets can then be combined to provide a desired coloring composition.

Thus, in another aspect of embodiments of the invention, there is provided a kit for coloring keratinous fibers, the kit comprising a plurality of sets of a solid formulation described herein. Each set consists of a plurality of substantially identical tablets differing in type of active agent and/or amount of active agent. Such sets may include, for example, one or more sets of tablets comprising at least one color imparting agent, one or more sets of tablets comprising at least one oxidizing agent, one or more sets of tablets comprising at least one alkalizing agent, and/or one or more sets of tablets comprising at least one thickening agent.

In some embodiments, at least a portion of the sets in the kit consist of solid formulations comprising at least one color imparting agent (e.g., as described herein).

In some embodiments, each of the sets in the kit consists of solid formulations comprising at least one color imparting agent (e.g., as described herein).

The color imparting agents of each set represent a "basic shade", as defined herein.

In some embodiments, the kit comprises at least 3 basic shades. In some embodiments, the kit comprises at least 4 basic shades. In some embodiments, the kit comprises at least 5 basic shades. In some embodiments, the kit comprises at least 6 basic shades. In some embodiments, the kit comprises at least 7 basic shades. In some embodiments, the kit comprises at least 8 basic shades. In some embodiments, the kit comprises at least 10 basic shades. In some embodiments, the kit comprises at least 15 basic shades. In some embodiments, the kit comprises at least 20 basic shades.

In some embodiments, the number of basic shades in a kit is in a range of from 3 to 36. In some embodiments, the number of basic shades in a kit is in a range of from 3 to 24. In some embodiments, the number of basic shades in a kit is in a range of from 6 to 18.

In some embodiments, the color imparting agents of the different basic shades in a kit are selected so as to be sufficiently different from one another so as to allow a large number of shades to be obtained by combination of basic shades in different proportions.

In some embodiments, the kit further comprises at least one set of solid formulations which does not comprise a color imparting agent (e.g., in addition to the basic shades). Such a set(s) may comprise, for example, at least one active agent other than a color imparting agent (e.g., alkalizing agent(s), oxidizing agent(s) and/or thickening agent(s)). In some embodiments, at least one set comprises an alkalizing agent as an active agent. In some embodiments, the set comprising an alkalizing agent is in addition to one or more sets for basic shades, as described herein.

In some embodiments, the sets of solid formulations in a kit are customized for coloring hair of an individual subject. The kit may be customized for a particular coloring process to be performed by an individual (e.g., a kit for coloring hair once, or a kit for performing the same coloring process multiple times), and/or for a plurality of different coloring processes which may be performed by an individual (e.g., a kit for coloring hair multiple times).

For example, the sets may be selected so as to take into account the initial hair color of an individual (e.g., basic shades may be deficient in shades close to the hair color of the individual), which may be affected by natural pigmentation, hair reflectance, previous coloring, and/or other chemical agents present in or on hair; the final color(s) desired by an individual (e.g., basic shades may be biased towards shades preferred by the individual); the type of hair of an individual (e.g., European, Asiatic, African, etc.; straight, wavy, curly, or kinky; thin or coarse; dry, normal or oily); a desired type of coloring process (e.g., permanent coloring, semi-permanent coloring, demi-permanent coloring, temporary coloring, and/or bleaching); and/or any sensitivities of an individual to (e.g., avoiding or minimizing components to which an individual is allergic or otherwise sensitive to). Customizing the basic shades based on an initial color and a desired color may be performed based on an analysis of how to go from an initial color to a desired color, as described herein.

In some embodiments, the sets of solid formulations are selected to be universal, that is they are intended to be as useful as possible to a wide variety of people with different needs (e.g., needs such described herein).

In some embodiments, the kit includes written or otherwise readable instructions describing how to obtain a desired color, for example, how to select basic shades and/or other active agents, how many tablets of each basic shade and/or other active agents to include in a composition, how to mix the basic shades with other active agents (e.g., tablets and/or media comprising active agents), and how to apply (e.g., for how long to apply) the obtained coloring composition.

Such instructions can be in a form of color coordinates or can be provided to an individual upon analyzing a hair of an individual and converting the analysis into the desired color coordinates. In some embodiments, analysis is made by means of an optical reader as described herein. In some embodiments, determining the coloring composition is made by means of the algorithmic methods as described herein.

In some embodiments, the kit further comprises a medium suitable for preparing a coloring composition (e.g., as described herein). The medium may optionally be included in the kit enclosed in a vessel recipient. In some embodiments, the medium is an aqueous medium.

In some embodiments, the medium is an oxidizing medium (e.g., an oxidizing medium described herein), that is, a medium comprising an oxidizing agent (e.g., an oxidizing agent described herein). Such a medium is particularly suitable, for example, when the kit does not include solid formulations comprising such an oxidizing agent.

In some embodiments, the medium is an alkalizing medium (e.g., an alkalizing medium described herein), that is, a medium comprising an alkalizing agent (e.g., an alkalizing agent described herein). Such a medium is particularly suitable, for example, when the kit does not include solid formulations comprising such an alkalizing agent.

In some embodiments, the medium is a color imparting medium (e.g., a color to imparting medium described herein), that is, a medium comprising at least one color imparting agent (e.g., color imparting agent(s) described herein). Such a medium is particularly suitable, for example, when the kit does not include solid formulations comprising such a color imparting agent(s).

In some embodiments, the medium is a carrier medium, that is, a medium which does not comprise a substantial amount of an oxidizing agent, color imparting agent, or alkalizing agent. In some embodiments, the carrier medium does not comprise a substantial amount of any active agent described herein. In some such embodiments, the kit comprises solid formulations comprising oxidizing agent(s), color imparting agent(s) and alkalizing agent(s).

In some embodiments, the medium is suitable for disintegration of the tablets of the kit (e.g., all the tablets in the kit).

In some embodiments, a viscosity of the medium is selected to be suitable for forming a composition for coloring by disintegrating the tablets in the medium. In some embodiments, an aqueous medium in the kit has a viscosity of 1 poise or less (as measured at a shear rate of 10 $s^{-1}$ and at a temperature of 25° C.).

In some embodiments, an alkalizing medium, a color imparting medium and/or an oxidizing medium in a kit is in a ready-to-use form, e.g., with respect to a concentration of active agent compatible with the type of coloring desired.

In some embodiments, an alkalizing medium, a color imparting medium and/or an oxidizing medium in a kit is provided as a high-concentration stock, which may be diluted to a desired concentration with suitable amounts of carrier medium. In some embodiments, such a carrier medium for dilution is included in the kit. In some embodiments, such a carrier medium for dilution is not included in the kit (e.g., where the carrier medium for dilution is water).

The rapidly disintegrating tablets described herein, when used for the preparation of a (customized) composition for treating keratinous fibers, can be measured and, when desired, mixed with the appropriate media, for providing a desired composition, as described herein. Selecting the type and amount of each active agent in the composition, whether the active agent is in a form of a tablet solid formulation or in any other form, measuring a desired amount and mixing, of desired, can be made manually or automatic ally.

In most cases, automation of dispensing desired sets of tablets or of single use custom hair coloring formulae at point-of-purchase or point-of-use is advantageous. Automated dispensing devices have various advantages. For example, automated dispensing devices can afford increased control over dosing accuracy and reproducibility, can rapidly prepare customized coloring preparations, and facilitate the introduction of computerized systems for color customization.

The use of tablets instead of traditional wet forms is generally advantageous since it saves storage space, allows for a cleaner working environment and improves the dosability of the color imparting agents, hence the accuracy and reproducibility of coloring formulae. Space saving can be further increased by having the relevant media in the form of rapidly disintegrating tablets.

The use of coated tablets and their free flowing nature facilitate their use within an automated or manual dispensing device during dispensing. The use of coated tablets significantly reduces the contact of coloring agents with internal portions of a dispensing device, minimizing the "contamination" of such parts by previously dispensed sets of coloring tablets, which can affect coloring formulae accuracy.

IV. The Dispensing Device:

The present inventors have designed a dispensing device for automatically dispensing a desired set of tablet formulation, to thereby produce a composition and/or a kit for treating keratinous fibers.

Although tablet dispensers are known in the field of pharmaceuticals, none were intended to mix specific amounts of various types of tablets on a customized basis and therefore this particular problem was not previously addressed.

In some embodiments, the dispensing device is designed to be suitable for providing customized compositions for treating keratinous fibers and in some embodiments, k for providing customized coloring composition (e.g., hair coloring composition). The device is able to dispense different combinations and quantities of tablet formulations such as those described herein, which can optionally be used in combination with any additional media and/or agents as described herein for forming a to coloring composition. The device can further be able to dispense both tablet formulations and liquid media or formulations for forming customized coloring composition.

According to an aspect of some embodiments of the present invention there is provided a device for preparing a composition for treating keratinous fibers, as described herein, whereby the composition is formed from a plurality of tablets. The device is configured such that it comprises a plurality of containers, or compartments, at least some of the compartments or containers have an outlet suitable for dispensing a solid formulation in a form of a tablet; and a dispensing unit configured for dispensing a pre-determined amount of tablets, the compartments or containers and the dispensing unit being attachable to one another.

By "being attachable" it is meant that the containers and the dispensing unit are in communication in a way that allows tablets to flow out of the container and to be dispensed through the dispensing unit. The dispensing unit and the containers and/or compartments can be attached to one another either directly or indirectly.

Thus, a device, according to embodiments of the present invention, is configured to be suitable for dispensing tablets, and may optionally be configured for dispensing solid formulations in a form other than tablets (e.g., powder or granules) and/or for dispensing liquid formulations (e.g., aqueous media or solutions), in addition to dispensing tablets.

In some embodiments, only of a portion of the containers in the dispensing device are containers suitable for containing and dispensing tablets. In some embodiments, all of the containers in the dispensing device are suitable for containing and dispensing tablets.

Those containers that are configured suitable for containing and dispensing tablets are referred to herein as tablet containers.

In the following, the term container may refer to an individual separate container or to an individual compartment within a multi-compartmented container, unless otherwise clear from context.

The Tablet Containers:

In some embodiments, each of the containers or compartments in the dispensing to device comprises a base, one or more walls, and a top. Each container, or individual compartment as described below, further comprises a container outlet. Tablet containers further comprise an outlet that is configured so as to allow tablets to be dispensed from the container. The outlet can be located on the container at any position suitable for the dispensing means (also referred to as dispensing element). When dispensing involves gravitational displacement of the content of the container (e.g., of tablets), the outlet via which tablets can be dispensed is preferably located on the container base.

Typically, the central axis (base to top) of the container is vertical, but deviations of up to 45° are possible as long as the selected angle of deviation of the container from verticality does not significantly affect the intra-container flow of tablets from the body of the container to the dispenser element. In some embodiments, only part of the container may deviate from typical horizontal and vertical orientations. For example, the base of the container, or part thereof, may be sloped (e.g., to improve flow toward the container outlet) thus departing from horizontally, whereas the walls are essentially vertical.

The base, wall(s) and top of a container may form an integral part or may remain separable. Sections of the wall(s) or the top of the tablet container can be movable or removable (e.g., hinged, screwed, slidable, pluggable, etc.) to allow re-filling of the container with tablets. This alternative is particularly suitable when the containers are non-reversibly attached to a platform, as described hereinafter. In addition, the container may comprise sections of different transparency or opacity levels. For example the container can be for most of its surface non-transparent, with one transparent "window" on top or along the walls allowing visual monitoring of the contents of the container and the level of tablets therein. Alternatively, most parts of the containers can be transparent.

In some embodiments of the invention, one or more of the tablet containers further comprise a desiccant, aimed at reducing the humidity of the environment inside the container. In some embodiments, the desiccant is enclosed within a suitable housing. In some embodiments, the desiccant is encapsulated or sachet packed in any permeable material allowing its activity, as standard in the field of desiccation.

The desiccant can be placed within the container or be attached by any suitable to means to the top of the container and/or to its walls, as long as the position of the desiccant does not affect the flow of tablets.

Alternatively and in addition, one or more desiccants can be located in other parts of the device suitable to reduce the extent to which the tablets are exposed to moisture, as long as the positioning of the desiccant housing does not impede tablet flow. A container comprising a desiccant is schematically illustrated in FIG. 6.

Suitable desiccants include, but are not limited to, silica gel, calcium sulfate, calcium chloride, potassium chloride, montmorillonite clay, activated alumina, and molecular sieves (such as aluminosilicate minerals, clays, microporous charcoals, zeolites, active carbons, or synthetic compounds). The containers to be used in the dispensing device can have any suitable shape which enables free intra-container motion of the tablets. Suitable horizontal cross sections of a container include any regular form such as a circle, an ellipse, a square, a rectangle, an oblong, a triangle or a polygon. Less regular or irregular cross sections may also be suitable as long as they are appropriate for the selected dispensing element and compatible with attachment of the containers to the dispensing means. For instance, containers having an approximate triangular cross-section with a convex face could fit like slices of a pie to form together an approximately cylindrical shaped conglomeration of containers.

Figure 5:
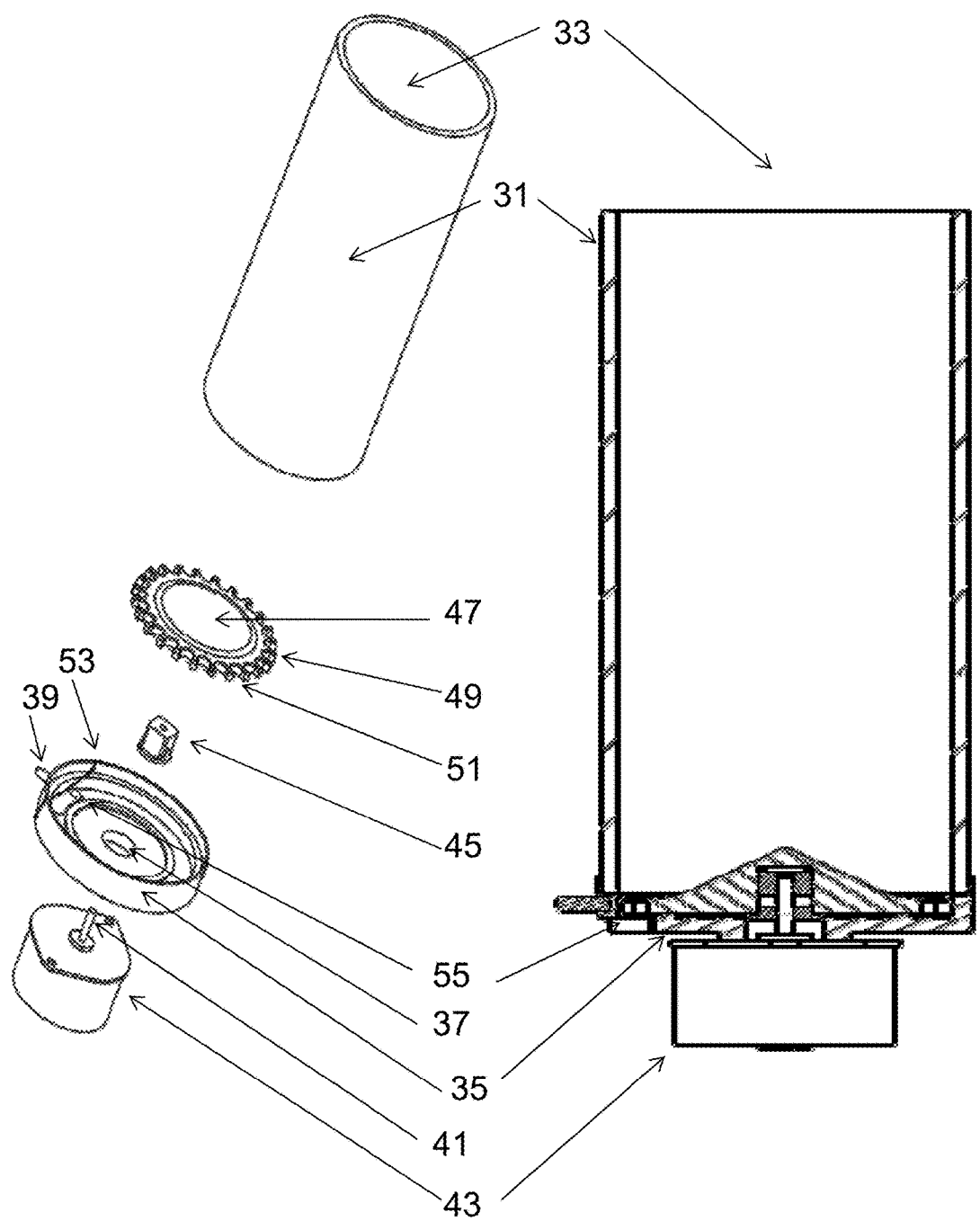
FIG. 5 shows an exploded view and a cross section view of a container and a dispenser element according to exemplary embodiments of the invention.
Figure 6:
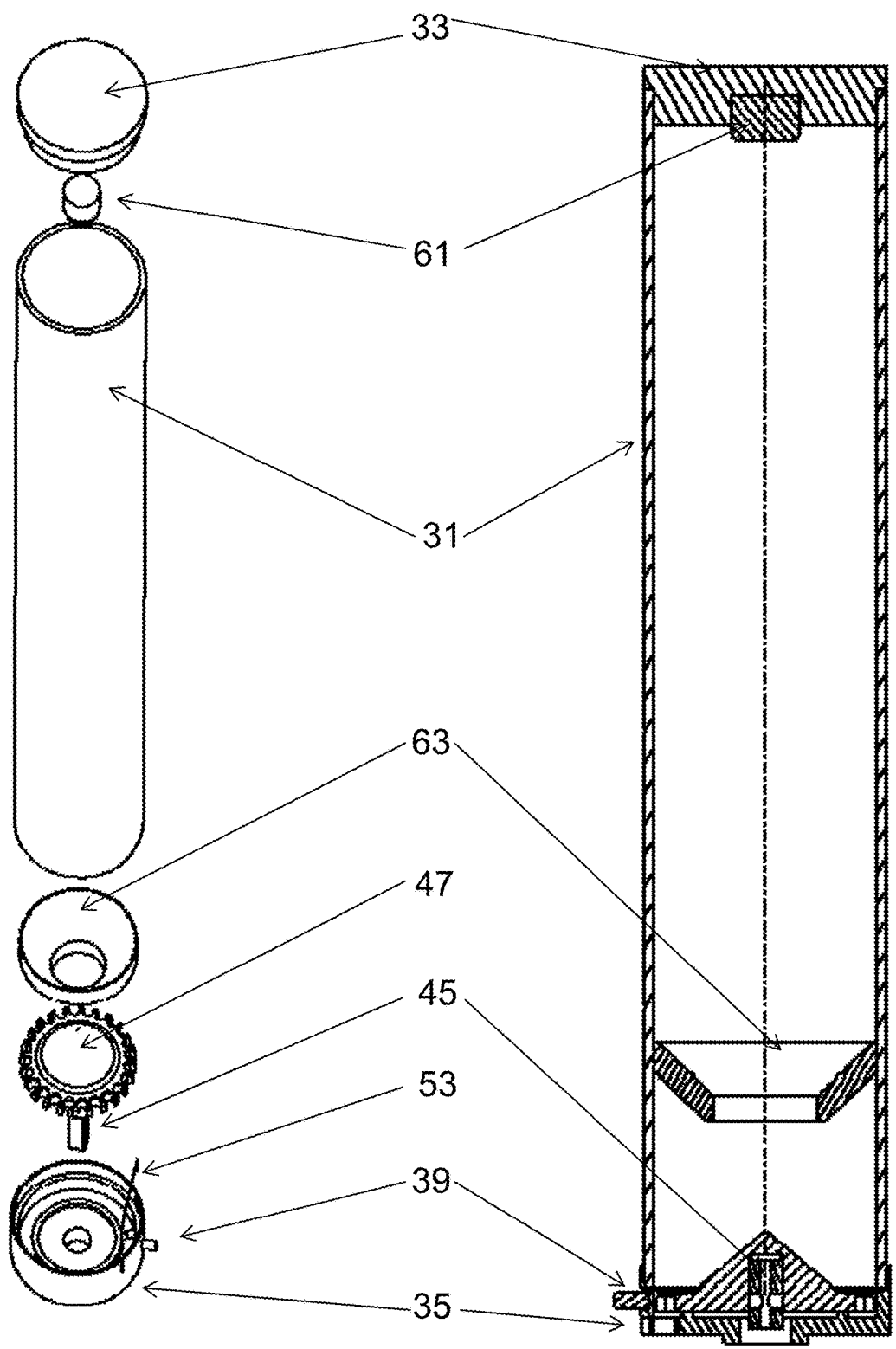
FIG. 6 shows an exploded view and a cross section view of a container and a dispenser element according to alternative exemplary embodiments of the invention.
Figure 7:
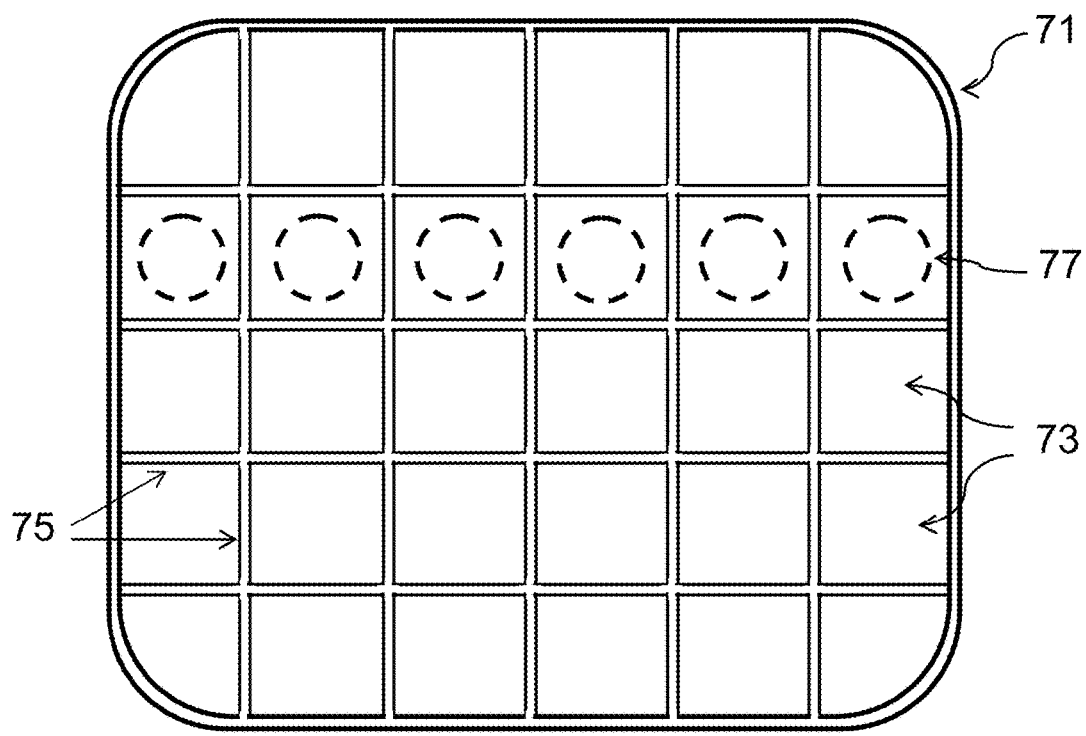
FIGS. 7A-B each shows a top view of a multi-compartmented container with various inner containers' combinations according to exemplary embodiments of the invention.
Figure 7:
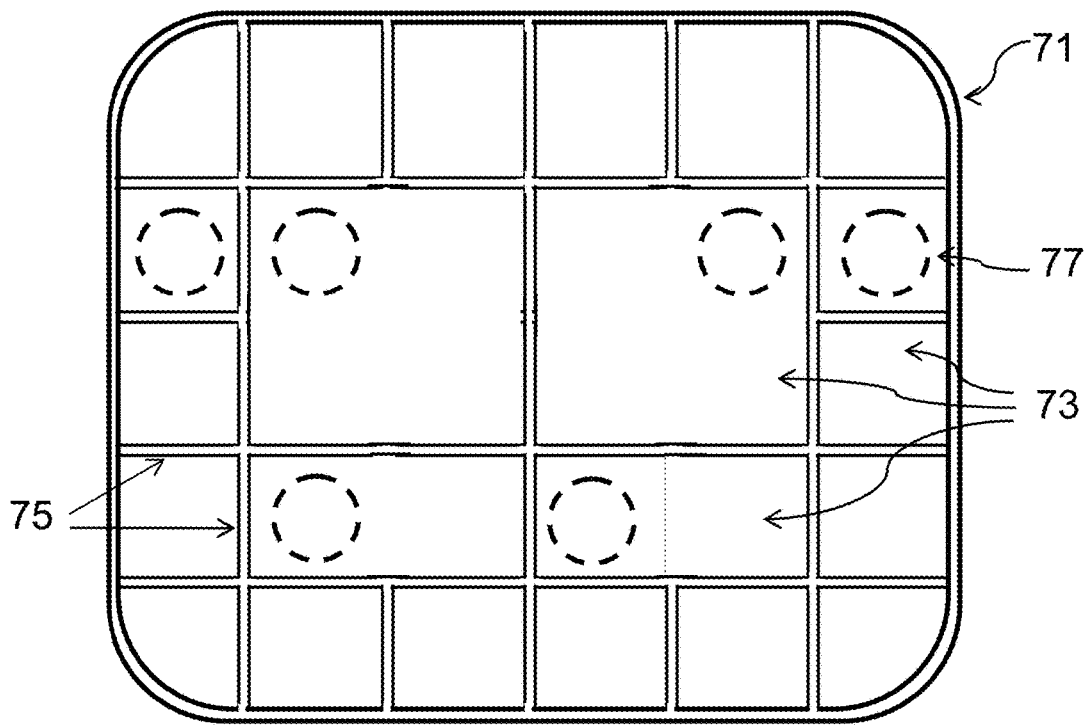

Examples of individual containers according to some embodiments of the invention are illustrated in FIGS. 4-6, and multi-compartmented containers are depicted in FIG. 7.

FIGS. 4A-4D show non-limiting examples of containers. FIGS. 4A and 4B both illustrate containers having the same shape along their base to top axis, differing from one another in height. In one exemplary embodiment of the invention, the containers displayed in FIGS. 4A and 4B have wall heights of 170 mm and 320 mm, respectively.

FIGS. 4C and 4D both show containers with different shapes along their base to top axis, differing from one another in height. In one exemplary embodiment of the invention, the containers displayed in FIGS. 4C and 4D have wall heights of 160 mm and 310 mm, respectively.

The floor of the wall section of the containers illustrated in FIGS. 4C and 4D is tilted toward the base section and the dispensing element to ensure that essentially all to tablets found in such containers can be dispensed.

As illustrated in FIGS. 7A and 7B, multi-compartment containers 71 may have a horizontal surface area and an overall volume corresponding approximately to the sum of the horizontal area and volume of each of its inner individual containers 73. The alternative features previously described for the separate individual containers apply to the inner individual containers of a multi-compartmented container, with the proviso that the selected parameters are compatible with the fact that adjacent inner containers may share part of the inner walls 75 dividing the overall cavity of the container into compartments.

The inner compartments, or containers 73, of a multi-compartment container 71 may have the same size, as schematically illustrated in FIG. 7A. Alternatively, the individual inner containers may have different sizes, as depicted in FIG. 7B. Inner containers of a multi-compartment container may share with each other, and optionally with all inner compartments of same larger container, the same base and/or the same top section. As for individual containers, each inner container of a larger multi-compartment container has an outlet schematically shown in FIGS. 7A and 7B as a dashed circle 77. For clarity, outlets are represented in only part of the inner containers. The multi-compartmented container can have in its top section a lid common to all inner containers. Alternatively, each inner container may be individually sealable allowing opening one container at a time.

In an exemplary embodiment of the dispensing device, all tablet containers have the same size and each contain a different type of tablets, as detailed hereinafter. However, as certain tablets may be used more frequently or may be used in larger numbers in preparation of a coloring composition or any other composition for treating keratinous fibers, the device can alternatively comprise one or more tablet container(s) having larger volume to accommodate a larger number of such tablets. This alternative could improve convenience by having relatively similar tablet refill or cartridge replacement rates. Alternatively and/or additionally, such frequently used tablets can be located in more than one container. An example of a more frequently used type of tablets is the Nature basic shade.

The cross section geometry may also vary within the same section of the container. For example, the wall section may have a smaller and/or different shape at a sub-section to ease gripping of the container and/or viewing of other containers' content.

The surface area of a container horizontal cross section can range from 1 cm$^2$ to 250 cm$^2$, or from about 10 cm$^2$ to about 200 cm$^2$ (and be the same or different along the base to top axis.

The volume of a container or an individual compartment within multi-compartmented container can be as desired and generally ranges from 250 cm$^3$ to 5,000 cm$^3$. Exemplary containers have a volume of about 500 cm$^3$, 1,000 cm$^3$, 2,000 cm$^3$, and 4,000 cm$^3$, with the term "about" meaning ±10%.

A container or compartment may contain an amount of tablets in a range of from about 100 grams to about 3,000 grams, including smaller and larger amounts, depending on the volume of the container and the shape and packing density of the tablets. Assuming a packing density of about 50%, exemplary containers enclose about 300 grams, about 600 grams, about 850 grams or about 2000 grams±10%.

In multi-compartmented containers, the horizontal surface area and an overall volume correspond approximately to the sum of the horizontal area and volume of each of its inner individual containers. Any of the features described for the separate individual containers apply to the inner individual compartment of a multi-compartmented container, as long as the selected parameters are compatible with the fact that adjacent inner containers may share part of the inner walls dividing the overall cavity of the container into compartments.

In order to facilitate the replacement of a container without the tablets pouring out when detached from the dispensing element, especially in the case when the dispensing element is not located on the container, a shutter means may be used that automatically closes the container outlet when the container is removed from its position.

FIGS. 41 and 43 illustrate two examples of such shutter means. In the example shown in FIG. 43, two partial spherical shells 240 and 242 are used, held closed by rubber-bands 244 when the container is out of the dispenser, but being opened when the container is inserted into the dispenser.

In FIG. 41, a rubber cap 246 perforated in its center is used, its perforation small enough to block tablets from falling out of the container. When inserted into dispenser 248, the perforation is stretched by a rigid tube 250 designed for that purpose, so that to beads can now pour through it from the container into the dispensing element.

The Dispensing Unit:

Each of the containers and/or compartments of the dispensing device is connected, directly or indirectly, to a unit for dispensing its contents. The device therefore comprises a dispensing unit for dispensing tablets from the tablet containers. In some embodiments, the device contains a unit for dispensing tablets in a pre-determined amount.

In some embodiments, the dispensing unit and the tablet container are attachable to one another.

The dispensing unit can be anything able to dispense tablets in a measurable and accurate manner (e.g., one by one). Suitable means include weighting and counting the tablets.

Thus, in some embodiments, the dispensing unit comprises means for weighing or counting the tablets to thereby provide a pre-determined amount of the tablets which is dispensed from each of the tablet containers.

Counting can be performed with the assistance of electronics (e.g., an electronic sensor) or using a mechanical implementation (e.g., a rotating cog wheel, as detailed hereinafter). In some embodiments, more than one of the above-described implementations can be combined. (e.g., the tablets are first counted by a mechanical system, and the number of tablets is further ascertained by electronics, or a combined electromechanical system is used.

Examples of electronic sensors include optical sensors, capacitive sensors and acoustic sensors, which can be positioned at any suitable point along the path of tablet delivery. When positioned at the level of the container outlet, each container needs to be monitored by at least one optical sensor, whereas acoustic sensors can monitor one or more containers. Preferably, corrective action can be taken in case of inaccurate dispensing.

To enhance accuracy, the dispensing unit may further comprise a separator element 222 preventing more than one tablet being dispensed at a time. In the case of a cog wheel, the separator element is positioned above the section of the cog wheel which overlaps the tablet container outlet. The separator element prevents tablets from immediately entering the cog-space from which a tablet was dispensed as long as the to cog-space is positioned above the outlet.

The separator element ensures that only the tablets located in the subsequent cog-spaces are dispensed, if so desired and controlled by rotation of the cog 220. To achieve this goal, the separator element 222 can be, for example, located at a height above the cog wheel, allowing the passage of a single tablet (i.e. slightly above the thickness of one tablet having entered a cog space), but preventing the passage of two tablets "stacked" over each other (i.e. below the thickness of two tablets, one being in a cog space). Any other positioning serving the goal of accurate dispensing is suitable.

While the separator 222 theoretically is an element of the dispensing means, in practice, according to some embodiments, the separator can form a part of the container, yet be in communication with the dispensing means. In an embodiment of the invention, the separator element is a wire, optionally passing through beads, or a thin rod attached between two points on the container inner walls, said wire or rod running above the cog wheel across the length of the container outlet. When the cog wheel 220 is located in the base portion of the container, the wire or rod can be attached to the inner walls of the base. Alternatively, the separator element can be a plastic rib attached to the interior of the tablet container or molded therein as a part of the tablet container.

Tablets can be dispensed from the containers either sequentially, one container only beginning dispensing after the previous container has completed dispensing, or concurrently, all relevant containers dispensing approximately at the same time.

The dispensing unit can be located within the container providing controlled access of the tablets to the container outlet, preferably by being located above the outlet. Alternatively, the dispensing mean can be located outside the container providing controlled exit of the tablets from the container outlet, preferably by being located below the outlet.

The dispensing unit can be positioned above or below a platform, as described hereinafter. When dispensing unit is composed of two parts and more, some part(s) can be positioned above the platform and other part(s) can be positioned below the platform.

An example of a dispensing unit comprising more than one part is a cog wheel having a motor rotating the wheel in a controlled manner.

FIG. 5 shows an exploded view and a cross section view of an exemplary container and dispensing means. For clarity, not all parts referenced in one view are necessarily indicated in the other view.

Shown in FIG. 5 is an exemplary cylindrical tablet container 11, which comprises container walls 31, a top 33, a container base 35 and a container outlet 55. Container base 35 has an aperture 37 allowing connection of the container to or through an optional platform (not shown herein and shown, for example, as element 17 in FIGS. 1 and 2). Attachment can be secured by way of a sprung pin 39. The container base aperture allows the passage of axle 41 of step motor 43. The motor axle 41 can be terminated by an axle head 45.

A dispensing element 13, consists of a cog wheel 47, comprising numerous cogs and cog-spaces in between adjacent cogs, as individually illustrated by cog 49 and cog-space 51. Cog wheel 47 can be connected to a motor axle 41 by matching to an axle head 45 through a socket of shape and size corresponding to the axle head. Such a socket being positioned underneath the cog wheel on the face facing the motor, is not shown in FIG. 5. Further shown in FIG. 5 is a separator element 53 which prevents access of a new tablet to the cog space(s) located above container outlet 55.

FIG. 6 shows an exploded view and a cross section view of alternative embodiments for the container and dispensing means. For clarity, not all parts referenced in one view are necessarily indicated in the other view. A container top 33 is shown as a plug that can be inserted at the top portion of container walls 31. This plug allows the insertion of a desiccant 61 within the container. In addition to the already described container base 35, sprung pin 39, axle head 45, cog wheel 47, and separator element 53, (see, e.g., FIG. 5), the device comprises an inside funnel 63. Inside funnel 63 is able to support part of the weight of the tablets, reducing pressure on cog wheel 47, and the height of tablets that could be displaced during cog wheel rotation. Inside funnel 63 can promote a prolonged service life to stepper motor 43 (see, FIG. 5) and the dispensing unit as a whole. Inside funnel 63 is preferably located closer to the base than to the top of a container, the narrow section of the funnel pointing downwards. The step motor and its axle that can be connected via the axle head to the cog wheel are not shown. Alternatively, the inside funnel may be located outside the container itself, in-between the container outlet and the dispensing unit (cog wheel).

Figure 8:
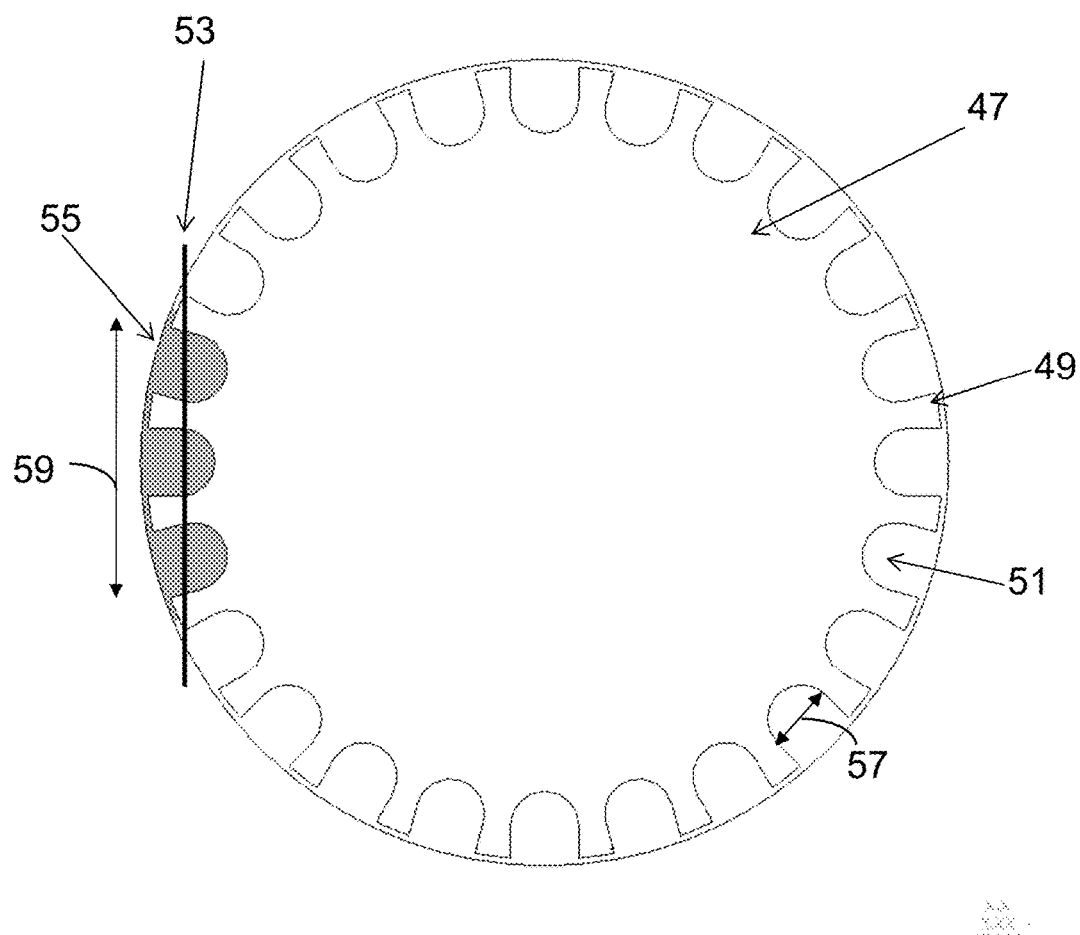
FIG. 8 shows a top view of a dispenser element according to exemplary embodiments of the invention.

FIG. 8 displays a top view of an exemplary cog wheel 47 allowing a more detailed view. In FIG. 8, the container outlet 55 is illustrated by a grey shape having to an approximate length 59. The circle surrounding the cog wheel can be a projection of the walls or base of the container. The general position of cog wheel 47 above the container base comprising the container outlet is arbitrary for the sake of illustration, since, as indicated hereinabove, the dispensing means could be positioned below the container outlet. A length 57 of a cog-space 51 being located between two adjacent cogs 49 is less than length 59 of the container outlet. Length 57 of the cog space is selected to allow dispensing of only one tablet and can be designed according to the size of the tablets to be dispensed. Length 59 of container outlet 55 is selected to allow rapid dispensing of tablets, taking into account the tangential speed of a tablet being rotated by the wheel (i.e., by the step motor), whilst allowing passage of only one tablet per controlled rotation of the wheel. Generally length 59 of the container outlet is up to about two to three times length 57 of one cog space and a length of one flanking tooth.

The prevention of uncontrolled passage of tablets through container outlet 55 is also achieved by means of separator element 53, as shown in FIG. 4 as a wire running between two points of the container along the length of container outlet 55.

The dispensing unit (or element) can be located within the container providing controlled access of the tablets to the container outlet, preferably by being located above the outlet. Alternatively, the dispensing mean can be located outside the container providing controlled exit of the tablets from the container outlet, preferably by being located below the outlet.

The dispensing means can be positioned above or below a platform, as described hereinafter. When dispensing means are composed of two parts and more, some part(s) can be positioned above the platform and other part(s) can be positioned below the platform.

An example of a dispensing unit comprising more than one part is a cog wheel having a motor rotating the wheel in a controlled manner.

Thus, in some embodiments, the dispensing unit comprises means for weighing or counting the tablets to thereby provide a pre-determined amount of the tablets which is dispensed from each of the tablet containers.

Reference is now made to FIG. 42, which shows in greater detail a possible embodiment of the tablet dispenser 200 of FIG. 40.

FIG. 42 illustrates an embodiment of the tablet dispenser in which the tablet container bases 215 (See FIG. 40) contain respective dispensing mechanisms 203 based on rotating cog wheels which are positioned above platform 205 to which they can be attached, whereas the corresponding stepper motors 207 are positioned below the platform 205. The container outlets are positioned above the platform apertures so that tablets are dispensed to chute 209 (see FIG. 40), located below the platform 205, and therefrom by gravity to tablet outlet 211. In this exemplary embodiment, the platform may be supported by a single leg.

As discussed in relation to earlier embodiments, the number of tablets being dispensed is proportional to the extent of rotation of the cog wheel 220 as controlled by a stepper motor. This number depends on the degree of rotation, the circumference of the cog wheel, the number of cogs on the wheel, the cog-space length, and the like, all being factors that can be readily adjusted by the person skilled in art is order to dispense the desired numbers of tablets. As the cog wheel rotates, tablets fall under gravity from the body of the tablet container to replace dispensed tablets, filling the cog-spaces of the cog wheel for subsequent dispending. For example, for a cog wheel having 24 cog spaces and rotating at a maximal speed of 120 RPM, as many as 48 tablets could be dispensed per second. Even lower dispensing rates of about 25 to 35 tablets per second ensure that all tablets necessary for the preparation of a desired coloration are provided by the device according to an exemplary embodiment of the invention in a short time not exceeding ten seconds. Such a rapid process advantageously replaces lengthy combinations of wet shades.

Reference is now made to FIG. 44 which is an exploded view and a cross sectional view of an exemplary container and dispensing unit. For clarity, not all parts referenced in one view are necessarily indicated in the other view.

Shown in FIG. 44 is an exemplary cylindrical tablet container housing 511, which comprises container housing walls 531, a platform 205 and a container outlet. Attachment can be secured by way of a sprung pin 539. The container base aperture allows the passage of axle 541 of stepper motor 207. The motor axle 541 can be terminated by an axle head 545

A dispensing element 513, consists of a cog wheel 547, comprising numerous cogs and cog-spaces in between adjacent cogs, as individually illustrated by cog 220 and cog-space 557 in FIG. 42. Cog wheel 203 can be connected to a motor axle 541 by matching to an axle head 545 through a socket of shape and size corresponding to the axle head and using rubber plate 230 and clutch 232 as shown in FIG. 42. Such socket being positioned underneath the cog wheel on the face facing the motor, is shown in FIG. 42. Further shown in FIG. 44, and more clearly in FIG. 42, is a separator element 222 which prevents access of a new tablet to the cog space(s) located above the container outlet.

FIG. 45 shows a top view of the tablet dispenser 200 of FIG. 40 and shows a container top 580 as a plug that can be inserted over the dispensers as shown in side view in FIG. 41.

FIGS. 3A-E show various possible combinations of containers on the platform of the dispensing device, according to some exemplary embodiments of the invention. Such exemplary containers can be used in various possible combinations in the devices of the invention. FIGS. 3A-E present non-limiting possible combinations of containers. In FIG. 3A, all containers have the same shape and size. In FIG. 3B, all containers have the same shape and have diverse sizes. In FIGS. 3C, 3D and 3E, containers differ in shape and in size.

Whenever the various combinations of containers are attached to a universal platform, the device can be designed to suit a variety of end uses and users. For example, small sized containers may be used for less frequently used shades, such as Blue, or for a small hair salon, and large sized containers for more frequently used shades or for supply stores.

Returning to the tablet dispenser and the outline of the cog wheel may be a projection of the walls or base of the container. The general position of cog wheel 220 above the container base comprising the container outlet is arbitrary for the sake of illustration, since, as indicated hereinabove, the dispensing means could be positioned below the container outlet. A length 557 of a cog-space 551 being located between two adjacent cog teeth 549 is less than the length of the container outlet. Length 557 of the cog space is selected to allow dispensing of only one tablet and can be designed according to the size of the tablets to be dispensed. The length of the container outlet is selected to allow rapid dispensing of tablets, taking into account the tangential speed of to a tablet being rotated by the wheel (i.e., by the step motor), whilst allowing passage of only one tablet per controlled rotation of the wheel. Generally the length of the container outlet is up to about two to three times length 557 of one cog space and a length of one flanking tooth 549.

The prevention of uncontrolled passage of tablets through the container outlet is also achieved by means of separator element 222, of which an alternative is shown in FIG. 4 as a wire running between two points of the container along the length of container outlet 55.

The Platform:

As mentioned hereinabove, in some embodiments, the dispensing unit further comprises a platform to which the containers and/or compartment are attached.

In some embodiments, the containers/compartments and the dispensing unit are attachable to one another through the platform, such that, for example, the containers are positioned above the platform and the dispensing means are positioned below the platform.

In other embodiments, both the containers and dispensing means are positioned above the platform.

In some embodiments, the tablet containers and/or the dispensing unit are each attachable to the platform. The attachment may be non-reversible, if permanent, or reversible, if the container can be attached to and detached from the platform more than once. Reversible attachment suits, for example, single use cartridges and/or allowing access for maintenance A single use cartridge is a disposable container pre-loaded with tablets of interest (basic shades or rapidly disintegrating media tablets).

The attachment to the platform cam be made by any suitable means, for instance by way of matching apertures in the platform, the containers and the dispensing means. For example, the containers and platform can be attached by way of spring-loaded pins and sockets. Alternatively or additionally, the attachment can be through the platform between device components located above the platform (e.g., the containers) and device components located below the platform (e.g., the dispensing means if so situated). For example, the shaft of a motor could connect the motor through a dispensing element to a corresponding container.

In some embodiments, the platform is perforated, so as to allow through-flow of to tablets from their respective containers. The perforated platform can either be suitable for one type of containers of given shape and dimension, or can alternatively accommodate more than one type of containers, hence serving as a "universal" platform.

The platform may be at various angles between horizontal and vertical and may comprise one or more leg supporting it in the desired angle relative to a horizontal work plan or to a vertical wall. The supporting leg(s) allow suitable positioning of the various components of the device in relation to the platform and to each other. Preferably, the containers are above the platform which is in turn in an elevated position relative to the funnel(s), tube(s), and tablet outlet(s). When the platform is vertical, the containers are above the platform by being tilted relative to the platform so that the top sections of the containers are in an elevated position relative to the platform, allowing tablets to flow down. The tablet or device outlets are positioned in a manner suitable for the convenient access of receiving vessel(s) below them when the device is in use.

The device can further comprise a device housing fully or partially enclosing some or all of the device components. In an alternative embodiment, the housing provides the support to the platform.

As mentioned, the platform of the device according to the invention can accommodate containers of different sizes and shapes. As described, all containers may be individual separate containers. Alternatively, all containers may be part of one or more multi-compartmented containers. In a further alternative, some of the containers are individual containers, whereas the other containers are parts of one or more multi-compartment containers.

Whenever the various combinations of containers are attached to a universal platform, the device can be designed to suit a variety of end uses and users. For example, small sized containers for less frequently used shades, such as Blue, or for small hair salon, and large sized containers for more frequently used shades or for supply stores).

Additional Components and Operation:

In some embodiments, the device comprises, in addition to the tablet containers, the tablet dispensing means and the optional platform, additional components, including, for example, legs supporting the platform, as described hereinabove, to housings able to enclose at least part of the device, as described hereinabove, one or more funnels and/or tubes to transfer dispensed tablets to one or more tablet outlet, one or more stands for receiving vessels able to contain the customized combination of tablets and optionally any additional media dispensed from the device or being in communication therewith, and user interfaces able to provide or retrieve information relating to the customized combination of tablets.

Figure 1:
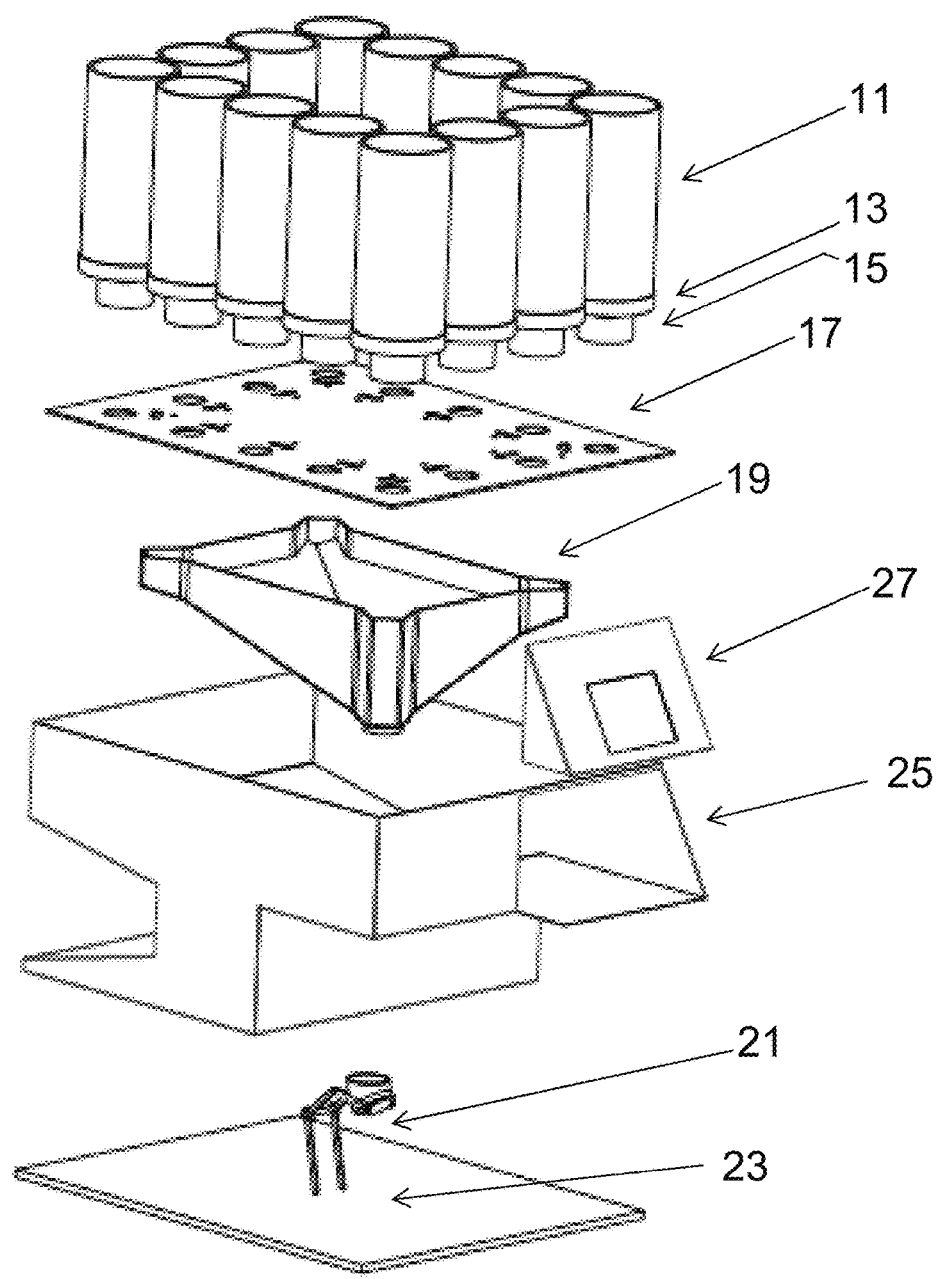
FIG. 1 shows an exploded view of a dispensing device according to exemplary embodiments of the invention.

FIG. 1 is an exploded view of an exemplary dispensing device according to some embodiments of the invention. Tablet containers 11 each comprise in their base portion a dispenser unit 13 composed of a rotating cog wheel and of a stepper motor 15. The containers and their respective dispensing means are positioned above platform 17 to which they can be attached. A funnel 19, located below the platform, guides via its slopes the dispensed tablets to tablet outlet 21. A receiving vessel (not shown in FIG. 1) can be placed on base 23, below tablet outlet 21 to collect the dispensed tablets. In this exemplary embodiment, the device comprises a housing 25 which supports the platform (and parts attached thereto) and encloses the funnel. Base 23 can provide for partial sealing of the housing. FIG. 1 schematically illustrates how a user interface 27 can be included in the device.

Figure 2:
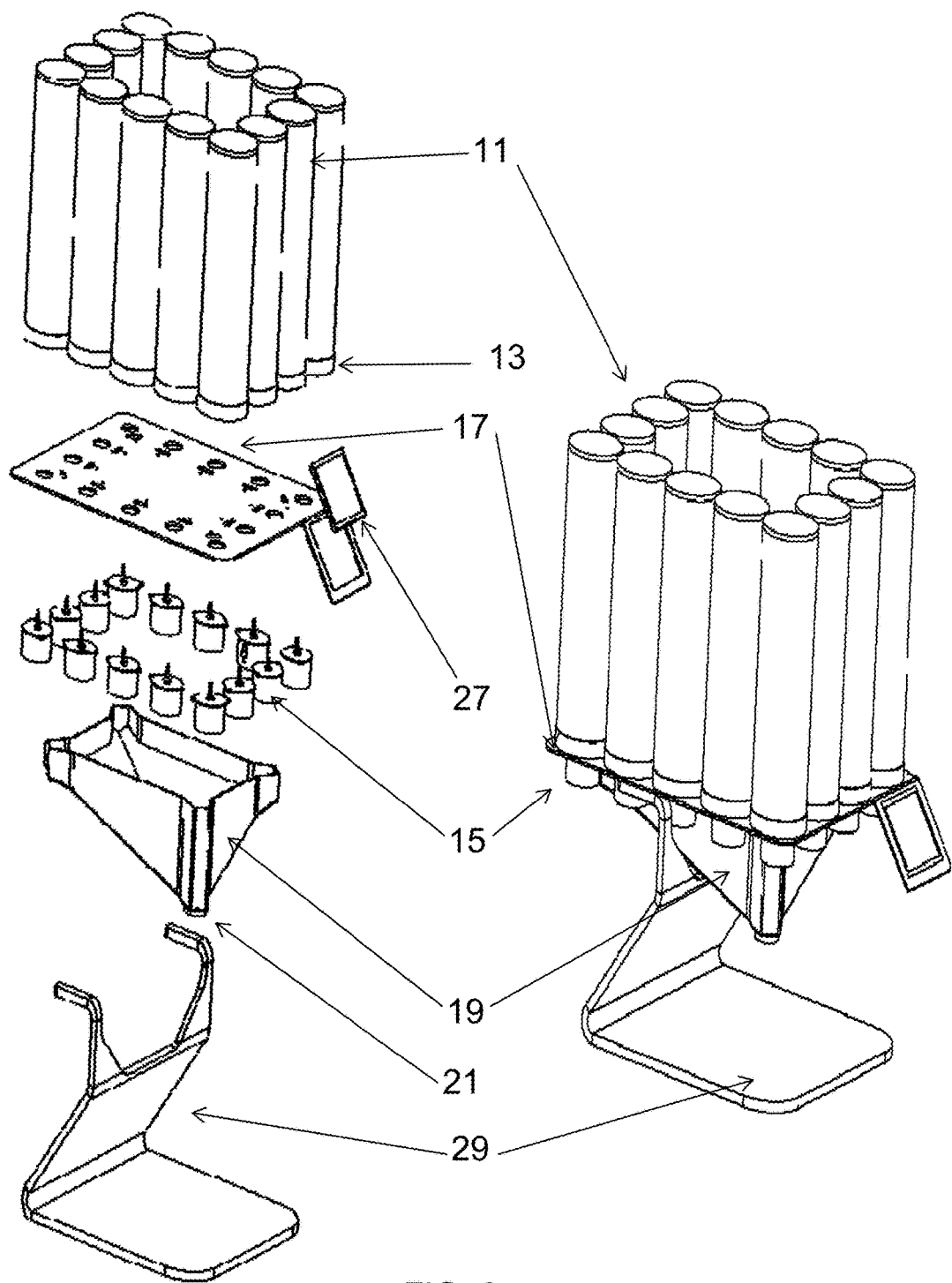
FIG. 2 shows an exploded view and a perspective view of a dispensing device according to alternative exemplary embodiments of the invention.
Figure 3:
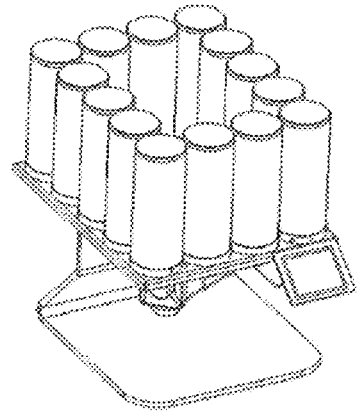
FIGS. 3A-E show various possible combinations of containers on the platform of the dispensing device, according to some exemplary embodiments of the invention.
Figure 3:
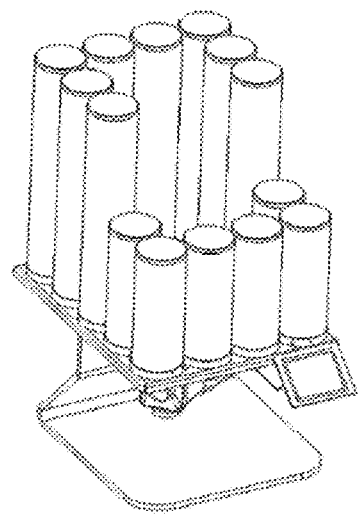
Figure 3:
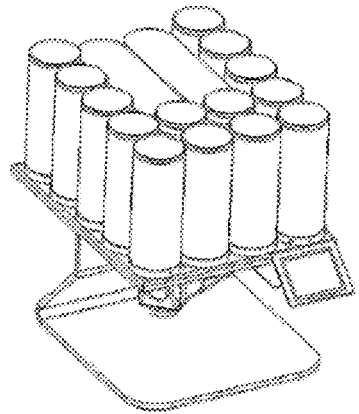
Figure 3:
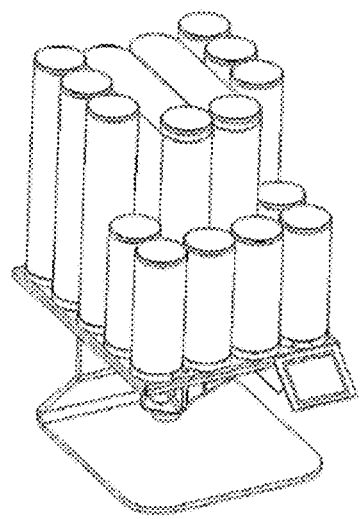
Figure 3:
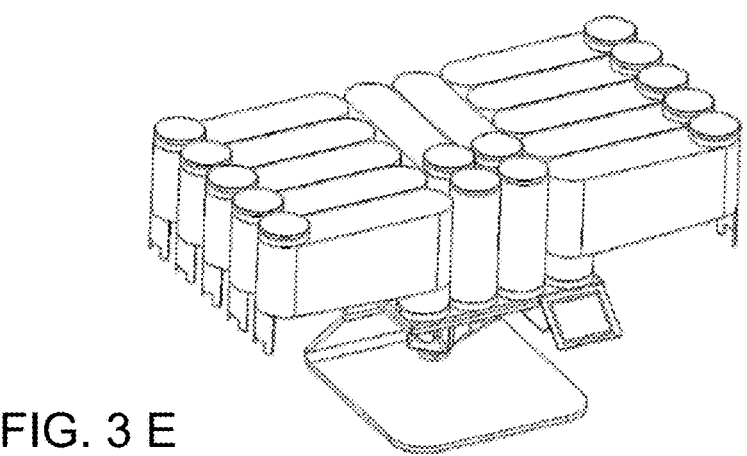

FIG. 2 shows alternative exemplary embodiments of the device, in exploded and perspective view. For clarity, not all parts referenced in one view are necessarily indicated in the other view. In this figure, the tablet containers 11 and their respective dispensing means 13 based on rotating cog wheels are positioned above platform 17 to which they can be attached, whereas the corresponding stepper motors 15 are positioned below the platform. The container outlets are positioned above the platform apertures so that tablets are dispensed to funnel 19, located below the platform, and therefrom by gravity to tablet outlet 21. In this exemplary embodiment, the platform is supported by a single leg 29.

Reference is now made to FIG. 40, which illustrates, in exploded view, an overall dispensing device according to the present embodiments comprising, a tablets dispenser 200, a media dispenser 210 and a receiving vessel 212.

In some embodiments, the dispensing unit 210 and the tablet dispenser 200 are attachable to one another.

The dispensing unit can be anything able to dispense tablets in a measurable and accurate manner (e.g., one by one). Suitable means include weighting and counting the tablets, as described herein.

Tablet containers 202 each are associated with respective a dispenser elements 203 composed of a rotating cog wheel and of a stepper motor 207. The containers and their respective dispensing means are positioned above platform 205 to which they can be attached. A shute 209, located below the platform, guides the dispensed tablets via its slopes to tablet outlet 211. A receiving vessel 212 can be placed below tablet outlet 211 to collect the dispensed tablets. In this exemplary embodiment, the device comprises 3*a*housing 213 which supports the platform (and parts attached thereto) and encloses the funnel. A base can provide for partial sealing of the housing.

The tablet dispenser 200 may comprise multiple containers 202 each having an approximately triangular cross-ssection with a convex face 204, which containers fit together like slices of a pie, and form together an approximately cylindrical shaped arrangement of containers. One or more containers may be placed in the space 208 that forms about the center of the cylindrical shaped arrangement. The additional containers may also have an approximate triangular cross-section with a convex face and may also fit like slices of a pie, and form together an approximately cylindrical shaped internal arrangement of containers, within a diameter which is smaller than the external cylindrical arrangement. Alternatively, the additional containers may have a different shape than the triangular shape, which fits the space formed about the center of the cylindrical shape.

In addition, the containers 202 and 206 may either be individual separate elements or parts of a larger container suitably divided with one or more inner walls to form a multi-compartmented element consisting of two or more individual containers.

The containers 202 and 206 may vary in geometry along the base to top axis. For example, the containers may have a circular cross section in the vicinity of the base portion (e.g., able to house dispensers of suitable geometry), another geometry further apart in the wall portion (e.g., oblong, rectangular, square, etc.) and optionally yet a different shape in the top portion (e.g., able to accommodate a lid).

In some embodiments, the dispensing device comprises, in addition to the tablet containers, a tablet dispensing mechanism and the optional platform as described herein, and one or more funnels and/or tubes configured for channeling tablets dispensed from the tablet container to an outlet.

Thus, in some embodiments, the tablets may flow under gravity, or mechanically, from the container outlet directly or indirectly to one or more funnels. Indirect flow indicates that a tube of suitable dimensions may be used at intermediate position between a container outlet and a funnel. The funnel can have sloped walls channeling a free flowing tablet to a funnel outlet. If more than one funnel is used, each funnel may independently channel tablets from one or more container outlets.

Alternatively, the tablets may be transferred from the dispensing unit to the collecting vessel 212 in a motorized fashion, e.g. a conveyor-belt. This in general would reduce dispenser overall height.

The tablets flow (e.g., under gravity) through the funnel(s) directly or indirectly to the respective tablet outlet of each funnel. Indirect flow indicates that a tube of suitable dimension may be used at intermediate position between the outlet of a funnel and the tablet outlet through which the suitable amount and types of tablets are dispensed to the receiving vessel.

In some embodiments, the device may further comprise one or more tubes connecting the tablet outlet to an inlet of a subsequently connected part through the device output.

If more than one funnel and/or tube is used to transfer the tablets being dispensed, the device may further comprise a converging funnel or tube channeling all tablet outlets to a single device output. If the device comprises a single funnel or tube, the single tablet outlet is alternatively referred to as the device output.

The outlets of any member of the device may further comprise a one-way valve. The one-way valves, whether controllable or not, allow the tablet to flow out of the corresponding device member when in an open position, while reducing access of eventual degradation factors when in a closed position.

The dispensed tablets can be channeled through the above described channels and/or tubes to a receiving vessel where they are mixed with an aqueous medium or media so as to provide a composition for treating keratinous fibers (e.g., a coloring to composition), as described herein.

The device may comprise a weighing unit for providing an additional indication of the amount of tablets being dispensed, further increasing the reliability of the dispenser.

The device may comprise a sensing unit that detects the absence of a receiving vessel at the device outlet, reducing the chance of dispensing tablets without collecting the tablets. The sensing unit may for example comprise optical, capacitive, electrical, magnetic and/or mechanical sensing.

The device may comprise a replacement mechanism for facilitating the replacement of a certain container (e.g. when it becomes empty), by moving the container to a specified location which is suitable for replacement. Referring again to FIG. 45, the replacement mechanism may comprise cog wheel 590, optionally driven by a motor.

The device may comprise container-recognition for reducing the chance of misplacing a certain container at a wrong position. The container-recognition may for example comprise optical means, RFID means and mechanical means.

In some embodiments of the invention, the device dispenses the desired set of tablets into the receiving vessel and then media is manually measured and added.

Alternatively, the device can further comprise one or more medium containers, and optionally one or more media dispensing elements configured to measure the amount of media being transferred from the media containers. In some embodiments, the device further comprises one or more funnels or tubes for transferring the dispensed media to one or more media outlet. The media outlets can dispense media into the same receiving vessels as the desired sets of tablets or into additional media receiving vessels.

In some embodiments, the device further comprises at least one additional container which comprises an aqueous solution and which is in communication with at least a portion of the compartments which comprises said at least active agent, the device being configured for generating a pre-determined amount of said medium upon contacting a type of said tablets with said aqueous solution.

The principles guiding the selection of media containers and dispensing suitable for devices according to the invention are as previously provided for the tablet to containers, with appropriate adjustments required for storing and dispensing liquids of relevant chemical reactivity and viscosity in a measurable manner. For example, the media can be dispensed using piston cylinder systems or pumps. In some embodiments, liquid media are delivered through an outlet separate from the dry tablet outlets. In some embodiments, liquid media are delivered through the tablet outlet, for example, by means of one or more tubes or funnels through which the liquid media passes and flows into the one or more funnels and tubes through which the tablets pass to the device outlet.

In some embodiments, the plurality of containers comprises two or more types of tablets, separately contained, such that a tablet container comprises one type of tablets. The dispensing device is operated such that a certain combination of two or more tablets is dispensed, thereby providing a desired combination for forming composition for treating keratinous fibers. The composition would comprise a pre-determined, desired combination of the two or more tablet types, each being dispensed from a different container.

In some embodiments, the containers all contain color imparting agents, which are dispensed so as to provide a pre-determined collection of color imparting agents.

In some embodiments, at least one type, and optionally all types of the tablets comprises rapidly disintegrating tablets, as described herein.

In some embodiments, one or more types of the tablets comprise an oxidizing agent, an alkalizing agent and/or a thickening agent.

Such tablets can be used either per se (e.g., for forming a bleaching composition) or in combination with tablets comprising a color-imparting agent or any other form of color-imparting agents.

Each of the above tablets can be co-dispensed or otherwise mixed with an aqueous medium or media, which can be simply an aqueous diluent or can comprise complement active agents for performing the desired treatment.

FIG. 46 shows in greater detail the media dispenser 210 and receiving vessel 212 parts of FIG. 40. Media dispenser 210 comprises funnel shaped media containers 580, also having dispensing mechanisms 582.

The media dispenser 210 may comprise a dispensing mechanism 582 for dispensing the media from the media containers 580. The dispensing mechanism 582 may comprise a piston (not shown in the figure) for pushing the media out of the containers 580. The piston may be activated using pneumatics, an electrical motor or electromagnetics or magnetics. The piston may be part of the container, or not. Alternatively, the media may be dispensed out of the container without the aid of a piston, by pneumatics or by gravity action.

The media dispenser may also comprise media valve/s for controlling the media dispensing, which may be attached to the media container, and unidirectional valve/s 584 for keeping the containers pressurized at all times in case of pneumatic operation. A valve actuator may be used for actuating the media valves by electrical, pneumatic or electromagnetic methods.

A single media valve and/or a single valve actuator may be used for dispensing media from all containers, by incorporating a mechanism that brings a specific media container into close proximity with the media valve and/or valve actuator. In one embodiment, the containers may be arranged in a circular fashion, and brought in close proximity with the media valve and/or valve actuator using an electrical motor that rotates the container arrangement 581 (See FIG. 45).

The media container 580 may be constructed from plastic, glass, metal or any other suitable material. It may comprise several material layers allowing for example: blocking atmospheric gases from penetrating into the container, blocking media gases from escaping the container, protecting the container and/or the cream from chemical reaction that might occur between the container and the media, blocking UV light, preventing media remains left on the container interior. In addition, the media container interior may be coated with oil, preferably thickened oil, for facilitating the media dispensing action and for allowing free flow of the media inside the media container without media remains left on the container interior.

The media dispenser may also comprise a prevention mechanism for preventing its operation in case a replaceable container has not been placed properly in its position by the user, thus preventing malfunction of the device.

The media container 580 may comprise a built-in aerosol mechanism known in the art, or any other built-in dispensing mechanism for dispensing the media from the container.

The media containers may be replaceable or fixed. If replaceable containers are used, containers-recognition means may be used for reducing the chance of misplacing a certain container at a wrong position. The containers-recognition may for example comprise optical means, RFID means and mechanical means.

The media valve/s may be any type of valve known in the art, suitable for the media in use. Preferably, the valve may be an aerosol valve, for example a high delivery valve suitable for thick materials.

The device may also comprise a weighing unit for further improving the accuracy of the dispensed media dosage. Such a unit may allow real-time close-loop control of the dispensed media dosage.

The device may also comprise an input\output apparatus known in the art, for operating the device, such as keyboard, mouse, screen, touch-screen, and printer.

The media dispenser may comprise a way of removing media remains remaining on the media valve. Such may comprise a way of generating air-jet/s about the media-valve, for example two counter-facing air-nozzles connected to a pneumatic system. An alternative comprises a tight wire that is placed such as to remove media remains by moving the wire in close proximity with the media valve.

The media dispenser may comprise a pneumatic system for driving the dispensing mechanism. The pneumatic system may comprise a pump, a compressor, electrically-controlled air-valve/s, unidirectional (no-return) air-valve/s, air-reservoir/s, air tube/s, and a pressure indicator/s.

The media dispenser and tablets dispenser may be arranged one on top of the other, one by the side of the other, or in any other suitable fashion. They may be rigidly connected, loosely connected, or totally separated. They may share a receiving vessel at identical physical position, share a receiving vessel at different physical position, or not share a receiving vessel.

The media and desired tablet set can be mixed manually or the device can further comprise mixing means which are able to mechanically mix the desired set of tablets with media automatically or manually dispensed. Mixing can be performed by rotation of an impeller within the receiving vessel containing the tablets and media, by to applying vibrations or oscillatory movements to the receiving vessel comprising the formula to be mixed or by any other suitable mixing method.

The mixing unit may comprise a driving unit, driving an impeller immersed into the coloring-mixture. Alternatively, the driving unit may drive the receiving vessel containing the coloring-mixture. A driving unit may comprise an electrical motor, a magnet or an electromagnet. The use of an electromagnet allows a mixing action without direct contact of the driving unit with the impeller and/or the receiving vessel, thus simplifying the mixing unit.

The driving unit may comprise a unit for driving a rotational movement in which the impeller and/or the receiving vessel rotates about its center. It may also comprise a unit for driving a circular motion, in which the impeller and/or the receiving vessel rotates about the receiving vessel center or any other center. It may also comprise a unit for driving linear movement, for example vertical, of the impeller and/or the receiving vessel.

The mixing unit may also comprise a unit for breaking or grinding the tablets before or after combined with the media, in case this is required.

The impeller can be specially designed for achieving the required mixing action. Several types of impellers may be used per the specific coloring-mixture being prepared. For example, the impeller may comprise the application tool used for applying the coloring-mixture onto the hair (e.g. brush). The receiving vessel may be designed to fit vessels currently used nowadays in manual preparation of coloring-mixture.

Optionally, a device according to various embodiments of the invention can further comprise heater elements able to heat the tablets and/or the media to temperatures that can increase the rate of disintegration of the tablets within the media, hence reducing the mixing time.

Optionally, a device according to various embodiments of the invention can dispense tablets whilst reducing or preventing premature exposure to degradation factors including for instance moisture, oxygen and UV light.

The device and its parts can be made of any material customary and appropriate for their intended purpose. For example, they can be made of any suitable material such to as glass, metals and alloys, for example aluminum, copper, iron and stainless steel, and plastic polymers, for example halogen containing polymers, such as polytetrafluoroethylene (PTFE) e.g., Teflon®, polyacrylates, such as polymethyl methacrylate (PMMA) e.g., Perspex®, polyoxyalkylenes, such as polyoxymethylene (POM) e.g., Delrine®, polycarbonates (PC), polyethylenes (PE), polypropylenes (PP), polystyrenes (PS), polyurethanes (PU), polyvinyl chlorides (PVC), and blends thereof.

The parts of the device containing the tablets or through which the tablets are dispensed (e.g., the containers, the connecting parts, the tubes, the funnels, the outlets, etc.) can further comprise an oxygen bather. Suitable oxygen protection can be achieved by using for the fabrication of these parts materials with low to null permeability to oxygen. For example, metal and glass generally have low gas permeability. For plastic polymers, their crystallinity, density, level of polymerization and copolimerization, and molecular weight can affect their gas permeability and these parameters can be selected to achieve reduced permeability to oxygen. Alternatively or additionally, materials may be similarly selected to have low to null moisture permeability, or any other desired permeability, or lack thereof, to a factor of interest.

Alternatively and in addition, the parts of the device involved in the containment and delivery of the tablets can be connected to one another in an air-tight manner and the containers and/or tubes and/or funnels and/or outlets (tablet and/or device) can be, for example, sealed by a one-way valve which opens, optionally in a controllable manner, only during actual dispensing of the tablets. Suitable one-way valves include for example a clack valve, a clapper valve and a flush valve (usually a leverable ball-shaped seal located over the relevant outlet when in closed position). In addition, connections between all said parts, or some of them, may be externally fastened with a sealant. Optionally, the device output and receiving vessel can comprise couplings allowing air-tight attachment and tablet dispensing.

In another embodiment, the containers and parts of the device involved in the delivery of the tablets are protected from light exposure (e.g., enclosed in a housing or made of UV blocking or shaded or opaque materials) or further comprise a UV light blocker. Many of the above-mentioned plastic polymers have grades that address this issue. For example, Perspex® VA and VE grades block out more than 99% of all UV radiation.

In addition, one or more of the aforementioned protections can be combined. For example, a container (and the relevant parts of the device through which the tablets are delivered) may be made of a non-oxygen-permeable material with reduced moisture permeability comprising a UV-light blocker and further comprise a desiccant within its body.

The device can further comprise one or more computerized systems including user interfaces allowing input of parameters pertinent to the preparation of custom coloring formulae, databases or algorithms for assessing the type and number of tablets including basic shades needed to obtain desired coloring and systems providing for the automation of tablets and/or media dispensing from each appropriate container. Parameters pertinent to the preparation of custom coloring formulae include, for example, information concerning the initial color of the fibers to be colored, the desired final color, individual properties of the fibers, the concentration of the color imparting agents per basic shade tablet, the strength of the suitable media or of the corresponding rapid disintegrating media tablets, and the like. In the case of human hair for instance, the individual properties of the keratinous fibers that can be of relevance include the type of hair (e.g., European, Asiatic, African, etc.), the texture of hair in general (e.g., straight, wavy, curly, kinky, etc.) and of individual fibers (e.g., thin, coarse, etc.), whether the hair is not artificially colored (natural) or already colored in full or partly, and other parameters such as dry, normal or oily hair types and the fact that the hair may be damaged. Additional information of relevance relates to the amount of coloring formula to be prepared and this amount may vary from one individual subject to another. For example, a lower amount of formula is needed for short hair than for long hair, or for coloring human hair than for coloring larger surfaces of non-human keratinous fibers (e.g., the fur or wool of an animal).

An additional option is to have a PH tester probing the coloring mixture after being prepared in the vessel, to further increase the reliability of the dispenser (e.g. not allowing over-dose of alkaline and/or oxidizing agents).

An additional option is to have the hair reader system or other spectrophotometric device, measuring the coloring mixture after being prepared in the vessel, to further increase the reliability of the dispenser (e.g. not allowing miss-dosing of certain coloring tablets).

The assessment of the types and number of basic shade tablets needed to obtain desired coloring can be performed by converting the initial and final colors of fibers to be colored to a color coordinate presentation (e.g., based on their respective reflectance spectrum). Color coordinate presentations include CIELAB, CIELUV, CIExyY, CIEXYZ, CMY, CMYK, HLS, HSI, HSV, HVC, LAb, LCC, NCS, PhotoYCC, RGB, Y'CbCr, Y'IQ, Y'PbPr and Y'UV. The CIELAB system, also termed Lab system, is commonly used in hair coloring, but any other color coordinates that exist or may be developed for this purpose can be suitable. Knowing the positive or negative contribution of one tablet of each basic shade to the color coordinate presentation, whether this contribution is linear or non-linear, one can calculate the expected change in color from the initial color coordinate to an intermediate coordinate presentation. This step is repeated for a tablet of same or different basic shade until the difference between the intermediate calculated color coordinate presentation and the desired color coordinate presentation is minimized. In other terms, the last step of the calculating process is reached when the Delta-E (dE) number that represents the "distance" between the calculated and desired colors is minimal. A delta-E of 5 or less is believed to be tolerable, a delta-E of less than 1 being generally considered unnoticeable to the human eye. If the coloring involves the use of oxidating or bleaching agents or media, the initial color coordinate of an individual subject will be corrected to take into account the lost of natural pigmentation, if any. Alkalizing agents and thickening agents may affect the penetration of the fibers and the efficacy of the lightening or coloring. Preferably, the contribution of each active agent when present in the final coloring formula is taken into account in the above-mentioned calculations. This method can provide the quantity and combination of basic shades to be dispensed to obtain the desired set of tablets.

The assignment of color coordinates to the initial and final colors can be done manually by visual selection from suitable databases or catalogs, of the known coordinates of the closest possible color. Alternatively, the assignment of color coordinates to the initial and final colors can be done automatically. For this purpose, the device can further comprise a color measurement system, alternatively termed a hair reader system. Advantageously, the hair reader system can also take into account the individual properties of the fibers to be colored. For instance, individuals having thinner to hair or a lighter initial shade may require lower amounts of color imparting agents than individuals having thicker hair or a darker initial shade. The optional ability to take into account the individual properties of the fibers to be colored further increases the likelihood of obtaining a desirable color result.

Alternatively or additionally, the hair reader system can measure the spectral reflectance of the hair to be colored, yet further increasing the likelihood of obtaining a desirable color result. The spectral range could be 200 nm to 1300 nm, preferably 300 nm to 1100 nm, preferably 380 nm to 970 nm. Measurement resolution could be 1 nm to 200 nm, preferably 2 nm to 10 nm, preferably 4 nm.

The device can further comprise a computerized system allowing tracking the amount of tablets and/or media consumed since cartridge attachment or filling of containers. Such monitoring system can trigger an alert when the remaining amount of tablets of a given type reaches a critical level requiring availability of stock for replacement or refill. The critical level can be set individually for each type of tablets (e.g., 10-time the average amount of tablets of a basic shade in coloring formulae) or can be set uniformly for all tablets (e.g., at about 100 tablets or 500 tablets etc.).

The device can further comprise memory and/or connectivity means to store and/or transfer desirable information. For example, the device can store for future use information concerning the set of tablets providing a desired coloring formula to a specific consumer. Such information can be stored independently at each hair-salon or retail-store attended by a consumer or centrally at an external database connectable from each device independent of location. Such connectivity from independent locations to information relevant to specific consumers can further improve the reproducibility of the coloring formulae or increase the likelihood of obtaining a desirable color result in case a change of hair color is desired by the customer. The device can also comprise a port allowing storage of desirable information to a portable memory system (e.g., to a USB key or swipe card of a consumer).

The connectivity of the computerized systems of the device can be to connectable units "internal" to the hair salon or retail store and to units external to said locations. For example, the system tracking the amount of consumed/remaining tablets can connect to an internal purchase system to trigger an alert and/or to a supplier of new stocks to directly place an order. Such connectivity (e.g., via a receiver-transmitter) can serve any to other desired goal, for example for billing purposes.

The device according to the invention may also comprise at least one printed circuit board (PCB) to mechanically support and electrically connect the electronic components of the device and any conventional part (e.g., connectivity to power grid etc.).

In some embodiments, the device as described herein is connected to a computational unit as described in greater detail hereinabove.

In some embodiments, the device is connected to an optical reader as described in greater detail hereinabove.

Selection of a Tablet Combination:

In the following, reference to tablets includes also oxidizing and alkalizing agents concentration, bleaching, treatment time and other parameters of the coloring treatment as well as tablet combination.

In any of the methods and devices described herein selection of a tablet combination can be generally effected by:

establishing the initial color and condition of the keratinous fibers (e.g., hair) fibers, and then selecting a desired customized color or other treatment suiting an individual subject. The customized treatment could be selected by the user from a collection of final shades or as desired. The system is then in a position to determine amounts of tablets suitable, in combination, for treating the fibers as desired by the customer.

Establishing said initial color may involve measuring an initial reflectance spectrum. Selecting the customized color may comprise determining a reflectance spectrum of the customized color, and the reflectance spectra may be independently converted to a color coordinate presentation.

The amount of tablet to be used may be determined by adding to the initial reflectance spectrum the positive or negative contribution of one tablet of one basic shade to obtain an intermediate calculated color coordinate presentation. Then iterations of the calculation step for a tablet of same or different basic shade may be carried out, until the difference between the intermediate calculated color and the desired color coordinate presentation is minimized The determination may take into consideration positive and/or negative contributions of an active agent such as an alkalizing agent, an oxidizing agent, or a thickening agent to the calculated color coordinate presentation.

The selecting may account for a contribution of individual properties of the keratinous fibers.

The selecting may be carried out by a computer implemented system.

The measuring may be carried out by the optical hair measurement device or hair reader. The hair reader may comprise an illumination unit for illuminating hair, and a measuring unit comprising at least one sensor for optically measuring the hair during illumination. The sensor and a beam from the illumination unit may respectively subtend a light diffusion angle at the hair being measured, thereby to ensure that the sensor principally measures light that is diffused or scattered by the hair.

The hair reader may include a main illumination source and subsidiary illumination sources, and processing electronics to use differential illumination results from the various sources to determine an angle of a hair relative to the main illumination source.

The main illumination source may used for spectroscopy, and a subsidiary illumination source may be used for angular measurement.

The sensor comprises sensitivity to the visible and near infrared parts of the electromagnetic spectrum.

Reference is now made to FIG. 47, which is a simplified diagram illustrating an embodiment in which a hair reader provides inputs for the color prediction, and the color prediction in turn controls the dispenser to dispense the dye that is needed to achieve the desired color.

In FIG. 47, hair reader 600 reads the hair, with particular attention to the specular reflection and scattering of the light, as explained since these provide extensive information as to the state of the hair. Furthermore information is obtained beyond the visible spectrum, as explained above.

The user requests a particular end result, a desired hair color, through user input 602.

The color prediction system 604 now has a user request and detailed information on the state of the user's hair at a variety of wavelengths. The color prediction system is now able to predict the resulting color if different dye mixtures were to be applied to the to user's hair, using the methodology described hereinabove.

Once a dye mixture is found whose prediction indicates the color required by the user, then the color prediction module outputs instructions to the dispenser 606 to dispense the necessary tablets and media and prepare the dye.

V. Methods of Treating Keratinous Fibers:

According to another aspect of embodiments of the invention, there is provided a method of treating keratinous fibers, as defined herein. In some embodiments, the method is effected by disintegrating at least one tablet comprising at least one an active agent (e.g., a tablet described herein) in an aqueous medium (e.g., an aqueous medium described herein), to thereby obtain a composition comprising at least one color imparting agent, and contacting the composition with the keratinous fibers for a time period suitable to provide a desired coloring.

In some embodiments, the method comprises contacting the fibers with a bleaching medium for a time period sufficient to lighten a color of the fibers. In some embodiments, contacting with a bleaching medium is performed prior to contacting the coloring composition with the fibers, for example, in order to reduce or eliminate an initial color (e.g., natural pigmentation) which may interfere with a desired color imparted by the coloring composition.

The bleaching medium may optionally comprise a bleaching agent described herein.

In some embodiments, a bleaching medium is prepared by disintegrating at least one tablet comprising a bleaching agent (e.g., a tablet described herein) in an aqueous medium (e.g., an aqueous medium described herein).

In some embodiments, the method further comprises mixing the tablet(s) comprising color imparting agent with at least one active agent selected from the group consisting of an alkalizing agent, an oxidizing agent, and a thickening agent, e.g., as such active agents are described herein. Such mixing may be before, during, and/or after disintegrating the tablet comprising color imparting agent.

In some embodiments, mixing with at least one alkalizing agent is effected by disintegrating at least one tablet comprising the alkalizing agent(s) (e.g., a tablet described herein) in an aqueous medium (e.g., a medium described herein). In some embodiments, the aqueous medium is the same medium in which the tablet(s) comprising color imparting agent is disintegrated.

In some embodiments, mixing with at least one oxidizing agent is effected by disintegrating at least one tablet comprising the oxidizing agent(s) (e.g., a tablet described herein) in an aqueous medium (e.g., a medium described herein). In some embodiments, the aqueous medium is the same medium in which the tablet(s) comprising color imparting agent is disintegrated.

In some embodiments, mixing with at least one thickening agent is effected by disintegrating at least one tablet comprising the thickening agent(s) (e.g., a tablet described herein) in an aqueous medium (e.g., a medium described herein). In some embodiments, the aqueous medium is the same medium in which the tablet(s) comprising color imparting agent is disintegrated.

In some embodiments, the tablet(s) comprising color imparting agent is mixed with an alkalizing medium comprising at least one alkalizing agent and a suitable carrier (e.g., an aqueous medium described herein). The alkalizing medium may optionally be prepared by disintegrating at least one tablet, as described herein. In some embodiments, a concentration of the alkalizing agent(s) in the alkalizing medium is in a range of from 0.1 to 15 weight percents. In some embodiments, the alkalizing medium is essentially the medium in which the tablet(s) comprising color imparting agent is disintegrated.

In some embodiments, the tablet(s) comprising color imparting agent is mixed with an oxidizing medium comprising at least one oxidizing agent and a suitable carrier (e.g., an aqueous medium described herein). The oxidizing medium may optionally be prepared by disintegrating at least one tablet, as described herein. In some embodiments, a concentration of the oxidizing agent(s) in the oxidizing medium is in a range of from 0.5 to 25 weight percents. In some embodiments, the oxidizing medium is essentially the medium in which the tablet(s) comprising color imparting agent is disintegrated.

In some embodiments, the oxidizing medium is a commercially available hydrogen peroxide solution. For example, solutions of 3%, 6%, 9%, 12%, and 24% hydrogen peroxide are commercially available, and may be suitable for use as an oxidizing medium according to embodiments of the invention. In some embodiments, the oxidizing medium is obtained by diluting an aforementioned commercially available to hydrogen peroxide solution (e.g., a 24% solution) to a desired concentration, using an appropriate amount of carrier medium (e.g., water).

In some embodiments, the tablet(s) comprising color imparting agent is mixed with a thickening medium comprising at least one thickening agent and a suitable carrier (e.g., an aqueous medium described herein). The thickening medium may optionally be prepared by disintegrating at least one tablet, as described herein. In some embodiments, the thickening medium is essentially the medium in which the tablet(s) comprising color imparting agent is disintegrated.

Mixture of the tablets with suitable media, as described herein, may be performed by any technique known in the art of color mixing. If mixing is performed manually, the process can be performed, for example, with a spatula, a brush, a spoon or any other suitable tool. If mixing is performed mechanically, such mixing can be performed, for example, by rotation of an impeller within the medium to be mixed, by applying vibrations or oscillatory movements to a receiving vessel containing the composition to be mixed, or by any other suitable method.

In some embodiments, the final coloring composition is mixed to homogeneity suitable for application to fibers within 10 minutes from addition of the tablets to the suitable medium. In some embodiments, the final coloring composition is mixed to homogeneity suitable for application to fibers within 5 minutes from addition of the tablets to the suitable medium.

In some embodiments, the tablet(s) comprising color imparting agent is mixed with at least one oxidizing agent (e.g., as described herein), and the resulting mixture is then mixed with at least one alkalizing agent (e.g., as described herein).

In some embodiments, the tablet(s) comprising color imparting agent is mixed with at least one alkalizing agent (e.g., as described herein). In some embodiments, the resulting mixture comprising an alkalizing agent is then mixed with at least one oxidizing agent (e.g., as described herein), so as to obtain a coloring composition comprising an alkalizing agent and an oxidizing agent. In some embodiments, the resulting mixture is then used (e.g., by mixing with a carrier medium) to prepare a coloring composition without an oxidizing agent (e.g., for coloring without an oxidation dye).

In some embodiments, the tablet(s) comprising color imparting agent is mixed to simultaneously with at least one oxidizing agent and at least one alkalizing agent. For example, the tablet(s) comprising color imparting agent may optionally be mixed with a medium which is both an oxidizing medium (e.g., as described herein) and an alkalizing medium.

For convenience, in some embodiments wherein an alkalizing medium and an oxidizing medium are used, a concentration of alkalizing agent and oxidizing agent in their respective media is such that one volume of oxidizing medium is suitable for use with one volume of alkalizing medium.

Similarly, in some embodiments, wherein an alkalizing medium is used without an oxidizing medium (e.g., when no oxidizing agent is used), a concentration of alkalizing agent in the alkalizing medium is such that no carrier medium needs to be added in order to obtain the desired concentration of alkalizing agent in a coloring composition, or alternatively, such that the desired concentration is obtained by adding one volume of carrier medium to one volume of alkalizing medium.

It is to be understood that additional volume ratios may be used (e.g., one volume of alkalizing medium for two volumes of oxidizing medium, if high bleaching is needed), as long as the concentrations of the active agents in the media are adjusted accordingly.

In some embodiments, the thickening agent(s) is mixed with the other ingredients of the composition after all other active agents have been mixed. In some embodiments, the thickening agent(s) is mixed concurrently with at least some other active agents, but no active agents are mixed after the thickening agent(s) has been added. Such sequences may be useful for avoiding interference by excess viscosity in the mixing of ingredients.

In some embodiments, the thickening agent(s) exhibits a substantial thickening effect only after being triggered by appropriate conditions. For example, some thickening agents exhibit a substantial thickening effect only at a suitable pH. A thickening effect of such agents may therefore be triggered by adjusting a pH to a suitable pH.

In some embodiments, the thickening agent is pH-sensitive, and a thickening effect thereof is triggered by adding alkalizing agent(s) such as described herein to a to relatively non-viscous composition comprising the thickening agent, for example, by adding an alkalizing medium (e.g., as described herein), and/or by adding one or more tablets comprising the alkalizing agent(s) (e.g., as described herein). Addition of the alkalizing agent results in a relatively viscous composition.

In some embodiments, a thickening effect of the thickening agent(s) is triggered after all other active agents have been mixed. In some embodiments, a thickening effect of the thickening agent(s) is triggered concurrently with at least some other active agents, but no active agents are mixed after a thickening effect of the thickening agent(s) has been triggered. Such timing of triggering may be useful for avoiding interference by excess viscosity in the mixing of ingredients Thus, in some embodiments wherein triggering is effected by the alkalizing agent(s), the alkalizing agent(s) is mixed with the other ingredients of the composition after all other active agents have been mixed, and/or concurrently with at least some other active agents, but no active agents are mixed after the alkalizing agent(s) has been added.

In some embodiments, a relatively non-viscous composition comprising the thickening agent(s) (e.g., prior to triggering) is sufficiently acidic such that the thickening agent(s) does not exhibit a substantial thickening effect. Such a composition may be in the form of a medium (e.g., oxidizing medium) such as described herein. In some embodiments, "sufficiently acidic" is a pH below 6. In some embodiments, "sufficiently acidic" is a pH below 5. In some embodiments, "sufficiently acidic" is a pH below 4. In some embodiments, "sufficiently acidic" is a pH below 3.

In some embodiments, the tablet(s) comprising color imparting agent is mixed with (e.g., disintegrated in) an oxidizing medium comprising at least one oxidizing agent, at least one thickening agent, and a suitable carrier (e.g., an aqueous medium described herein), to obtain a mixture comprising color imparting agent, oxidizing agent and thickening agent. The oxidizing medium may optionally be prepared by disintegrating at least one tablet comprising an oxidizing agent and/or at least one tablet comprising a thickening agent, as described herein. In some embodiments, a thickening agent in a form of a powder and/or suspension (e.g., aqueous suspension, non-aqueous suspension) is added to an oxidizing medium such as described herein.

In some embodiments, the oxidizing medium is sufficiently acidic (e.g., as described herein) such that the thickening agent(s) does not exhibit a substantial thickening effect. In some embodiments, the mixture comprising color imparting agent, oxidizing agent and thickening agent remains sufficiently acidic (e.g., as described herein) such that the thickening agent(s) does not exhibit a substantial thickening effect.

In some such embodiments, the alkalizing agent(s) is mixed with the aforementioned mixture comprising the other active agents, and a thickened coloring composition is obtained with a suitable pH, texture and viscosity (e.g., as described herein). In some embodiments, addition of the alkalizing agent(s) is effected by adding an alkalizing medium (e.g., as described herein) to the mixture. In exemplary embodiments, the alkalizing medium has a pourable consistency (e.g, a lotion, a pourable cream).

In exemplary embodiments, concentrations of active agents in the alkalizing and oxidizing media are selected such that the alkalizing medium and oxidizing medium with thickening agent are provided in a 1:1 volume ratio.

In some embodiments, a concentration of the thickening agent(s) in the oxidizing medium is in a range of from 0.1 to 10 weight percents. In some embodiments, a concentration of the thickening agent(s) in the oxidizing medium is in a range of from 0.2 to 7 weight percents. In some embodiments, a concentration of the thickening agent(s) in the oxidizing medium is in a range of from 0.2 to 5 weight percents.

Examples of suitable thickening agents for inclusion in an oxidizing medium include, without limitation, acrylate polymers and copolymers thereof, acrylate derivative polymers and copolymers thereof, polyvinyl pyrrolidone and copolymers thereof, and polyvinyl pyrrolidone derivative and copolymers thereof. By "Derivative" are encompassed polymers in which at least a portion of the acrylate or PVP backbone units are substituted by one or more substituents.

In some embodiments, a concentration of alkalizing agent in the composition comprising at least one color imparting agent (e.g., after mixing) is 10 weight percents or less.

In some embodiments wherein an alkalizing agent comprises ammonium, a concentration of alkalizing agent in the composition is in a range of from 0.5 to 5 weight percents. In some such embodiments, the concentration is in a range of from 1 to 3 weight percents.

In some embodiments, an amount of alkalizing agent is selected such that a pH of the final coloring composition is in a range of from 7.0 to 11.5. In some embodiments, the pH is in a range of from 7.5 to 10.0.

The concentration of alkalizing agent in a coloring composition, and the pH thereof, may affect the permanence of the coloring obtained with the composition.

In some embodiments, an amount of alkalizing agent is selected such that a pH of the final coloring composition is in a range of from 7.0 to 8.0, the coloring composition being for temporary coloring.

In some embodiments, an amount of alkalizing agent is selected such that a pH of the final coloring composition is in a range of from 8.0 to 9.0, the coloring composition being for semi-permanent and/or demi-permanent coloring.

In some embodiments, an amount of alkalizing agent is selected such that a pH of the final coloring composition is above 9.0, the coloring composition being for permanent coloring.

As a pH of a composition may change after application of the composition to fibers, the pH values described herein refer to the pH of a composition prior to application.

In some embodiments, a concentration of oxidizing agent in the composition comprising at least one color imparting agent (e.g., after mixing) is 10 weight percents or less.

In some embodiments wherein an oxidizing agent is hydrogen peroxide, a concentration of the oxidizing agent in the composition is in a range of from 1 to 6 weight percents.

A concentration of oxidizing agent(s) in a coloring composition may be selected to be suitable for a desired type of coloring. In some embodiments, no oxidizing agent is used in a composition for temporary coloring.

In addition, a concentration of oxidizing agent(s) may depend on the initial color and desired color. For example, lower concentrations may be used when coloring a light-colored fiber with a darker color than when coloring a dark-colored fiber with a to light color. In some embodiments, no oxidizing agent is used when coloring a light-colored fiber with a dark color (e.g., when the color imparting agent(s) is not an oxidation dye).

In some embodiments, a concentration of alkalizing agent and a concentration of oxidizing agent in the composition comprising at least one color imparting agent are each 10 weight percents or less.

In some embodiments, the ingredients being mixed and amounts thereof are selected such that the obtained coloring composition is characterized by a viscosity suitable for providing sufficient time of contact between the composition and the fibers, to thereby facilitate coloring.

A suitable viscosity of a coloring composition may be obtained by a selecting suitable amount of thickening agent (if present), a suitable ratio of liquid medium to solid ingredients, and/or a suitable viscosity of one or more media used to prepare the composition.

A suitable viscosity may depend on the type of coloring which is intended. For example, a composition for temporary coloring may be characterized by a low viscosity (e.g., a composition in the form of a "wash"), whereas effective permanent coloring typically requires a higher viscosity such that composition will remain in contact with the fibers for a longer time period.

In some embodiments, the final coloring composition has a viscosity of at least 50 poise or at least 60 poise (as measured at a shear rate of $10 \text{ s}^{-1}$, at a temperature of 25° C.).

In some embodiments, a composition for temporary coloring has a viscosity of up to 1 poise (as measured at a shear rate of 10 at about 25° C.).

The different media used to prepare the composition (e.g., alkalizing, oxidating and/or carrier media) may optionally each have viscosities similar to that of the final composition. Alternatively, each medium can have a distinct viscosity, as long as the media remain mixable and the viscosity of the final coloring composition is suitable. In some embodiments, an alkalizing medium is more viscous than an oxidizing medium.

In some embodiments, the method comprises disintegrating at least 2 tablets (e.g., tablets described herein), optionally at least 3, optionally at least 4, optionally at to least 5, optionally at least 10, optionally at least 20, optionally at least 50, optionally at least 100, optionally at least 150, and optionally at least 200 tablets.

In some embodiments, the method comprises disintegrating no more than 150 tablets to thereby obtain the desired color imparting agent(s). In some embodiments, the method comprises disintegrating no more than 100 tablets to thereby obtain the desired color imparting agent(s).

In some embodiments, the method comprises disintegrating no more than 150 tablets to thereby obtain all the desired active agents described herein (i.e., color imparting agents, oxidizing agents, thickening agents, and/or alkalizing agents). In some embodiments, the method comprises disintegrating no more than 100 tablets to thereby obtain all the desired active agents described herein.

A medium used for preparing a composition (e.g., an alkalizing medium, oxidizing medium and/or carrier medium described herein) may optionally further comprise additional ingredients, for example, an anti-dandruff agent, an anti-foam agent, anti-oxidants, a chelating agent, a conditioning agent, an emollient, an emulsifying agent, a fragrance, a free-radical scavenger, a hair care agent, a humectant, an odor masking agent, an opacifier, a pearlizing agent, a pH adjusting agents, a preservative, a stabilizing agent, a surfactant, a vitamin, a vitamin precursor, and a wetting agent (e.g., as described herein).

The coloring composition prepared as described herein may optionally be applied to hair by any conventional method, for instance by using a brush, a comb, a cloth, a sponge, a squeeze bottle or an applicator, including applicators comprising reservoirs for the coloring formula.

In some embodiments, the coloring composition is left on the hair from about 5 to 60 minutes, although certain types of temporary coloring could be achieved in a shorter time.

It is to be appreciated that the time for which a coloring composition should be left on fibers depends on temperature, which affects the rate of the coloring process. In some embodiments, coloring may be effected at a temperature in a range of from 15° C. to 45° C. In some embodiments, the coloring process of human hair lasts for about 10 to 45 minutes at room temperature.

The selection of a tablet may be based on:
establishing the initial color of the hair fibers, and then selecting a desired customized color suiting an individual subject. The customized color could be selected by the user from a collection of final shades. The system is then in a position to determine amounts of tablets suitable, in combination, for changing the color of the fibers to the color desired by the customer.

Establishing said initial color may involve measuring an initial reflectance spectrum. Selecting the customized color may comprise determining a reflectance spectrum of the customized color, and the reflectance spectra may be independently converted to a color coordinate presentation.

The amount of tablet to be used may be determined by adding to the initial reflectance spectrum the positive or negative contribution of one tablet of one basic shade to obtain an intermediate calculated color coordinate presentation. Then iterations of the calculation step for a tablet of same or different basic shade may be carried out, until the difference between the intermediate calculated color and the desired color coordinate presentation is minimized.

The determination may take into consideration positive and/or negative contributions of an active agent such as an alkalizing agent, an oxidizing agent, or a thickening agent to the calculated color coordinate presentation.

The selecting may account for a contribution of individual properties of the keratinous fibers.

The selecting may be carried out by a computer implemented system.

The measuring may be carried out by the optical hair measurement device or hair reader. The hair reader may comprise an illumination unit for illuminating hair, and a measuring unit comprising at least one sensor for optically measuring the hair during illumination. The sensor and a beam from the illumination unit may respectively subtend a light diffusion angle at the hair being measured, thereby to ensure that the sensor principally measures light that is diffused or scattered by the hair.

The hair reader may include a main illumination source and subsidiary illumination sources, and processing electronics to use differential illumination results from the various sources to determine an angle of a hair relative to the main illumination source.

The main illumination source may be used for spectroscopy, and a subsidiary to illumination source may be used for angular measurement.

The sensor may comprise sensitivity to the visible and near infrared parts of the electromagnetic spectrum.

In some embodiments, measuring an initial reflectance spectrum is performed while using an optical reader as disclosed in detail herein. However, any other hair readers are also contemplated.

According to some embodiments of the present invention, a method of performing a customized treatment of keratinous fibers, is effected by:
obtaining optical measurements of the keratinous fibers;
predicting a result of treating the keratinous fibers with a pre-determined combination of active agents and selecting, based on the predicting, a customized combination of the active agents for effecting a desired treatment of the keratinous fibers and/or customized conditions for applying the active agents;
preparing a composition comprising the customized combination of active agents; and
contacting the keratinous fibers with the composition.

In some embodiments, obtaining the optical measurements is effected using an optical reader as described herein. However, any other optical readers are contemplated.

In some embodiments, the predicting is in accordance with the methods as described herein.

In some embodiments, at least one of the active agents is formulated as a tablet (a solid formulation such as described herein), and selecting the combination comprises selecting a combination of the tablets. Selecting the combination can further comprise selecting a suitable medium to be mixed with the tablets to provide a desired composition, as described herein.

According to some embodiments preparing the composition is effected dispensing the combination of tablets from a dispensing device, such as described herein According to some embodiments, the dispensing device is interfaced with the computer implemented unit.

According to some embodiments of the present invention, the dispensing device to is as described herein.

In any of these embodiments, the active agents include color imparting agents, thickening agents, oxidizing agents and/or alkalizing agents, as described herein.

In any of the above aspects, the selecting is further of conditions for contacting the composition with the keratinous fibers, wherein the conditions include, but are not limited to, rate, duration and temperature, as described herein.

According to some embodiments, any of the methods described herein are executed while using any of the systems as described herein.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion. Certain marks referenced herein may be common law or registered trademarks of third parties. Use of these marks is by way of example and shall not be construed as descriptive or limit the scope of this invention to material only associated with such marks.

Example 1

Tablet Compositions

Materials and Methods:
Tablets were formulated to provide a range of basic shades which can be combined to provide a custom coloring composition.

The ingredients were purchased at pharmaceutical or cosmetic grade, as applicable.

The color imparting agents were generally purchased from Jarocol.

The tablet ingredients (including the color imparting agents) were mixed together.

Prior to mixing, one or more of the tablet ingredients was optionally ground with a cutting mill (Fritsch Pulverisette 19, with an insert sieve of 250 micron) under operating conditions, so as to obtain a similar size distribution for all tablet ingredients. In a typical procedure, for a batch of 400 grams, ingredients were ground for about 2 hours at a power of 2,000 W, although longer times can be used for ingredients made of hard bulk material and/or having large initial size were eventually ground for up to 4 hours.

The obtained particles were then optionally sieved by vibration techniques with meshes having openings of 212 μm, 150 μm and 45 μm (Retsch Vibratory Sieve Shaker, AS 200) to predominantly obtain particles having a size ranging from 45 μm to 150 μm.

The tablet ingredients, whether or not ground and/or sieved, were then transferred to an oven set to 50° C. to homogeneously dry the particles. After twenty four hours, desired amounts of the dried particles of the various tablet ingredients were thoroughly mixed for at least twenty minutes using a motorized V-shape blender (Model GHJ-10V, Jiangyin Longchang Machinery Manufacture Co.).

The obtained powdered mixture was then tableted, using either a manual or an automatic tabletting machine.

In the manual tabletting setup, 1.5 Kg of the mixture was introduced into a stainless steel AISI 316 cylinder having an inner diameter of about 25 mm. The corresponding piston was placed over the powdered mixture, which was then compressed with a manual hydraulic press (Mazzola, W20) applying a pressure of 25 N on the resulting tablet, which had an average thickness of about 3 mm A 10-station rotary tablet press machine (TPC-10-B, Dynamic Exim Corp.) was used for the automated process, with tooling of modified ball configuration having a to diameter of 4.5 mm or 5.0 mm (iHolland). The modified ball punches were adjusted to allow for the production of tablets having a maximal thickness similar to the tablet diameter, hence for the preparation of approximately spherical tablets having a diameter of 4.5 mm or 5.0 mm The average weight of a spheroid tablet of 5.0 mm typically ranged from about 70 mg to about 90 mg, depending on the formulation used.

The applied compression was generally between 5 kN and 7.5 kN for a single tip punch, generally resulting in a hardness of 3.0 kgf to 5.0 kgf (as further detailed in Example 3 hereinbelow).

Tablet Formulations: Using the above described methods, various tablets were prepared. Tables 1A to 1C below present the tablet's composition as weight percents of each component of the total weight of an uncoated tablet. Table 1A presents compositions of control tablets devoid of color imparting agents, which are also referred to herein as placebo tablets; Table 1B presents compositions of basic shade tablets comprising color imparting agents (which were prepared at both 4.5 and 5.0 mm approximate diameter); and Table 1C presents compositions of rapidly disintegrating media tablets comprising oxidizing agents (see, Tablet Nos. 201-204), thickening agents (see, Tablet Nos. 205-208) and alkalizing agents (see, Tablet No. 209).

The various grades of Avicel® (FMC Corporation) and Comprecel correspond to various types of microcrystalline cellulose; GalenIQ™ grades (Palatinit) and Isomalt™ correspond to various preparations of isomalt; LH-21 and LH-22 (Shin Etsu) are types of low substituted hydroxypropyl cellulose (HPC); Ludiflash® (BASF) and Parteck® M and ODT grades are based on mannitol, whereas Parteck® SI grades (Merck) are based on sorbitol; and PEO N-10 (DOW) is a polyethylene oxide. Ludiflash® comprises in addition to mannitol, PVA, PVP and polyvidone. SuperTab® 11SD is a spray dried form of lactose and all previously mentioned ingredients from Avicel® to SuperTab® serve alone or in combination as bulk excipients (e.g., binder, filler), though some of them may also be considered as auxiliary disintegrants (e.g., LH-21, LH-22, SuperTab® 11SD). AC-Di-Sol® SD711 is a type of sodium croscarmellose, Polyplasdone® grades (ISP) correspond to various types of crosslinked polyvinylpyrrolidone and Primojel® comprises sodium starch glycolate. The latter to group of ingredients serves as superdisintegrants. A third series of ingredients serve as additives such as antioxidants (ascorbic acid) and lubricants/anti-adherents/glidants (magnesium stearate, Alubra™, which comprises sodium stearyl fumarate, and Parteck® LUB CST, LUB MST and LUB STA 50 of Merck, which respectively comprise calcium stearate, magnesium stearate and stearic acid).

Formulations prepared without lubricants were manually tableted. Such formulations were adapted to automatic tabletting by adding a lubricant (e.g., 1% Mg stearate or any other suitable amount of appropriate ingredient) and decreasing the amount of bulk excipient by the same quantity.

Some basic shade tablets were prepared in two versions, one comprising only dye precursors and couplers, and another comprising the same precursors and couplers in the same amount together with direct dyes, in which case the amount of bulk excipient was decreased accordingly. The version with the direct dyes are presented in Table 1B, the version without the direct dye is denoted by the same tablet number followed by an apostrophe (e.g., Tablet No. 103 corresponds to the Red shade comprising 0.08% of HC Red No. 10 & 11, whereas Tablet No. 103' corresponds to a Red shade lacking said direct dyes and comprising 60.5% of Avicel® PH-102).

TABLE 1A

| Ingredient | Tablet No. | | | | | | | |
|---|---|---|---|---|---|---|---|---|
| | 1 | 2 | 3 | 4 | 5 | 6 | 7 | 8 |
| Avicel ® CE-15 | 99.50 | 99.00 | — | — | — | — | — | — |
| Avicel ® HFE-102 | — | — | 99.50 | — | — | — | — | — |
| Avicel ® PH-101 | — | — | — | 99.00 | 99.00 | 64.50 | 64.50 | 64.50 |
| SuperTab ® 11SD | — | — | — | — | — | 33.00 | 33.00 | 33.00 |
| AC-Di-Sol ® SD711 | 0.50 | — | 0.50 | — | — | 2.00 | 2.00 | 2.00 |
| Polyplasdone ® INF-10 | — | — | — | — | — | — | — | — |
| Polyplasdone ® XL | — | 1.00 | — | 1.00 | — | — | — | — |
| Polyplasdone ® XL-10 | — | — | — | — | 1.00 | — | — | — |
| Parteck ® LUB CST | — | — | — | — | — | 0.50 | — | — |

TABLE 1A-continued

| Ingredient | | | | | | | | |
|---|---|---|---|---|---|---|---|---|
| Parteck ® LUB MST | — | — | — | — | — | — | 0.50 | — |
| Parteck ® LUB STA 50 | — | — | — | — | — | — | — | 0.50 |

| | Tablet No. | | | | | | | |
|---|---|---|---|---|---|---|---|---|
| Ingredient | 9 | 10 | 11 | 12 | 13 | 14 | 15 | 16 |
| Avicel ® PH-101 | 65.00 | — | — | — | — | — | — | — |
| Avicel ® PH-102 | — | 70.00 | 70.00 | — | — | — | — | — |
| Avicel ® PH-102 SCG | — | — | — | 99.50 | 99.00 | — | — | — |
| Avicel ® PH-105 | — | — | — | — | — | 99.00 | 99.00 | 99.00 |
| SuperTab ® 11SD | 33.00 | 27.00 | 22.00 | — | — | — | — | — |
| AC-Di-Sol ® SD711 | 2.00 | 2.00 | 2.00 | 0.50 | — | 1.00 | — | — |
| Polyplasdone ® INF-10 | — | — | — | — | — | 1.00 | — | — |
| Polyplasdone ® XL | — | — | — | — | 1.00 | — | 1.00 | — |
| Polyplasdone ® XL-10 | — | — | — | — | — | — | — | 1.00 |
| Ascorbic acid | — | — | 5.00 | — | — | — | — | — |
| Magnesium stearate | — | 1.00 | 1.00 | — | — | — | — | — |

| | Tablet No. | | | | | | | |
|---|---|---|---|---|---|---|---|---|
| Ingredient | 17 | 18 | 19 | 20 | 21 | 22 | 23 | 24 |
| Avicel ® PH-105 | 99.50 | — | — | — | — | — | — | — |
| Avicel ® PH-200 | — | 99.50 | — | — | — | — | — | — |
| Avicel ® PH-301 | — | — | 99.50 | 99.00 | 99.00 | 97.50 | — | — |
| Avicel ® PH-302 | — | — | — | — | — | — | 99.50 | 99.00 |
| AC-Di-Sol ® SD711 | 0.50 | 0.50 | 0.50 | — | — | 0.50 | 0.50 | — |
| Polyplasdone ® XL | — | — | — | 1.00 | — | — | — | 1.00 |
| Polyplasdone ® XL-10 | — | — | — | — | 1.00 | 2.00 | — | — |

| | Tablet No. | | | | | | | |
|---|---|---|---|---|---|---|---|---|
| Ingredient | 25 | 26 | 27 | 28 | 29 | 30 | 31 | 32 |
| Avicel ® PH-302 | 99.00 | 97.00 | 97.50 | 65.00 | 70.00 | — | — | — |
| Comprecel M101 | — | — | — | — | — | 97.00 | 99.50 | — |
| Comprecel M102 | — | — | — | — | — | — | — | 97.00 |
| GalenIQ ™ 721 | — | — | — | 34.50 | — | — | — | — |
| SuperTab ® 11SD | — | — | — | — | 27.00 | — | — | — |
| AC-Di-sol ® SD711 | — | — | 0.50 | 0.50 | 2.00 | — | 0.50 | — |
| Polyplasdone ® XL | — | — | — | — | — | 3.00 | — | 3.00 |
| Polyplasdone ® XL-10 | 1.00 | 3.00 | 2.00 | — | — | — | — | — |
| Magnesium stearate | — | — | — | — | 1.00 | — | — | — |

| | Tablet No. | | | | | | | |
|---|---|---|---|---|---|---|---|---|
| Ingredient | 33 | 34 | 35 | 36 | 37 | 38 | 39 | 40 |
| Comprecel M102 | 99.50 | — | — | — | — | — | — | — |
| GalenIQ ™ 720 | — | 97.00 | 99.00 | — | — | — | — | — |
| GalenIQ ™ 721 | — | — | — | 97.00 | 99.00 | — | — | — |
| GalenIQ ™ 800 | — | — | — | — | — | 97.00 | 99.00 | — |
| GalenIQ ™ 810 | — | — | — | — | — | — | — | 97.00 |
| AC-Di-sol ® SD711 | 0.50 | — | 1.00 | — | 1.00 | — | 1.00 | — |
| Polyplasdone ® INF-10 | — | — | — | — | — | — | — | — |
| Polyplasdone ® XL | — | 3.00 | — | 3.00 | — | 3.00 | — | 3.00 |

| | Tablet No. | | | | | | | |
|---|---|---|---|---|---|---|---|---|
| Ingredient | 41 | 42 | 43 | 44 | 45 | 46 | 47 | 48 |
| GalenIQ ™ 810 | 99.00 | — | — | — | — | — | — | — |
| GalenIQ ™ 960 | — | 97.00 | 99.00 | — | — | — | — | — |
| Isomalt ™ GS | — | — | — | 75.40 | 43.40 | — | — | — |
| LH-21 (HPC) | — | — | — | 9.60 | — | — | — | — |
| LH-22 (HPC) | — | — | — | — | 48.00 | — | — | — |
| Ludiflash ® | — | — | — | — | — | 100.0 | — | — |
| Parteck ® Delta M | — | — | — | — | — | — | 99.50 | — |
| Parteck ® M 100 | — | — | — | — | — | — | — | 99.50 |
| PEO N-10 | — | — | — | 15.00 | 8.60 | — | — | — |
| AC-Di-sol ® SD711 | 1.00 | — | 1.00 | — | — | — | 0.50 | 0.50 |
| Polyplasdone ® XL | — | 3.00 | — | — | — | — | — | — |

| | Tablet No. | | | | | | | |
|---|---|---|---|---|---|---|---|---|
| Ingredient | 49 | 50 | 51 | 52 | 53 | 54 | 55 | 56 |
| Avicel ® PH-102 | — | — | — | — | — | — | 69.60 | 70.40 |
| Parteck ® M 200 | 99.50 | — | — | — | — | — | — | — |

TABLE 1A-continued

| | | | | | | | | |
|---|---|---|---|---|---|---|---|---|
| Parteck ® ODT | — | 99.50 | — | — | — | — | — | — |
| Parteck ® SI 200 | — | — | 99.50 | — | — | — | — | — |
| Parteck ® SI 400 | — | — | — | 99.50 | — | — | — | — |
| Parteck ® SI 450 | — | — | — | — | 99.50 | — | — | — |
| SuperTab ® 11SD | — | — | — | — | — | 97.00 | 26.40 | 26.60 |
| AC-Di-sol ® SD711 | 0.50 | 0.50 | 0.50 | 0.50 | 0.50 | 2.00 | — | 2.00 |
| Primojel ® | — | — | — | — | — | — | 3.00 | — |
| Alubra ™ PG-100 | — | — | — | — | — | — | — | 1.00 |
| Magnesium stearate | — | — | — | — | — | 1.00 | 1.00 | — |

TABLE 1B

| | Tablet No. | | | | | | | | |
|---|---|---|---|---|---|---|---|---|---|
| | 101 | 102 | 103 | 104 | 105 | 106 | 107 | 108 | 109 |
| | Shade | | | | | | | | |
| Ingredient | Rose | Orange | Red | Gold | Violet | Blue | Ash | Nature | Green |
| Avicel ® PH-102 | 67.71 | 63.32 | 60.43 | 67.50 | 58.87 | 63.01 | 68.93 | — | 60.70 |
| Avicel ® PH-200 | — | — | — | — | — | — | — | 58.74 | — |
| SuperTab ® 11SD | 25.63 | 23.96 | 22.90 | 25.54 | 22.33 | 23.85 | 26.09 | 22.23 | 23.17 |
| AC-Di-sol ® SD711 | 2.00 | 2.00 | 3.00 | 2.00 | 3.00 | 2.00 | 2.00 | 2.00 | 2.00 |
| Magnesium stearate | 1.00 | 1.00 | 1.00 | 1.00 | 1.00 | 1.00 | 1.00 | 1.00 | 1.00 |
| Ascorbic acid | 1.00 | 1.00 | 3.00 | 1.00 | 3.00 | 1.00 | 1.00 | 1.00 | 1.00 |
| p-aminophenol | 1.17 | — | — | — | — | — | — | — | — |
| 4-amino-m-cresol | — | 0.30 | — | — | — | — | — | — | — |
| 1-hydroxyethyl-4,5-diamino pyrazole sulfate | — | — | 6.30 | — | — | — | — | — | — |
| n,n-bis(2-hydroxy-ethyl)-p-phenylene-diamine sulfate | — | — | — | — | 8.30 | 4.96 | — | — | — |
| toluene-2,5-diamine sulfate | — | — | — | — | — | — | 0.50 | 10.13 | 3.80 |
| 4-amino-2-hydroxytoluene | 1.50 | 0.30 | 3.30 | — | 3.50 | — | — | — | — |
| 2,4-diamino-phenoxy-ethanol diHCl | — | — | — | — | — | 4.04 | 0.40 | — | — |
| m-aminophenol | — | — | — | — | — | — | — | 0.47 | — |
| Resorcinol | — | — | — | — | — | — | — | 4.43 | — |
| hydroxyethyl-3,4-methylene dioxyaniline HCl | — | — | — | — | — | — | 0.10 | — | 3.80 |
| 2-amino-6-chloro-4-nitrophenol | — | 8.14 | — | 3.00 | — | — | — | — | — |
| HC Red No. 10 & 11 | — | — | 0.08 | — | — | — | — | — | — |
| HC Blue No. 15 | — | — | — | — | — | 0.16 | — | — | 0.03 |
| HC Yellow No. 13 | — | — | — | — | — | — | — | — | 4.00 |
| 2,6-diamino-3-((pyridin-3-yl)azo)pyridine | — | — | — | — | — | — | — | — | 0.50 |

TABLE 1C

| | Tablet No. | | | | | | | | |
|---|---|---|---|---|---|---|---|---|---|
| Ingredient | 201 | 202 | 203 | 204 | 205 | 206 | 207 | 208 | 209 |
| Urea Hydrogen Peroxide | 35.00 | 97.00 | 50.00 | 50.00 | — | — | — | — | — |
| Carbopol ® Ultrez 20 | — | — | — | — | 10.00 | — | — | — | — |
| Stabileze ® QM | — | — | — | — | — | 6.00 | 7.00 | 12.00 | — |
| (NH$_4$)$_2$CO$_3$ | — | — | — | — | — | — | — | — | 30.00 |
| Avicel ® PH-102 | — | — | 47.00 | 34.10 | 53.60 | 65.30 | 63.10 | 59.50 | 48.60 |
| SuperTab ® 11SD | 62.00 | — | — | 12.90 | 20.30 | 24.70 | 23.90 | 22.50 | 18.40 |
| AC-Di-sol ® SD711 | 2.00 | 2.00 | 2.00 | 2.00 | 2.00 | 3.00 | — | — | 2.00 |
| Polyplasdone ® XL | — | — | — | — | — | — | 5.00 | 5.00 | — |
| Citric acid | — | — | — | — | 7.00 | — | — | — | — |
| Sodium bicarbonate | — | — | — | — | 6.10 | — | — | — | — |
| Magnesium stearate | 1.00 | 1.00 | 1.00 | 1.00 | 1.00 | 1.00 | 1.00 | 1.00 | 1.00 |

Tables 1D and 1E present exemplary improved formulations, prepared in order to allow accurate coloring and analysis with an algorithm system as described herein, by containing one color imparting agent.

The ratio of the oxidation dye precursor to the coupler was finely tuned (as being less than 1) in order to avoid possible formation of harmful compounds.

TABLE 1D

| | Tablet No. | | | | | | | | |
|---|---|---|---|---|---|---|---|---|---|
| | 1 | 2 | 3 | 4 | 5 | 6 | 7 | 8 | 9 |
| | | | | | Shade | | | | |
| Ingredient | Natural | Gold | Orange | Red | Violet | Ash | Rose | Green | Blue |
| Avicel ® PH-200 | 58.9% | 68.5% | 60.5% | 60.4% | 57.8% | 68.8% | 69.1% | 61.2% | 61.3% |
| SuperTab ® 11SD | 22.2% | 25.9% | 22.9% | 22.9% | 22% | 26.2% | 26.2% | 23.1% | 23.2% |
| AC-Di-sol ® SD711 | 2% | 2% | 2% | 3% | 3% | 2% | 2% | 2% | 2% |
| Magnesium stearate | 1% | 1% | 1% | 3% | 3% | 1% | 1% | 1% | 1% |
| Ascorbic acid | 1% | 1% | 1% | 1% | 1% | 1% | 1% | 1% | 1% |
| Toluene-2,5-diamine sulfate | 9.93% | | | | | 0.24% | | 3.8% | |
| 1-hydroxyethyl-4,5-diamino-pyrazole sulfate | | | | 6.3% | | | | | |
| N,N-Bis(2-hydroxyethyl)-p-phenylene-diamine sulfate | | | | | 9.25% | | | | 6.2% |
| 4-Amino-m-cresol | | | 0.43% | | | | | | |
| p-Aminophenol | | | | | | | 0.35% | | |
| 4-Amino-2-hydroxytoluene | | | 0.43% | 3.3% | 3.9% | | 0.45% | | |
| 2,4-Diamino-phenoxy-ethanol 2HCl | | | | | | 0.22% | | | 5.05% |
| m-Aminophenol | 0.91% | | | | | | | | |
| Resorcinol | 4.05% | | | | | | | | |
| Hydroxyethyl-3,4-methylene-dioxyaniline HCl | | | | | | 0.46% | | 3.8% | |
| 2-amino-6-chloro-4-nitrophenol | | 1.55% | 11.7% | | | | | | |
| HC Red No. 10 & 11 | | | | 0.075% | | | | | |
| HC Yellow No. 13 | | | | | | | | 4% | |
| 2,6-diamino-3-((pyridin-3-yl)azo) pyridine | | | | | | | | | |
| HC Blue No. 15 | | | | | | | | 0.03% | 0.2% |

TABLE 1E

| | Tablet No. | | | | | | | | |
|---|---|---|---|---|---|---|---|---|---|
| | 10 | 11 | 12 | 13 | 14 | 15 | 16 | 17 | 18 |
| | | | | | Shade | | | | |
| Ingredient | Natural | Gold | Orange | Red | Violet | Ash | Rose | Green | Blue |
| Avicel ® PH-102 | 58.9% | 68.5% | 60.5% | 60.4% | 57.8% | 69.3% | 69.1% | 63.9% | 61.3% |
| SuperTab ® 11SD | 22.2% | 25.9% | 22.9% | 22.9% | 22% | 26.2% | 26.2% | 23.1% | 23.2% |
| AC-Di-sol ® SD711 | 2% | 2% | 2% | 3% | 3% | 2% | 2% | 2% | 2% |
| Magnesium stearate | 1% | 1% | 1% | 3% | 3% | 1% | 1% | 1% | 1% |
| Ascorbic acid | 1% | 1% | 1% | 1% | 1% | 1% | 1% | 1% | 1% |
| Toluene-2,5-diamine sulfate | 9.93% | | | | | 0.24% | | 3.46% | |
| 1-hydroxyethyl-4,5-diamino-pyrazole sulfate | | | | 6.3% | | | | | |
| N,N-Bis(2-hydroxyethyl)-p-phenylene-diamine sulfate | | | | | 9.25% | | | | 6.2% |
| 4-Amino-m-cresol | | | 0.43% | | | | | | |
| p-Aminophenol | | | | | | | 0.35% | | |
| 4-Amino-2-hydroxytoluene | | | 0.43% | 3.3% | 3.9% | | 0.45% | | |
| 2,4-Diamino-phenoxy-ethanol 2HCl | | | | | | 0.22% | | | 5.05% |
| m-Aminophenol | 0.91% | | | | | | | | |

TABLE 1E-continued

| | Tablet No. | | | | | | | | |
|---|---|---|---|---|---|---|---|---|---|
| | 10 | 11 | 12 | 13 | 14 | 15 | 16 | 17 | 18 |
| | | | | | Shade | | | | |
| Ingredient | Natural | Gold | Orange | Red | Violet | Ash | Rose | Green | Blue |
| Resorcinol | 4.05% | | | | | | | | |
| Hydroxyethyl-3,4-methylene-dioxyaniline HCl | | | | | | 0.46% | | 3.43% | |
| 2-amino-6-chloro-4-nitrophenol | | 1.55% | 11.7% | | | | | | |
| HC Red No. 10 & 11 | | | | 0.075% | | | | | |
| HC Yellow No. 13 | | | | | | | | 2% | |
| 2,6-diamino-3-((pyridin-3-yl)azo)pyridine | | | | | | | | 0.025% | |
| HC Blue No. 15 | | | | | | | | 0.025% | 0.2% |
| Base/coupler ratio | 0.99 | — | 0.99 | 0.98 | 0.93 | 0.99 | 0.87 | 0.99 | 0.95 |

Tables 1D and 1E each present a combination of exemplary formulations for a variety of basic shades, which are may be combined to form a wide variety of shades. The exemplary formulations comprise, as color imparting agents, a combination of one or more dye precursors with one or more dye couplers, and/or one or more direct dyes. The dye precursors used include toluene-2,5-diamine, 1-hydroxyethyl-4,5-diamino-pyrazole, N,N-bis(2-hydroxyethyl)-p-phenylene-diamine, 4-amino-m-cresol, and p-aminophenol. The dye couplers used include 4-amino-2-hydroxytoluene, 2,4-diamino-phenoxy-ethanol, m-aminophenol, resorcinol, and hydroxyethyl-3,4-methylene-dioxyaniline. The direct dyes used include 2-amino-6-chloro-4-nitrophenol, HC Red No. 10 & 11, HC Yellow No. 13, 2,6-diamino-3-((pyridin-3-yl)azo)pyridine, and HC Blue No. 15).

In the formulation presented in Table 1E, the molar ratio between the base dye (dye precursor) and the dye coupler was finely controlled so as not to exceed 1.0.

Example 2

Tablet Coatings

The tablets prepared as described in Example 1 were, when desired, further coated, for instance, to enhance the tablet hardness, reduce the undesired oxygen and/or moisture penetration and prolong the shelf-life of the tablets.

The tablets were spray-coated using a perforated pan coater (Freund Vector, Laboratory LDCS Hi-Coaters®) with electropolished fully perforated pan 2.5 L. The coating solutions were generally sprayed using Schlick ABC spray gun at average inlet temperature of 74-77° C. and average exhaust temperature of 45-50° C. for up to 105 minutes, depending on the concentration of the coating solution, the spraying rate and the desired thickness. The thickness of the resulting coatings was assessed by cutting the tablet and measuring the thickness of the coating in the resulting cross section under an optical microscope (Olympus BX51). The reported average thickness is the mean of four measurements made on two tablets of the same batch. Alternatively, the thickness of the coating could be estimated according to the weight gained by the tablet following coating, by approximating the tablet shape to a sphere. By assuming that the coating and the tablet have the same density, the tablet percent weight increase ΔW, given by equation 1, allows estimation of the thickness $r_2-r_1$, wherein $r_1$ is the initial radius of the uncoated tablet and $r_2$ is the final radius of the coated tablet:

$$100\left(\frac{r_2^3 - r_1^3}{r_1^3}\right) = \Delta W \qquad [\text{Eq. 1}]$$

The weight gain percentage presented in Table 2A, is calculated by equating the weight gain of the tablets to the weight of applied coating. In Table 2B it is calculated by measuring the weight of 100 tablets before and after coating using an analytical weight (ML204/01, Mettler Toledo).

The coating solutions were prepared by dissolving the coating agent of interest to in deionised water, typically by steadily adding the powder to a vortex formed by a propeller stirrer (Ultra-Turrax® T50 Basic with R 1402 Dissolver accessories, Ika Werke). Once all the powder was added, the propeller speed was reduced from 2,000 RPM to 500 RPM, which nearly eliminated the vortex, and the solution was further mixed for 30 minutes. The coating agents, when applicable with color identifiers, were purchased at pharmaceutical or edible grade. Opadry® coatings were obtained from Colorcon, and Kollicoat® coatings were obtained from BASF. These coatings were generally based on hydroxypropylmethylcellulose (HPMC), polyethylene glycol (PEG), polyvinyl alcohol (PVA), polyvinyl alcohol-polyethylene glycol graft copolymer (PVA-PEG), or mixtures thereof. Rapid Subcoat SD-9600, based on sucrose, PEG and xanthan gum, was purchased from Colorcon and used at a concentration of 5%. Typically inlet temperatures of about 74° C. were used for sucrose, HPMC and PVA-PEG copolymer based coatings and inlet temperatures of about 77° C. were used for PVA based coatings.

Batches of 1.2-1.6 kg of desired tablets were entered into the 2.5 liter perforated pan which was rotated at 18 RPM. The content of the pan was heated by the incoming warm air and the exhaust air temperature was monitored as an indicator of tablets' temperature. Once the tablets were preheated to about 45-50° C., coating solutions were peristalticly pumped to the system at the desired rate and generally sprayed at an air flow rate of 90-100 m³/hour with a spray gun atomization pressure of 700 to 900 mbar and a pattern air of 1,000 to 1,600 mbar. Various coated tablets were prepared by this method, including control tablets devoid of color imparting agents. The compositions of the coating solutions (in weight percents of the total weight of the coating solution), the spraying rate of the coating solution (in gram/minute), the duration of the coating (in minutes), the final solid contribution of the coating (as weight percents of the uncoated tablet) and the measured or calculated thickness of the resulting coatings (in microns) are presented in Tables 2A and 2B.

The coating experiments reported in Table 2A were performed at a coating rate of about 7 grams/minute, except for coating Nos. 4, 8 and 12 which were prepared at a rate of about 4 gram/minute. In additional experiments reported in Table 2B, the coating solutions were sprayed for about 45 minutes at a rate of 9-10 g/min. The coating to thickness reported in Table 2A was measured using optical microscopy and in Table 2B was both measured and calculated according to Equation 1.

TABLE 2A

| | Coat. # | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| Opadry ® II HPMC Blue | 5% | — | — | — | 5% | — | — | — | 5% | — | — | — |
| Opadry ® II PVA Yellow | — | 5% | — | — | — | 5% | — | — | — | 5% | — | — |
| Kollicoat ® IR Brilliant Blue | — | — | 5% | 1% | — | — | 5% | 1% | — | — | 5% | 1% |
| Kollicoat ® Protect | — | — | — | 4% | — | — | — | 4% | — | — | — | 4% |
| Coating Duration (min) | | 75 | | | | 90 | | | | 105 | | |
| Coating Amount (wt %) | 2.1 | 2.1 | 2.1 | 1.3 | 2.6 | 2.6 | 2.6 | 1.5 | 3.0 | 3.0 | 3.0 | 1.8 |
| Coating mean thickness (μm) | 15 | 13 | 17 | 10 | 20 | 19 | 23 | 12 | 25 | 24 | 25 | 15 |

TABLE 2B

| | Coat. # | | | | | | | | |
|---|---|---|---|---|---|---|---|---|---|
| | 13 | 14 | 15 | 16 | 17 | 18 | 19 | 20 | 21 |
| Kollicoat ® IR Black | — | — | — | — | — | — | 0.1% | — | |
| Kollicoat ® IR Carmine | 0.4% | 0.3% | — | — | — | 0.15% | — | — | |
| Kollicoat ® IR White | 0.6% | 0.4% | — | 0.7% | — | — | 0.7% | — | 0.6% |
| Kollicoat ® IR Sunset Yellow | — | 0.3% | 1% | 0.3% | — | — | — | 0.75% | 0.2% |
| Kollicoat ® IR Brilliant Blue | — | — | — | — | 1% | 0.85% | 0.2% | 0.25% | 0.2% |
| Kollicoat ® Protect | 4% | 4% | 4% | 4% | 4% | 4% | 4% | 4% | 4% |
| Coating Amount (wt %) | 1.60 | 1.70 | 1.62 | 1.79 | 1.95 | 1.64 | 1.74 | 1.56 | 1.78 |
| Coating mean thickness (μm) | 17 | 16 | 18 | 18 | 21 | 16 | 13 | 15 | 17 |
| Calc. Coating thickness (μm) | 13 | 14 | 13 | 15 | 16 | 14 | 14 | 13 | 15 |

The variation in average weights of coated tablets was of at most 10% for tablets of a given formulation and batch. This variability, however, which stems from the coating process, does not affect accuracy of doses, since the core tablets that provide the color imparting agents or the other desired active ingredients (e.g., alkalizing, oxidizing, bleaching, thickening agents) have a very low deviation from the average weight of each rapidly disintegration tablet or shade (i.e. below 2%).

In order to enhance number of suitable coating colors, and in order to obtain high stability of a coating towards UV light, alternative procedures for coating were developed.

Coating utilized the following aqueous coating formulation: 4% (w/w) polyvinyl alcohol (Kollicoat IR coating polymer, BASF); 1% (w/w) synthetic pigment, and 95% water. The polyvinyl alcohol and pigments were mixed together in powder form, and then added to water stirred by an IKAT-50 homogenizer equipped with a 1402 dissolver tool, to obtain an aqueous coating solution.

Figure 10A:
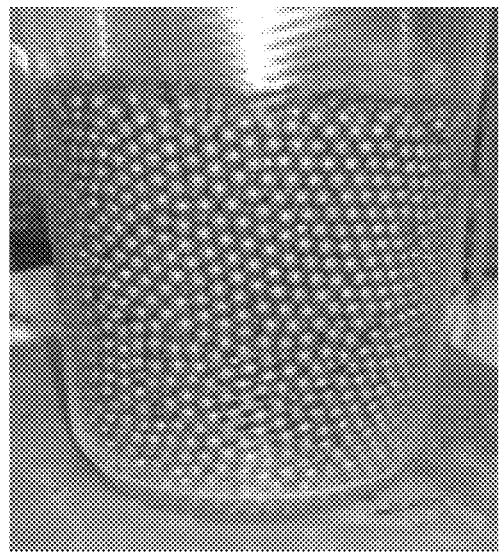
FIGS. 10A-B are images of exemplary coated tablets comprising a polyvinyl alcohol coating with Pigment Green 7 (FIG. 10A) or Pigment Yellow 73 (FIG. 10B)
Figure 10B:
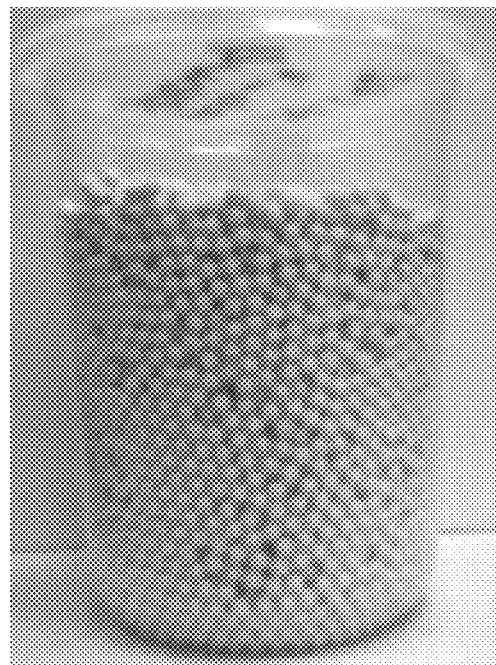

Tablets were then coated by spraying the aqueous solution onto uncoated (core) tablets. Typical examples of tablets coated by these procedures are shown in FIGS. 10A and 10B.

Figure 11:
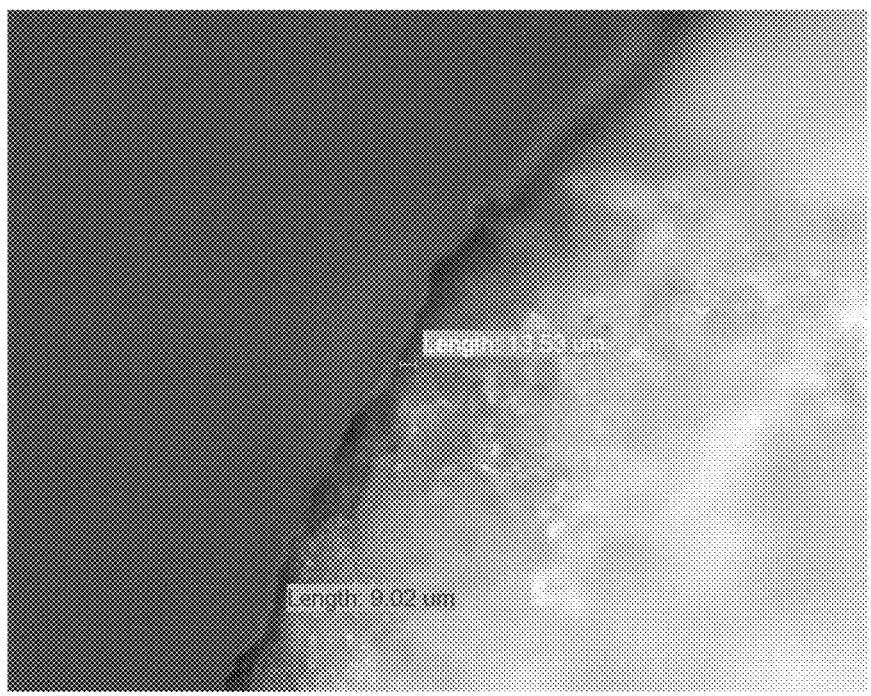
FIG. 11 is a light microscopy image of a coated tablet in which the coating thickness (length) is measured in two regions in order to obtain an average value.

The thickness of the tablet coating was determined using a light microscope and camera software analysis, as described in Example 2. A representative image of a coated tablet is shown in FIG. 11. Five tablets of formulation No. 14 (see, Table 1E) were sampled, and the thickness was determined in 10 locations for each tablet.

Figure 12:
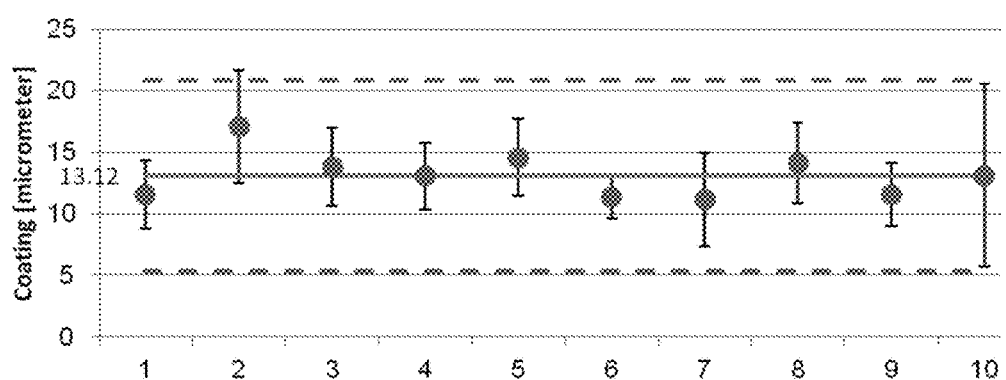
FIG. 12 is a graph showing the average coating thickness as measured at 10 measurements, for 5 tested tablets each time, with average thickness of the tablets being 13.12 micrometers, with the error bars showing deviation of coating thickness for each measurement, and the dotted line shows the envelope of two standard deviations around the average value of coating thickness, in which thickness of 95% of the tablets is encompassed.
Figure 13A:
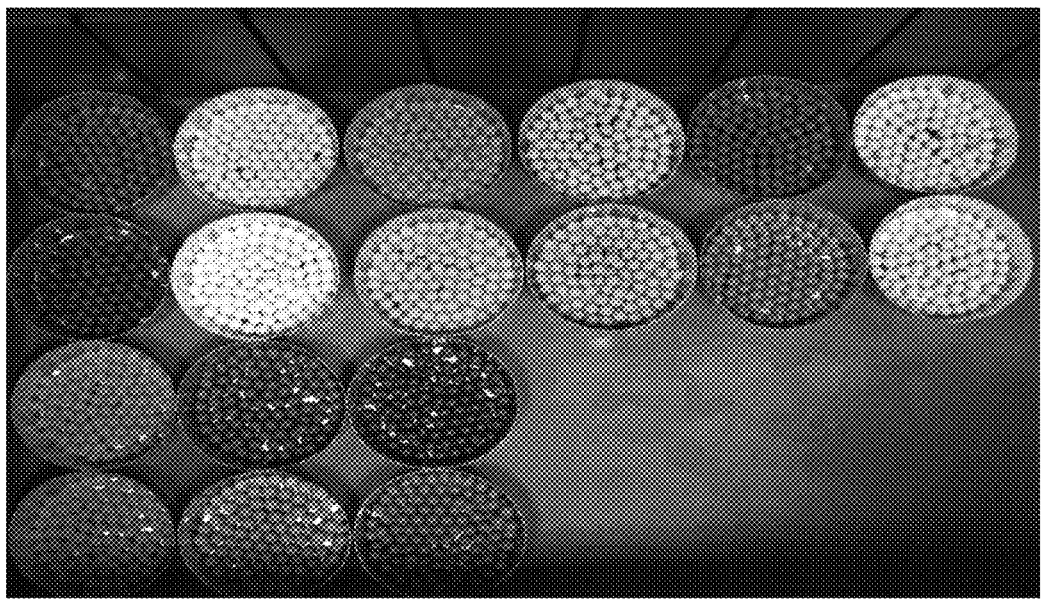
Figure 13B:
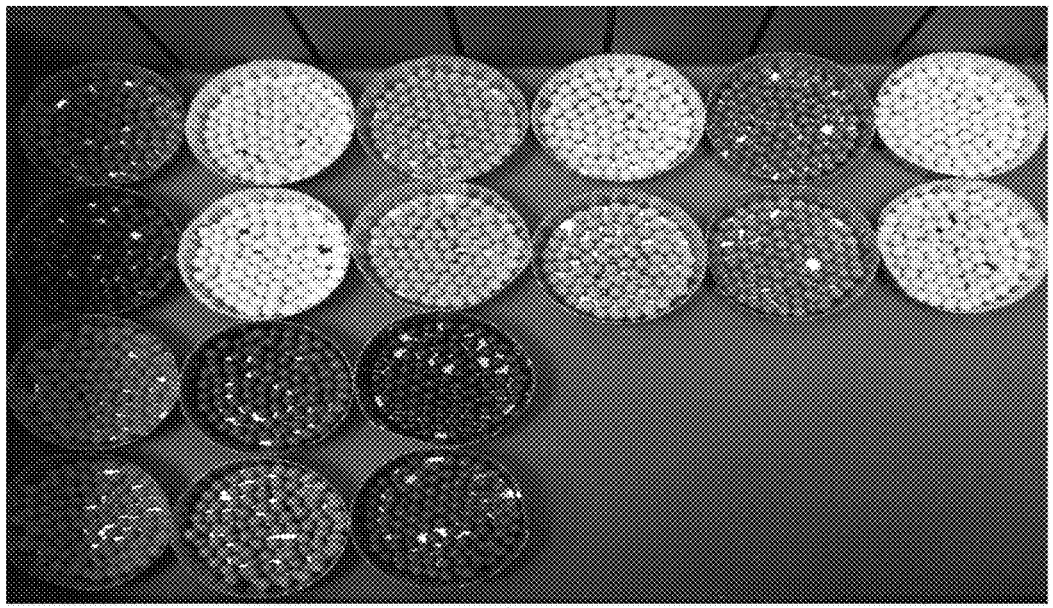
Figure 13C:
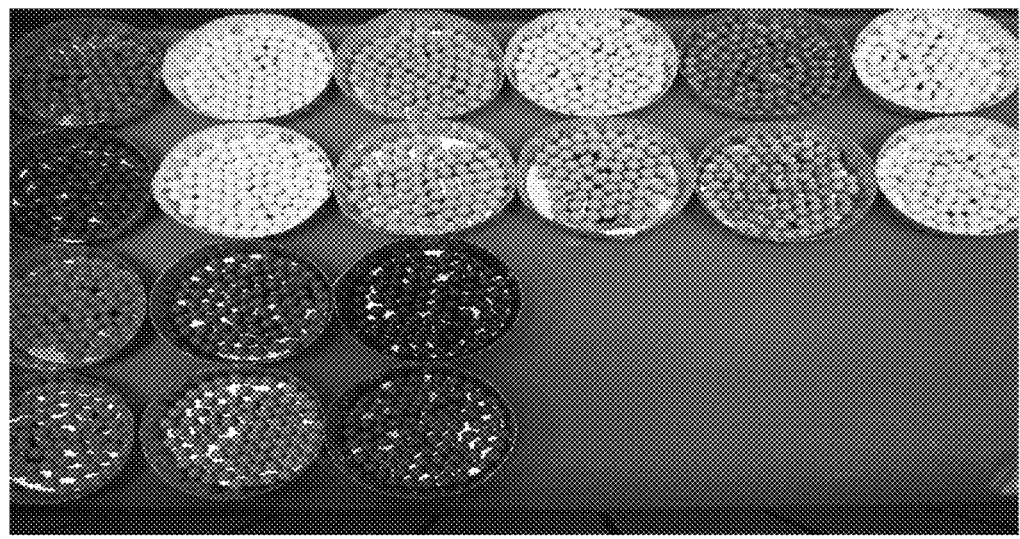
Figure 13D:
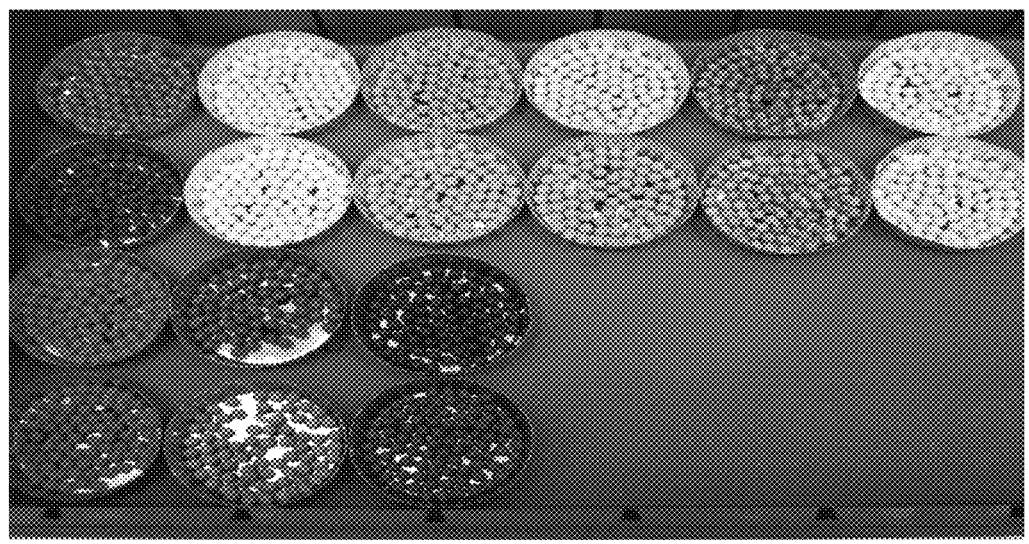
Figure 13E:
Figure 13F:
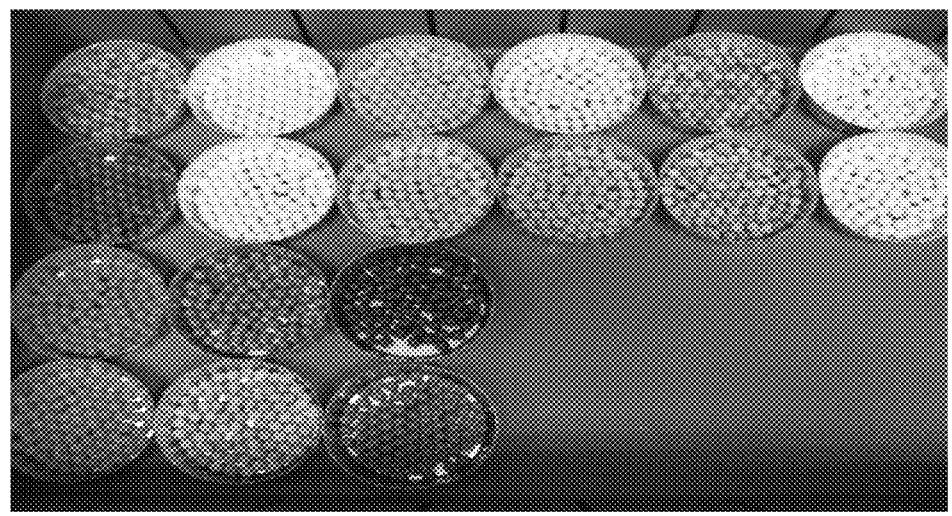

As shown in FIG. 12, the coating exhibited an average thickness of 13.12 micrometers, with the average thickness for each of the 10 tested tablets being in a range of approximately 11-17 micrometers.

These results indicate that the coating procedure provides a reasonably uniform tablet coating.

Example 3

Tablet Properties

Coated and uncoated tablets prepared as described in Examples 1 and 2 were submitted to numerous tests to assess certain properties.

The mechanical properties were measured using a tablet hardness tester (HT-50P), a friability test apparatus (FTA-20), and a disintegration tester (TD-20S), all of Thermonik Campbell Electronics. These properties were assessed at various time points following the preparation of the tablets.

The stability of the tablets was assessed under normal and accelerated conditions. The accelerated conditions were produced by incubating the tested tablets in an environmental chamber (KBF115, Binder). Tablets were removed from the environmental chamber after different durations and their performance with time were compared to baseline values established closely following tabletting and/or coating (time point 0). Unless otherwise indicated, the environmental chamber maintained a stable temperature of 25° C. and relative humidity of 65% (RH).

The chemical stability of the color imparting agents was assessed by scanning spectrometry (Cary 300 UV-Vis Spectrophotometer, Agilent Technologies).

As a rule, at least 3 tablets were used for each test and/or the test was repeated.

To assess hardness, one tablet was placed in the tester until the tablet broke. The reported value indicates the force needed to break the tablet. To assess friability, ten tablets were inserted in the tester's chamber, which was then rotated 25 times at a speed of 25 RPM. The weights of the tablets before and after the test were analytically measured and compared, the friability value being the percent of weight lost.

To assess disintegration, tablets were placed in a perforated basket that was moved up and down at constant speed in a beaker containing 500 ml of test medium at ambient temperature of about 25° C. The time until total disintegration was measured. When disintegration was tested in a non-viscous medium, total disintegration was set to occur when no visible fragments of the tablets remained in the basket. When tested in viscous medium, the swollen tablets could not necessarily spontaneously pass through the mesh of the basket and total disintegration was set to occur when no fragments of the tablets remained in the basket after an operator gently pressed the swelled tablet through the mesh (i.e. no remaining core).

The medium used to test disintegration rate was either deionized water (pH 7.0, viscosity of 1 cp), or a commercially available emulsion of hydrogen peroxide (6% $H_2O_2$, pH 3.0, viscosity of less than 0.5 poise) or an emulsion of hydrogen peroxide (Welloxon 9% $H_2O_2$) diluted at a ratio of 30:70 weight by weight with deionized water (final viscosity of 0.5 poise, pH 4.0). It must be noted that disintegration time was assessed with no manual mixing. Therefore the durations reported below represent upper limits, expected to be reduced upon additional mixing. To assess the chemical stability of the dyes, one tablet was dissolved in 250 ml of deionized water and a 2 ml sample was transferred in a quartz cuvette to the spectrophotometer. The volume of dissolution was selected to achieve an optical density of at most about 1.

In a first set of experiments, control tablets containing 70% Avicel® PH 102 microcrystalline cellulose, 27% SuperTab® 11SD spray dried lactose, 2% Ac-Di-Sol® SD-711 croscarmellose sodium and 1% magnesium stearate were tested before and after coating. The coating solutions were prepared at 5% concentration in deionized water and sprayed at similar rate of 6.8 grams/minute, with the exception of the B coating which was sprayed at about 4.1 grams/minute. The tested coating agents were Kollicoat® Brilliant Blue, Kollicoat® IR Brilliant Blue+Kollicoat® Protect (1%+4%) and Opadry® II coatings based on either HPMC or PVA, respectively A, B, C and D in Table 3A. Tablets were sampled every 15 minutes up to 105 minutes of coating.

Additional experiments are reported in Table 3B, the tablet number referring to the information provided in Table 1B in Example 1 and the coating number referring to the information provided in Example 2. For reference, the disintegration time of the to uncoated versions of these tablets in water was below thirty seconds for all basic shade tablets. The friability of the coated basic shades was established at time point 0 and the chemical stability was monitored for the duration of the preliminary environmental chamber test. All shades were tested for at least 5 days.

Tables 3A and 3B report the tablet properties measured by these methods. The time points are given in days, weeks or months, as the case may be. Hardness is given in kgf, friability is given in percent of weight loss, disintegration time is given in seconds (Table 3A) or min:sec (Table 3B). For reference, all uncoated versions of the reported tablets had baseline hardness between 2.0 and 4.5 kgf. When applicable, the chemical stability is given as 0 or 1, where 1 stands for a spectrum identical or almost identical to baseline spectrum and 0 stands for spectrum where the dyes peak have reduced area and/or have disappeared and/or have shifted position and/or new peaks have appeared. Stability graded as 0 as far as the optical spectrum is concerned may not necessarily mean that the residual dyes cannot achieve hair coloring to some extent that may still be satisfactory.

TABLE 3A

|  |  | 0 | 15' | 30' | 45' | 60' | 75' | 90' | 105' |
|---|---|---|---|---|---|---|---|---|---|
| Thickness (μm) | A | 0 | 8 | 11 | 13 | 16 | 17 | 23 | 25 |
|  | B | 0 | 4 | 6 | 7 | 9 | 10 | 12 | 15 |
|  | C | 0 | 7 | 10 | 10 | 13 | 15 | 20 | 25 |
|  | D | 0 | 6 | 8 | 10 | 12 | 13 | 19 | 24 |
| Hardness (kgf) | A | 4.00 | 4.04 | 4.10 | 4.51 | 4.55 | 4.77 | 4.40 | 5.45 |
|  | B | 4.00 | 4.18 | 5.18 | 4.56 | 6.62 | 6.03 | 6.58 | 7.53 |
|  | C | 4.00 | 3.90 | 4.18 | 4.28 | 4.28 | 4.28 | 4.70 | 4.80 |
|  | D | 4.00 | 4.08 | 4.40 | 4.39 | 4.36 | 4.75 | 5.58 | 5.29 |
| Disintegration Time in $H_2O_2$ (seconds) | A | 88 | 121 | 118 | 136 | 128 | 162 | 171 | 149 |
|  | B | 88 | 146 | 116 | 143 | 142 | 153 | 168 | 153 |
|  | C | 88 | 131 | 154 | 188 | 189 | 191 | 239 | 265 |
|  | D | 88 | 91 | 125 | 136 | 160 | 160 | 165 | 169 |

TABLE 3B

| | Tablet No. | | | | | | | | |
|---|---|---|---|---|---|---|---|---|---|
| | 101 | 102 | 103' | 104 | 105 | 106 | 107 | 108 | 109' |
| | Coating No. | | | | | | | | |
| | 13 | 14 | 15 | 16 | 17 | 18 | 19 | 20 | 21 |
| Time point | 0 | 0 | 0 | 0 | 0 | 0 | 0 | 0 | 0 |
| Hardness (kgf) | 5.67 | 5.10 | 4.80 | 6.55 | 5.17 | 4.38 | 5.56 | 4.72 | 4.71 |
| Friability (%) | 0.00 | 0.00 | 0.37 | 0.13 | 0.00 | 0.24 | 0.13 | 0.00 | 0.01 |
| Disintegration time in $H_2O$ | 00:19 | 00:20 | 00:24 | 00:17 | 00:28 | 00:40 | 00:18 | 00:44 | 00:18 |
| Disintegration time in $H_2O_2$ (minutes) | 01:24 | 01:24 | 03:00 | 01:15 | 03:00 | 02:00 | 01:30 | 01:54 | 01:35 |
| Time point | 5d | 5d | 5d | 5d | 5d | 5d | 5d | 5d | 5d |
| Chemical stability | 1 | 1 | 1 | 1 | 1 | 1 | 1 | 1 | 1 |
| Hardness (kgf) | 2.68 | 2.73 | 2.60 | 2.48 | 3.40 | 2.27 | 2.13 | 2.12 | 2.47 |
| Time point | 13 d | 13 d | 13 d | 13 d | 13 d | 13 d | 13 d | 13 d | 13 d |
| Chemical stability | 1 | 1 | 1 | 1 | 1 | 1 | 1 | 1 | 1 |
| Hardness (kgf) | 2.17 | 2.95 | 2.50 | 2.30 | 3.16 | 2.50 | 2.41 | 1.94 | 2.27 |

(d = days)

The results of Tables 3A and 3B show that coated tablets prepared according to some embodiments of the invention undergo rapid disintegration in absence of mixing. The disintegration time, which was correlated with the type and thickness of the coating, was between 01:30 and 04:25 for the placebo tablets having coating thicknesses of up to about 25 μm. It must be emphasized that these durations were achieved in a viscous medium comprising hydrogen peroxide and not in plain water. The basic shade tablets, which were coated with diverse types of coatings, achieved disintegration between 01:15 and 03:00 minutes in the same viscous medium. For comparison, basic shade tablets of the same type added to water achieved disintegration at least twice more rapidly (see Tablet No. 108) and up to seven-fold more rapidly (see Tablet No. 103), with an average of about 4.7-fold more rapidly for all the tested basic shades.

The difference in disintegration time of the diverse tested basic shades may stem from the type and thickness of coating or from the composition of the core tablet. Interestingly, it was found that ascorbic acid also had a positive impact on disintegration time. A tablet formulation comprising 59% Avicel® PH-102, 24.85% SuperTab® SD-11, 2% Ac-Di-Sol® SD711, 1% magnesium stearate, 9.25% n,n-bis (2-hydroxy-ethyl)-p-phenylene-diamine sulfate and 3.9% 4-amino-2-hydroxytoluene, provided for uncoated tablets disintegration times of about 04:30 minutes in $H_2O_2$ emulsion. A similar formulation wherein 3% of SuperTab® SD-11 were replaced by 3% of ascorbic acid led to tablets disintegrating more rapidly in about 01:30 minute only. When these tablets were coated with a 5% solution of Kollicoat® IR Brilliant Blue, the disintegration times increased to about 9 minutes for the formulation lacking ascorbic acid, whereas the formulation comprising ascorbic acid provided tablets which disintegrated in only 3 minutes in the $H_2O_2$ emulsion without mixing.

The mechanical properties of the tablets as measured following manufacturing were satisfactory. The hardness of the coated placebo and basic shade tablets ranged from 3.90 kgf to 7.53 kgf depending on the type of coating and its thickness. The tested tablets had a friability of at most 0.5%, with coated placebo tablets having a friability to of less than 0.44% and basic shades having a friability between 0.00% and 0.37%.

The preliminary stability testing of the tablets showed a decrease in hardness under accelerated conditions. The hardness decreased to about half of its original value, within 5 days. After this initial diminution, the hardness of the tablets remained approximately steady with average fluctuations of about 2% between day 5 and at least day 13. It must be emphasized that the conditions of the environmental chamber testing are harsher than suggested by the apparently mild temperature and the relative humidity of 65%. These accelerated conditions have been reported to be surprisingly more challenging than testing done at 40° C. and 80% RH. The decrease in hardness observed in accelerated storing conditions led to coated basic shades hardnesses of at least 2 kgf and of about 2.5 kgf on average of tested basic shades. Such values are suitable for use in dispensing devices such as the dispensing device as described herein.

Importantly, the preliminary stability testing of the tablets showed that there was no observable chemical degradation of the color imparting dyes over the duration of the test.

In additional tests, tablet formulations as presented in Table 1E were tested and disintegration was assessed in an oxidizing medium (3% hydrogen peroxide, MAG Cosmetics), having a viscosity of about 1.4 cpoise measured using a Brookfield viscometer at about 25° C., 50 rpm. For comparison, the disintegration time was also assessed in deionized water. Results of these experiments are provided in Table 3C below.

TABLE 3C

| Shade | Tablet No. in Table 1E | Disintegration time for coated tablets in aqueous hydrogen peroxide (seconds) | Disintegration time for coated tablets in water (seconds) | Hardness (Kgf) |
|---|---|---|---|---|
| Blue | 18 | 9 | 10 | 3.7 |
| Violet | 14 | 18 | 6 | 3.8 |
| Red | 13 | 10 | 10 | 3.3 |

TABLE 3C-continued

| Shade | Tablet No. in Table 1E | Disintegration time for coated tablets in aqueous hydrogen peroxide (seconds) | Disintegration time for coated tablets in water (seconds) | Hardness (Kgf) |
|---|---|---|---|---|
| Green | 17 | 4 | 3 | 3.1 |
| Natural | 10 | 15 | 8 | 3.2 |
| Rose | 16 | 3 | 3 | 3.7 |
| Ash | 15 | 4 | 4 | 3.8 |
| Gold | 11 | 4 | 4 | 3.4 |
| Orange | 12 | 9 | 2 | 3.5 |

FIGS. 9A and 9B present images of the tablet formulation denoted as Tablet 15 in Table 1E, when placed in a 6% (w/w) solution of hydrogen peroxide. at t=0 (FIG. 9A) and at t=3 seconds (FIG. 9B), demonstrating the fast disintegration time of this exemplary tablet formulation.

In additional sets of experiments, the physical and chemical stability of coated to tablets under several conditions was determined by testing physical parameters at different time intervals.

The conditions used for testing were: under a $N_2$ atmosphere; under open air (relative humidity of approximately 50%, at 24° C.); in oven at a temperature of 40° C.); in an incubator (relative humidity 65%, at 25° C.); and packed under dry silica gel (dry conditions).

The measured physical parameters were hardness, weight, disintegration time in water and in 75% water with 25% $H_2O_2$, diameter, friability, appearance and color.

In a typical experiment the coated tablets are placed in a volumetric flask glass (i.e., under open air (52% relative humidity, 22.8° C.)), and the following physical parameters are measured at time intervals of two weeks and one month. Initial results ($T_0$) and results obtained after one month (1 m) are presented in Table 3D below, with results after one month being presented as the change relative to initial results.

TABLE 3D

| | Hardness | | Weight | | Disintegration time in $H_2O$ (seconds) | | Disintegration time in $H_2O/H_2O_2$ (seconds) | | Diameter | |
|---|---|---|---|---|---|---|---|---|---|---|
| | $T_0$ | 1m | $T_0$ | 1m | $T_0$ | 1m | $T_0$ | 1m | $T_0$ | 1m |
| Blue | 4.11 | −36% | 0.5957 | 2.5% | 54 | −48% | 205 | −72% | 4.59 | 2.8% |
| Green | 4.62 | −48% | 0.6192 | 1.88% | 19 | −12% | 94 | −41% | 4.60 | 3.7% |
| Red | 5.00 | −44% | 0.6155 | 1.64% | 37 | −0.9% | 169 | −60% | 4.61 | 2.0% |
| Natural | 3.8 | −49% | 0.6074 | 1.8% | 44 | −49% | 164 | −56% | 4.59 | 3.0% |
| Violet | 5.8 | −39% | 0.6309 | 2.1% | 102 | −50% | 181 | −42% | 4.52 | 3.2% |
| Rose | 4.8 | −47% | 0.5817 | 2.3% | 16 | −10% | 94 | −7.8% | 4.67 | 3.2% |
| Ash | 4.9 | −46% | 0.588 | 2% | 18 | −15% | 89 | −69% | 4.68 | — |
| Gold | 5.8 | −46% | 0.6158 | 2.17% | 32 | −5.2% | 104 | — | 4.64 | 3.0% |
| Orange | 5.3 | −33% | 0.6181 | 1.73% | 33 | −2.9% | 108 | −19% | 4.58 | 2.8% |

As shown in Table 3D, the increases in weight and diameter are relatively small.

These results indicate that little water is absorbed from the atmosphere, and therefore suggest good stability in storage.

As further shown in Table 3D, disintegration time is relatively short and decreases over time.

These results suggest that the tablets readily disintegrate in water or in aqueous solution of $H_2O_2$, as is advantageous, regardless of storage time.

The light fastness stability of the tablet coatings was also tested. Overall, 18 coating solutions were prepared and applied to placebo tablets having the following formulation:
Avicel® PH-102: 68%; SuperTab® 11SD:25%; AC-Di-Sol® SD711: 3%; Magnesium Stearate: 1%; and Ascorbic acid: 3%.

The tablets were coated using coating solutions which comprise organic and inorganic pigments.

In a typical stability experiment, several grams of coated tablets are placed in a small vessel and then placed under the ATLAS instrument. Analysis is done using SUNTEST CPS+/XLS+, Software documentation Version 1.4, which simulates direct sunlight (UV light) on the illuminated beads. One hour of illumination corresponds to direct illumination of one month under glass of 3 mm thickness. Since a typical glass thickness in a typical hair salon has 8 mm thickness, the tablets are covered with glass of 5 mm thickness to mimic the effect of 8 mm glass thickness.

Table 3E presents the results as obtained by visual inspection (by eye). FIGS. 13A-F present images of the illuminated coated tablets through one year of illumination.

TABLE 3E

|  | Blue | Gold | Orange | Ash | Red | Green | Natural |
|---|---|---|---|---|---|---|---|
| 1 month | ✓ | ✓ | ✓ | ✓ | ✓ | ✓ | ✓ |
| 3 months | ✓ | ✓ | ✓ | ✓ | ✓ | ✓ | ✓ |
| 6 months | — | ✓ | ✓ | ✓ | ✓ | ✓ | ✓ |

✓ indicates that the tablet coating color did not fade (tests are done by eye)
— indicates that the tablet coating color slightly fade (tests are done by eye)

As shown in Table 3E, all tested tablet formulations exhibited stability for at least 6 months.

These results demonstrate that the compositions and processes disclosed herein result in tablet formulations which exhibit desirable properties.

Example 4

Hair Coloring

The tablets prepared as described in Examples 1 and 2 were mixed with suitable media for the preparation of hair coloring formulae. The formulae were applied on natural yak hair and the change in fibers' colors was assessed.

In a first series of experiments, the oxidizing and alkalizing media were relatively viscous as customary or the oxidizing medium was less viscous and the alkalizing medium more viscous, so that the mixtures obtained therefrom had similar suitable viscosity. Typically, up to 150 tablets of a single basic shade or up to about 300 tablets for mixtures were added to 60 grams of commercially available 6% $H_2O_2$ oxidizing medium having a viscosity of less than 50 cps, as provided by the manufacturer (MAG Cosmetics) or to 60 grams of the previously mentioned diluted Welloxon (2.7% $H_2O_2$ and viscosity of 50 cps). The tablets were allowed to spontaneously disintegrate for at most about two minutes for the highest number of tablets. The disintegrated tablets were then manually brush mixed to homogeneity with the oxidizing medium. Sixty grams of a commercially available ammonia-based cream (Wella Pure Cream, having a viscosity of 300 poise, or MAG Cosmetics 2% Ammonia Cream having a viscosity of more than 300 poise) were added to previous mixture and further mixed to homogeneity. Generally, all mixing steps took no more than 3 minutes.

In a second series of experiments, some of the media were prepared using tablets able to rapidly disintegrate or dissolve to form a desired medium. In a first experiment, the oxidizing medium was made of water and rapidly disintegrating tablets prepared as described herein. Sixty tablets of the rapidly disintegrating oxidizing tablet according to Tablet No. 201 of Table 1C and 60 tablets of Nature shade (see Tablet No. 108) were added to 60 grams of deionized water and allowed to disintegrate as above-described. Sixty grams of Pure Cream were added and further mixed to homogeneity. In a second experiment, 3 grams of oxidizing tablets according to Tablet No. 204 were added to 10 grams of water, allowed to disintegrate and then mixed with 10 grams of Pure Cream. The decoloring effect of this formulation having a hydrogen peroxide concentration of 2.3% was tested on bundles of naturally pigmented dark human hair and compared to a formulation prepared by mixing 10 grams of 6% $H_2O_2$ Welloxon with 10 grams of Pure Cream. In a third experiment, 17 thickening tablets according to Tablet No. 208 were added to 14 grams of water and allowed to disintegrate. Six alkalizing tablets according to Tablet No. 209 were added to previous solution and mixed until formation of a creamy formulation.

The final hair coloring preparations, which all had suitable viscosity independently of the oxidizing and alkalizing media used, were generously applied and massaged in thoroughly so as to completely cover tufts of Yak body hair about 7.5 cm long (Cat. No. 826401, Kerling International). When testing the decoloring effect, the light colored Yak hair sample was replaced by pigmented human hair. Unless otherwise indicated, the coloring formulation was applied for 30 minutes and then washed away, the hairs were thoroughly rinsed in water and allowed to air dry at ambient temperature.

The coloration of the dried hairs was assessed visually and reference coordinates to were also generated by a hair reader (AvaMouse spectrophotometric measurement, Avantes) measuring the Lab color space and the color spectrum from 380 nm to 750 nm. The measured data was analyzed using Lab Tool Ver. 6.

Results of these experiments are reported in Tables 4A and 4B. For reference, yak hairs treated with the mixture of oxidizing and alkalizing media in the absence of tablets have a baseline shade corresponding to a Lab spectrum of L: 79.04, a: −0.52 and b: 4.63. Uncolored and untreated yak hairs displayed similar results (L: 77.13, a: −0.09 and b: 7.09).

Table 4A reports the types of tablets tested in this Example and each type is assigned for convenience a formulation number (Form. #). The Tablet number refers to the composition of the core of the tablet as presented in Table 1B of Example 1 hereinabove for the relevant tablet number. The Coat number refers to the coating of the tablet as provided in Table 2 of Example 2 hereinabove for the relevant coating number.

Table 4B reports for each type of tablets used in the preparation of the coloring formulae as above-described, first the number of tablets used and below the resulting Lab values ("L" on first line, "a" on second line and "b" on third line of each cell). The reported Lab values represent the average of 5 measurements performed on each sample of colored tufts.

TABLE 4A

| Form. No. | 1 | 2 | 3 | 4 | 5 | 6 | 7 | 8 | 9 |
|---|---|---|---|---|---|---|---|---|---|
| Shade | Rose | Orange | Red | Gold | Violet | Blue | Ash | Nature | Green |
| Tablet No. | 101 | 102 | 103 | 104 | 105 | 106 | 107 | 108 | 109' |
| Coating No. | 13 | 14 | 15 | 16 | 17 | 18 | 19 | 20 | 21 |

TABLE 4B

| | \multicolumn{8}{c}{No. of Rose} | | | | | | | |
|---|---|---|---|---|---|---|---|---|
| | 3 | 6 | 8 | 11 | 14 | 17 | 19 | 22 |
| Rose Lab | 77.71 | 77.40 | 75.80 | 76.72 | 75.05 | 71.78 | 72.79 | 71.54 |
| | 0.95 | 2.54 | 5.52 | 3.57 | 5.85 | 9.72 | 8.38 | 8.92 |
| | 5.95 | 7.38 | 10.73 | 8.15 | 10.79 | 14.78 | 13.85 | 14.27 |
| | \multicolumn{8}{c}{Orange No.} | | | | | | | |
| | 13 | 26 | 40 | 53 | 66 | 79 | 93 | 106 |
| Orange Lab | 61.27 | 55.02 | 50.16 | 49.82 | 47.50 | 47.80 | 46.33 | 44.53 |
| | 24.88 | 33.30 | 37.68 | 39.07 | 40.60 | 40.76 | 42.48 | 42.21 |
| | 50.74 | 55.90 | 54.54 | 54.98 | 52.07 | 52.20 | 50.06 | 48.01 |
| | \multicolumn{8}{c}{No. of Red} | | | | | | | |
| | 18 | 37 | 55 | 74 | 92 | 111 | 129 | 148 |
| Red Lab | 52.69 | 48.21 | 47.79 | 47.11 | 45.00 | 41.23 | 43.80 | 38.42 |
| | 36.02 | 39.58 | 41.63 | 41.10 | 41.69 | 43.14 | 42.78 | 44.83 |
| | 30.13 | 33.29 | 35.21 | 32.87 | 35.36 | 35.53 | 34.87 | 35.24 |
| | \multicolumn{8}{c}{Gold No.} | | | | | | | |
| | 5 | 10 | 14 | 19 | 24 | 29 | 33 | 38 |
| Gold Lab | 74.89 | 72.38 | 69.71 | 67.47 | 65.66 | 63.94 | 64.30 | 61.36 |
| | 5.64 | 9.24 | 14.35 | 17.72 | 19.23 | 19.83 | 20.70 | 24.31 |
| | 24.37 | 31.14 | 38.56 | 43.36 | 46.34 | 45.79 | 46.60 | 50.96 |
| | \multicolumn{8}{c}{Violet No.} | | | | | | | |
| | 10 | 21 | 31 | 41 | 51 | 62 | 72 | 82 |
| Violet Lab | 44.95 | 35.99 | 28.21 | 30.33 | 25.96 | 24.68 | 21.89 | 22.66 |
| | 7.45 | 10.63 | 12.76 | 11.45 | 12.56 | 11.12 | 11.96 | 11.91 |
| | −18.96 | −23.09 | −23.75 | −23.34 | −24.13 | −22.00 | −22.64 | −22.21 |
| | \multicolumn{8}{c}{No. of Blue} | | | | | | | |
| | 12 | 23 | 35 | 46 | 58 | 69 | 81 | 92 |
| Blue Lab | 44.23 | 34.25 | 30.89 | 27.35 | 25.71 | 24.41 | 25.96 | 22.42 |
| | −4.90 | −1.80 | 0.19 | 1.38 | 2.33 | 1.53 | 1.40 | 3.27 |
| | −23.26 | −24.86 | −25.19 | −24.44 | −24.94 | −21.97 | −22.58 | −22.50 |
| | \multicolumn{8}{c}{Ash No.} | | | | | | | |
| | 5 | 9 | 14 | 18 | 23 | 28 | 32 | 37 |
| Ash Lab | 75.19 | 68.15 | 66.36 | 62.97 | 58.23 | 56.38 | 52.62 | 50.60 |
| | −0.49 | −0.17 | −1.04 | −1.17 | −0.84 | −0.73 | −0.46 | 0.21 |
| | 1.30 | −3.08 | −5.24 | −7.66 | −10.01 | −10.84 | −11.49 | −13.52 |
| | \multicolumn{8}{c}{Nature No.} | | | | | | | |
| | 9 | 28 | 37 | 46 | 65 | 74 | 83 | 102 |
| Nature Lab | 58.29 | 36.90 | 35.53 | 35.45 | 29.91 | 28.45 | 27.20 | 22.82 |
| | 2.95 | 4.45 | 4.83 | 4.54 | 4.61 | 4.38 | 4.38 | 3.88 |
| | 11.31 | 13.28 | 13.92 | 15.48 | 13.32 | 12.11 | 10.98 | 9.25 |
| | \multicolumn{8}{c}{Green No.} | | | | | | | |
| | 9 | 18 | 28 | 37 | 46 | 55 | 65 | 74 |
| Green Lab | 55.49 | 46.15 | 40.01 | 37.05 | 32.77 | 31.17 | 29.35 | 27.79 |
| | −0.18 | −0.15 | 0.14 | −0.39 | −0.23 | 0.16 | −0.01 | 0.07 |
| | 10.50 | 11.79 | 11.08 | 12.70 | 11.01 | 10.94 | 9.29 | 8.90 |

The results presented in Table 4B show that the lightness component of the color presentation, L decreases with increasing number of tablets. The chromaticity components "a" and "b", also termed opponent color axes, were differently affected by increasing number of tablets depending on the basic shades being tested. For information, the "a" component represents, roughly, the color progression between red/magenta colors (positive) and green colors (negative), whereas the "b" component is indicative of the evolution from the yellow colors (positive) to the blue colors to (negative). Relations between Lab values at different tested points need not be linear, as this color presentation method is intended to mimic the nonlinear response of the eye. Visual assessment of the dried colored hair tufts showed a nice coloration, which progressed with increasing number of tablets from the lighter to darker shades of each basic shade. The colored tufts corresponding to the above-mentioned experiments are pictured in FIGS. 15A-15I. The number of tablets used in the final formula is indicated at the base of each bundle of yak hair and the shade and formulation number is indicated for each panel.

In a separate set of experiments, a preparation equivalent to Formulation 9 was prepared by weighting the individual ingredients and incorporating them into the media in powder form instead of in tablet form. Coloration was performed and monitored as previously described. The results were similar to those obtained by the corresponding tablet formulation, indicating that the tablet formulations as described herein do not affect the coloring efficiency of the color imparting agents comprised therein.

Mixtures of basic shades of different types also resulted in pleasing coloring. A combination of Red (Formulation No. 3) and Violet (Formulation No. 5) resulted, when applied on the yak hair, in a darker purple shade, whereas combination of Blue to (Formulation No. 6) and Nature (Formulation No. 8) resulted in a darker blue shade. Mixtures of up to five basic shades were prepared and their Lab values were measured. A first mixture comprising 175 tablets of Nature, 29 tablets of Orange, 18 tablets of Gold, 10 tablets of Ash and 6 tablets of Violet (Formulation No. 10) prepared in a final volume of 120 grams of coloring formula led to a chestnut coloring with L: 19.01, A: 7.38 and b: 11.37. A second mixture comprising 130 tablets of Red, 115 tablets of Nature, 43 tablets of Orange, 10 tablets of Gold and 6 tablets of Violet (Formulation No. 11) led to a warm reddish brown coloring with L: 19.53, a: 17.53 and b: 9.68. A third mixture comprising 105 tablets of Nature, 100 tablets of Red, 11 tablets of Violet and 7 tablets of Orange (Formulation No. 12) led to a Mahogany coloring with L: 18.39, a: 15.93 and b: 6.09.

The media tablets allowed for the preparation of formulations enabling coloring or decoloring as desired. The coloring formulation prepared with Nature basic shade and oxidizing agents in the form of rapidly disintegrating tablets yielded the expected natural chestnut coloring with Lab values of L: 24.81, a: 5.23 and b: 11.74. These results are comparable to the Lab values obtained with 65 tablets of the same basic shade when the oxidizing agent was supplied in a commercially available emulsion of hydrogen peroxide.

The decoloring tablet formulation prepared lightened the shade of the sample human hair in a manner comparable to the control formulation made of commercially available oxidizing and alkalizing media. Untreated human hair displayed baseline Lab values of L: 20.84, a: 3.49 and b: 4.51, whereas hair treated with a corresponding tablet formulation displayed Lab values of L: 23.48, a: 6.97 and b: 8.54 and hair treated with a commercially available formula displayed Lab values of L: 21.48, a: 5.84 and b: 7.65. In the experiment performed with thickening tablets which were allowed to first disintegrate before alkalizing tablets were added showed that the viscosity of the media could be controlled by addition of the tablets as described herein.

These results demonstrate that basic shades and media tablets prepared according to some embodiments of the invention can serve for the preparation of coloring formulae. The coloring formulae, whether comprising increasing number of tablets of a given shade or mixtures of basic shades, effectively modified the color of the fibers being tested.

These results further demonstrate that rapidly disintegrating to tablets as described herein, when used in combination with water, can replace the traditional media used in coloring procedures.

Further experiments were performed to assess the effect of hair type on hair coloring.

In one series of experiments, single shade colorings were performed on natural human laboratory hair of different types: blond Caucasian hair, dark blond Caucasian hair, and brunette Caucasian hair. Each shade was tested with three different quantities of tablets. For example, natural shade was applied using 1, 34 or 67 tablets in 60 ml alkaline medium and 60 ml oxidizing medium, and green shade was applied using 1, 101 or 200 tablets in 60 ml alkaline medium and 60 ml oxidizing medium.

In another series of experiments, all possible combinations of two shades in a wide range of ratios was applied to different hair types, ranging from the lightest Caucasian hair to the darkest Asian hair, as well as yak hair. Exemplary combinations included 1 tablet of orange shade with 100 tablets of violet shade; 100 tablets of orange shade with 1 tablet of violet shade; and 100 tablets of orange shade with 100 tablets of violet shade. XEach of the aforementioned combinations of tablets was added to 60 ml medium and 60 ml of hydrogen peroxide solution. The peroxide solution and a 2% ammonia cream medium were obtained from MAG Cosmetics. The resulting color obtained for each type of hair exhibited an impact of the natural pigmentation, and the concentration of coloring agent (i.e., the number of tablets used).

In all of these experiments, tablets denoted number 3 (Orange), number 8 (Green) and number 5 (Violet) in Table 1D, were used.

FIG. 16A shows the hair color obtained with three concentrations of green shade, when applied to natural dark blond Caucasian hair As shown in FIG. 16B, following application of a combination of orange shade and violet shade, orange shade had little impact when applied in low amounts (sample 1), violet shade had little impact when applied in low amounts (sample 2), and both shades had a considerable impact when applied in similar amounts (sample 3).

As shown in FIG. 17, human natural red hair was colored red-copper using a commercially available Koleston Perfect tube (red copper shade), mixed 1:1 with Welloxon Hydrogen Peroxide 6% cream. After coloring with the Koleston shade, to further application of violet shade tablets resulted in a bordeaux color.

These results indicate that the color obtained using exemplary tablets is a function of the number of tablets used and the initial hair color (which depends on natural hair pigmentation and previous coloring, if any).

Example 5

Drying of Tablets

A process for drying tablets was developed in order to increase stability and shelf life.

In a typical procedure, coated tablets having the formulations presented in Table 1E, coated with a PVA coating purchased from Colorcon Opadry 200, were placed in a vacuum oven for 20 hours. Water content was measured using a Sartorius moister analyzer MA 150 by manually grinding 1 gram of tablets (from each sample) and measure the weight change at 120° C. at 30 mbar for 1 hour.

As shown in Table 5A below, the water content of the tablets of all the basic shades was reduced to less than 3% and even less than 1%.

TABLE 5A

| Shade | Water content after drying process (weight percents) |
|---|---|
| Green | 0.9 |
| Orange | 1.8 |
| Gold | 1.9 |
| Rose | 2.1 |
| Ash | 2.0 |
| Blue | 2.5 |
| Natural | 2.3 |
| Red | 1.8 |
| Violet | 2.6 |

These results indicate that the water content of tablets according to some embodiments of the invention can be reduced to low levels (e.g., less than 3%), thereby enhancing tablet stability, despite the presence of hygroscopic ingredients.

Example 6

Microbiological Stability of Tablets

In order to test the stability of exemplary tablets towards microbiological to contamination, tablet samples were stored under relatively dry conditions (2% relative humidity, 25° C.) for a time period in a range of from 3 to 24 weeks. All tablets had a formulation as presented in Table 1E. In each sample, both the initial and final concentration of colony-forming units (CFU) was less than 10 CFU/gram.

These results indicate that tablets described herein exhibit microbiological stability, particularly when stored under relatively dry conditions.

Example 7

HPLC Analysis of Coloring Agents

In view of repeated use of the exemplary coloring agents described in the Examples herein, an analytically sensitive method of detecting coloring agent amounts was developed using HPLC (high performance liquid chromatography). Such a method can be useful, for example, for precisely quantifying chemical stability of tablets containing coloring agents (e.g., tablets described herein).

A Sepax® chromatographic column (GP C718 4.6×250 mm 5 u; 120 A) was used with phosphate buffer (50 mM, pH 3.0) as mobile phase. The gradient flow was as described in Table 7A.

TABLE 8A

| % B = Acetonitrile | % A = Phosphate buffer | Time (minutes) |
|---|---|---|
| 0 | 100 | 0 |
| 0 | 100 | 3 |
| 50 | 50 | 30 |
| 50 | 50 | 33 |
| 0 | 100 | 33.1 |
| 0 | 100 | 40 |

A LaChrom HPLC system (Hitachi) was used with an L-7100 solvent pump, L-7200 auto-sampler, L-7300 column oven, and DA-L7455 photodiode array detector. The flow rate was 1.0 ml/minute; the injection volume was 10 μl; detection between 200-400 nm.

Samples were dissolved (usually at 1 mg/ml) in water or a water/acetonitrile solution in a 100 ml volumetric flask. The flask was shaken to fully dissolve the coloring agent, and an injection vial was prepared using a suitable filter (e.g., a PTFE filter).

The retention time of exemplary agents used in formulations described herein is presented in Table 8B below, and a representative HPLC spectrum is shown in FIG. 14.

TABLE 7B

| Retention time (minutes) | Compound |
|---|---|
| 4.13 | Toluene-2,5-diaminosulfate |
| 3.04 | 1-Hydroxyethyl-4,5-diaminopyrazole sulfate |
| 10.50 | N,N-Bis(2-hydroxyethyl)-p-phenylenediamine sulfate |
| 6.26 | 4-Amino-3-methylphenol |
| 4.02 | 1-Hydroxy-4-aminobenzene |
| 13.33 | 5-Amino-2-methylphenol |
| 6.72 | 2,4-Diaminophenoxy-ethanol |
| 6.69 | m-Aminophenol |
| 15.20 | Resorcinol |
| 13.76 | Hydroxyethyl-3,4-methylene dioxyaniline HCl |
| 25.84 | 2-Amino-6-chloro-4-nitrophenol |
| 20.00 | HC red No. 10 |
| 17.30 | HC red No. 11 |
| 22.34 | HC Yellow No. 13 |
| — | 2,6-diamino-3-pyridine-3-yl-azo-pyridine |
| 29.52 | HC Blue No. 15 |
| 4.85 | Ascorbic Acid |

These results indicate that amounts of exemplary agents can be determined quantitatively with precision.

Example 8

Exemplary Alkalizing and Oxidizing Media 10 grams of a commercially available 1% ammonia cream (MAG Cosmetics), having a viscosity of more than 300 centipoise, were diluted with water at a weight ratio to of 1:2 (cream:water), by slowly adding the water to the cream during continuous hand mixing. 30 grams of an ammonia-based alkalizing medium in the form of a pourable cream was obtained.

30 grams of a 6% hydrogen peroxide solution (containing 1% EDTA, pH adjusted to 2.8 with phosphoric acid) were then added in bulk to the pourable cream alkalizing medium, and mixed vigorously by hand. The result was a very dilute cream with lotion consistency, which thickened slightly with time, but remained quite pourable.

In a further experiment, 0.9 gram of Novethix™ L-10 Polymer (Lubrizol, suspension of 30% by weight polymer in aqueous solution), an acrylates/beheneth-25 methacrylate copolymer, was added to 29.1 grams of the abovementioned 6% hydrogen peroxide solution (pH 2.8), to obtain 30 grams of an oxidizing medium comprising 3 weight percents of the thickening agent polymer This thickening agent is an anionic polymer which has little effect on viscosity under acidic conditions, when the polymer is in a protonated, non-ionic state. Thus, addition of the thickening agent did not substantially change the consistency of the acidic oxidizing medium. This oxidizing medium with thickening agent was added in bulk to 30 grams of the above-described alkalizing medium, and mixed vigorously for 30 seconds. The mixture thickened immediately, and after about 2 minutes turned into a thick cream.

Example 9

Exemplary Dispensing Device

A device able to dispense measured amounts of tablets contained in separate containers was built as schematically illustrated in FIG. 2, with containers as shown in FIG. 6 and dispensing means as partly displayed in FIG. 8. The device had overall dimensions of 345 mm (width)*345 mm (depth) *525 mm (height, including the containers). The device had 16 roughly cylindrical containers made of Polyethylene terephthalate (PET) manufactured by blow molding. The diameter of a container was about 60 mm and its walls had a height of about 200 mm Each container was equipped with a shutter mechanism as shown in FIG. 43, facilitating the quick and convenient replacement of a container while preventing tablets from pouring out. The two partial spherical shells constituting the shutter mechanism were plastic-made, manufactured by injection-molding. The plastic-made cog-wheel, manufactured by injection molding, was positioned outside the container. Above the tablets outlet of each cog-wheel, a steel wire was mounted, preventing tablets from being accidently dispensed out directly (i.e. not by the cog-wheel mechanism).

The step motors were positioned under their respective containers below the stainless steel platform in a manner that allowed free flow of the dispensed tablets into a single 4-sloped wall plastic funnel which was prepared by plastic rapid prototyping. A shutter mechanism at the funnel outlet provided control of the actual moment in which tablets are being dispensed out of the device. The shutter mechanism consisted of a rubber ball that unless pulled up by electro-mechanical actuator, blocked the funnel outlet. Two additional optical detectors were placed about the position of the receiving vessel, aimed at providing indication of its presence in order to prevent tablets dispensing out of the device while no vessel is in place. The step motors (Permanent Magnet step motor 42, having a step angle of 15° and a holding torque of 800 g. cm) allowed dispensing at a rate of up to 2,880 tablets per minute (using a cog wheel with 24 cog spaces at a maximal rotation of 120 RPM). Generally, repeatability tests were performed at up to 80 RPM using spheroidal placebo tablets having an average diameter of about 5 mm.

The device comprises two optical sensors (Everlight Photodetector Transistor, PT204-6B) for each container outlet. The step motors and their corresponding photodiodes were mounted on a single PCB shaped so as to match the containers lateral to arrangement. Additional PCB contained all controlling electronics as well as connectivity means to a personal computer installed inside the dispenser. Additional PCB was used for controlling a touch-screen LCD that serves as a user interface configured to allow manual entering of the number of tablets desired from each specific container. Numerous experiments were successfully performed. Repeatability tests, where the number of tablets dispensed was each time confirmed by manual counting, established that the device was accurate and feasible.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of treating keratinous fibers, the method comprising:
disintegrating at least one solid formulation in a first aqueous medium, to thereby obtain an aqueous composition; and
contacting said composition with the keratinous fibers for a time period suitable to treat the keratinous fibers, wherein: (i) said formulation is in a form of a tablet and comprises at least one water-insoluble superdisintegrant, and at least one active agent selected from the group consisting of a color imparting agent, an alkalizing agent, an oxidizing agent, and a thickening agent, said superdisintegrant being characterized by a water absorption ratio of at least 0.5; (ii) said aqueous composition comprises said active agent.

2. The method of claim 1, wherein said at least solid formulation comprises at least one color imparting agent, the method being for coloring the keratinous fibers.

3. The method of claim 2, further comprising, prior to contacting the composition with the fibers, contacting the fibers with a bleaching medium for a time period sufficient to lighten a color of said fibers.

4. The method of claim 3, further comprising mixing said at least one solid formulation, before, during and/or after said disintegrating, with an active agent selected from the group consisting of an alkalizing agent, an oxidizing agent, and a thickening agent.

5. A device for preparing a customized composition for treating keratinous fibers, the composition comprising a plurality of solid formulations in a tablet form, the device comprising
a plurality of containers, each container having an outlet suitable for dispensing a tablet; and a dispensing unit for dispensing a pre-determined amount of tablets, said containers and said dispensing unit being attachable to one another.

6. The device of claim 5 wherein a plurality of tablets are disposed in each said container, each table comprising at least one water-insoluble superdisintegrant, and at least one active agent selected from the group consisting of a color imparting agent, an alkalizing agent, an oxidizing agent, and a thickening agent, said superdisintegrant being characterized by a water absorption ratio of at least 0.5.

7. A device for optical measurement of keratinous fibers, comprising:
an illumination unit for illuminating keratinous fibers;
a measuring unit comprising at least one sensor for optically measuring said keratinous fibers during illumination by said illumination unit; wherein the sensor and a beam from the illumination unit respectively subtend a light diffusion angle at the keratinous fibers being measured, thereby to ensure that said sensor principally measures light of said illumination beam that is diffused or scattered by said keratinous fibers.

8. The device of claim 7, wherein the measuring unit comprises a plurality of sensors located around said keratinous fibers at an elevation from the azimuth and said illumination unit is positioned perpendicularly to said keratinous fibers.

9. The device of claim 7, wherein said illumination unit comprises a plurality of illumination sources respectively configured to illuminate said keratinous fibers from a plurality of substantially azimuthal angles.

10. The device of claim 9, wherein said illumination unit comprises two substantially opposing illumination directions along a hair axis, such that a differential comparison between detections of each respective direction provides an indication of a condition of a hair scapula.

11. The device of claim 7, wherein said light diffusion angle is between 45 and 135 degrees.

12. The device of claim 7, wherein said illumination unit comprises a light source parallel to a keratinous fibers axis, or at least two illumination sources wherein at least two of said illumination sources illuminate the keratinous fibers from respectively different azimuthal angles.

13. The device of claim 12, wherein said illumination sources are configured to illuminate the keratinous fibers at different times or at different positions, thereby allowing illumination from respective sources to be measured separately.

14. The device of claim 13, further comprising a main illumination source and subsidiary illumination sources, and processing electronics to use differential illumination results from respective sources to determine an angle of a hair relative to the main illumination source, or said processing electronics is configured to use said keratinous fibers angle to correct a spectrum of said keratinous fibers, or said processing electronics is configured to use said differential illumination results from said multiple illumination sources to distinguish between specular and diffuse light from said keratinous fibers, or wherein at least said main illumination source is used for spectroscopy and at least one subsidiary illumination source is used for angular measurement, or wherein at least a second illumination source is used for spectroscopy.

15. The device of claim 7, wherein there are four illumination sources at a same elevation angle relative to a plane perpendicular to a detection axis, and wherein an azimuth angle with respect to a keratinous fibers axis is 30° for two of said four illumination sources and 150° for a third and a fourth of said illumination sources.

16. The device of claim 7, wherein said sensor comprises sensitivity to the visible and near infrared parts of the electromagnetic spectrum, or wherein said sensor comprises sensitivity to at least the 350-1500 nm wavelength range, or wherein said sensor comprises sensitivity to the 350-750 nm wavelength range, or wherein said sensor comprises sensitivity to at least the 400-950 nm wavelength range, or wherein said sensor comprises at least one calibration region for receiving calibration light and calibrating said optical readings, or said device further comprising a controllably polarizing element, or further comprising a controllably analyzing element, or further comprising grips for holding keratinous fibers in position for measurement.

* * * * *